(12) United States Patent
Pitram et al.

(10) Patent No.: US 8,710,180 B2
(45) Date of Patent: Apr. 29, 2014

(54) VEGF-SPECIFIC CAPTURE AGENTS, COMPOSITIONS, AND METHODS OF USING AND MAKING

(75) Inventors: Suresh Mark Pitram, La Jolla, CA (US); Heather Dawn Agnew, Culver City, CA (US); Tsun Yin Lai, Culver City, CA (US); Rosemary Dyane Rohde, Pasadena, CA (US); Paul Edward Kearney, Seattle, WA (US)

(73) Assignee: Indi Molecular, Inc., Culver City, CA (US)

( * ) Notice: Subject to any disclaimer, the term of this patent is extended or adjusted under 35 U.S.C. 154(b) by 0 days.

(21) Appl. No.: 13/601,023

(22) Filed: Aug. 31, 2012

(65) Prior Publication Data

US 2013/0156692 A1    Jun. 20, 2013

Related U.S. Application Data

(60) Provisional application No. 61/529,872, filed on Aug. 31, 2011, provisional application No. 61/556,713, filed on Nov. 7, 2011, provisional application No. 61/675,298, filed on Jul. 24, 2012, provisional application No. 61/585,590, filed on Jan. 11, 2012.

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61K 51/00* | (2006.01) |
| *A61M 36/14* | (2006.01) |
| *G01N 33/00* | (2006.01) |
| *G01N 33/564* | (2006.01) |
| *A61K 38/18* | (2006.01) |
| *A61K 38/12* | (2006.01) |

(52) U.S. Cl.
USPC ......... 530/300; 424/1.11; 435/7.92; 436/501; 514/8.1; 530/317

(58) Field of Classification Search
None
See application file for complete search history.

(56) References Cited

U.S. PATENT DOCUMENTS

| | | |
|---|---|---|
| 2008/0242587 A1 | 10/2008 | Kim et al. |
| 2009/0035317 A1 | 2/2009 | Daugherty et al. |
| 2010/0009896 A1* | 1/2010 | Agnew et al. ............... 514/2 |
| 2011/0263515 A1* | 10/2011 | Agnew et al. ............... 514/21.3 |
| 2012/0202219 A1* | 8/2012 | Agnew et al. ............... 435/7.4 |

FOREIGN PATENT DOCUMENTS

WO   WO2010064207   6/2010

OTHER PUBLICATIONS

Rudikoff et al "Single amino acid substitution altering antigen-binding specificity" Pro Natl Acad Sci 79:1979-1983. Published Mar. 1982.*

(Continued)

*Primary Examiner* — Cecilia J Tsang
*Assistant Examiner* — Zachary J Miknis
(74) *Attorney, Agent, or Firm* — Lathrop & Gage LLP

(57) ABSTRACT

The present application provides biligand and triligand protein-catalyzed capture (PCC) agents that specifically bind VEGF, as well as the use of these capture agents as detection, diagnosis, and treatment agents.

35 Claims, 96 Drawing Sheets

(56) References Cited

OTHER PUBLICATIONS

Agnew, H.D., et al. "Iterative In Situ Click Chemistry Creates Antibody-like Protein-Capture Agents", Angew Chem. Int. Ed., 48:4944-4948 (2009).
Bell, A., et al. "Differential tumor-targeting abilities of three single-domain antibody formats", Cancer Letters, 289:81-90 (2010).
Dhara, D., et al., "Electrophoretic Transport of Poly(ethylene glycol) Chains through Poly(acrylamide) Gel", J. Phys. Chem. B., 103:8458-8461 (1999).
D'Andrea, Luca Domenico, et al., "Peptide-based Molecules in Angiogenesis", Chem. Biol. Drug Des., 67:115-126 (2006).
Erlanson, D.A., et al., "Site-directed ligand discovery", PNAS, 97(17):9367-9372 (2000).
Fairbrother, W.J., et al., "Novel Peptides Selected to Bind Vascular Endothelial Growth Factor Target the Receptor-Binding Site", Biochemistry, 37:17754-17764 (1998).
Fields, G.B., et al., "Solid phase peptide synthesis utilizing 9-fluorenylmethoxycargbonyl amino acids", Int. J. Peptide Protein Res., 35:161-24 (1990).
Hosten, B., et al., "Effect of Interleukin-2 Pretreatment on Paclitaxel Absorption and Tissue Disposition after Oral and Intravenous Administration in Mice", Drug Metabolism and Disposition, 36(8):1729-1735 (2008).
International Search Report, International Application No. PCT/US2012/053388, Korean Intellectual Property Office, Nov. 16, 2012.
Jencks, William P., "On the attribution and additivity of binding energies", Proc. Natl. Acad. Sci. USA, 78(7):4046-4050 (1981).
Kurfürst, M. M., et al., "Detection and Molecular Weight Determination of Polyethylene Glycol-Modified Hirudin by Staining after Sodium Dodecyl Sulfate-Polyacrylamide Gel Electrophoresis", Anal. Biochem., 200:244-248 (1992).
Kwong, G.A., et al., "Modular Nucleic Acid Assembled p/MHC Microarrays for Multiplexed Sorting of Antigen-Specific T Cells", J. Am. Chem. Soc., 131(28):9695-9703 (2009).
Lam, K.S., et al., "A new type of synthetic peptide library for identifying ligand-biding activity", Nature, 354:82-84 (1991).
Lee, S.S., "Rapid Microwave-Assisted CNBr Cleavage of Bead-Bound Peptides", J. Comb. Chem., 10(6):807-809 (2008).
Lee, S.S., "Accurate MALDI-TOF/TOF Sequencing of One-Based-One-Compound Peptide Libraries with Application to the Identification of Multi-ligand Protein Affinity Agents Using In Situ Click Chemistry Screening", Anal. Chem., 82(2):672-679 (2010).
Liang, W.C., "Cross-species Vascular Endothelial Growth Factor (VEGF)-blocking Antibodies Completely Inhibit the Growth of Human Tumor Xenografts and Measure the Contribution of Stromal VEGF", J. Biol. Chem., 281:951-961 (2006).
Manetsch, R., et al., "In Situ Click Chemistry: Enzyme Inhibitors Made to Their Own Specifications", J. Am. Chem. Soc., 126:12809-12818 (2004).
Mocharla, V.P., "In Situ Click Chemistry: Enzyme-Generated Inhibitors of Carbonic AnhydraseII", Angew. Chem. Int. Ed., 44:116-120 (2004).
Murray, C.W., "The consequences of translational and rotational entropy lost by small molecules on binding to proteins", J. Computer-Aided Mol. Design, 16:741-753 (2002).
Nagengast, W.B., et al., "VEGF-SPECT with 111_In-bevacizumab in stage III/IV melanoma patients", Eur. J. Cancer, 47:1595-1602 (2011).
Pakkala, Mikka, et al., "Activity and stability of human kallikrein-2-specific linear and cyclic peptide inhibitors", J. Pept. Sci., 13:348-353 (2007).
Paudyal, B., et al., "Positron emission tomography imaging and biodistribution of vascular endothelial growth factor with 64_Cu-labeled bevacizumab in colorectal cancer xenografts", Cancer Sci., 102(1):117-121 (2011).
Peterson, K.J., et al. "A Florescence Polarization Assay for Identifying Ligands that Bind to Vascular Endothelial Growth Factor", Anal. Biochem., 378(1):8-14 (2008).
Shi, J., et al., "Improving Tumor Uptake and Pharmacokinetics of 64_Cu-labeled Cyclic RGD Peptide Dimers wiht Gly_3 and PEG_4 Linkers", Bioconjug. Chem., 20(4):750-759 (2009).
Shuker, S.B., et al., "Discovering High-Affinity Ligands for Proteins: SAR by NMR", Science, 274(5292):1531-1534 (1996).
Stollman, T.H., "Specific imaging of VEGF-A expression with radiolabeled anti-VEGF monoconolal antibody", Int. J. Cancer, 122:2310-2314 (2008).
Watt, A.P., "Higher Throughput Bioanalysis by Automation of a Protein Precipitation Assay Using a 96-Well Format with Detection by LC-MS/MS", Anal. Chem. 72:979-984 (2000).
Whiting, M., et al., "Inhibitors of HIV-1 Protease by Using In Situ Click Chemistry", Angew. Chem. Int. Ed., 45:1435-1439 (2006).
Zimmerman, S. B., et al., "ELectrophoresis of Polyethylene Glycols and Related Materials as Sodium Dodecyl Sulfate Complexes", Anal. Biochem., 234:190-193 (1996).

* cited by examiner

Figure 16
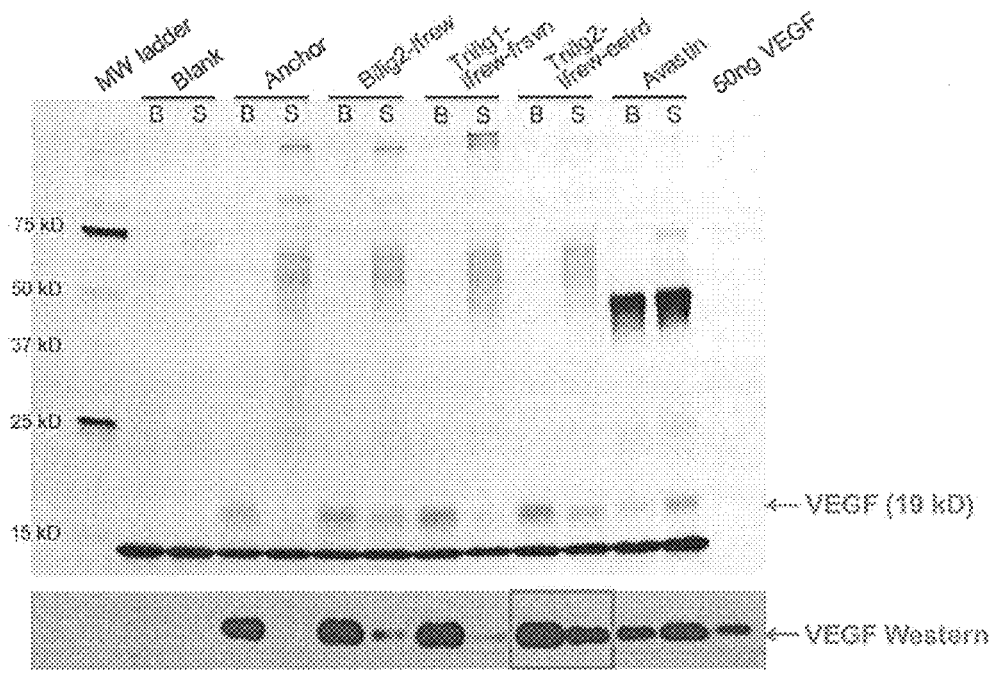
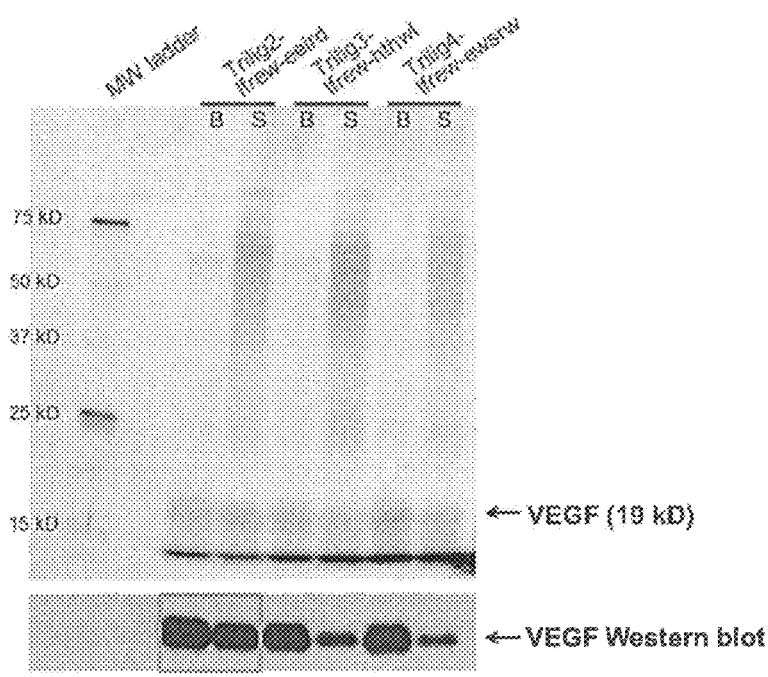

X-Anchor-Tz4-Ifrew-Tz4-eeird
(X = Biotin-PEG$_{n=3}$)

Figure 44
A.
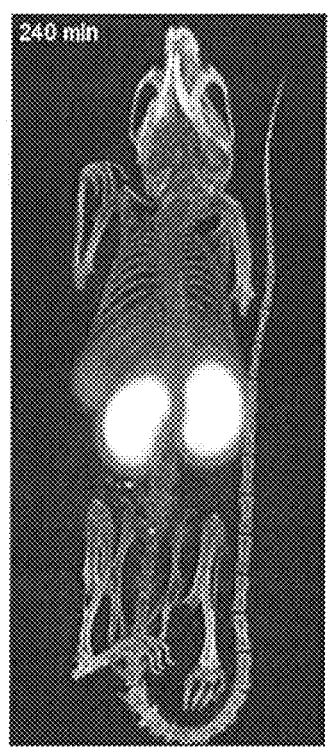
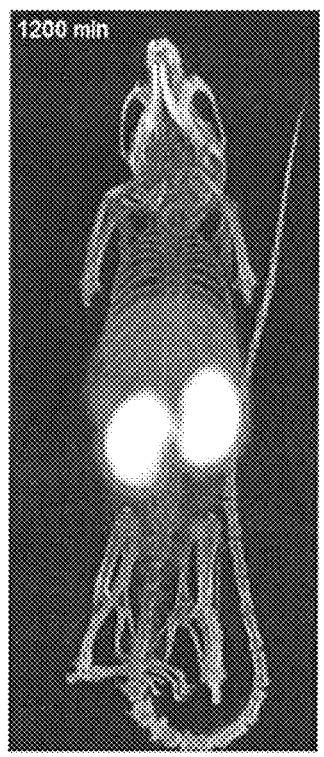
B.
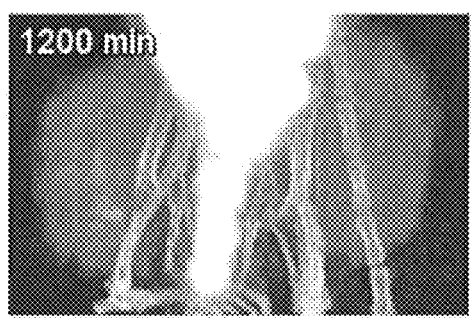

Figure 44C.
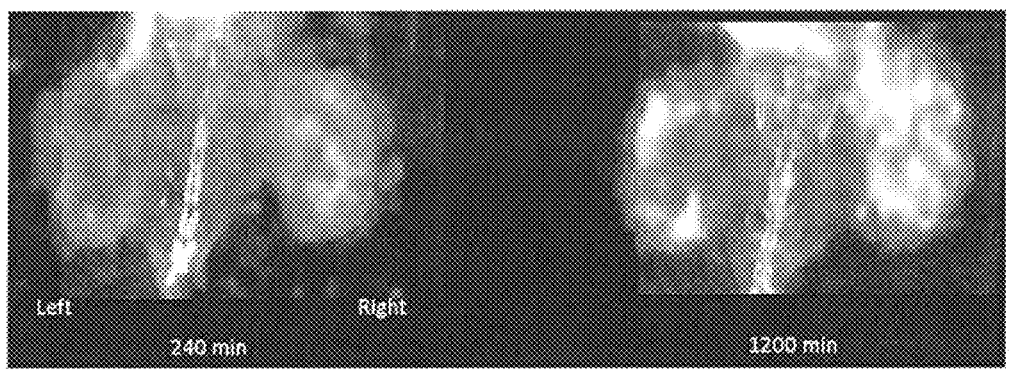
D.
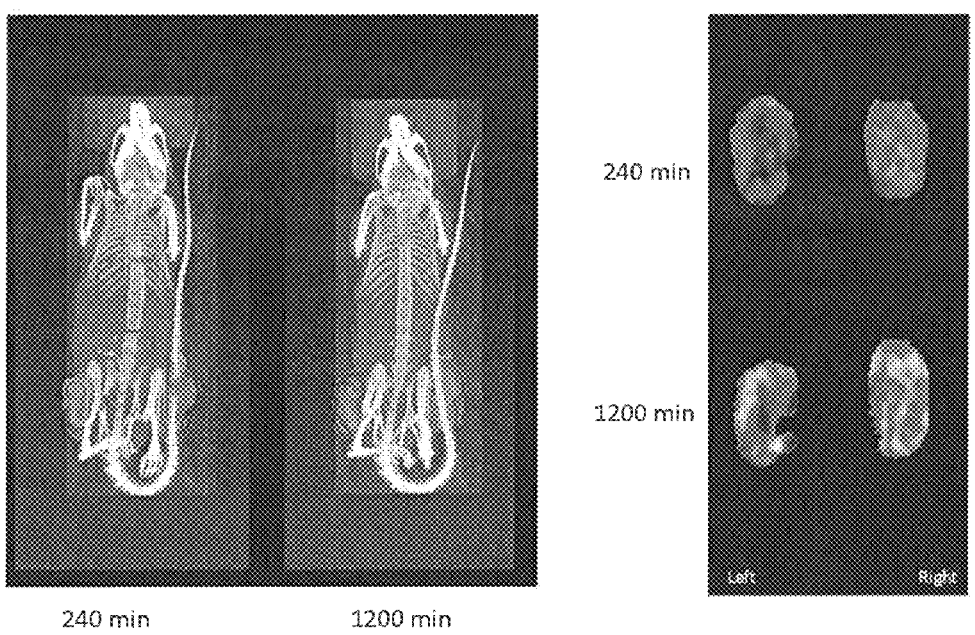
240 min    1200 min

Figure 44E.
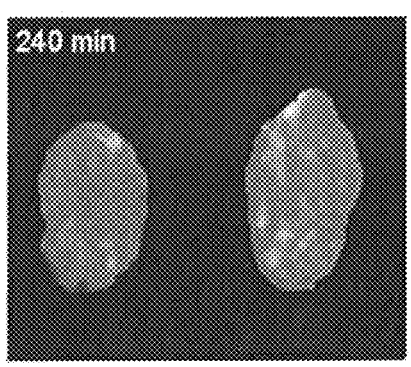 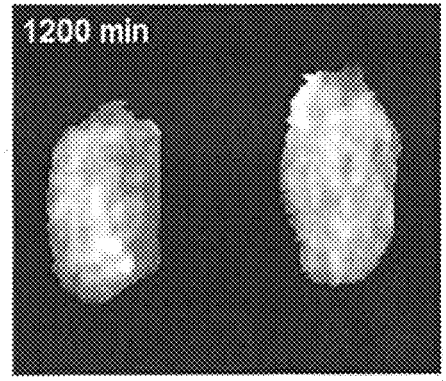

Figure 45
A.
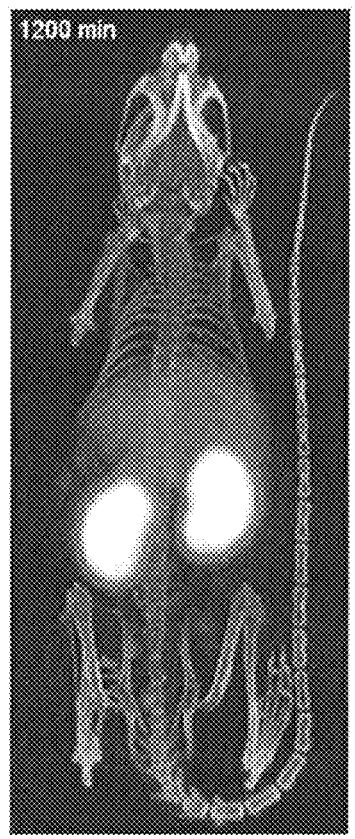
B.
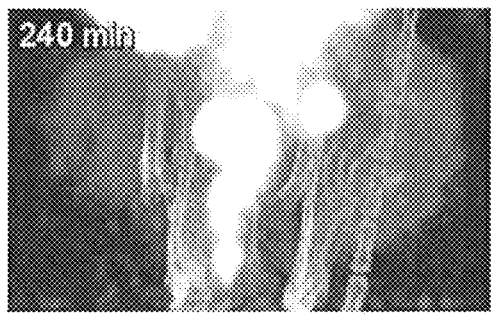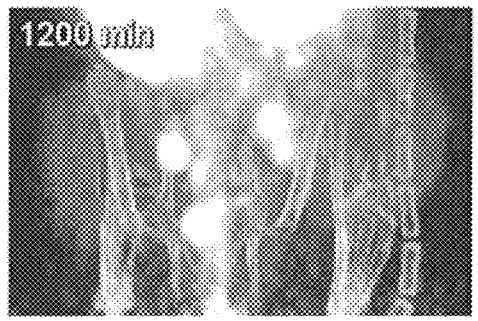

Figure 45C.
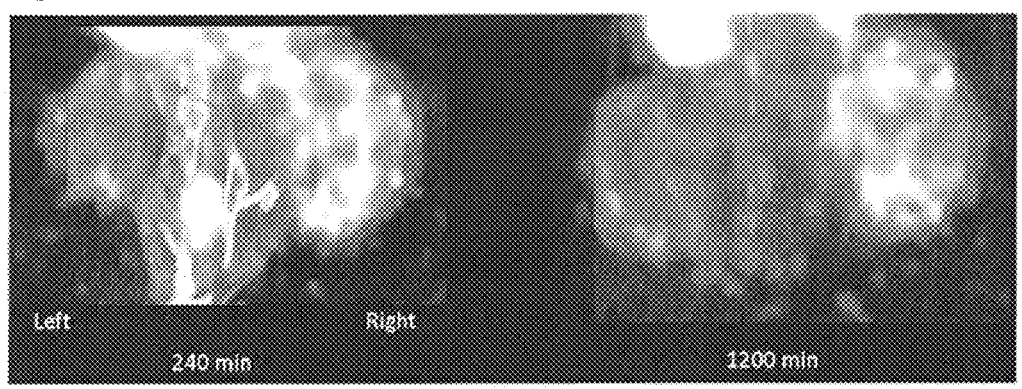
D.
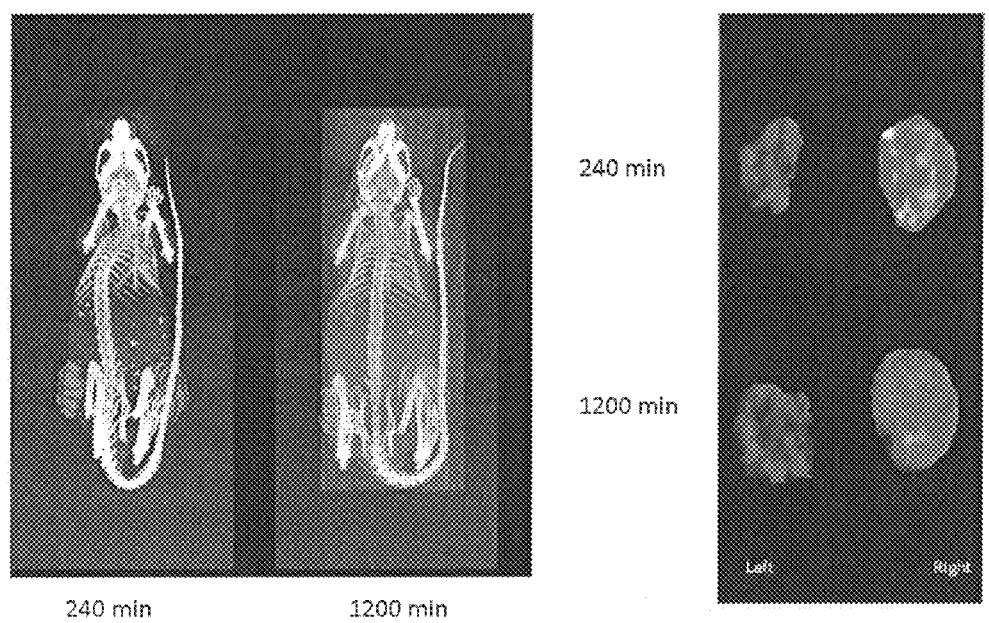

Figure 46
A.
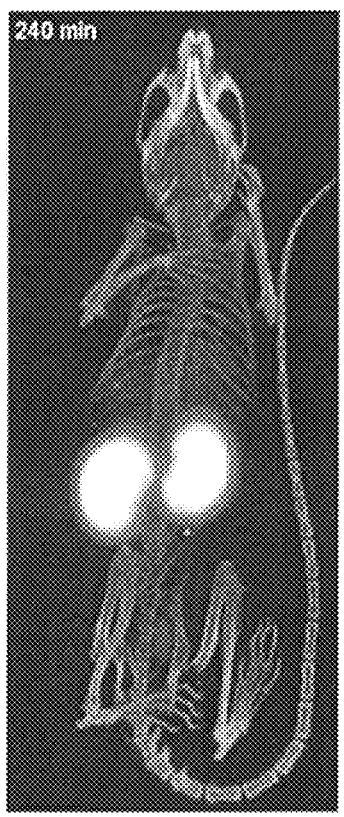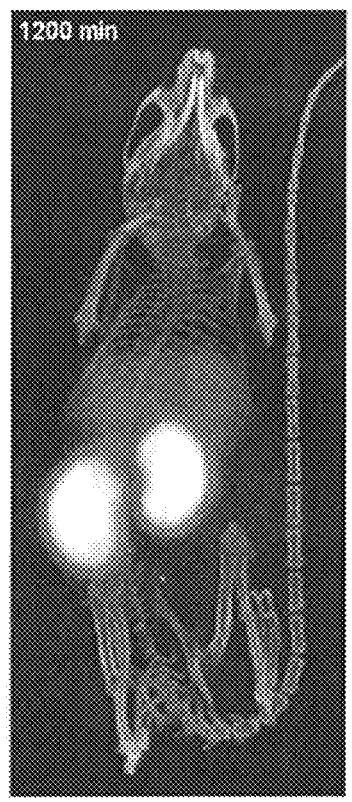
B.
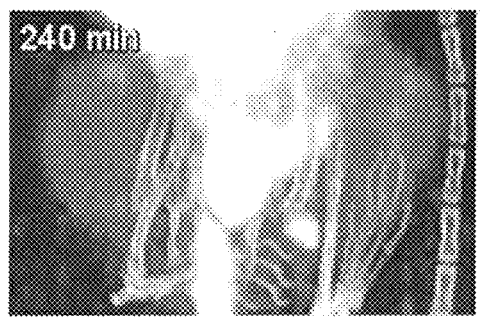

Figure 46C.
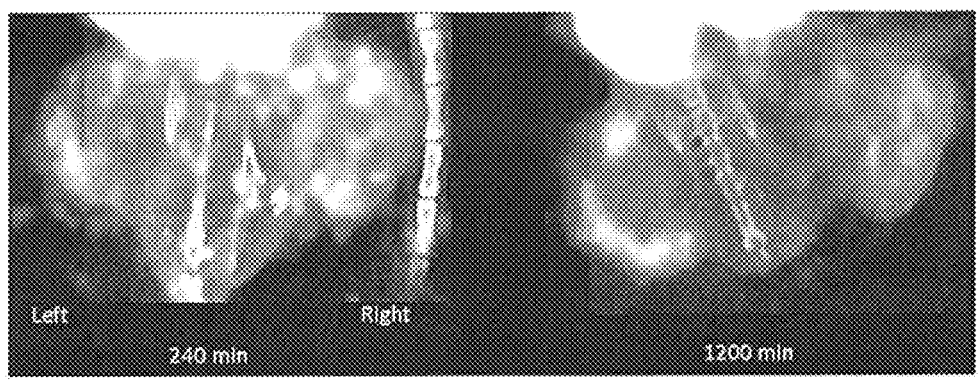
D.
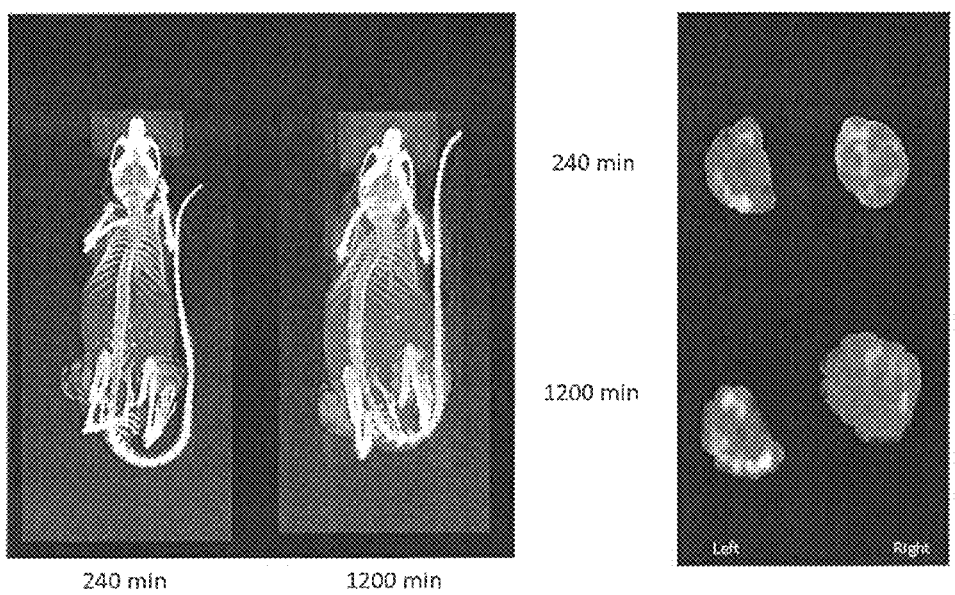

A.

Figure 47B.
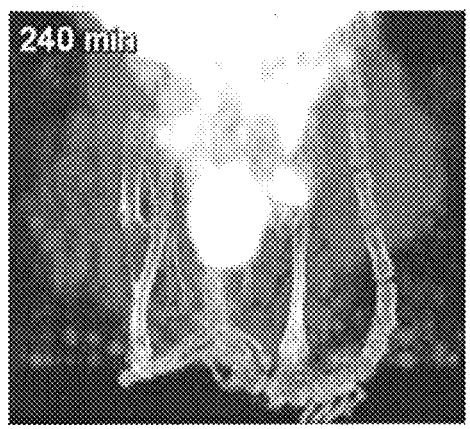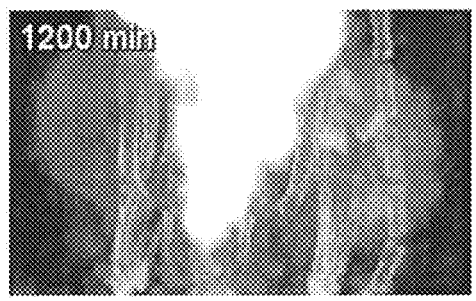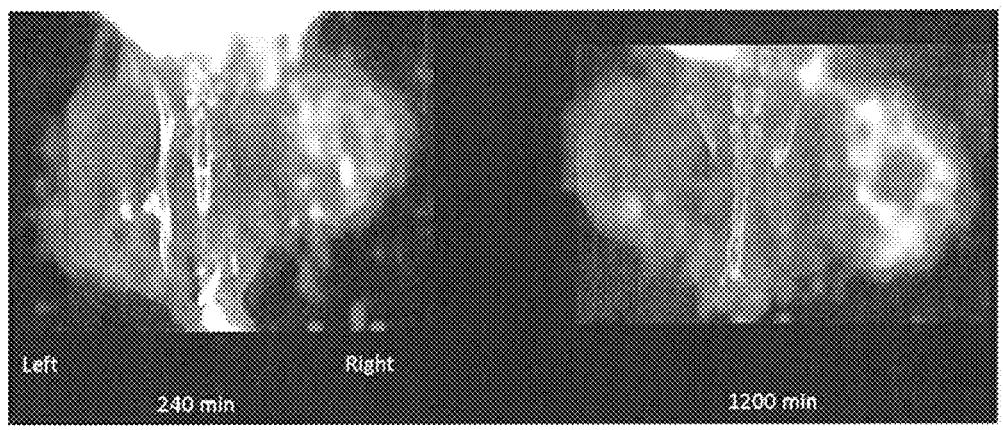

Figure 47D.
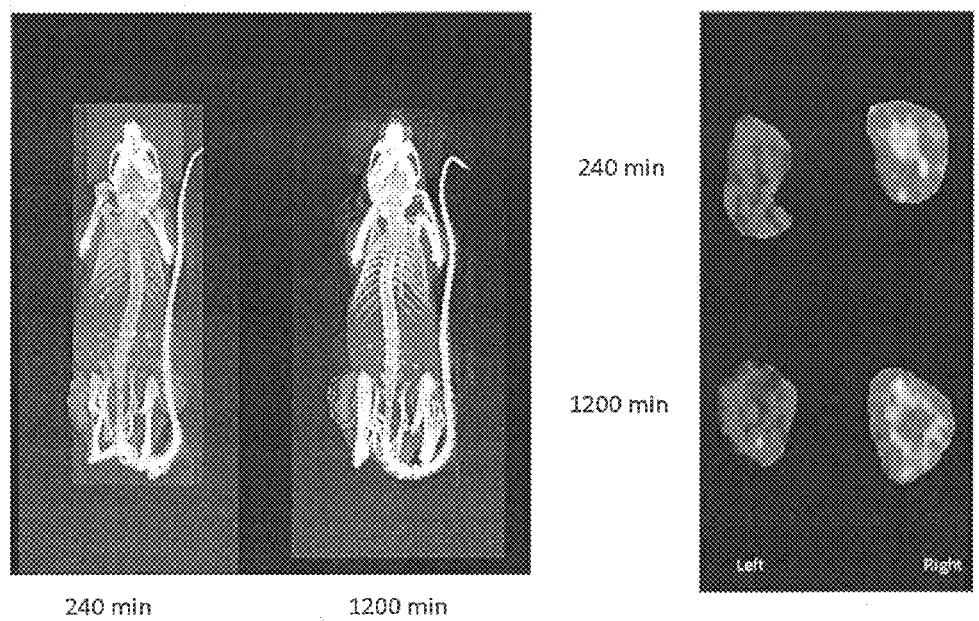
240 min          1200 min
E.
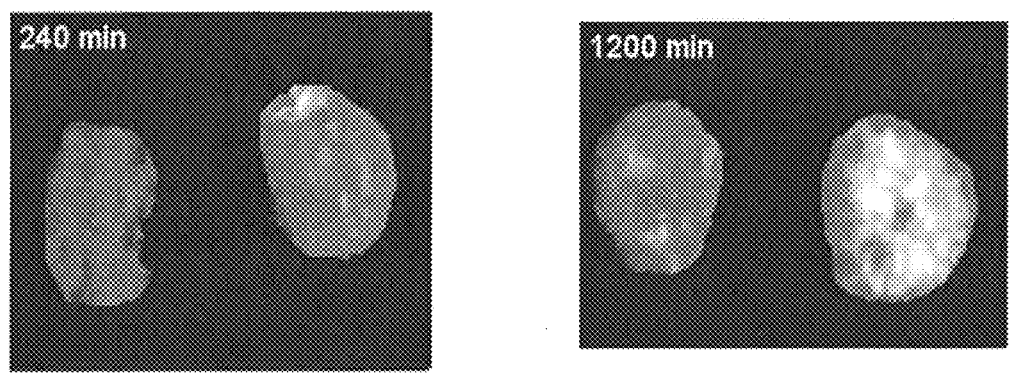

Figure 48
A.
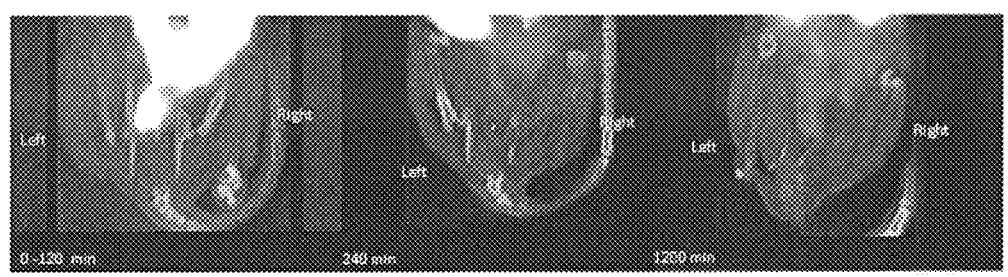
B.
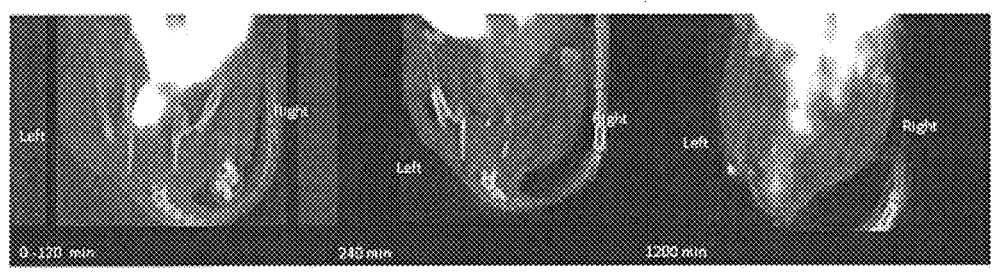

Figure 49
A.
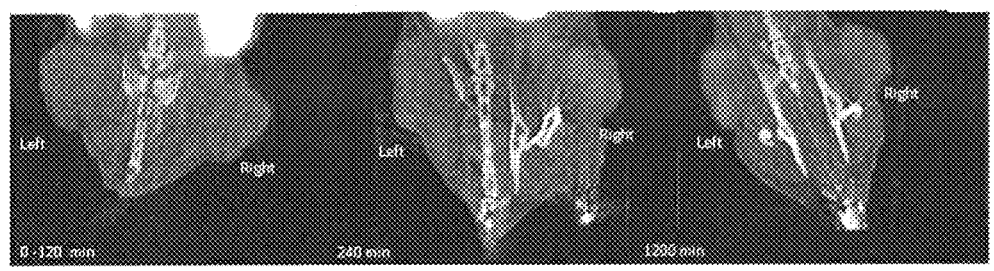
B.
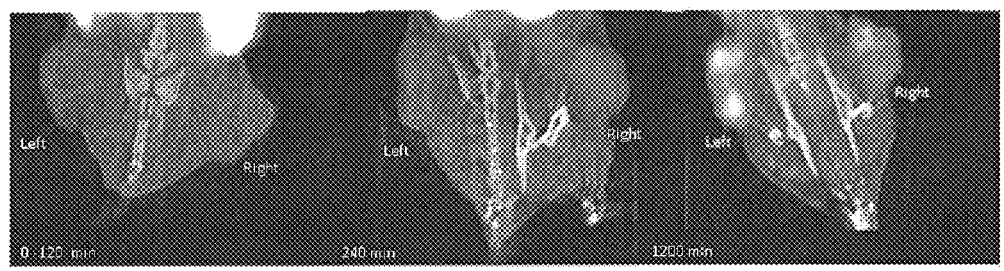

Figure 58
A.
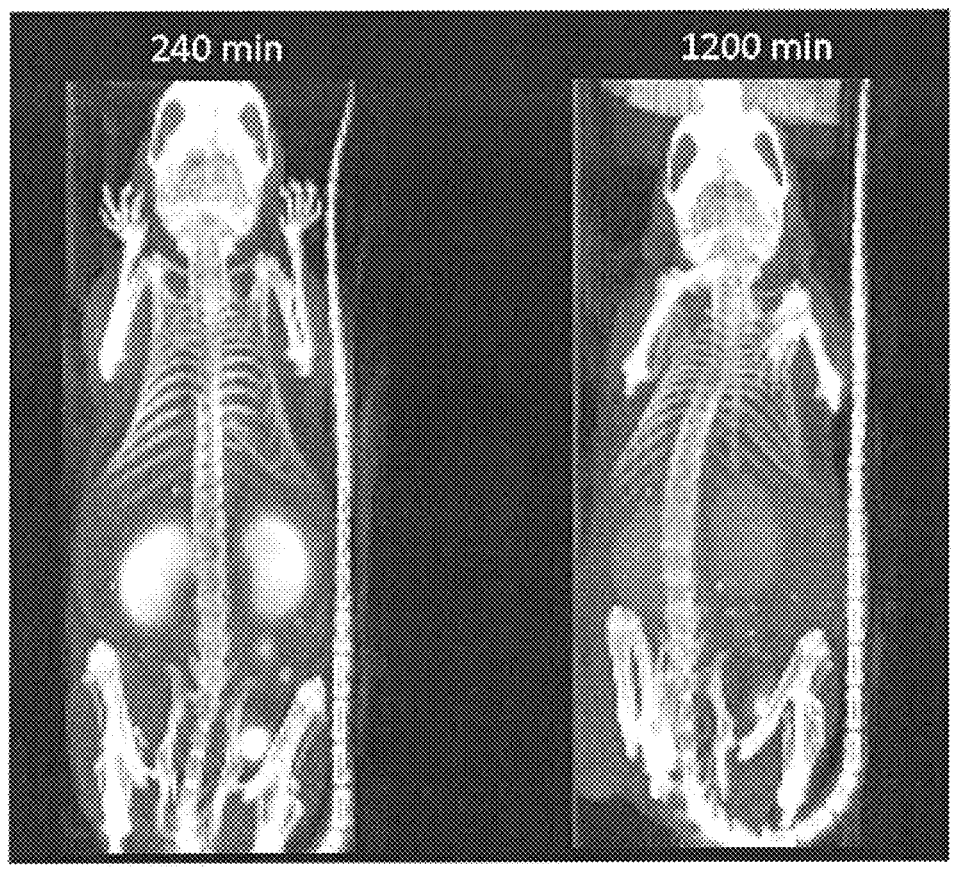
B.
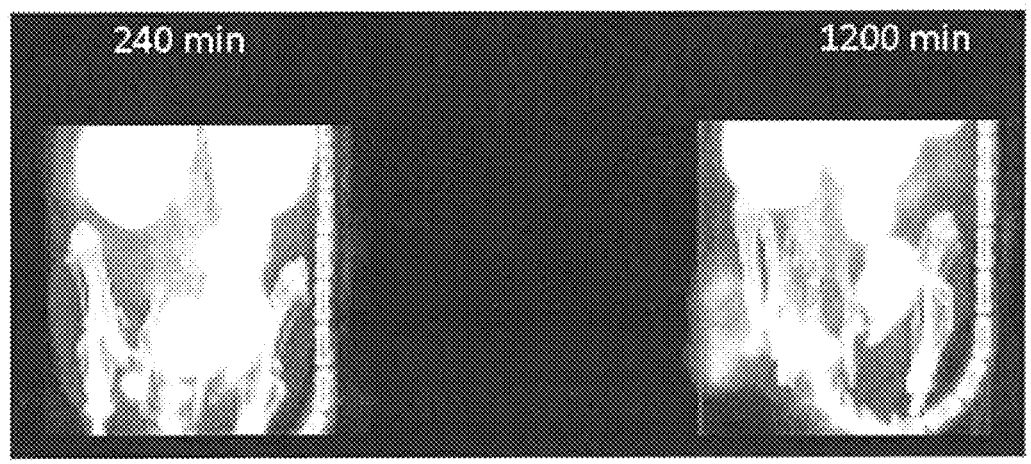

Figure 58C.
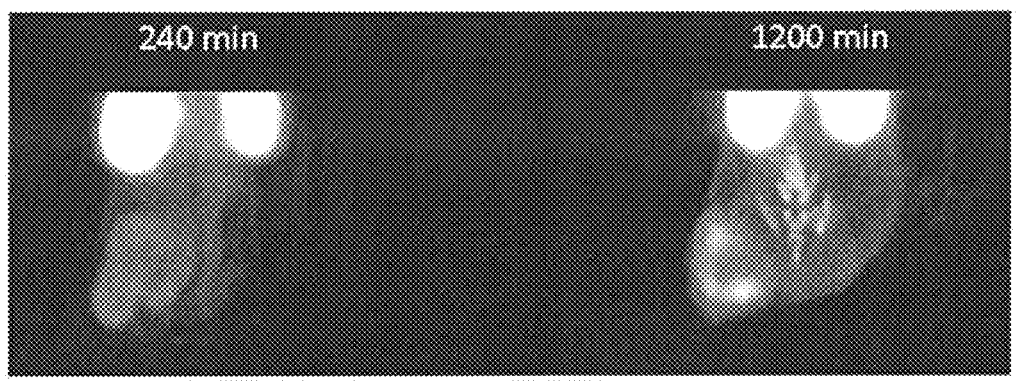
D.
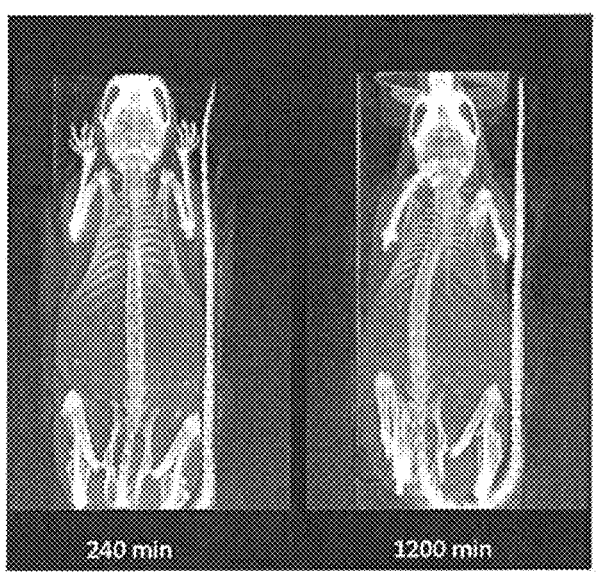
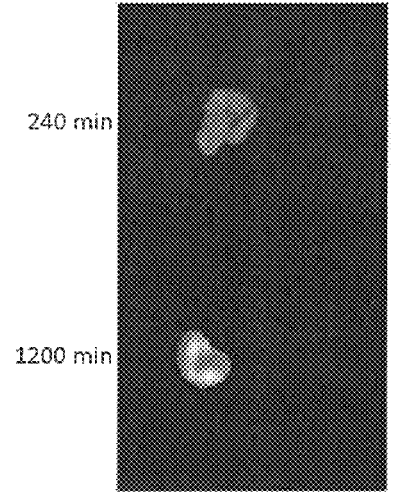

Figure 59
A.
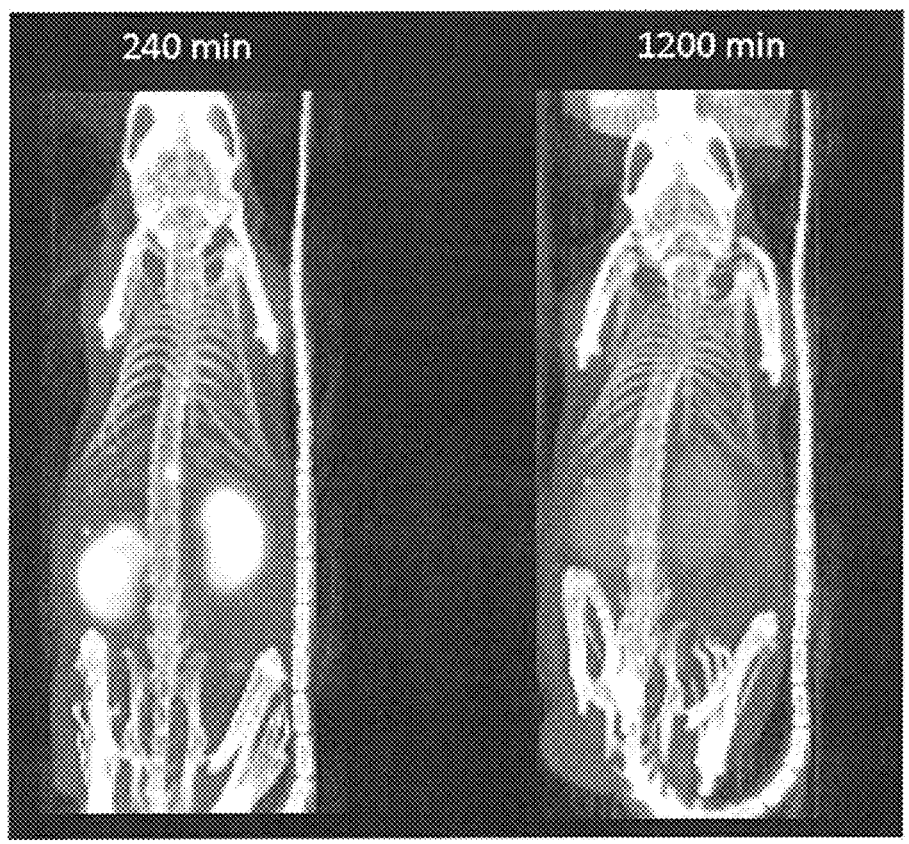
B.
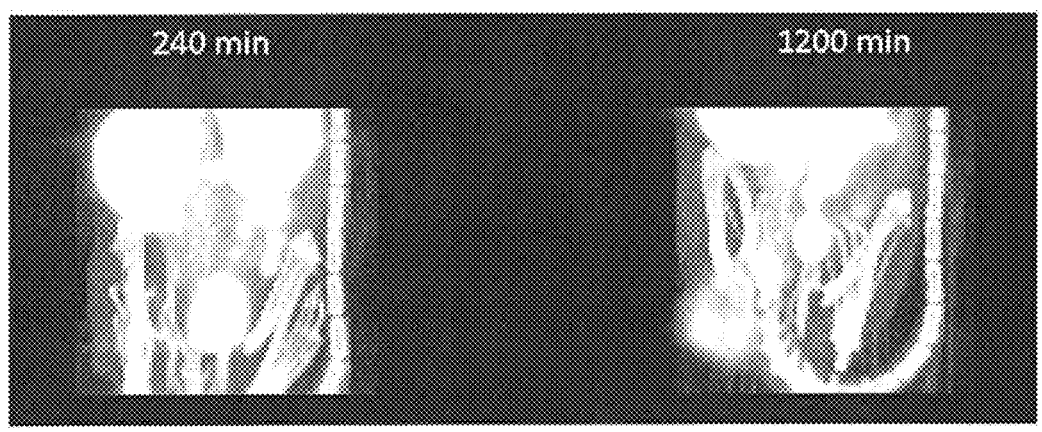

Figure 59C.
D.
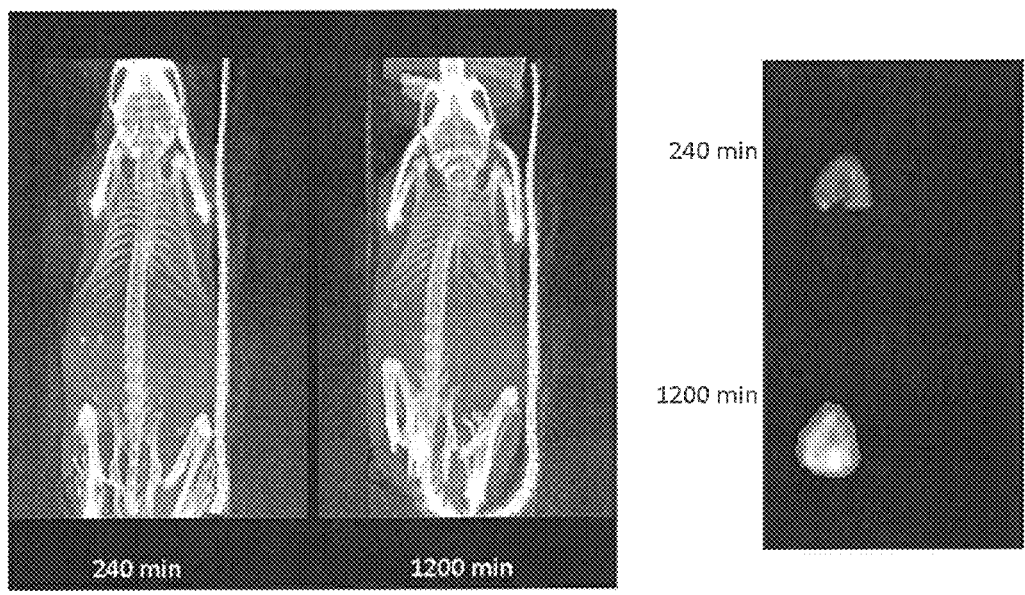

Figure 60
A.
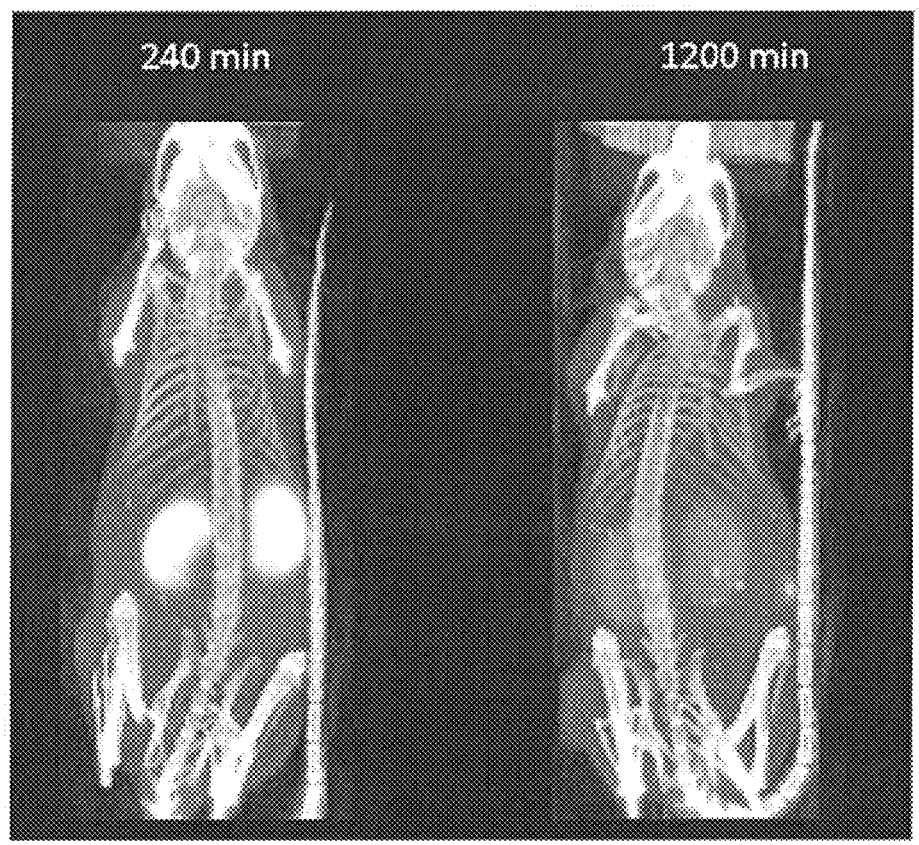
B.
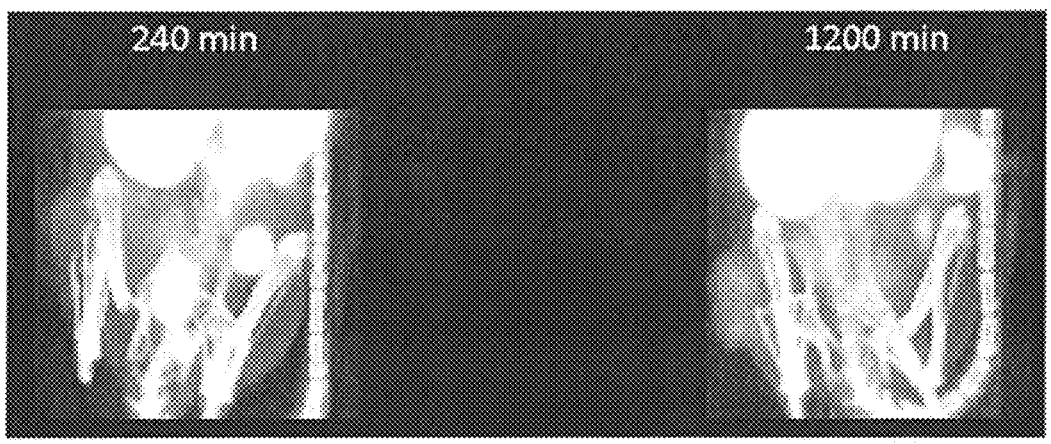

Figure 60C.
D.
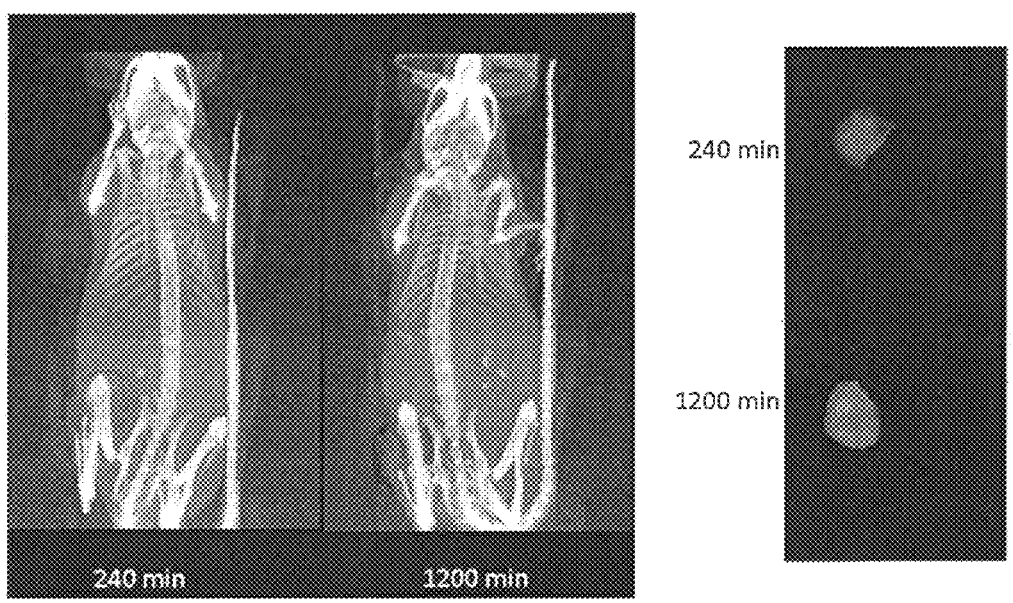

Figure 61
A.
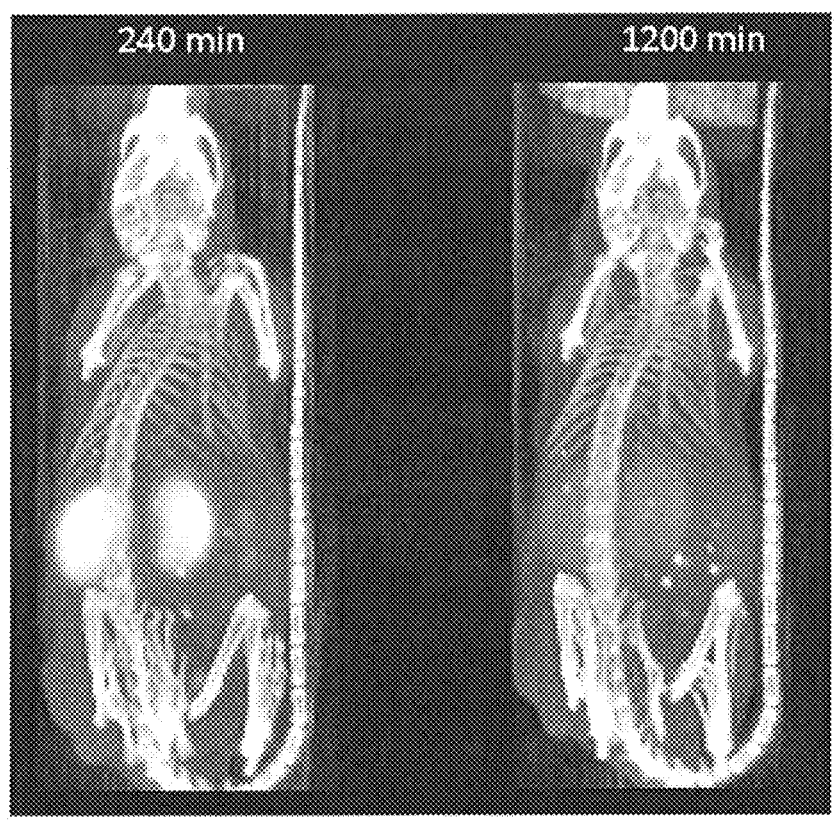
B.

Figure 61C.
D.
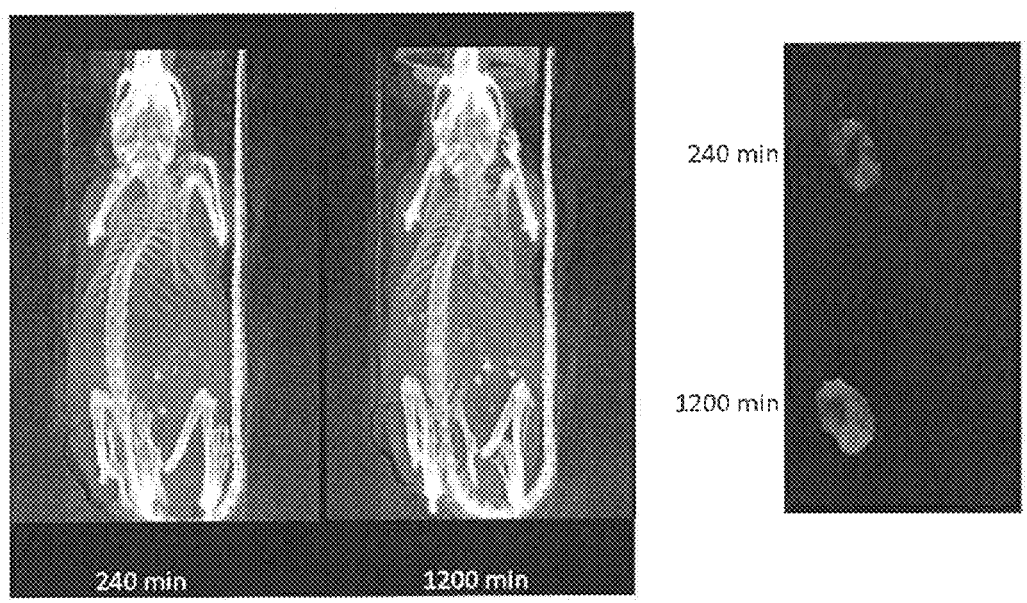

Figure 62
A.
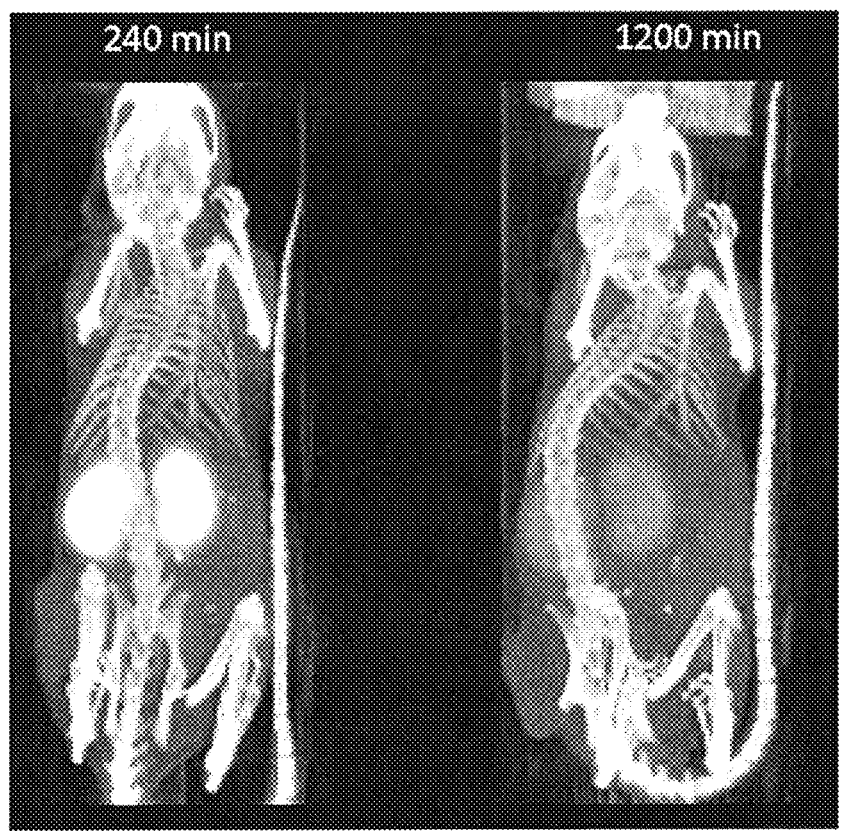
B.

Figure 62C.
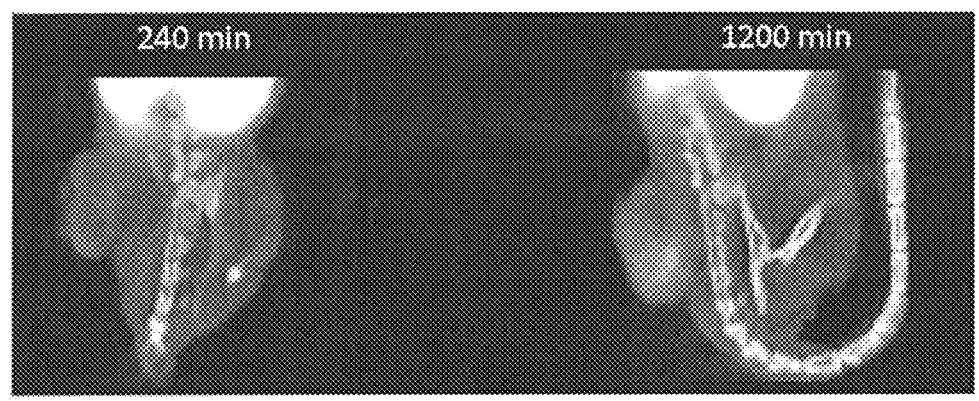
D.
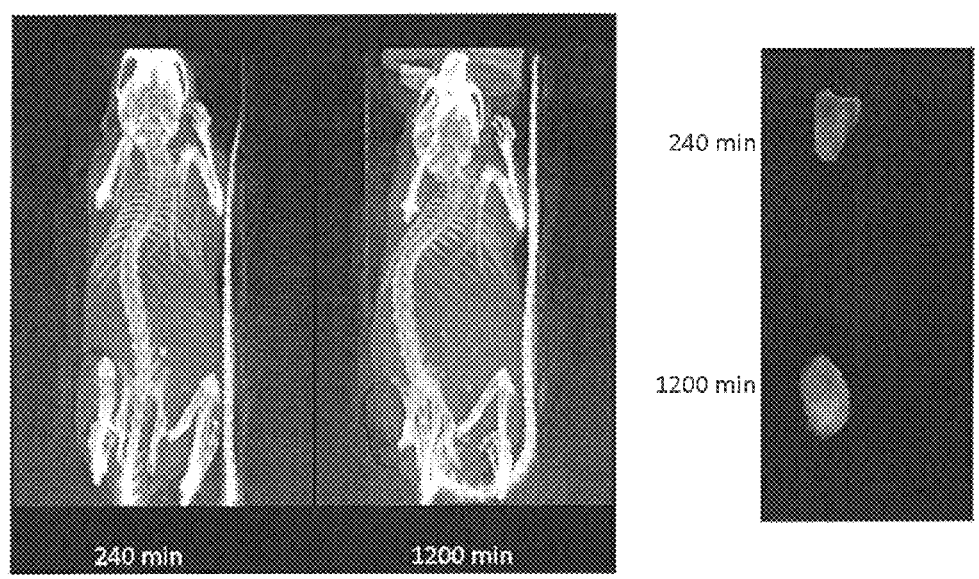

Figure 63
A.
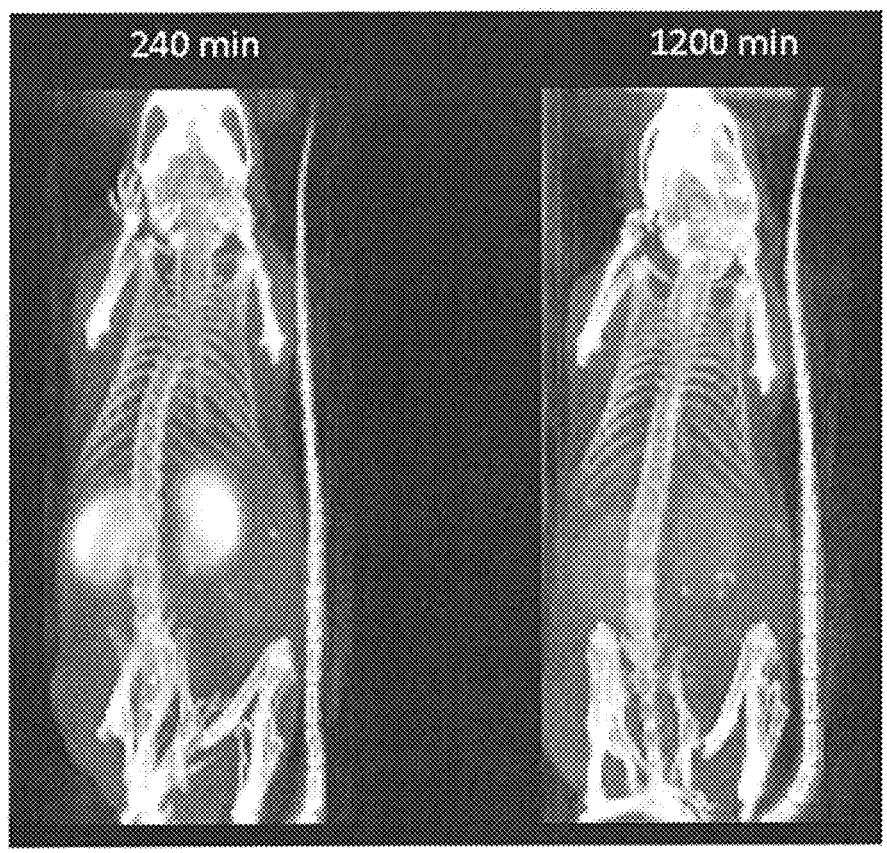
B.
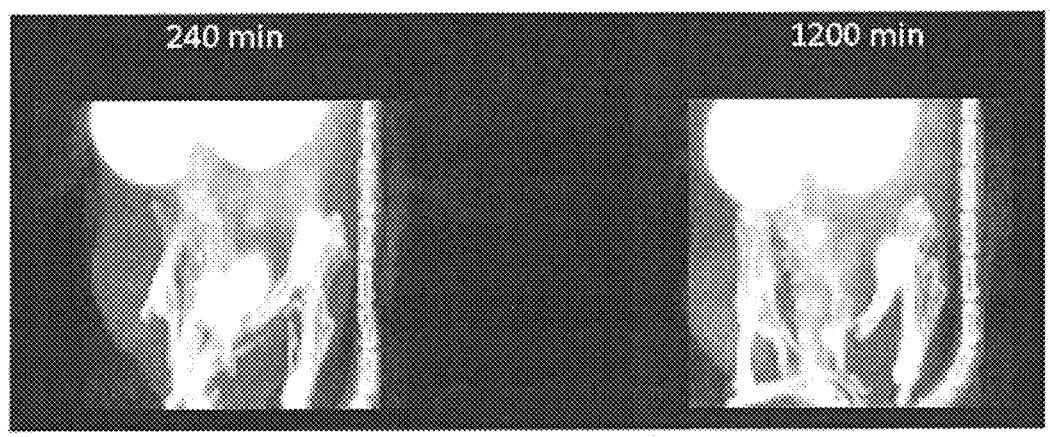

Figure 63C.
D.
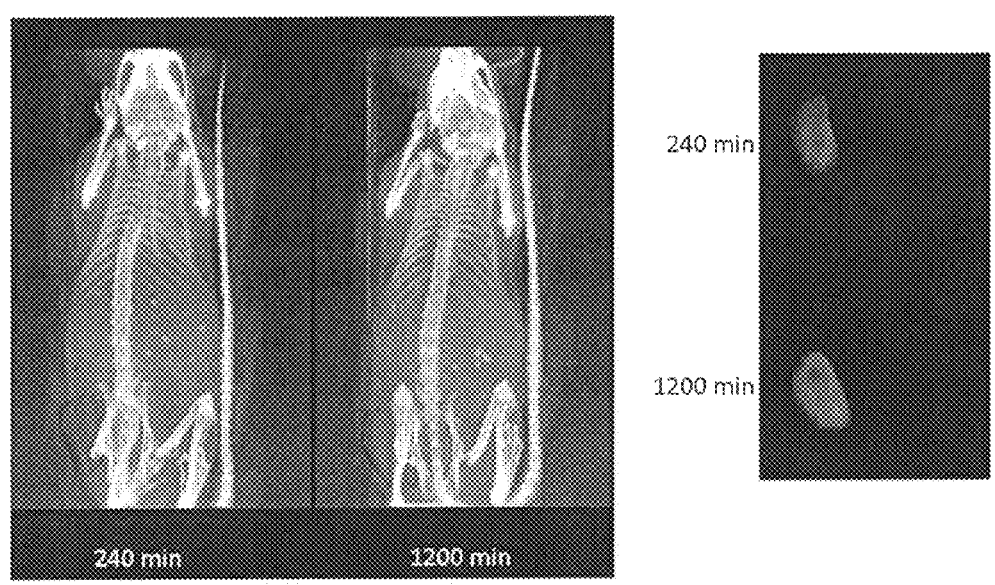

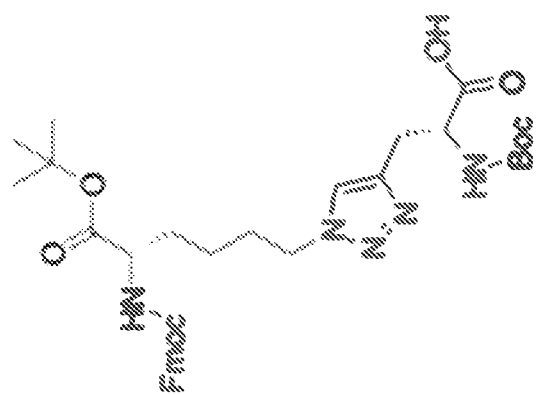
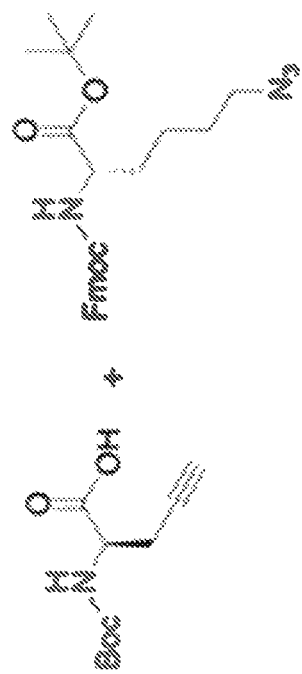
Fig. 65

Figure 66
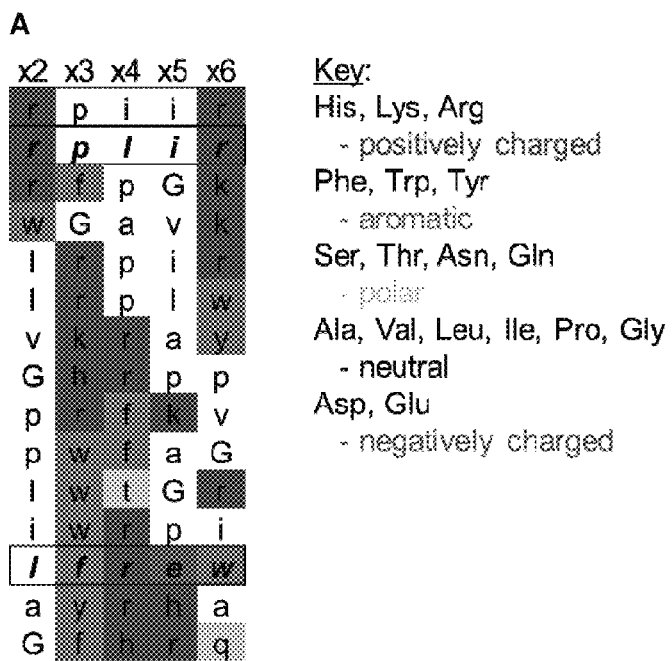
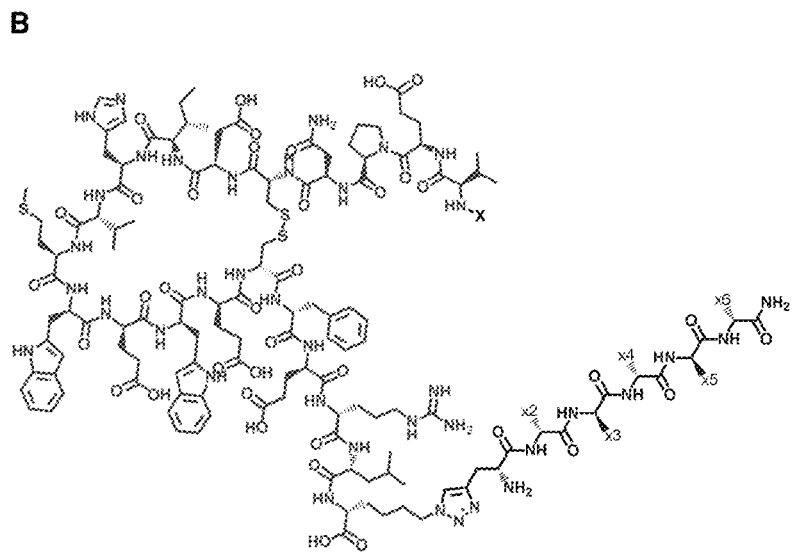

VEGF-SPECIFIC CAPTURE AGENTS, COMPOSITIONS, AND METHODS OF USING AND MAKING

RELATED APPLICATIONS

This application claims priority to U.S. Provisional Patent Application No. 61/529,872, filed Aug. 31, 2011; U.S. Provisional Patent Application No. 61/556,713, filed Nov. 7, 2011; U.S. Provisional Patent Application No. 61/585,590, filed Jan. 11, 2012 and U.S. Provisional Patent Application No. 61/675,298, filed Jul. 24, 2012. The contents of the aforementioned applications are hereby incorporated herein by reference in their entireties.

BACKGROUND

Detection of disease at the earliest stages requires multiplex measurements of key protein biomarkers in biological samples. The availability of high-affinity, highly selective compositions that recognize biomarkers from complex biological mixtures is a critical component for accurate detection of proteins that may indicate disease or changes in health.

Vascular endothelial growth factor A (VEGF) is a potent endothelial cell-specific mediator of angiogenesis and vasculogenesis. VEGF is involved pathologically in cancer, proliferative retinopathy, disease pathology of wet form age-related macular degeneration (AMD), and rheumatoid arthritis, and as such represents an important diagnostic and therapeutic target. VEGF signaling modulates angiogenesis, and VEGF levels are elevated in a variety of tumor types. As such, VEGF presents an attractive candidate for imaging, detection and treatment of cancer.

SUMMARY

Provided herein in certain embodiments are stable, synthetic VEGF capture agents that specifically bind VEGF.

In certain embodiments, the VEGF capture agents provided herein comprise a designed anchor ligand and a designed secondary ligand, both of which selectively bind VEGF. In certain embodiments, the capture agents further comprise a designed tertiary ligand.

In certain embodiments, the VEGF capture agents provided herein are biligands. In certain of these embodiments, the biligands comprise an anchor ligand comprising the amino acid sequence of SEQ ID NO:1 and a secondary ligand comprising the amino acid sequence of SEQ ID NOs:2, 3, or 4. In certain embodiments, the anchor ligand comprises an amino acid sequence, 80, 81, 82, 83, 84, 85, 86, 87, 88, 89, 90, 91, 92, 93, 94, 95, 96, 97, 98 or 100% identical to the amino acid sequence set forth in SEQ ID NO:1. In other embodiments, the anchor ligand comprises a fragment of the amino acid sequence of SEQ ID NO:1. In certain embodiments, this fragment contains 5, 6, 7, 8, 9, 10, 11, 12, 13, 14, 15, 16, 17 or 18 amino acids. In other embodiments, this fragment contains 5-18, 10-18, 5-15, 7-15, 9-15 or 3-16 amino acids. In certain embodiments, the secondary ligand comprises a formula of X2-X3-X4-X5-X6. In certain embodiments, X2 is selected from a positively charged D-amino acid, an aromatic D-amino acid and a neutral D-amino acid. In other embodiments, X2 is selected from D-arginine, D-tryptophan, D-leucine, D-valine, glycine, D-proline, D-isoleucine and D-alanine. In other embodiments, X3 is selected from a neutral D-amino acid, an aromatic D-amino acid or a positively charged amino acid. In certain embodiments, X3 is selected from D-proline, D-phenylalanine, glycine, D-arginine, D-lysine, D-histidine, D-tryptophan and D-tyrosine. In other embodiments, X4 is selected from a neutral D-amino acid, a positively charged D-amino acid, an aromatic D-amino acid and a polar D-amino acid. In certain embodiments, X4 is selected from D-isoleucine, D-leucine, D-proline, D-alanine, D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from D-isoleucine, glycine, D-valine, D-leucine, D-alanine, D-proline, D-lysine, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-lysine, D-tryptophan, D-tyrosine, D-proline, D-valine, glycine, D-isoleucine, D-alanine and D-glutamine.

In certain embodiments, X2 is selected from a positively charged D-amino acid and an aromatic D-amino acid. In other embodiments, X2 is selected from D-arginine and D-tryptophan. In other embodiments, X3 is selected from a neutral D-amino acid and an aromatic D-amino acid. In certain embodiments, X3 is selected from D-proline, D-phenylalanine and glycine. In other embodiments, X4 is a neutral D-amino acid. In certain embodiments, X4 is selected from D-isoleucine, D-leucine, D-proline and D-alanine. In other embodiments, X5 is a neutral D-amino acid. In certain embodiments, X5 is selected from D-isoleucine, glycine and D-valine. In other embodiments, X6 is a positively charged D-amino acid. In certain embodiments, X6 is selected from D-arginine and D-lysine.

In certain embodiments, X2 is a neutral D-amino acid. In other embodiments, X2 is selected from D-leucine, D-valine, glycine and D-proline. In other embodiments, X3 is a positively charged amino acid. In certain embodiments, X3 is selected from D-arginine, D-lysine and D-histidine. In other embodiments, X4 is selected from a neutral D-amino acid, a positively charged D-amino acid and an aromatic D-amino acid. In certain embodiments, X4 is selected from D-proline, D-arginine and D-phenylalanine. In other embodiments, X5 is selected from a neutral D-amino acid and a positively charged D-amino acid. In certain embodiments, X5 is selected from D-leucine, D-isoleucine, D-alanine, D-proline and D-lysine. In other embodiments, X6 is selected from a positively charged D-amino acid, an aromatic D-amino acid and a neutral D-amino acid. In certain embodiments, X6 is selected from D-arginine, D-tryptophan, D-tyrosine, D-proline and D-valine.

In certain embodiments, X2 is a neutral D-amino acid. In other embodiments, X2 is selected from D-leucine, glycine, D-proline, D-isoleucine and D-alanine. In other embodiments, X3 is an aromatic D-amino acid. In certain embodiments, X3 is selected from D-tryptophan, D-phenylalanine and D-tyrosine. In other embodiments, X4 is selected from a positively charged D-amino acid, an aromatic D-amino acid and a polar D-amino acid. In certain embodiments, X4 is selected from D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from glycine, D-alanine, D-proline, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-tryptophan, glycine, D-isoleucine, D-alanine and D-glutamine.

In other embodiments, the secondary ligand comprises an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence, wherein one amino acid differs from an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence wherein the amino acid sequence consists of an amino acid sequence selected from SEQ ID NOs:2, 3, 4, 9, 10, 11, 12, 13, 14, 15, 16, 17, 18, 19, 20 and 21.

In certain embodiments, the anchor ligand and secondary ligand are linked together via a 1,4-disubstituted-1,2,3-triazole (Tz4) linkage. In certain embodiments, the biligands comprise a structure selected from:

(SEQ ID NO: 67)
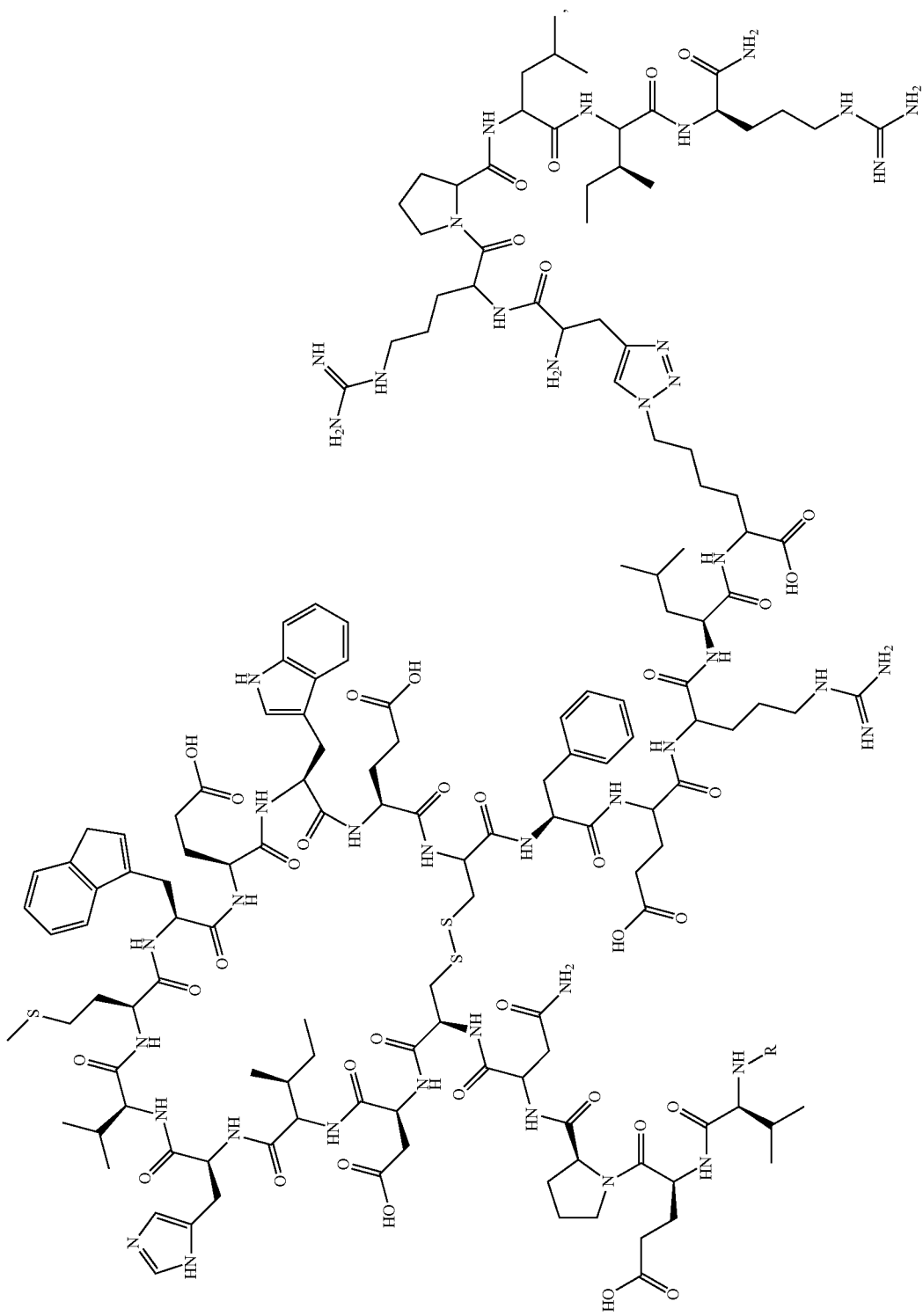

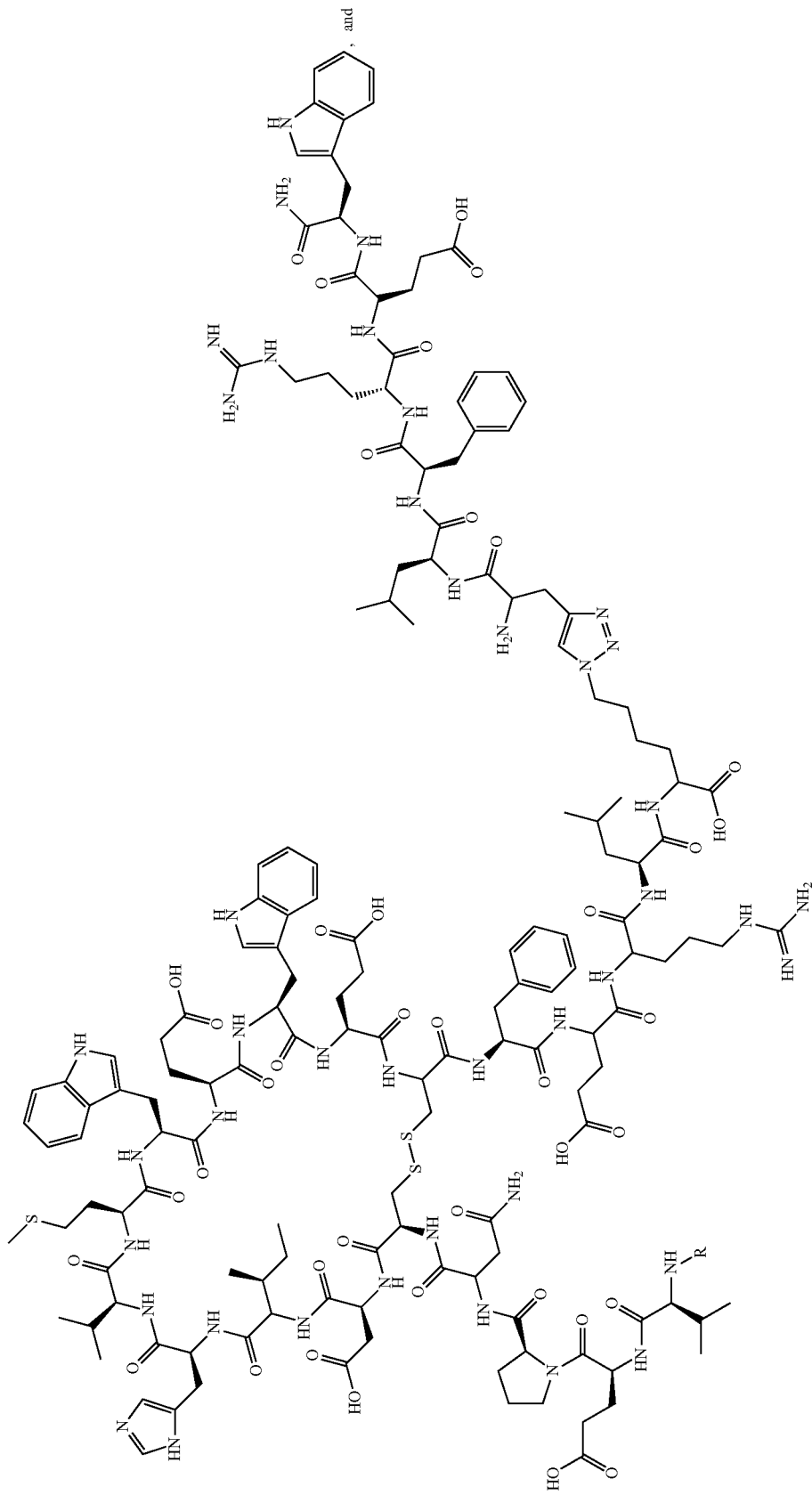
(SEQ ID NO: 68)

(SEQ ID NO: 69)
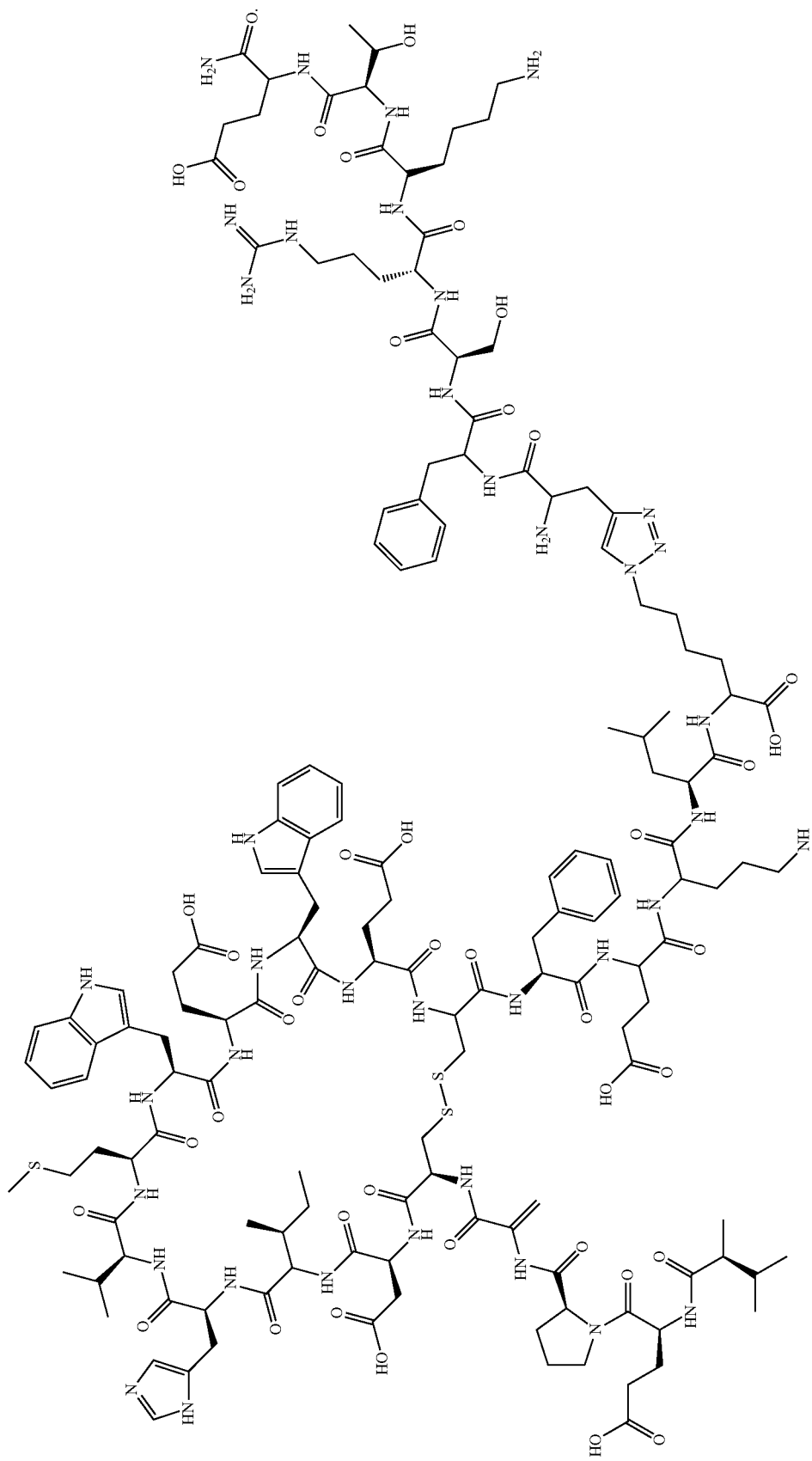

In certain embodiments, the VEGF capture agents provided herein are triligands. In certain of these embodiments, the triligands comprise an anchor ligand comprising the amino acid sequence of SEQ ID NO:1, a secondary ligand comprising the amino acid sequence of SEQ ID NO:3, and a tertiary ligand comprising the amino acid sequence of SEQ ID NOs:5, 6, 7, or 8. In other embodiments, the anchor ligand comprises an amino acid sequence, 80, 81, 82, 83, 84, 85, 86, 87, 88, 89, 90, 91, 92, 93, 94, 95, 96, 97, 98 or 100% identical to the amino acid sequence set forth in SEQ ID NO:1. In other embodiments, the anchor ligand comprises a fragment of the amino acid sequence of SEQ ID NO:1. In certain embodiments, this fragment contains 5, 6, 7, 8, 9, 10, 11, 12, 13, 14, 15, 16, 17 or 18 amino acids. In other embodiments, this fragment contains 5-18, 10-18, 5-15, 7-15, 9-15 or 3-16 amino acids. In certain embodiments, the secondary ligand comprises a formula of X2-X3-X4-X5-X6. In certain embodiments, X2 is selected from a positively charged D-amino acid, an aromatic D-amino acid and a neutral D-amino acid. In other embodiments, X2 is selected from D-arginine, D-tryptophan, D-leucine, D-valine, glycine, D-proline, D-isoleucine and D-alanine. In other embodiments, X3 is selected from a neutral D-amino acid, an aromatic D-amino acid or a positively charged amino acid. In certain embodiments, X3 is selected from D-proline, D-phenylalanine, glycine, D-arginine, D-lysine, D-histidine, D-tryptophan and D-tyrosine. In other embodiments, X4 is selected from a neutral D-amino acid, a positively charged D-amino acid, an aromatic D-amino acid and a polar D-amino acid. In certain embodiments, X4 is selected from D-isoleucine, D-leucine, D-proline, D-alanine, D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from D-isoleucine, glycine, D-valine, D-leucine, D-alanine, D-proline, D-lysine, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-lysine, D-tryptophan, D-tyrosine, D-proline, D-valine, glycine, D-isoleucine, D-alanine and D-glutamine.

In certain embodiments, X2 is selected from a positively charged D-amino acid and an aromatic D-amino acid. In other embodiments, X2 is selected from D-arginine and D-tryptophan. In other embodiments, X3 is selected from a neutral D-amino acid and an aromatic D-amino acid. In certain embodiments, X3 is selected from D-proline, D-phenylalanine and glycine. In other embodiments, X4 is a neutral D-amino acid. In certain embodiments, X4 is selected from D-isoleucine, D-leucine, D-proline and D-alanine. In other embodiments, X5 is a neutral D-amino acid. In certain embodiments, X5 is selected from D-isoleucine, glycine and D-valine. In other embodiments, X6 is a positively charged D-amino acid. In certain embodiments, X6 is selected from D-arginine and D-lysine.

In certain embodiments, X2 is a neutral D-amino acid. In other embodiments, X2 is selected from D-leucine, D-valine, glycine and D-proline. In other embodiments, X3 is a positively charged amino acid. In certain embodiments, X3 is selected from D-arginine, D-lysine and D-histidine. In other embodiments, X4 is selected from a neutral D-amino acid, a positively charged D-amino acid and an aromatic D-amino acid. In certain embodiments, X4 is selected from D-proline, D-arginine and D-phenylalanine. In other embodiments, X5 is selected from a neutral D-amino acid and a positively charged D-amino acid. In certain embodiments, X5 is selected from D-leucine, D-isoleucine, D-alanine, D-proline and D-lysine. In other embodiments, X6 is selected from a positively charged D-amino acid, an aromatic D-amino acid and a neutral D-amino acid. In certain embodiments, X6 is selected from D-arginine, D-tryptophan, D-tyrosine, D-proline and D-valine.

In certain embodiments, X2 is a neutral D-amino acid. In other embodiments, X2 is selected from D-leucine, glycine, D-proline, D-isoleucine and D-alanine. In other embodiments, X3 is an aromatic D-amino acid. In certain embodiments, X3 is selected from D-tryptophan, D-phenylalanine and D-tyrosine. In other embodiments, X4 is selected from a positively charged D-amino acid, an aromatic D-amino acid and a polar D-amino acid. In certain embodiments, X4 is selected from D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from glycine, D-alanine, D-proline, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-tryptophan, glycine, D-isoleucine, D-alanine and D-glutamine.

In other embodiments, the secondary ligand comprises an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence, wherein one amino acid differs from an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence wherein the amino acid sequence consists of an amino acid sequence selected from SEQ ID NOs:2, 3, 4, 9, 10, 11, 12, 13, 14, 15, 16, 17, 18, 19, 20 and 21.

In certain embodiments of the biligand and triligand capture agents provided herein, the tertiary ligand comprises a formula of X2-X3-X4-X5-X6. In certain embodiments, X2 is a positively charged D-amino acid. In other embodiments, X2 is selected from D-histidine, D-arginine and D-lysine. In other embodiments, X3 is selected from a polar D-amino acid, a neutral D-amino acid and a negatively charged amino acid. In certain embodiments, X3 is selected from D-threonine, D-asparagine, D-leucine, D-proline, D-isoleucine, D-alanine, and D-glutamate. In other embodiments, X4 is selected from a positively charged D-amino acid, an aromatic D-amino acid and a neutral D-amino acid. In certain embodiments, X4 is selected from D-histidine, D-lysine, D-arginine, D-tryptophan, D-phenylalanine, D-proline, D-leucine and D-tyrosine. In other embodiments, X5 is selected from a neutral D-amino acid, a positively charged D-amino acid, an aromatic D-amino acid and a polar D-amino acid. In certain embodiments, X5 is selected from D-valine, D-proline, D-histidine, D-phenylalanine, D-tryptophan, D-asparagine, D-glutamine, D-serine and D-tyrosine. In other embodiments, X6 is selected from a positively charged D-amino acid, an aromatic D-amino acid, a polar D-amino acid and a neutral D-amino acid. In certain embodiments, X6 is selected from D-arginine, D-tyrosine, D-asparagine, D-glutamine, D-leucine, D-proline, D-lysine and D-histidine.

In certain embodiments, X2 is an aromatic D-amino acid. In other embodiments, X2 is selected from D-tyrosine, D-phenylalanine and D-tryptophan. In other embodiments, X3 is selected from a neutral D-amino acid and a positively charged amino acid. In certain embodiments, X3 is selected from D-proline, D-alanine, glycine, D-leucine, D-lysine, D-arginine and D-histidine. In other embodiments, X4 is selected from a positively charged D-amino acid, an aromatic D-amino acid, a negatively charged D-amino acid, a neutral D-amino acid and a polar D-amino acid. In certain embodiments, X4 is selected from D-arginine, D-histidine, D-tryptophan, D-phenylalanine, D-glutamate, D-proline, D-serine and D-threonine. In other embodiments, X5 is selected from a neutral D-amino acid, a negatively charged D-amino acid, a positively charged D-amino acid, an aromatic D-amino acid and a polar D-amino acid. In certain embodiments, X5 is selected from D-proline, D-aspartate, D-lysine, D-arginine, D-tyrosine, D-histidine, D-alanine, D-valine, D-leucine and D-asparagine. In other embodiments, X6 is selected from a positively charged D-amino acid, a polar D-amino acid, a neutral D-amino acid, a negatively charged D-amino acid and an aromatic D-amino acid. In certain embodiments, X6 is selected from D-histidine, D-lysine, D-asparagine, D-threonine, D-glutamine, D-leucine, D-aspartate, D-serine, D-tyrosine, D-arginine, D-tryptophan, D-glutamate and D-valine.

In certain embodiments, X2 is negatively charged D-amino acid. In other embodiments, X2 is selected from D-glutamate and D-aspartate. In other embodiments, X3 is selected from a negatively charged D-amino acid, an aromatic D-amino acid, a positively charged amino acid and a polar D-amino acid. In certain embodiments, X3 is selected from D-glutamate, D-phenylalanine, D-tryptophan, D-histidine, D-lysine, D-asparagine and D-serine. In other embodiments, X4 is selected from a neutral D-amino acid, a positively charged D-amino acid, a polar D-amino acid, a negatively charged D-amino acid and an aromatic D-amino acid. In certain embodiments, X4 is selected from D-isoleucine, D-proline, D-alanine, D-arginine, D-serine, D-aspartate, D-asparagine, D-proline, D-phenylalanine, D-tyrosine and D-histidine. In other embodiments, X5 is selected from a positively charged D-amino acid, an aromatic D-amino acid and a neutral D-amino acid. In certain embodiments, X5 is selected from D-arginine, D-tyrosine, glycine, D-tryptophan, D-lysine, D-histidine, D-alanine, D-asparagine and D-leucine. In other embodiments, X6 is selected from a negatively charged D-amino acid, a neutral D-amino acid, an aromatic D-amino acid and a polar D-amino acid. In certain embodiments, X6 is selected from D-aspartate, D-proline, D-tryptophan, D-tyrosine, D-leucine, D-asparagine, D-serine and D-threonine.

In other embodiments, the tertiary ligand comprises an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64. In other embodiments, the secondary ligand comprises an amino acid sequence, wherein one amino acid differs from an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64. In other embodiments, the secondary ligand comprises an amino acid sequence wherein the amino acid sequence consists of an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64.

In certain embodiments, the anchor ligand and secondary ligand and/or the secondary ligand and tertiary ligand are linked together via a Tz4 linkage. In certain embodiments, the triligands comprise a structure selected from:

(SEQ ID NO: 70)

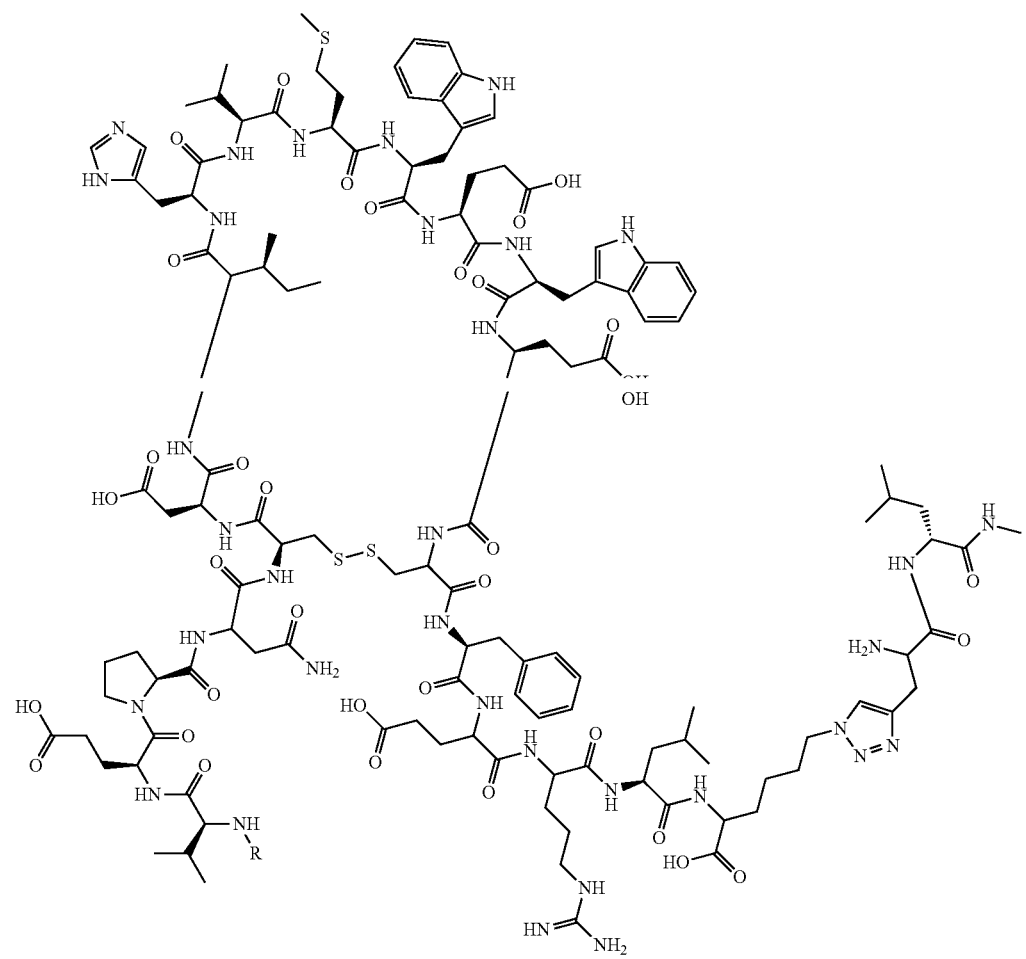

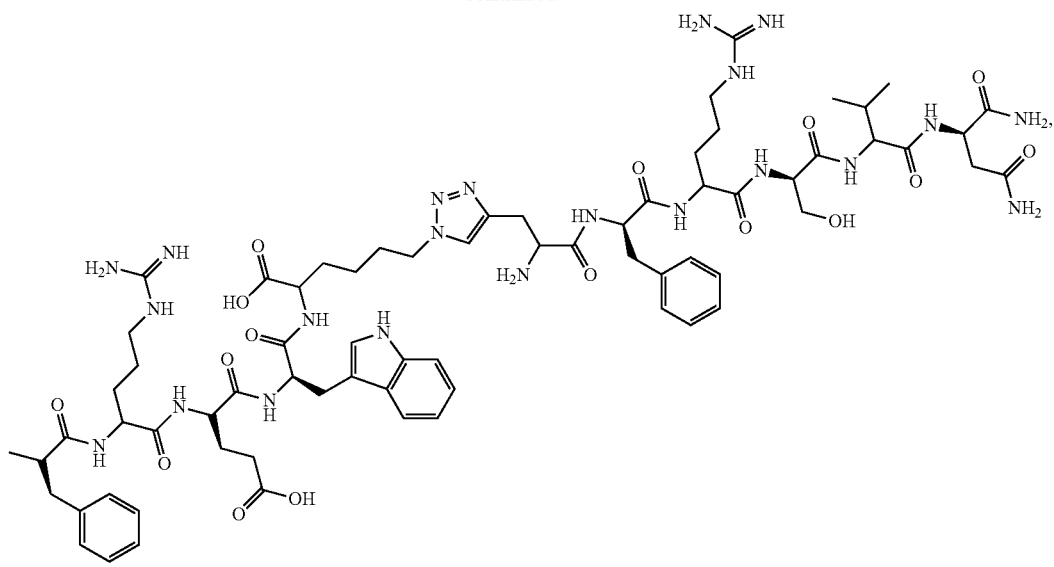
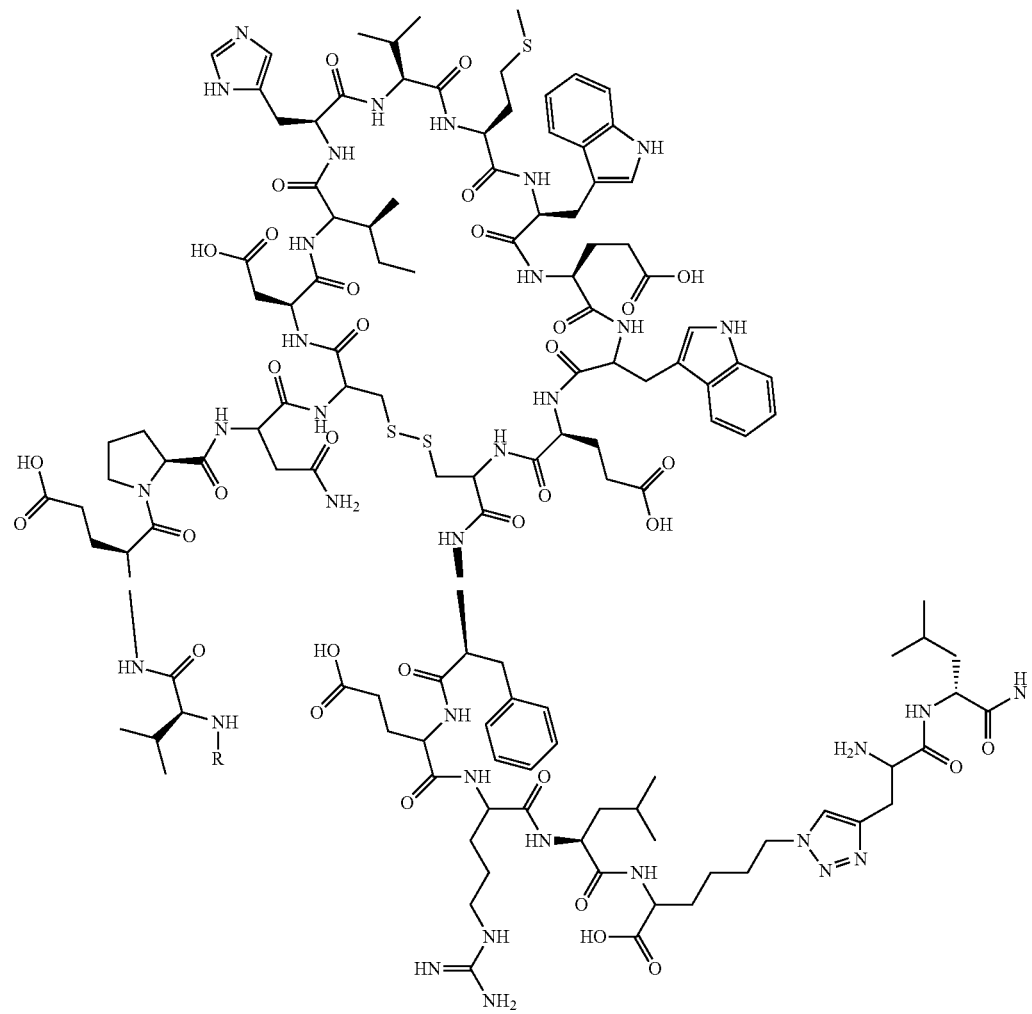
(SEQ ID NO: 71)

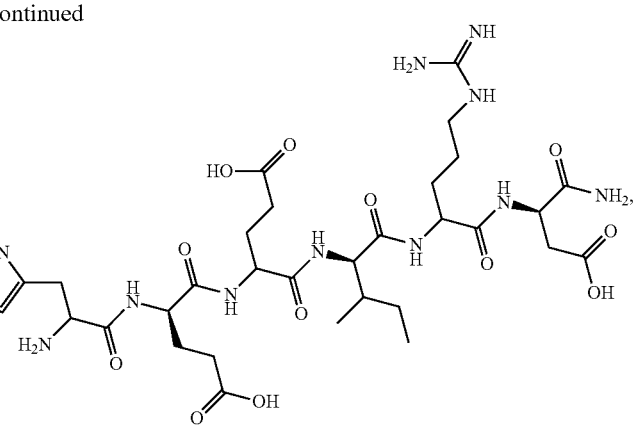
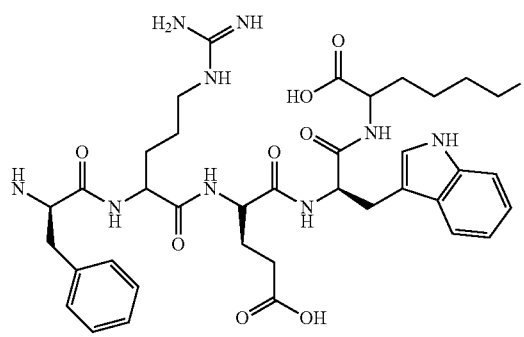
(SEQ ID NO: 72)
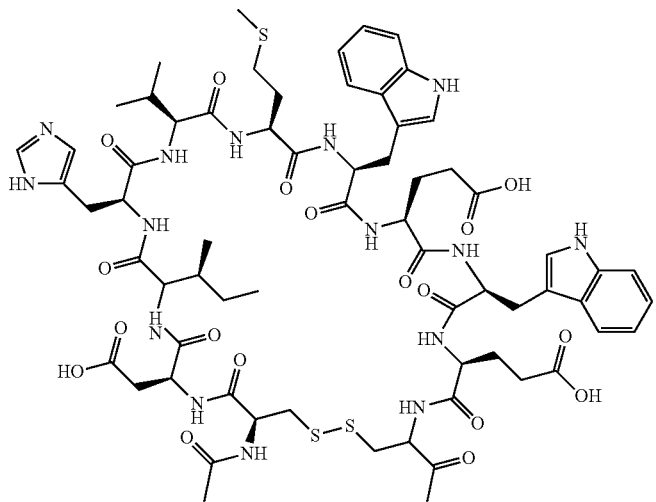
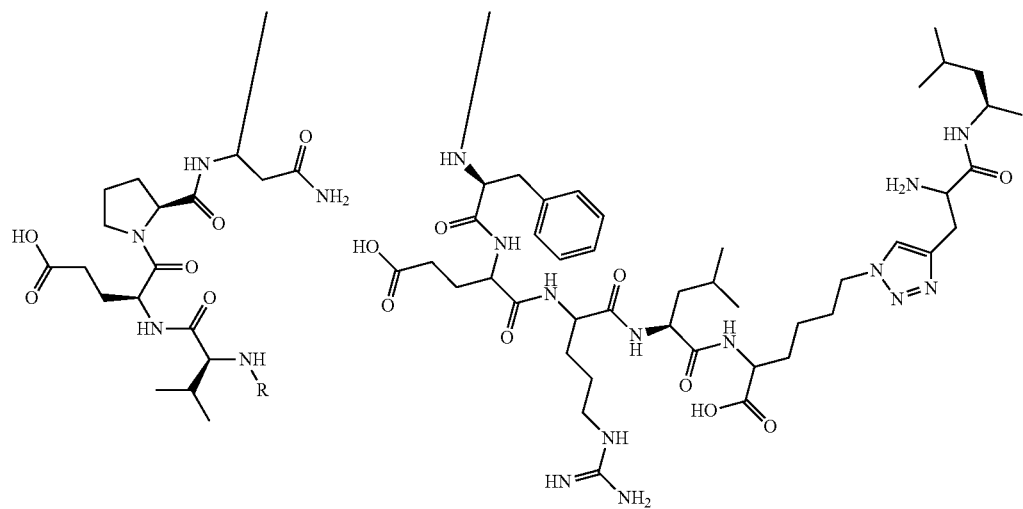

-continued
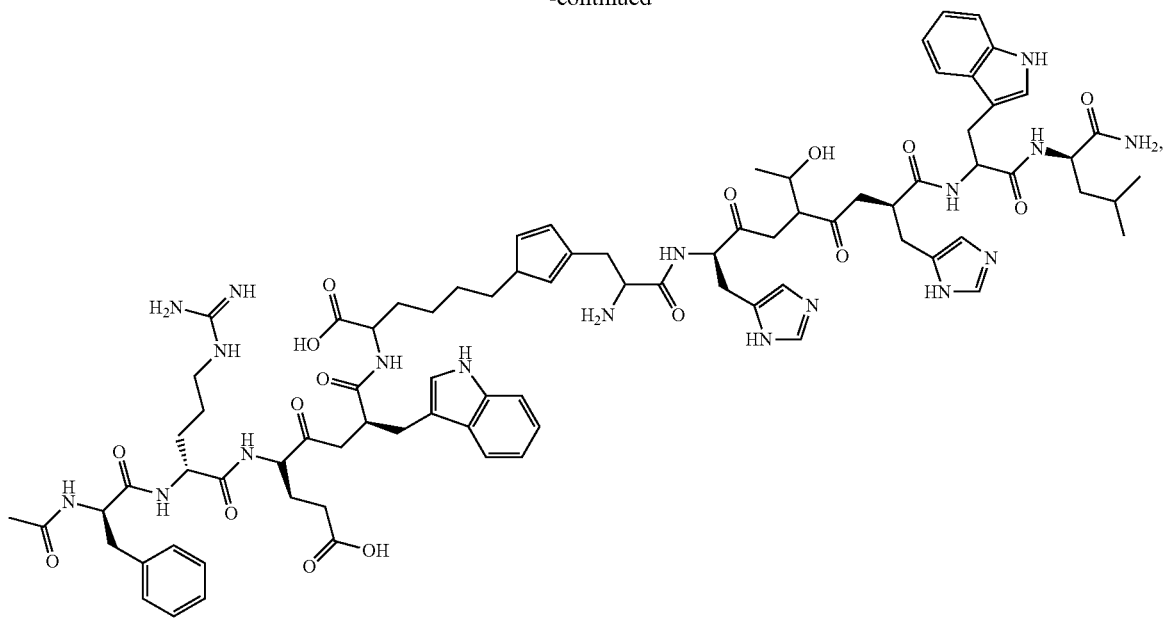
and
(SEQ ID NO: 73)
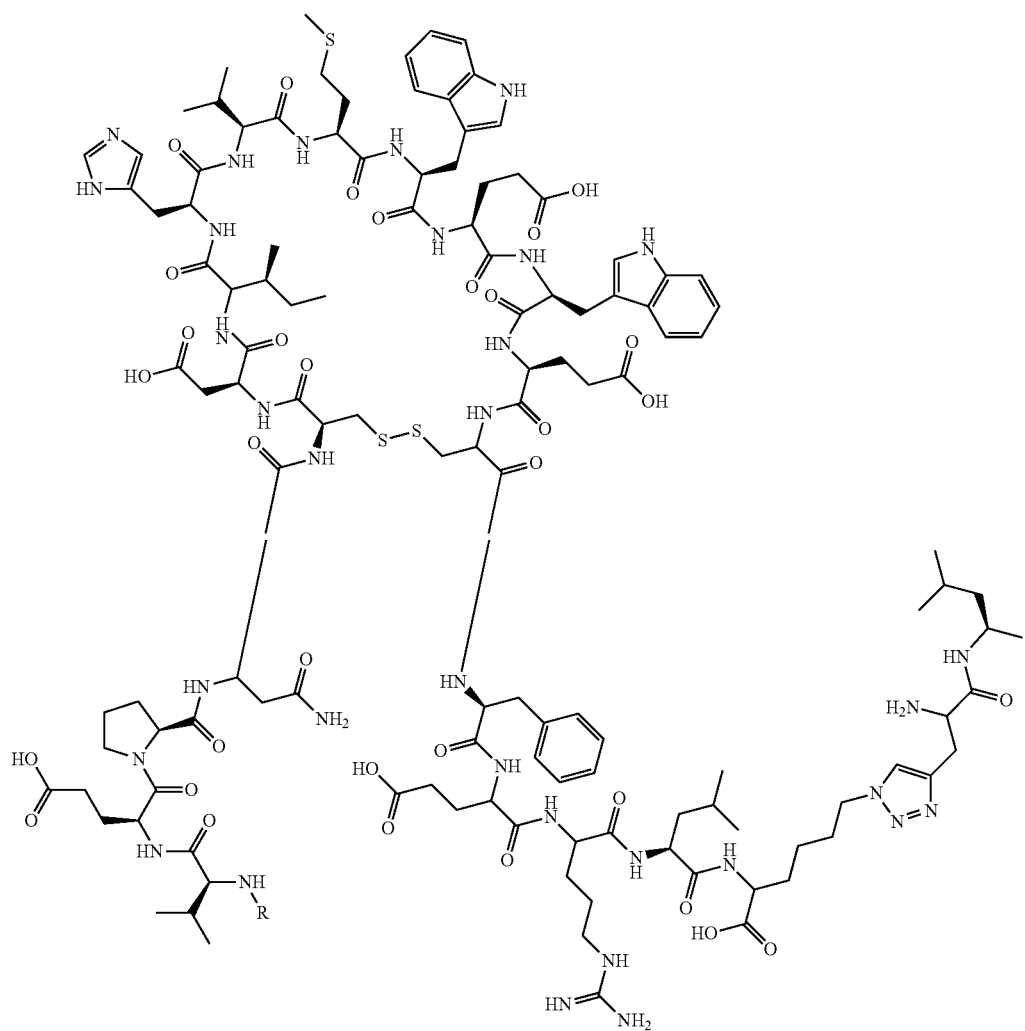

-continued

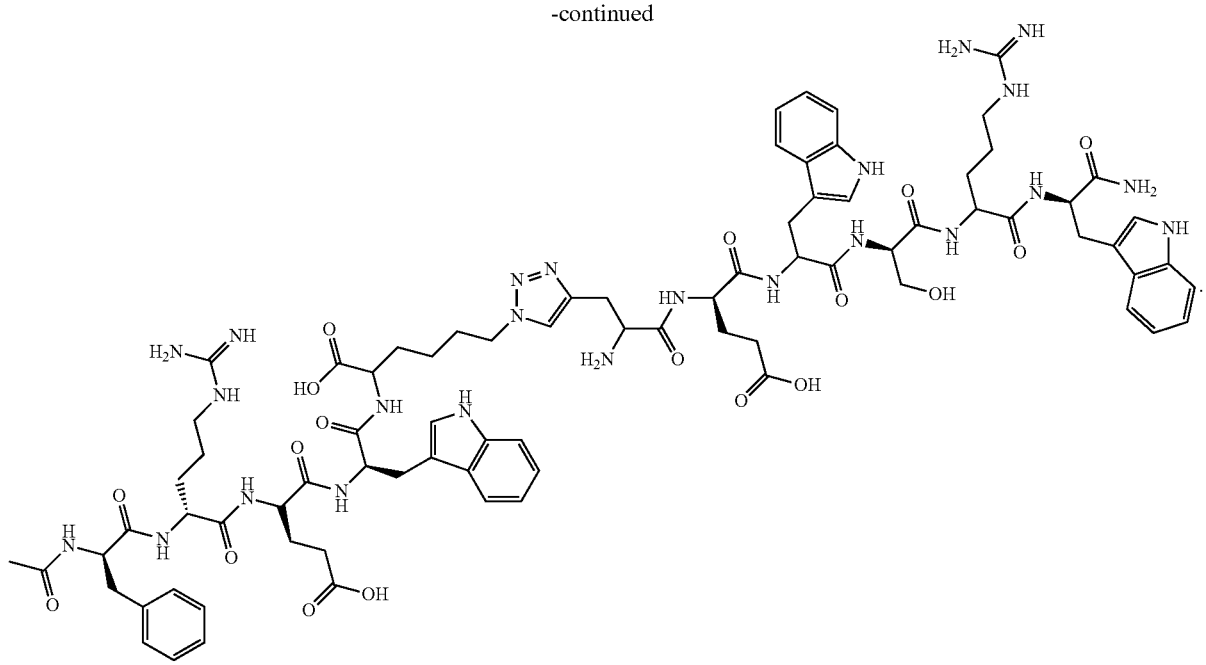

In certain embodiments, the VEGF capture agents provided herein are stable across a wide range of temperatures, pH's, storage times, storage conditions, and reaction conditions, and in certain embodiments the capture agents are more stable than a biologic. In certain embodiments, the capture agents are stable in storage as a lyophilized powder. In certain embodiment, the capture agents are stable in storage at a temperature of about −80° C. to about 40° C. In certain embodiments, the capture agents are stable in storage at room temperature. In certain embodiments, the capture agents are stable in human serum for at least 24 hours. In certain embodiments, the capture agents are stable at a pH in the range of about 3 to about 8.

In certain embodiments, the VEGF capture agents provided herein comprise one or more detectable labels. In certain of these embodiments, the label is copper-DOTA. In other embodiments, the label is a fluorescent label. In other embodiments, the detectable label is $^{64}$Cu DOTA, $^{68}$Ga DOTA, $^{18}$F, $_{64}$Cu, $^{68}$Ga, $^{89}$Zr, $^{124}$I, $^{86}$Y, $^{94m}$Tc, $^{110m}$In, $^{11}$C or $^{76}$Br.

In certain embodiments, kits are provided that comprise one or more of the VEGF capture agents provided herein. In certain of these embodiments, the kits include instructions for use.

In certain embodiments, methods are provided for identifying, detecting, quantifying, or separating VEGF in a biological sample using the capture agents provided herein. In certain embodiments, these methods are immunoassays where the VEGF capture agent is used as a replacement for an antibody or its equivalent. In certain embodiments, the immunoassay is a Western blot, pull-down assay, dot blot, or ELISA.

In certain embodiments, methods are provided for diagnosing or classifying a condition associated with increased VEGF expression and/or activity in a subject in need thereof using the capture agents provided herein. In certain of these embodiments, the condition is cancer, and the methods are used to diagnose and/or stage the cancer. In certain embodiments, this condition is selected from cancer, proliferative retinopathy, disease pathology of wet form age-related macular degeneration (AMD), or rheumatoid arthritis.

In certain embodiments, methods are provided for treating a condition associated with increased VEGF expression and/or activity in a subject in need thereof. In certain embodiments, these methods comprise administering to a subject a therapeutically effective amount of a VEGF capture agent as provided herein. In certain embodiments, the condition being treated is cancer, proliferative retinopathy, disease pathology of wet-form AMD, or rheumatoid arthritis. In certain embodiments, the VEGF capture agents provided herein function as immunotherapeutics.

In certain embodiments, methods are provided for inhibiting VEGF activity in vivo or in vitro using a VEGF capture agent as provided herein.

In certain embodiments, methods are provided for inhibiting binding of VEGF to VEGF receptor (VEGFR) using a VEGF capture agent as provided herein.

In certain embodiments, methods are provided for inhibiting VEGFR signaling using a VEGF capture agent as provided herein.

In certain embodiments, the use of one or more VEGF capture agents is provided for use in preparing a medicament for treating a condition associated with increased VEGF expression and/or activity in a subject in need thereof.

In certain embodiments, methods are provided for synthesizing the VEGF capture agents disclosed herein.

BRIEF DESCRIPTION OF DRAWINGS

FIG. 16: Binding of Triligand 1 ("Trilig1-Ifrew-frsvn"), Triligand 2 ("Trilig2-Ifrew-eeird"), Triligand 3 ("Trilig3-Ifrew-hthwl"), Triligand 4 ("Trilig4-Ifrew-ewsrw"), Biligand 2 ("Bilig2-Ifrew"), the anchor ligand ("Anchor") component of the bi- and triligands, and Avastin® to VEGF165 as measured by capture agent immunoprecipitation from VEGF165-spiked buffer ("B") and VEGF165-spiked human serum ("S"). Results were analyzed by silver stain (top panel) and Western blot (bottom panel).

FIG. 44: Biodistribution study results for mouse 1009. A. Maximum intensity projections (MIPs). Gaussian filter (0.200 mm FWHM) applied to the images, scaled to fixed percentile of image. B. Cropped MIPs. Gaussian filter (0.100 mm FWHM) applied to the images, scaled to fixed percentile of image. C. Cropped coronal slices. Gaussian filter (0.100 mm FWHM) applied to the images. D. Tumors extracted using 3D ROI Tool in vivoQuant™. Left tumor is in red, right tumor is in green. E. MIP of extracted tumors. At 240 minutes, the color scale min (black) was 0 and the color scale max (white) was $3.9 \times 10\text{-}5$ μCi. At 1200 minutes, the color scale min (black) was 0 and the color scale max (white) was $1.63 \times 10\text{-}5$ μCi (corrected for isotope decay).

FIG. 48: Biodistribution results for mouse 1102. A. Cropped coronal slices. Left=HT29, right MSTO-211 H. Gaussian filter (0.100 mm FWHM) applied to the images, scaled to fixed max. B. Cropped coronal slices. Left=HT29, right MSTO-211 H. Gaussian filter (0.100 mm FWHM) applied to the images, scaled to decay-corrected fixed max.

FIG. 49: Biodistribution results for mouse 1004. A. Cropped coronal slices. Left=HT29, right MSTO-211 H. Gaussian filter (0.100 mm FWHM) applied to the images, scaled to fixed max. B. Cropped coronal slices. Left=HT29, right MSTO-211 H. Gaussian filter (0.100 mm FWHM) applied to the images, scaled to decay-corrected fixed max.

FIG. 65: Copper catalyzed azide/alkyne cycloaddition (CuAAC) between a fully protected alkyne containing amino acid and a fully protected azide containing amino acid to provide a protected 1,4-triazole linked dipeptide.

FIG. 66: (A) Hit sequences obtained from the biligand screen with a comprehensive library. These sequences are SEQ ID NOs:9, 2, 10, 11, 12, 13, 14, 15, 16, 17, 18, 19, 3, 20 and 21 reading from top to bottom. (B) Biligand structure of SEQ ID NO: 84 illustrating the anchor (red) and selected secondary ligands (blue).

DETAILED DESCRIPTION OF THE INVENTION

Figure 1:
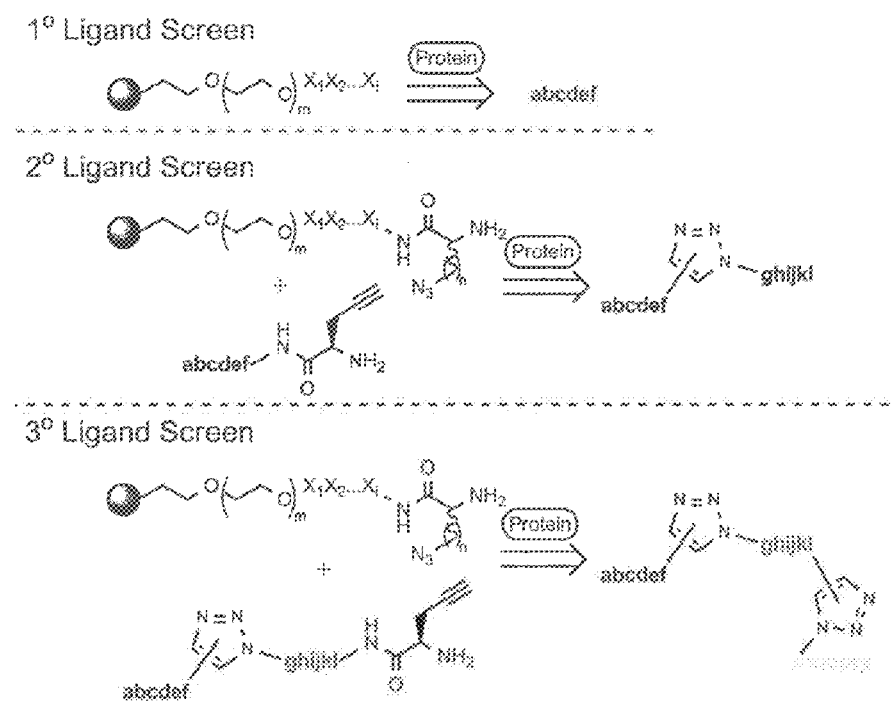
FIG. 1: In situ click chemistry protocol.

The following description of the invention is merely intended to illustrate various embodiments of the invention.

As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Abbreviations

AMD, age-related macular degeneration; Az4, 6-azido-L-norleucine; CuAAC, copper catalyzed azide/alkyne cycloaddition; DIEA, N-hydroxy-7-aza-benzotriazole (HOAt), or diisopropylethylamine; HATU, O-(7-azabenzotriazol-1-yl)-N,N,N',N'- tetramethyluronium hexafluorophosphate; HBTU, O-Benzotriazole-N,N,N',N'- tetramethyl-uronium-hexafluoro-phosphate; NMP, 1-methyl-2-pyrrolidinone; OBOC, one-bead-one-compound; TIS, triisopropylsilane; TFA, trifluoroacetic acid; Tz4, 1,4-disubstituted 1,2,3-triazole; VEGF, vascular endothelial growth factor; VEGFR, vascular endothelial growth factor receptor.

Definitions

The term "capture agent" as used herein refers to a protein-catalyzed capture (PCC) agent that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to non-random binding of a binding agent such as a capture agent to an epitope on a predetermined antigen. Typically, the binding agent binds with an affinity (KD) of approximately less than 10-'M, such as approximately less than $10^{-8}$ M, $10^{-9}$ M or $10^{-10}$ M or even lower.

The term "KD" as used herein refers to the dissociation equilibrium constant of a particular interaction between a binding agent such as a capture agent and its antigen. Typically, the capture agents of the invention bind to VEGF with a dissociation equilibrium constant (KD) of less than approximately 10-'M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the capture agent, so that when the KD of the capture agent very low (that is, the capture agent is highly specific), then the amount with which the affinity for the antigen is lower than the affinity for a non-specific antigen may be at least 10,000 fold.

The term "kd" (sec') as used herein refers to the dissociation rate constant of a particular binding agent-antigen interaction. Said value is also referred to as the koff value.

The term "ka" (M-'xsec ') as used herein refers to the association rate constant of a particular binding agent-antigen interaction.

The term "KD" (M) as used herein refers to the dissociation equilibrium constant of a particular binding agent-antigen interaction.

The term "KA" (M-') as used herein refers to the association equilibrium constant of a particular binding agent-antigen interaction and is obtained by dividing the ka by the kd.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein with regard to a condition refer to preventing the condition; slowing the onset, occurrence, or rate of development of the condition; reducing the risk of developing or experiencing the condition; preventing or delaying the development of symptoms associated with the condition; permanently or temporarily reducing or ending symptoms associated with the condition; lessening the severity of the condition; or some combination thereof.

A "therapeutically effective amount" as used herein refers to an amount effective, at dosages and for periods of time necessary, to achieve a desired therapeutic result. A therapeutically effective amount may vary according to factors such as disease state, age, sex, and weight of the individual, and the ability of the capture agent to elicit a desired response in the individual.

The term "vascular endothelial growth factor" or "VEGF" as used herein refers to any splicing isoform of VEGF-A, including VEGF121, VEGF165, VEGF189, and VEGF206, or a portion thereof such as an epitope.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')2 and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent or pharmaceutical formulation thereof means that the agent or formulation maintains structural and functional integrity for a sufficient period of time to be useful in the methods described herein.

The term "synthetic" as used herein with regard to a capture agent means that the capture agent has been generated by chemical rather than biological means. Synthetic capture agents are specifically designed using bioinformatic analytical tools to define aspects of the structure. The anchor ligands are selected from a pool of potential anchor ligands based on inherent properties.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Development of VEGF Capture Agents:

In situ click chemistry (Manetsch 2004; Mocharla 2004; Whiting 2006) is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The enzyme promotes the click reaction only between those library components that bind to the protein in the right orientation. The resultant inhibitor can exhibit far superior affinity characteristics relative to the initial inhibitor that formed the basis of the two libraries (Jencks 1981; Murray 2002).

Sequential in situ click chemistry extends the in situ click chemistry concept to enable the discovery of multiligand capture agents. This process was used previously to produce a triligand capture agent against the model protein carbonic anhydrase II (CAII) (Agnew 2009). Sequential in situ click chemistry has several advantages. First, structural information about the protein target is replaced by the ability to sample a very large chemical space to identify the ligand components of the capture agent. For example, an initial ligand may be identified by screening the protein against a large (>$10^6$ element) one-bead-one-compound (OBOC) (Lam 1991) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described (Shuker 1996; Erlanson 2000), most require detailed structural information on the target to guide the screening strategy, and most (such as the original in situ click approach), are optimized for low-diversity small molecule libraries.

As disclosed herein, an iterative in situ click chemistry approach was utilized to synthesize biligand and triligand capture agents that specifically bind VEGF. The biligand capture agents exhibited improved VEGF binding affinity and specificity versus their anchor ligand, and also showed the ability to inhibit HUVEC proliferation mediated by VEGF binding to VEGFR2. The triligand capture agents exhibited improvements in VEGF binding affinity and specificity beyond that of the biligands, and also showed the ability to inhibit VEGF binding to VEGFR2. Three of the triligand capture agents were found to share a binding epitope with Avastin®. All the capture agents exhibited a high degree of stability in serum. Multimeric forms of the capture agents were also developed, with certain of these multimeric capture agents displaying improved affinity, specificity, and/or efficacy.

Based on the results disclosed herein, the present application provides biligand and triligand VEGF capture agents and multimers thereof, as well as methods of using these capture agents to identify, detect, quantify, and separate VEGF and to diagnose, classify, and treat various conditions associated with increased VEGF expression and/or activity.

VEGF Capture Agents:

Provided herein in certain embodiments are synthetic biligand VEGF capture agents comprising two target-binding moieties. The first target-binding moiety is referred to as an anchor ligand, and the second is referred to as a secondary ligand.

Provided herein in certain embodiments are synthetic triligand VEGF capture agents comprising three target-binding moieties. The first target-binding moiety is referred to as an anchor ligand, the second is referred to as a secondary ligand, and the third is referred to as a tertiary ligand.

Provided herein in certain embodiments are multimeric forms of the biligand and/or triligand VEGF capture agents disclosed herein. In certain embodiments, these multimeric capture agents comprise dimers, trimers, or tetramers of the biligands and/or triligands disclosed herein. In certain embodiments, the multimeric capture agents are homomultimers, meaning that all of the biligand and/or triligand components of the multimer are identical. In other embodiments, the multimeric capture agents are heteromultimers, meaning that they comprise two or more different biligands and/or triligands.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted 1,2,3-triazole.

In certain embodiments, the anchor ligand and secondary ligand in the biligand and triligand capture agents provided herein are linked to one another via a covalent linkage. Similar, in certain embodiments the secondary ligand and tertiary ligand in the triligand capture agents provided herein are linked to one another via a covalent linkage. In certain of the above embodiments, the covalent linkage is an amide bond or a 1,4- disubstituted-1,2,3-triazole linkage as shown below:

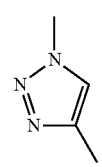

1,4-disubstituted-1,2,3-triazole linkage

In those embodiments where one or more target-binding moieties are linked to one another via a 1,4-disubstituted-1,2,3-triazole linkage, the 1,4-disubstituted -1,2,3- triazole linkage may be formed by copper-catalyzed azide/alkyne cycloaddition (CuAAC).

In certain embodiments, the anchor and secondary ligands and/or the secondary and tertiary ligands are linked to one another by a Tz4 linkage having the following structure:

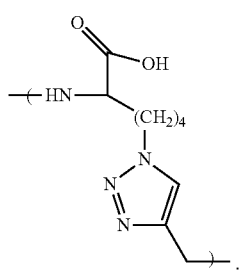

In those embodiments wherein one or more of the anchor, secondary, and tertiary ligands are linked to one another via amide bonds, the amide bond may be formed by coupling a carboxylic acid group and an amine group in the presence of a coupling agent (e.g., O-(7-azabenzotriazol-1-yl)-N,N,N', N'-tetramethyluronium hexafluorophosphate (HATU), N-hydroxy-7-aza-benzotriazole (HOAt), or diisopropylethylamine (DIEA) in DMF).

In certain embodiments of the biligand and triligand capture agents provided herein, the anchor ligand comprises the amino acid sequence set forth in SEQ ID NO:1. In other embodiments, the anchor ligand comprises an amino acid sequence, 80, 81, 82, 83, 84, 85, 86, 87, 88, 89, 90, 91, 92, 93, 94, 95, 96, 97, 98 or 100% identical to the amino acid sequence set forth in SEQ ID NO:1. In other embodiments, the anchor ligand comprises a fragment of the amino acid sequence of SEQ ID NO:1. In certain embodiments, this fragment contains 5, 6, 7, 8, 9, 10, 11, 12, 13, 14, 15, 16, 17 or 18 amino acids. In other embodiments, this fragment contains 5-18, 10-18, 5-15, 7-15, 9-15 or 3-16 amino acids.

Figure 3:
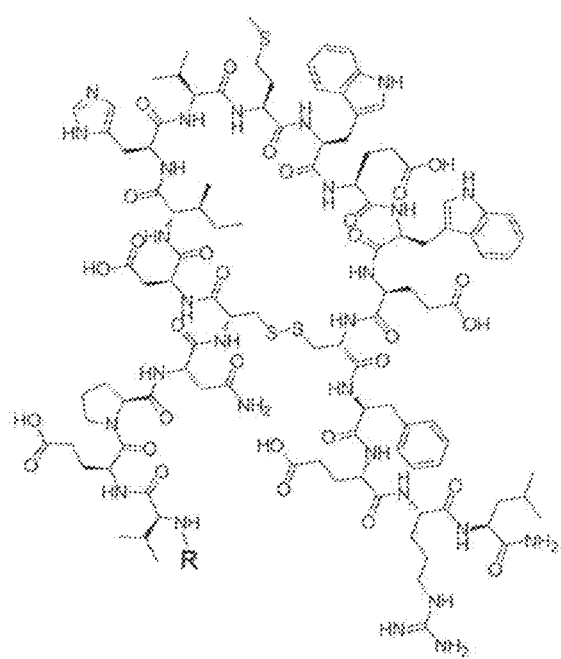
FIG. 3: Structure of anchor ligand comprising the amino acid sequence of SEQ ID NO:1 (VEPNCDIHVMWEWECFERL). The underline represents disulfide restrained residues.
Figure 4:
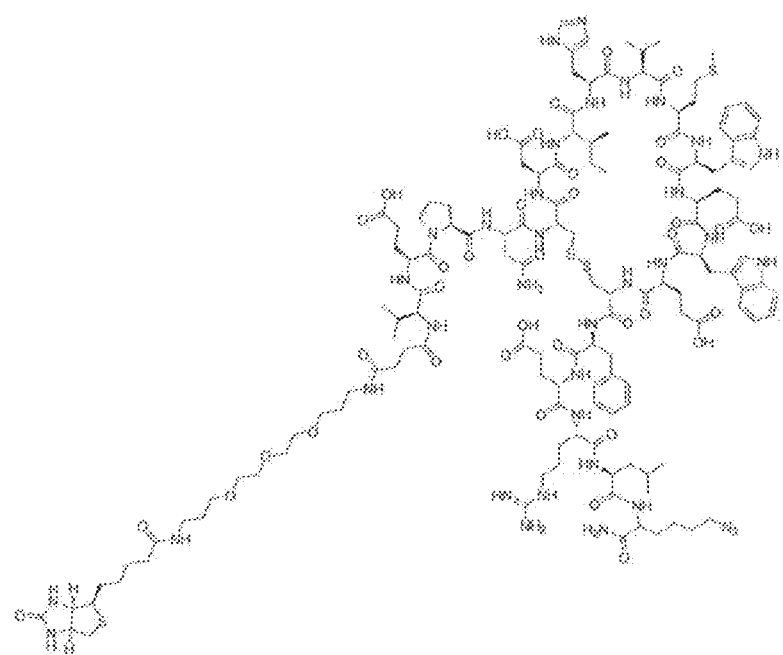
FIG. 4: Structure of the anchor ligand construct Biotin-PEG-anchor ligand-Az4 (SEQ ID NO: 65).

In certain embodiments of the biligand and triligand capture agents provided herein, the anchor ligand has the structure set forth in FIG. 3 or 4.

In certain embodiments of the biligand and triligand capture agents provided herein, the secondary ligand comprises a formula of X2-X3-X4-X5-X6. In certain embodiments, X2 is selected from a positively charged D-amino acid, an aromatic D-amino acid and a neutral D-amino acid. In other embodiments, X2 is selected from D-arginine, D-tryptophan, D-leucine, D-valine, glycine, D-proline, D-isoleucine and D-alanine. In other embodiments, X3 is selected from a neutral D-amino acid, an aromatic D-amino acid or a positively charged amino acid. In certain embodiments, X3 is selected from D-proline, D-phenylalanine, glycine, D-arginine, D-lysine, D-histidine, D-tryptophan and D-tyrosine. In other embodiments, X4 is selected from a neutral D-amino acid, a positively charged D-amino acid, an aromatic D-amino acid and a polar D-amino acid. In certain embodiments, X4 is selected from D-isoleucine, D-leucine, D-proline, D-alanine, D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from D-isoleucine, glycine, D-valine, D-leucine, D-alanine, D-proline, D-lysine, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-lysine, D-tryptophan, D-tyrosine, D-proline, D-valine, glycine, D-isoleucine, D-alanine and D-glutamine.

In certain embodiments, X2 is selected from a positively charged D-amino acid and an aromatic D-amino acid. In other embodiments, X2 is selected from D-arginine and D-tryptophan. In other embodiments, X3 is selected from a neutral D-amino acid and an aromatic D-amino acid. In certain embodiments, X3 is selected from D-proline, D-phenylalanine and glycine. In other embodiments, X4 is a neutral D-amino acid. In certain embodiments, X4 is selected from D-isoleucine, D-leucine, D-proline and D-alanine. In other embodiments, X5 is a neutral D-amino acid. In certain embodiments, X5 is selected from D-isoleucine, glycine and D-valine. In other embodiments, X6 is a positively charged D-amino acid. In certain embodiments, X6 is selected from D-arginine and D-lysine.

In certain embodiments, X2 is a neutral D-amino acid. In other embodiments, X2 is selected from D-leucine, D-valine, glycine and D-proline. In other embodiments, X3 is a positively charged amino acid. In certain embodiments, X3 is selected from D-arginine, D-lysine and D-histidine. In other embodiments, X4 is selected from a neutral D-amino acid, a positively charged D-amino acid and an aromatic D-amino acid. In certain embodiments, X4 is selected from D-proline, D-arginine and D-phenylalanine. In other embodiments, X5 is selected from a neutral D-amino acid and a positively charged D-amino acid. In certain embodiments, X5 is selected from D-leucine, D-isoleucine, D-alanine, D-proline and D-lysine. In other embodiments, X6 is selected from a positively charged D-amino acid, an aromatic D-amino acid and a neutral D-amino acid. In certain embodiments, X6 is selected from D-arginine, D-tryptophan, D-tyrosine, D-proline and D-valine.

In certain embodiments, X2 is a neutral D-amino acid. In other embodiments, X2 is selected from D-leucine, glycine, D-proline, D-isoleucine and D-alanine. In other embodiments, X3 is an aromatic D-amino acid. In certain embodiments, X3 is selected from D-tryptophan, D-phenylalanine and D-tyrosine. In other embodiments, X4 is selected from a positively charged D-amino acid, an aromatic D-amino acid and a polar D-amino acid. In certain embodiments, X4 is selected from D-arginine, D-phenylalanine, D-threonine and D-histidine. In other embodiments, X5 is selected from a neutral D-amino acid, a positively charged D-amino acid and a negatively charged D-amino acid. In certain embodiments, X5 is selected from glycine, D-alanine, D-proline, D-glutamate, D-histidine and D-arginine. In other embodiments, X6 is selected from a positively charged D-amino acid, an aromatic D-amino acid, a neutral D-amino acid and a polar D-amino acid. In certain embodiments, X6 is selected from D-arginine, D-tryptophan, glycine, D-isoleucine, D-alanine and D-glutamine.

In other embodiments, the secondary ligand comprises an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence, wherein one amino acid differs from an amino acid sequence selected from SEQ ID NOs:2, 3, 4, 9, 10, 11, 12, 13, 14, 15, 16, 17, 18, 19, 20 and 21. In other embodiments, the secondary ligand comprises an amino acid sequence wherein the amino acid sequence consists of an amino acid sequence selected from SEQ ID NOs:2, 3, 4, 9, 10, 11, 12, 13, 14, 15, 16, 17, 18, 19, 20 and 21.

In certain embodiments of the biligand and triligand capture agents provided herein, the secondary ligand comprises the amino acid sequence set forth in SEQ ID NOs:2, 3, or 4.

In certain embodiments of the biligand and triligand capture agents provided herein, the tertiary ligand comprises a formula of X2-X3-X4-X5-X6. In certain embodiments, X2 is a positively charged D-amino acid. In other embodiments, X2 is selected from D-histidine, D-arginine and D-lysine. In other embodiments, X3 is selected from a polar D-amino acid, a neutral D-amino acid and a negatively charged amino acid. In certain embodiments, X3 is selected from D-threonine, D-asparagine, D-leucine, D-proline, D-isoleucine, D-alanine, and D-glutamate. In other embodiments, X4 is selected from a positively charged D-amino acid, an aromatic D-amino acid and a neutral D-amino acid. In certain embodiments, X4 is selected from D-histidine, D-lysine, D-arginine, D-tryptophan, D-phenylalanine, D-proline, D-leucine and D-tyrosine. In other embodiments, X5 is selected from a neutral D-amino acid, a positively charged D-amino acid, an aromatic D-amino acid and a polar D-amino acid. In certain embodiments, X5 is selected from D-valine, D-proline, D-histidine, D-phenylalanine, D-tryptophan, D-asparagine, D-glutamine, D-serine and D-tyrosine. In other embodiments, X6 is selected from a positively charged D-amino acid, an aromatic D-amino acid, a polar D-amino acid and a neutral D-amino acid. In certain embodiments, X6 is selected from D-arginine, D-tyrosine, D-asparagine, D-glutamine, D-leucine, D-proline, D-lysine and D-histidine.

In certain embodiments, X2 is an aromatic D-amino acid. In other embodiments, X2 is selected from D-tyrosine, D-phenylalanine and D-tryptophan. In other embodiments, X3 is selected from a neutral D-amino acid and a positively charged amino acid. In certain embodiments, X3 is selected from D-proline, D-alanine, glycine, D-leucine, D-lysine, D-arginine and D-histidine. In other embodiments, X4 is selected from a positively charged D-amino acid, an aromatic D-amino acid, a negatively charged D-amino acid, a neutral D-amino acid and a polar D-amino acid. In certain embodiments, X4 is selected from D-arginine, D-histidine, D-tryptophan, D-phenylalanine, D-glutamate, D-proline, D-serine and D-threonine. In other embodiments, X5 is selected from a neutral D-amino acid, a negatively charged D-amino acid, a positively charged D-amino acid, an aromatic D-amino acid and a polar D-amino acid. In certain embodiments, X5 is selected from D-proline, D-aspartate, D-lysine, D-arginine, D-tyrosine, D-histidine, D-alanine, D-valine, D-leucine and D-asparagine. In other embodiments, X6 is selected from a positively charged D-amino acid, a polar D-amino acid, a neutral D-amino acid, a negatively charged D-amino acid and an aromatic D-amino acid. In certain embodiments, X6 is selected from D-histidine, D-lysine, D-asparagine, D-threonine, D-glutamine, D-leucine, D-aspartate, D-serine, D-tyrosine, D-arginine, D-tryptophan, D-glutamate and D-valine.

In certain embodiments, X2 is negatively charged D-amino acid. In other embodiments, X2 is selected from D-glutamate and D-aspartate. In other embodiments, X3 is selected from a negatively charged D-amino acid, an aromatic D-amino acid, a positively charged amino acid and a polar D-amino acid. In certain embodiments, X3 is selected from D-glutamate, D-phenylalanine, D-tryptophan, D-histidine, D-lysine, D-asparagine and D-serine. In other embodiments, X4 is selected from a neutral D-amino acid, a positively charged D-amino acid, a polar D-amino acid, a negatively charged D-amino acid and an aromatic D-amino acid. In certain embodiments, X4 is selected from D-isoleucine, D-proline, D-alanine, D-arginine, D-serine, D-aspartate, D-asparagine, D-proline, D-phenylalanine, D-tyrosine and D-histidine. In other embodiments, X5 is selected from a positively charged D-amino acid, an aromatic D-amino acid and a neutral D-amino acid. In certain embodiments, X5 is selected from D-arginine, D-tyrosine, glycine, D-tryptophan, D-lysine, D-histidine, D-alanine, D-asparagine and D-leucine. In other embodiments, X6 is selected from a negatively charged D-amino acid, a neutral D-amino acid, an aromatic D-amino acid and a polar D-amino acid. In certain embodiments, X6 is selected from D-aspartate, D-proline, D-tryptophan, D-tyrosine, D-leucine, D-asparagine, D-serine and D-threonine.

In other embodiments, the tertiary ligand comprises an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64. In other embodiments, the secondary ligand comprises an amino acid sequence, wherein one amino acid differs from an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64. In other embodiments, the secondary ligand comprises an amino acid sequence wherein the amino acid sequence consists of an amino acid sequence selected from SEQ ID NOs: 5, 6, 7, 8, 22, 23, 24, 25, 26, 27, 28, 29, 30, 31, 32, 33, 34, 35, 36, 37, 38, 39, 40, 41, 42, 43, 44, 45, 46, 47, 5, 48, 49, 50, 51, 52, 53, 54, 55, 56, 57, 58, 59, 60, 61, 62, 63 and 64.

For all of the above embodiments, glycine is considered to be a member of the genus of neutral D-amino acids, despite the achirality of glycine.

In certain embodiments of the triligand capture agents provided herein, the tertiary ligand comprises the amino acid sequence set forth in SEQ ID NOs: 5, 6, or 7.

In certain embodiments, the biligand capture agents provided herein have the structure set forth in FIG. 6, 8, 9, or 10.

In certain embodiments, the triligand capture agents provided herein have the structure set forth in FIG. 11, 12, 13, or 14.

In certain embodiments, the capture agents provided herein are stable across a range of reaction conditions and/or storage times. A capture agent that is "stable" as used herein maintains the ability to specifically bind to a target protein and is at least partially resistant to proteolytic degradation.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than a biologic binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than a biologic binding to the same target protein, and/or remain stable at a specific temperature for a longer time period than a biologic binding to the same target protein.

In certain embodiments, the pH of a capture agent provided herein is in the range of about 3.0 to about 12.0. In certain of these embodiments, the pH of the capture agent is in the range of about 5.0 to about 9.0. The pH of a capture agent may be adjusted to a physiologically compatible range using methods known in the art. For example, in certain embodiments the pH of the capture agent may be adjusted to the range of about 6.5 to about 8.5.

In certain embodiments, the capture agents provided herein are stable in blood serum for more than 12 hours. In certain of these embodiments, the capture agents are stable in blood serum for more than 18 hours, more than 24 hours, more than 36 hours, more than 48 hours, or more than 96 hours. In certain embodiments, the capture agents provided herein are stable for a longer period of time in blood serum than a biologic binding to the same target protein.

In certain embodiments, the capture agents provided herein may comprise one or more detection labels, including for example biotin, copper-1,4,7,10-tetraazacyclododecane-1,4, 7,10-tetraaceticacid (copper-DOTA), desferrioxamine B (DFO), a ligand for radiolabeling with $^{68}$Ga, or other radiolabeled products that may include gamma emitters, proton emitters, positron emitters, tritium, or covered tags detectable by other methods (i.e., gadolinium) among others.

In certain embodiments, the capture agents provided herein comprise one or more detectable labels. In certain of these embodiments, the label is copper-DOTA. In other embodiments, the detectable label is selected from $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the detectable label is selected from $^{123}$I, $^{131}$I, $^{67}$Ga, $^{111}$In and $^{99m}$Tc. In other embodiments, the label is a fluorescent label.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Provided herein in certain embodiments are pharmaceutical formulations comprising one or more of the capture agents provided herein. In certain embodiments, these pharmaceutical formulations comprise one or more pharmaceutically acceptable carriers, excipients, or diluents. These carriers, excipients, or diluents may be selected based on the intended use and/or route of administration of the formulation.

Provided herein in certain embodiments are kits comprising one or more of the capture agents disclosed herein. In certain embodiments, these kits may be used for identifying, detecting, quantifying, and/or separating VEGF, and in certain of these embodiments the kits may be used in the diagnosis and/or staging of a condition associated with increased VEGF expression and/or activity. In certain embodiments, a kit as provided herein comprises: (a) a substrate comprising an adsorbent thereon, wherein the adsorbent is suitable for binding VEGF, and (b) a washing solution or instructions for making a washing solution, wherein the combination of the adsorbent and the washing solution allows detection of VEGF. In other embodiments, the kits provided herein may be used in the treatment of a condition associated with increased VEGF expression and/or activity.

In certain embodiments, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as provided herein comprises (a) one or more VEGF capture agents that specifically bind VEGF; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of VEGF detected in a sample is an amount consistent with a diagnosis of a particular condition.

Methods of Using VEGF Capture Agents:

Provided herein in certain embodiments are methods of using the VEGF capture agents disclosed herein to identify, detect, quantify, and/or separate VEGF in a biological sample. The VEGF capture agents disclosed herein can serve as a drop-in replacement for monoclonal antibodies in biochemical assays. Therefore, in certain embodiments the methods provided herein utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, blood serum, plasma, urine, sputum, saliva, stool, spinal fluid, cerebral spinal fluid, lymph fluid, skin secretions, respiratory secretions, intestinal secretions, genitourinary tract secretions, tears, and milk.

Provided herein in certain embodiments are methods of identifying, detecting, quantifying, and/or localizing VEGF in vivo. In certain of these embodiments, the capture agents may be used as an imaging agent. In these embodiments, the capture agents may comprise one or more detection labels as discussed above.

Provided herein in certain embodiments are methods of using the VEGF capture agents disclosed herein to inhibit VEGF activity. In certain of these embodiments, the capture agents inhibit VEGF activity by blocking binding of VEGF to VEGFR, thereby inhibiting VEGFR activity. Accordingly, further provided herein are methods of using the VEGF capture agents disclosed herein to inhibit binding of VEGF to VEGFR and/or inhibit VEGFR activity. In certain of these embodiments, the VEGFR is VEGFR2.

Provided herein in certain embodiments are methods of using the VEGF capture agents disclosed herein to diagnose and/or classify (e.g., stage) a condition associated with increased VEGF expression and/or activity, including for example various cancers. In certain embodiments, these methods comprise (a) obtaining a biological sample from a subject; (b) measuring the presence or absence of VEGF in the sample with the VEGF capture agent; (c) comparing the levels of VEGF to a predetermined control range for VEGF; and (d) diagnosing a condition associated with increased VEGF expression based on the difference between VEGF levels in the biological sample and the predetermined control.

In certain embodiments of the diagnosis and/or classification methods provided herein, the VEGF capture agents may be used to diagnose a change in health status in a subject, wherein the change in health status is a predictor of a disease or event. In certain of these embodiments, the methods may be utilized to predict the development of a disease or event in a subject who does not yet exhibit any symptoms of the disease or event. In certain embodiments, the change in health status may be an increase in VEGF levels.

Provided herein in certain embodiments are methods of treating a condition associated with increased VEGF expression and/or activity in a subject in need thereof by administering a therapeutically effective amount of one or more of the capture agents or pharmaceutical formulations disclosed herein. In certain of these embodiments, the capture agent(s)

may be linked to one or more additional therapeutic agents, including for example a chemotherapeutic agent. In preferred embodiments, the capture agent is administered as a pharmaceutical composition. In certain embodiments, the condition being treated is a disease selected from the group consisting of cancer, proliferative retinopathy, disease pathology of wet form AMD, or rheumatoid arthritis.

A capture agent or pharmaceutical formulation may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

A capture agent or pharmaceutical formulation may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Provided herein in certain embodiments is the use of the capture agents disclosed herein in the preparation of a medicament for treating a condition associated with increased VEGF expression and/or activity.

Methods of Making Capture Agents:

In certain embodiments, methods are provided for synthesizing a capture agent as provided herein. In certain embodiments, these methods comprise:
  a) preparing a synthesis block of a target-binding moiety, the synthesis block comprising the target-binding moiety and at least one reactive group that can form a desired linkage with another synthesis block, wherein:
    i) the linkage is selected from the group consisting of amide linkage, 1,4-disubstituted 1,2,3-triazole linkage, and 1,5-disubstituted 1,2,3-triazole linkage; and
    ii) all other active functional groups of the target-binding moiety are protected to avoid undesired reactions; and
  b) coupling the synthesis blocks of the target-binding moieties to provide the capture agent.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Synthesis of VEGF Capture Agents

Three anti-VEGF biligand capture agents and four anti-VEGF triligand capture agents were identified using an in situ click chemistry approach.

Reagents. Fmoc-D-X-OH (Fmoc, fluoren-9-ylmethoxycarbonyl) (X=Ala, Arg(Pbf) (Pbf, pentamethyldihydrobenzofuran-5-sulfonyl), Asn(Trt) (Trt, trityl), Asp(OtBu) (tBu, tert-butyl), Glu(OtBu), Gln(Trt), Gly, His(Trt), Ile, Leu, Lys(Boc) (Boc, tert-butyloxycarbonyl), Met, Phe, Pro, Ser(tBu), Thr (tBu), Trp(Boc), Tyr(tBu), and Val) (Anaspec; San Jose, Ga.). Amino acid coupling reactions were performed in 1-methyl-2-pyrrolidinone (NMP, 99%) with O-Benzotriazole-N,N,N', N'-tetramethyl-uronium- hexafluoro-phosphate (HBTU; AAPPTec) and DIEA. For removal of Na-Fmoc protecting groups, a solution of 20% piperidine in NMP was used. For final deprotection of the peptide libraries, trifluoroacetic acid (TFA, 98% min. titration) and triisopropylsilane (TIS) were used. All solvents and reagents were purchased from Sigma-Aldrich (St. Louis, Mo.).

Construction of peptide libraries. Randomized OBOC libraries of pentapeptides were synthesized using a Titan 357 automatic synthesizer (AAPPTec) via standard split-mix methods on polyethylene glycol-grafted polystyrene beads (TentaGel S—NH$_2$, 90 pm, 0.29 mmol/g, 2.86×10$^6$ beads/g). In a typical library construction, non-natural D-stereoisomers were used at each position in the peptide sequence. For the coupling steps, a standard solid-phase peptide synthesis method with Fmoc chemistry (Fields 1990) was used. The resin was swelled in NMP for two hours in the collection vessel (CV). The coupling of Fmoc-methionine (4 equiv) was initiated by addition of 3.8 equiv of HATU (Chem Pep) and 12 equiv of DIEA. The coupling reaction was run for 30 minutes. Following the coupling step, the beads were thoroughly washed (4×NMP) and treated with 20% piperidine in NMP (5 minutes followed by a 15 minute wash with a fresh aliquot of deprotection solution). The resin was thoroughly washed (4×NMP, 4×DCM) and divided into multiple equal-mass aliquots for the next cycle of coupling in the reaction vessel (RV). With the coupling and Fmoc deprotection completed, the resins were combined in the collection vessel. The procedures were repeated until the desired length of peptide was attained. The amino acid side chain protective groups were then removed by incubation in TFA (94%), water (3%), and TIS (3%) for two hours. The library resin was then washed thoroughly with dichloromethane (DCM; 5×), methanol (MeOH; 5×), water (5×), MeOH (5×), DCM (5×), and diethyl ether (5×). The resulting resin was dried under vacuum and stored at 4° C.

Figure 2:
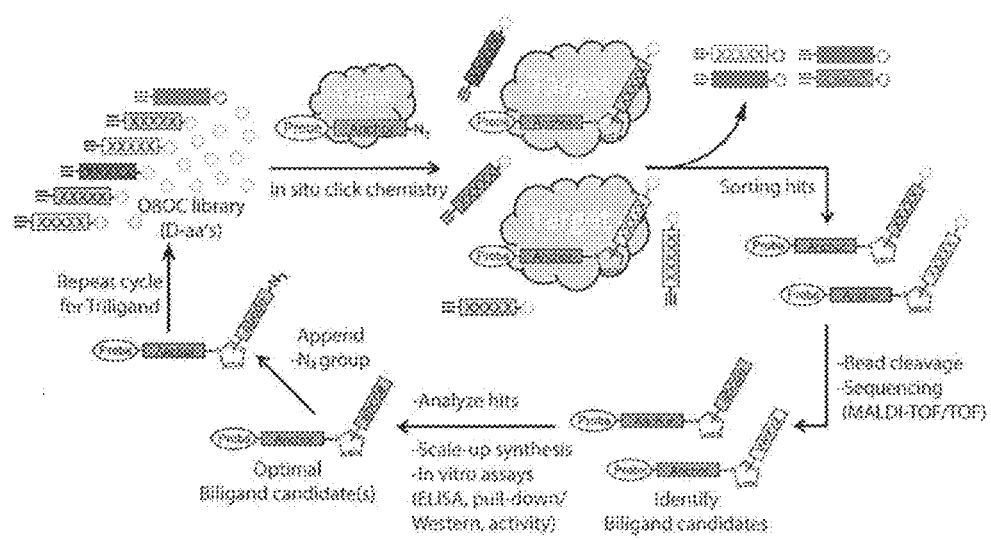
FIG. 2: In situ click chemistry protocol.

Biligand selection. Selection was carried out using an in situ click chemistry technique where the target protein acts as the catalyst that conjugates azide to alkyne candidate ligands (FIGS. 1 and 2; Agnew 2009). For the screen, a 200-mg portion of the OBOC library, coupled with D-propargylglycine at the N-terminus, was transferred into an 8-mL capacity Alltech vessel and pre-incubated in a blocking solution consisting of 0.05% NaN$_3$, 0.1% Tween 20, and 0.1% BSA in PBS buffer (pH 7.4), for two hours on a 360° rotator at 25° C. Separately, a 3 mL volume of 10 nM human VEGF165A (#ab56620; Abcam, MA) diluted in blocking solution was pre-incubated with the anchor ligand construct Biotin-PEG-VEPNCDIHVMWEWECFERL-Az4 (SEQ ID NO: 65), where PEG=3× ethylene glycol linker, Az4=6-azido-L-norleucine, VEPNCDIHVMWEWECFERL=amino acid sequence of SEQ ID NO:1 (FIG. 3), and underlining=disulfide constrained residues (FIG. 4) (Fairbrother 1998), for two hours on a 360° rotator at 25° C.

Anchor ligand was supplied at a 3000-fold molar excess of the protein. After draining the blocking solution from the OBOC library, the pre-incubated solution of 10 nM VEGF165A and anchor ligand was added to the library resin and incubated for four hours on a 360° rotator at 25° C. The screen was washed with 3×5 mL of the blocking solution, and 3 mL of 1:10,000 AP-linked Streptavidin (#V5591; Promega) was incubated for 45 minutes at 25° C. AP-linked streptavidin distinguished those beads which contain a biotin label, and therefore products of VEGF-templated in situ click biligand conjugation. To eliminate non-specifically bound proteins, the screen was washed with 5×3 mL Blocking Solution, 5×3 mL Wash 1 Buffer (25 mM Tris-Cl, 10 mM $MgCl_2$, 700 mM NaCl, pH 7.5), and 5×3 mL Wash 2 Buffer (25 mM Tris-Cl, pH 7.5), and drained by vacuum. BCIP:NBT (#S3771; Promega), freshly prepared in Alkaline Phosphatase Buffer (100 mM Tris-HCl, pH 9.0, 150 mM NaCl, 1 mM $MgCl_2$), was used to develop the screen. The most intensely colored purple beads ("hits") were selected manually. Selected beads were treated with 7.5 M guanidine hydrochloride (pH 2.0) to remove bound proteins and then decolorized with NMP. Anti-screens were separately performed to eliminate beads that displayed non-specific binding to the reagents used to visualize the screen. Following this refinement, sequencing of authentic hits was performed with MALDI-TOF/TOF and a semi-automated algorithm (Lee 2010). Biligand hit sequences obtained from screening VEGF against a comprehensive library are shown in FIG. 66.

Figure 5:
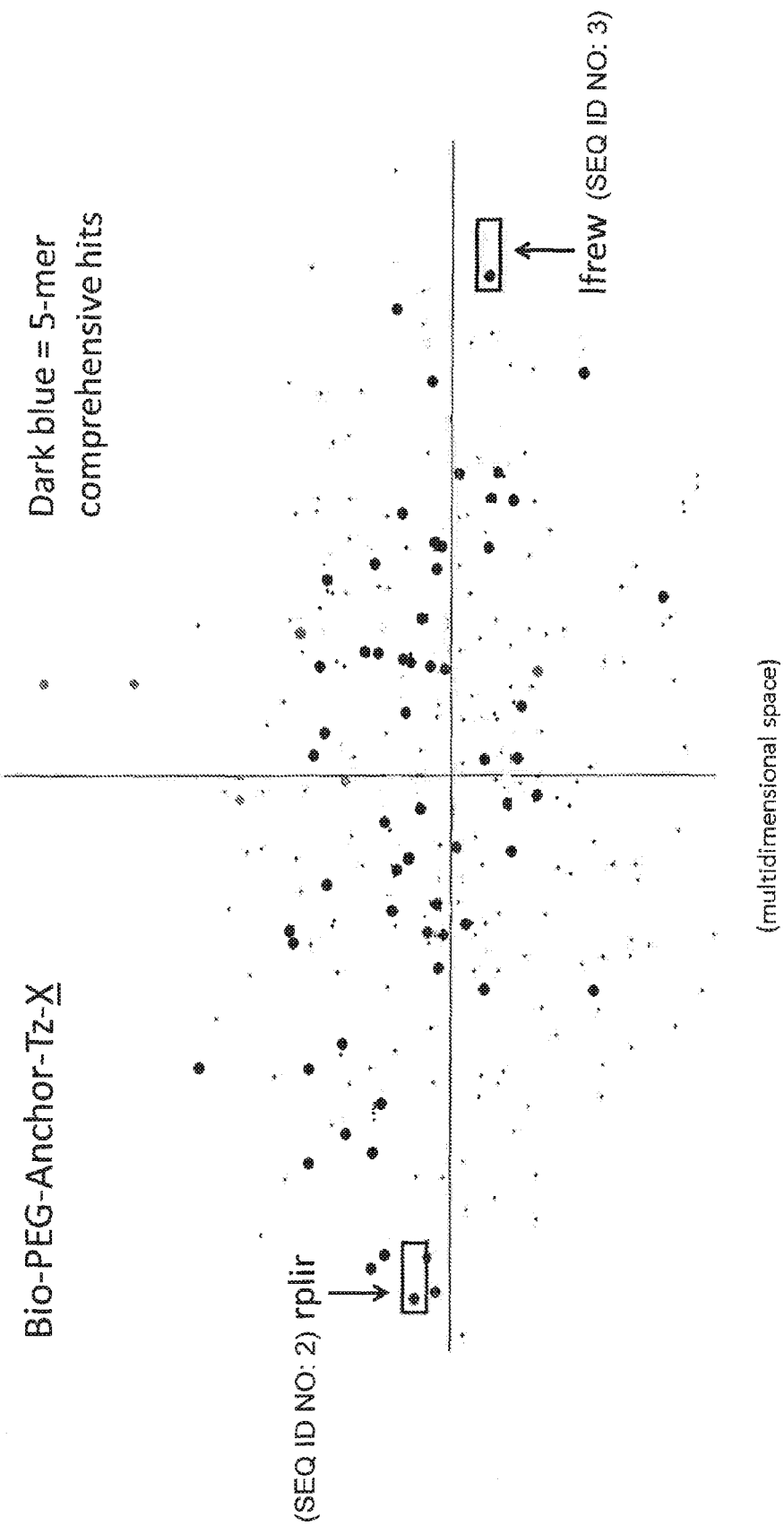
FIG. 5: Informatic clustering guides candidate selection for secondary and tertiary ligands. Different regions of the protein epitope are suggested to be sampled by different clusters. Dark blue=5-mer secondary ligand hits from biligand screen.
Figure 6:
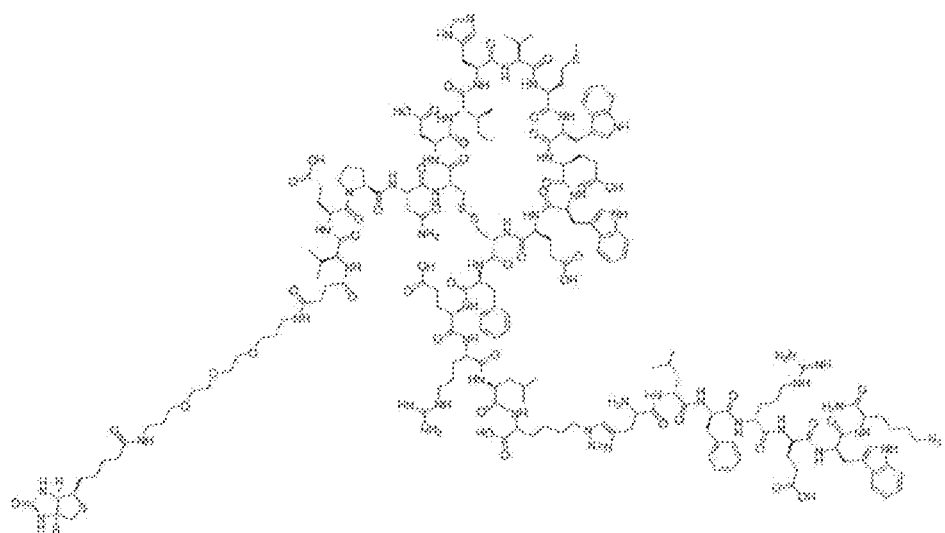
FIG. 6: Structure of the biligand construct Biotin-PEG-VEPNCDIHVMWEWECFERL-Tz4-Ifrew-Az4 (SEQ ID NO: 66).

Candidate biligands against VEGF were analyzed and grouped by similar charges and similar conserved motifs using a proprietary Integrated Diagnostics bioinformatic clustering program. Candidate peptides were grouped together based on physicochemical features (FIG. 5). This bioinformatic clustering method was used to rationally guide biligand candidate selection, as non-randomly selected ligands occur on the extremes of the universe of physiochemical properties. Different classes of hits were also identified through this multidimensional representation (i.e., different clusters may sample different regions of the protein epitope).

Biligand candidates containing the 1,4-substituted-1,2,3-triazole were then synthesized individually, and biological assays were performed to determine the biligand with the largest improvement in VEGF binding affinity and specificity versus the anchor ligand.

The selected biligand capture agents comprised the anchor ligand of SEQ ID NO:1 and a secondary ligand comprising the amino acid sequence of SEQ ID NO:2 (rplir; "Biligand 1"), 3 (lfrew; "Biligand 2"), or 4 (fsrkte; "Biligand 3"). The structures of Biligands 1, 2, and 3 are set forth in FIGS. 8, 9, and 10, respectively.

Triligand selection. A 200-mg portion of the OBOC library, coupled with D-propargylglycine at the N-terminus, was transferred into an 8-mL capacity Alltech vessel and pre-incubated in a blocking solution consisting of 0.05% $NaN_3$, 0.1% Tween 20, and 0.1% BSA in PBS buffer (pH 7.4), for two hours on a 360° rotator at 25° C. Separately, a 3 mL volume of 1 nM VEGF165A diluted in blocking solution was pre-incubated with the Biligand 2 construct Biotin-PEG-VEPNCDIHVMWEWECFERL-Tz4-Ifrew-Az4 (SEQ ID NO: 66), where PEG=3× ethylene glycol linker (FIG. 6), for two hours on a 360° rotator at 25° C.

Figure 69:
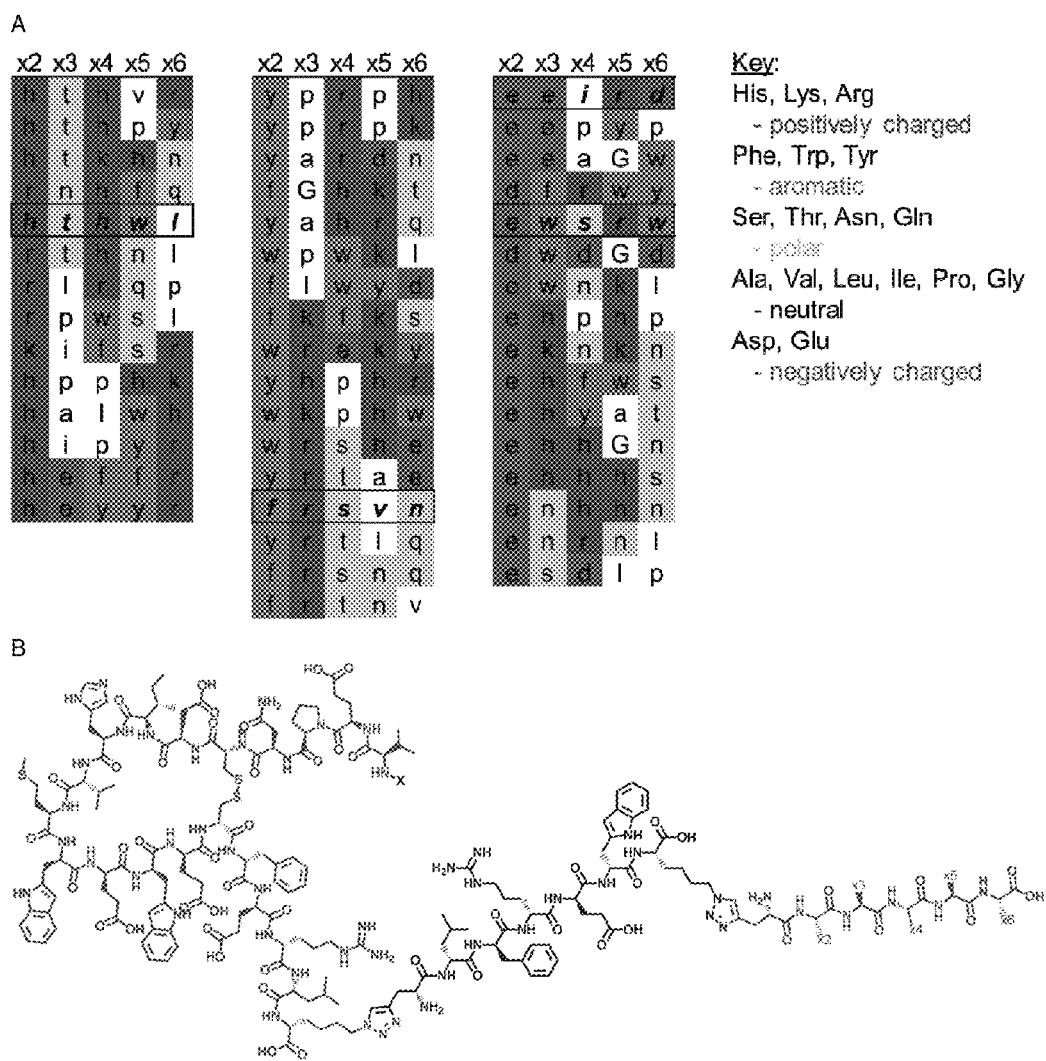
FIG. 69: (A) Hit sequences obtained from the triligand screen with a comprehensive library. These sequences are SEQ ID NOs:22, 23, 24, 25, 7, 26, 27, 28, 29, 30, 31, 32, 33, 34, 35, 36, 37, 38, 39, 40, 41, 42, 43, 44, 45, 46, 47, 5, 48, 49, 50, 6, 51, 52, 53, 8, 54, 55, 56, 57, 58, 59, 60, 61, 62, 63 and 64 reading from top to bottom and left to right across the three columns. (B) Triligand structure of SEQ ID NO: 85 illustrating the anchor (red), secondary ligand (blue), and selected tertiary ligands (green).

The biligand was supplied at a 5000-fold molar excess of the protein. After draining the blocking solution from the OBOC library, the pre-incubated solution of 1 nM VEGF165A and biligand was then added to the library resin and incubated for four hours on a 360° rotator at 25° C. Product screens and anti-screens implementing AP-linked Streptavidin were performed as described above. Sequencing of authentic hits was performed with MALDI-TOF/TOF and a semi-automated algorithm (Lee 2010). Triligand hit sequences obtained from screening VEGF against a comprehensive library are shown in FIG. 69.

Figure 7:
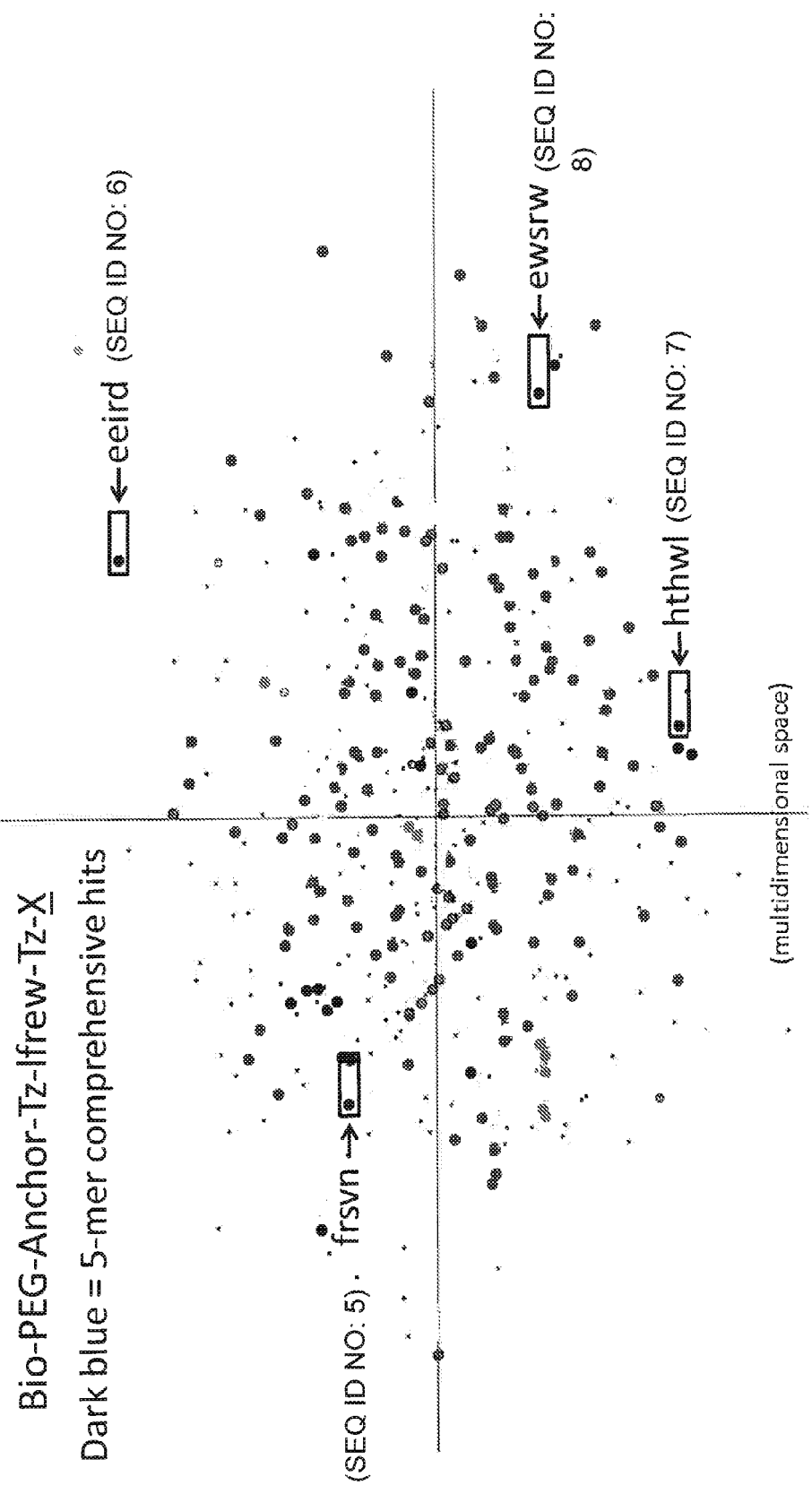
FIG. 7: Informatic clustering guides candidate selection for secondary and tertiary ligands. Different regions of the protein epitope are suggested to be sampled by different clusters. Dark blue=5-mer tertiary ligand hits from triligand screen.
Figure 8:
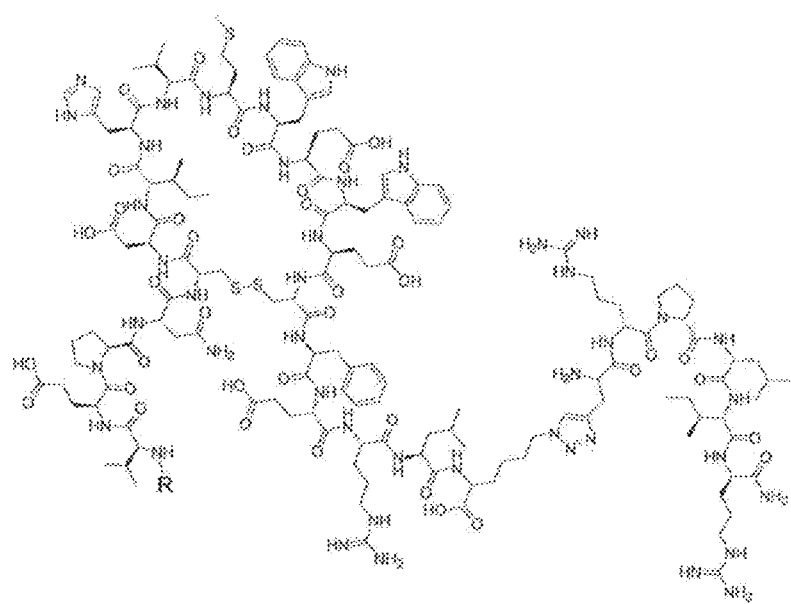
FIG. 8: Structure of Biligand 1 (SEQ ID NO: 67), which comprises the anchor ligand of SEQ ID NO:1 and the secondary ligand of SEQ ID NO:2 (rplir).
Figure 9:
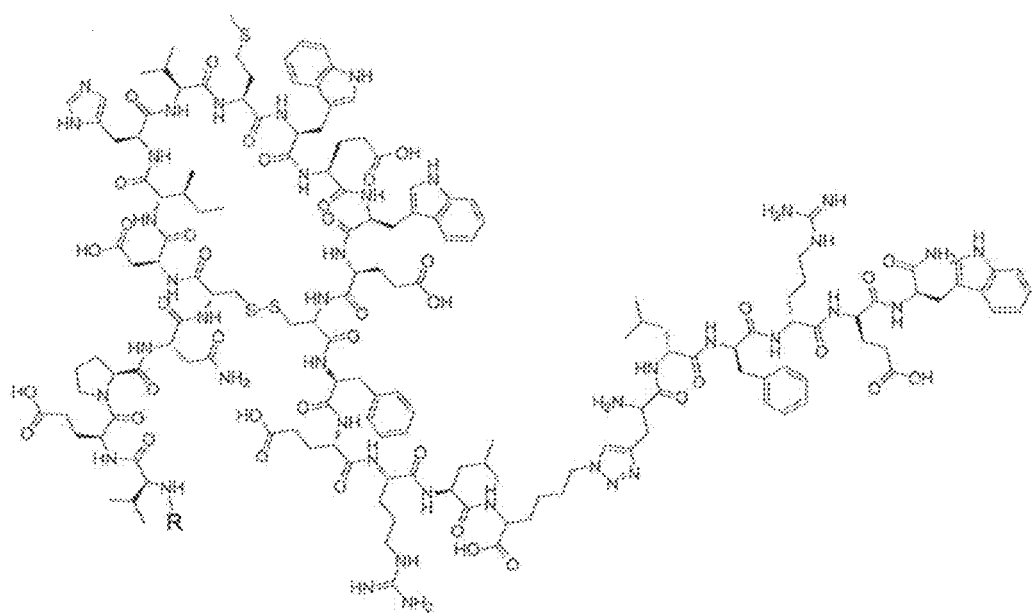
FIG. 9: Structure of Biligand 2 (SEQ ID NO: 68), which comprises the anchor ligand of SEQ ID NO:1 and the secondary ligand of SEQ ID NO:3 (lfrew).
Figure 10:
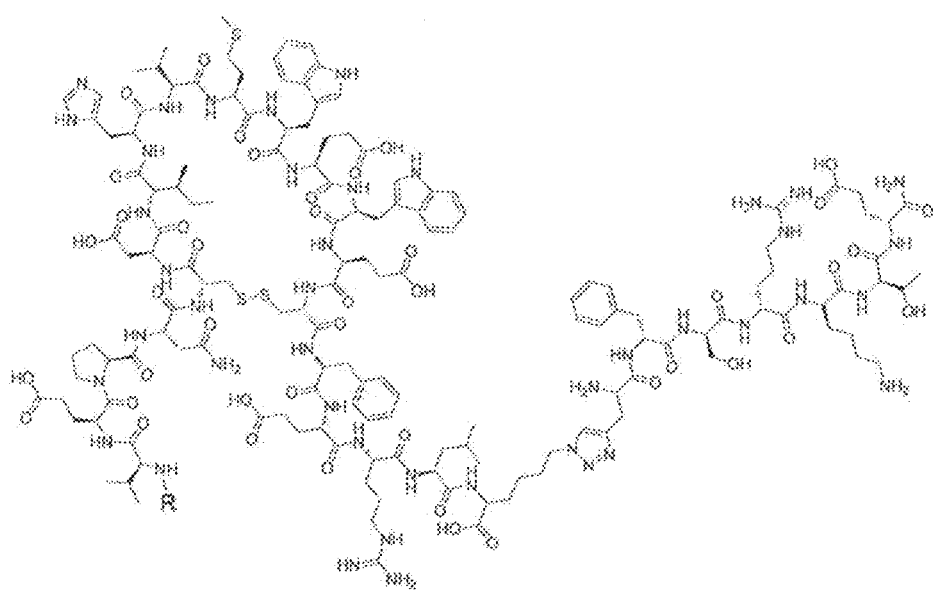
FIG. 10: Structure of Biligand 3 (SEQ ID NO: 69), which comprises the anchor ligand of SEQ ID NO:1 and the secondary ligand of SEQ ID NO:4 (fsrkte).
Figure 11:
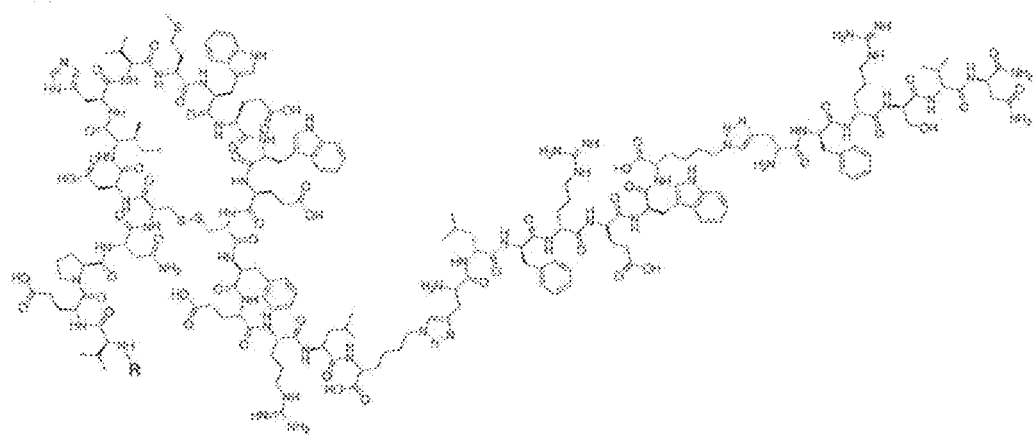
FIG. 11: Structure of Triligand 1 (SEQ ID NO: 70), which comprises the anchor ligand of SEQ ID NO:1, the secondary ligand of SEQ ID NO:3, and the tertiary ligand of SEQ ID NO:5 (frsvn).
Figure 12:
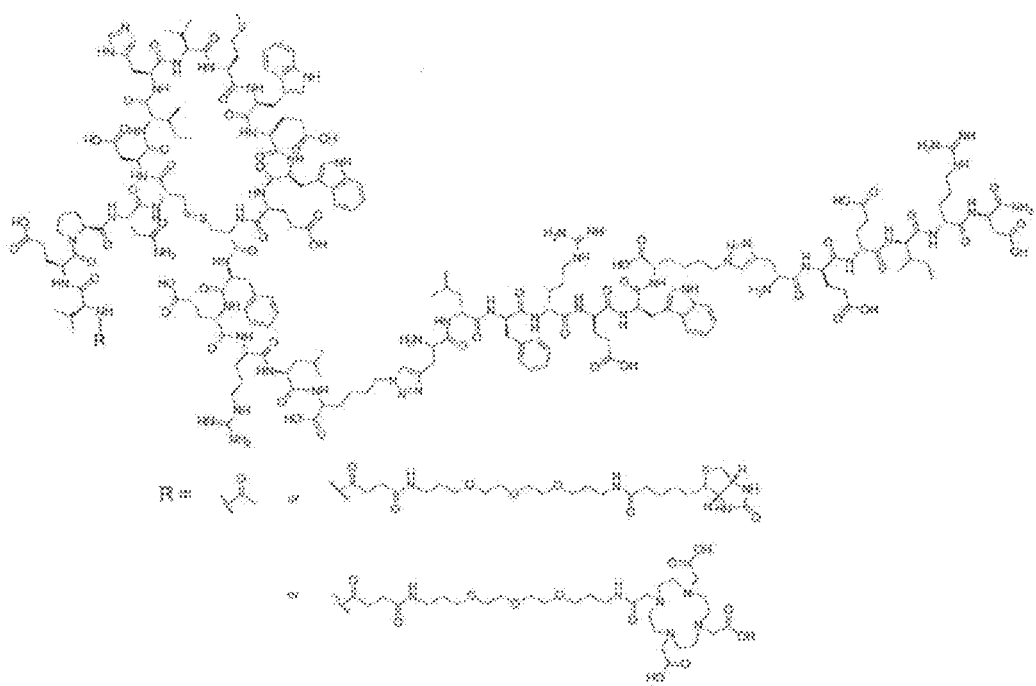
FIG. 12: Structure of Triligand 2 (SEQ ID NO: 71), which comprises the anchor ligand of SEQ ID NO:1, the secondary ligand of SEQ ID NO:3, and the tertiary ligand of SEQ ID NO:6 (eeird).
Figure 13:
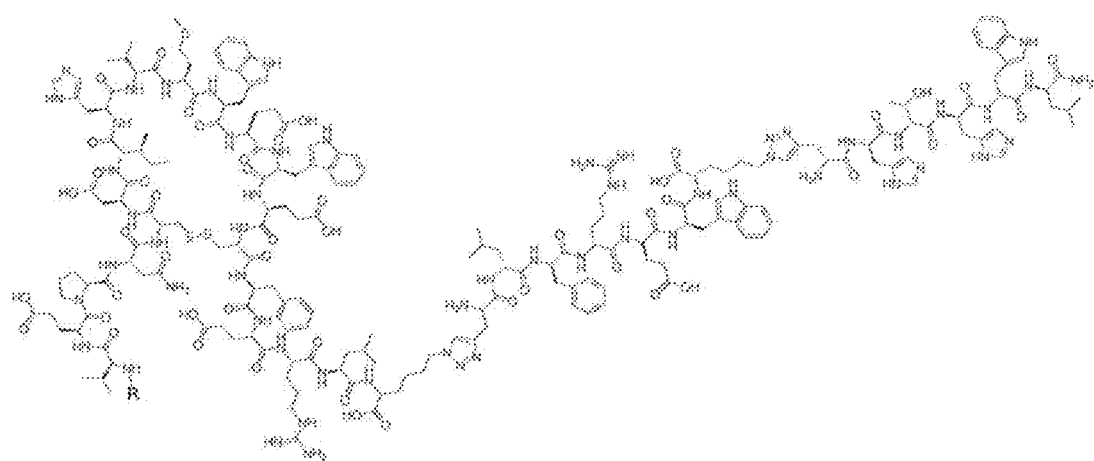
FIG. 13: Structure of Triligand 3 (SEQ ID NO: 72), which comprises the anchor ligand of SEQ ID NO: 1, the secondary ligand of SEQ ID NO:3, and the tertiary ligand of SEQ ID NO:7 (hthwl).
Figure 14:
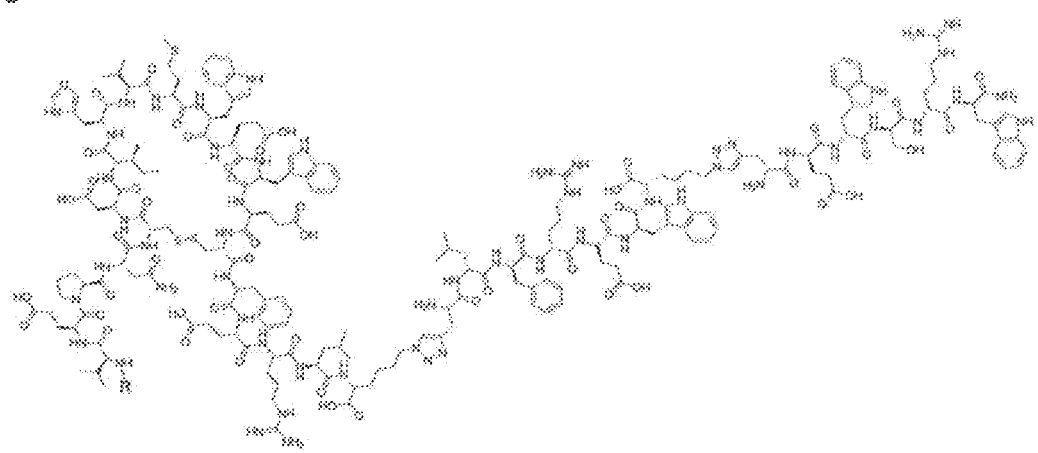
FIG. 14: Structure of Triligand 4 (SEQ ID NO: 73), which comprises the anchor ligand of SEQ ID NO:1, the secondary ligand of SEQ ID NO:3, and the tertiary ligand of SEQ ID NO:8 (ewsrw).

Hit sequences were analyzed using the proprietary Integrated Diagnostics bioinformatic clustering algorithm that was used to guide triligand candidate selection. Candidate peptides were grouped together based on physicochemical features (FIG. 7).

Triligand candidates containing the 1,4-substituted-1,2,3-triazole were then synthesized individually, and biological assays were performed to determine the triligands with the largest improvements in VEGF binding affinity and specificity versus the biligand. Competitive assays were also implemented to characterize inhibitory effects of triligands on VEGF binding to VEGFR2 and other species.

The selected triligand capture agents comprise Biligand 2 linked to a tertiary ligand comprising the amino acid sequence of SEQ ID NO:5 (frsvn; "Triligand 1"), 6 (eeird; "Triligand 2"), 7 (hthwl; "Triligand 3"), or 8 (ewsrw; "Triligand 4"). The structures of Triligands 1-4 are set forth in FIGS. 11-14, respectively.

CNBr Cleavage of "Hit" Peptides from Single Beads. A single bead was transferred to a microcentrifuge tube containing pure water (10 μL). After addition of CNBr (10 μL, 0.50 M in 0.2 N HCl solution) the reaction vessel was purged with argon and then placed under microwave for one minute (Lee 2008). The resulting solution was concentrated under centrifugal vacuum for 2 hours at 45° C.

MALDI-MS and MS/MS Analysis of "Hit" Peptides Cleaved from Single Beads. To each tube was added a-cyano-4-hydroxycinnamic acid CHCA (0.5 μL, 5 mg/mL matrix solution in acetonitrile/water (70:30) containing 0.1% TFA (v/v)). The mixture solution was taken up to be spotted onto a 384-well MALDI plate, which was allowed to stand for 15 minutes to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each sample in LIFT™ mode.

Example 2

Large-Scale Production of VEGF Capture Agents

Large scale production of the VEGF capture agents identified in Example 1 was required for biological assays. Each triligand was prepared using a combination of conventional and microwave-assisted Fmoc-based solid phase peptide synthesis (SPPS). Specifically, the differing tertiary ligands of each triligand were synthesized in parallel onto rink amide resin using an AAPPTEC Titan 357 peptide synthesizer. Each amino acid coupling reaction incorporated 4 equiv of Fmoc-amino acid, 4 equiv of HBTU, and 10 equiv of DIEA. Deprotection of the Fmoc group required 20% piperidine/NMP.

The rink amide bound tertiary ligands were transferred to a CEM Liberty 1 microwave peptide synthesizer for the preparation of the anti-VEGF (X-VEPNCDIHVM-WEWECFERL-Tz4-Ifrew-Tz4 (SEQ ID NO: 87), where X is a pegylated reporter tag (e.g., biotin-PEG, DOTA-PEG, etc.)). Each amino acid, PEG linker, and reporter coupling reaction incorporated 4 equiv of Fmoc-amino acid, 4 equiv of HBTU, and 10 equiv of DIEA. Coupling conditions of the two Tz4 linkers were modified using 4 equiv of Fmoc-amino acid, 4 equiv of HATU and 10 equiv of DIEA. Deprotection of the Fmoc group required 20% piperidine/NMP. If no pegylated reporter was required, the resin bound triligands were capped at the N-termini using $Ac_2O$/DIEA. Capture agents were purified by reversed phase HPLC using a C18 column and a linear gradient (Solvent A: H$_2$O+0.1% TFA, Solvent B: ACN+0.1% TFA).

Example 3

Binding Affinity Analysis

A direct, solid-phase microplate enzyme-linked immunosorbent assay (ELISA) was used to measure in vitro binding of capture agents to VEGF165 (#ab56620; Abcam, Mass.). Binding was also measured for the whole IgG and Fab fragment (prepared by papain digestion) of the anti-VEGF monoclonal antibody Bevacizumab (Avastin®). The ELISA was found to be highly sensitive and reliable for detecting binding over a range of capture agent concentrations. The equilibrium dissociation constant (KD) for the capture agents may be estimated as the concentration corresponding to half-maximal fluorescent emission. Assaying multiple capture agents in parallel permits relative and absolute comparison of in vitro binding.

NUNC MAXISORP™ microtiter plates were coated with 2 µg/mL VEGF165 (#ab56620; Abcam, Mass.) in PBS pH 7.4 over 2 hour at 25° C. After washing each well with PBS (3×), the plate was filled with 5% non-fat dry milk in TBS (25 mM Tris, 150 mM NaCl, pH 7.25) containing 0.1% (v/v) Triton X-100 and blocked for 2 hours at 25° C. The plate was washed with 1% non-fat dry milk in TBS containing 0.1%(v/v) Triton X-100 (3×), and then serially diluted biotinylated capture agent in 1% non-fat dry milk in TBS containing 0.1% (v/v) Triton X-100 was incubated for 3 hours at 25° C. After washing all microwells with TBS/0.1%(v/v) Triton X-100 (5×), 0.1 µg/mL Streptavidin Poly-HRP conjugate (Pierce, Ill.) in TBS/0.1%(v/v) Triton X-100 was incubated for 30 minutes at 25° C. The plate was aspirated and washed with TBS/0.1% (v/v) Triton X-100 (5×), followed by TBS (5×), and then developed by adding QuantaRed™ Enhanced Chemifluorescent HRP Substrate. Using an excitation wavelength of 535 nm, fluorescent emission at 595 nm was recorded by Beckman Coulter DTX880 photometer (Brea, Calif.) as a function of capture agent concentration. The titration curves were fit using a four-parameter regression curve fitting program (Origin 8.5, Northampton, Mass.).

Figure 15:
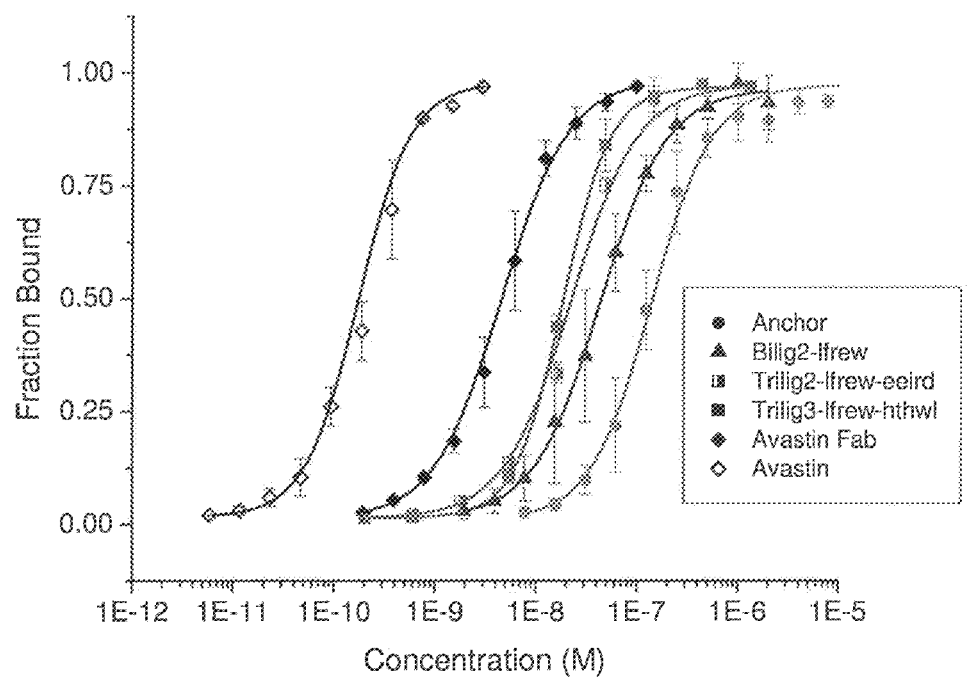
FIG. 15: Binding of Triligand 2 ("Trilig2-Ifrew-eeird"), Triligand 3 ("Trilig3- hthwl-hthwl"), Biligand 2 ("Bilig2-Ifrew"), the anchor ligand ("Anchor") component of the bi- and triligands, Avastin®, and Avastin® Fab to VEGF165 as measured by ELISA.
Figure 67:
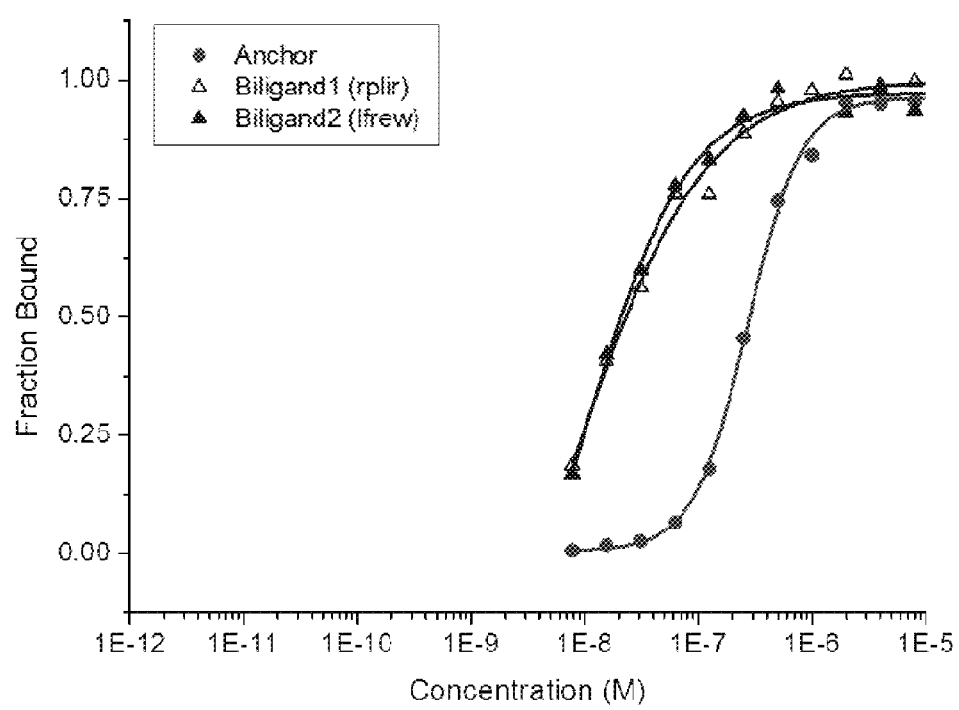
FIG. 67: Affinities of anti-VEGF PCC biligand candidates versus anchor. VEGF165A was immobilized on NUNC Max- iSorp plates and incubated with varying concentrations of biotinylated peptide. All values were normalized to the binding observed at saturation.
Figure 68:
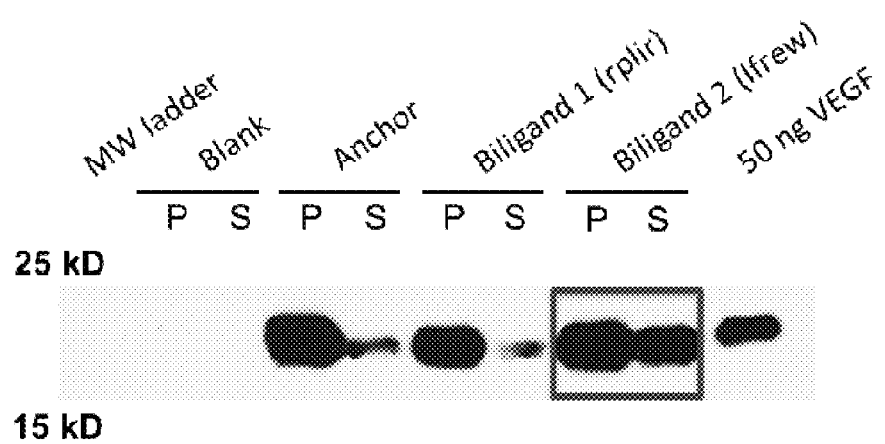
FIG. 68: Immunoprecipitation by anti-VEGF PCC biligand candidates vs. anchor from buffer and human serum. Biotinylated ligands were incubated with 0.5 µg/mL VEGF165A in PBS pH 7.4 (P) or 25% (v/v) human serum (S) for 16 h at 4° C., after which DynaBeads® M-280 Streptavidin were added for 3 h at 4° C. Beads were washed exhaustively, eluted with SDS-PAGE Laemmli sample buffer, and analyzed for VEGF165A by Western blotting compared to control (50 ng VEGF).
Figure 70:
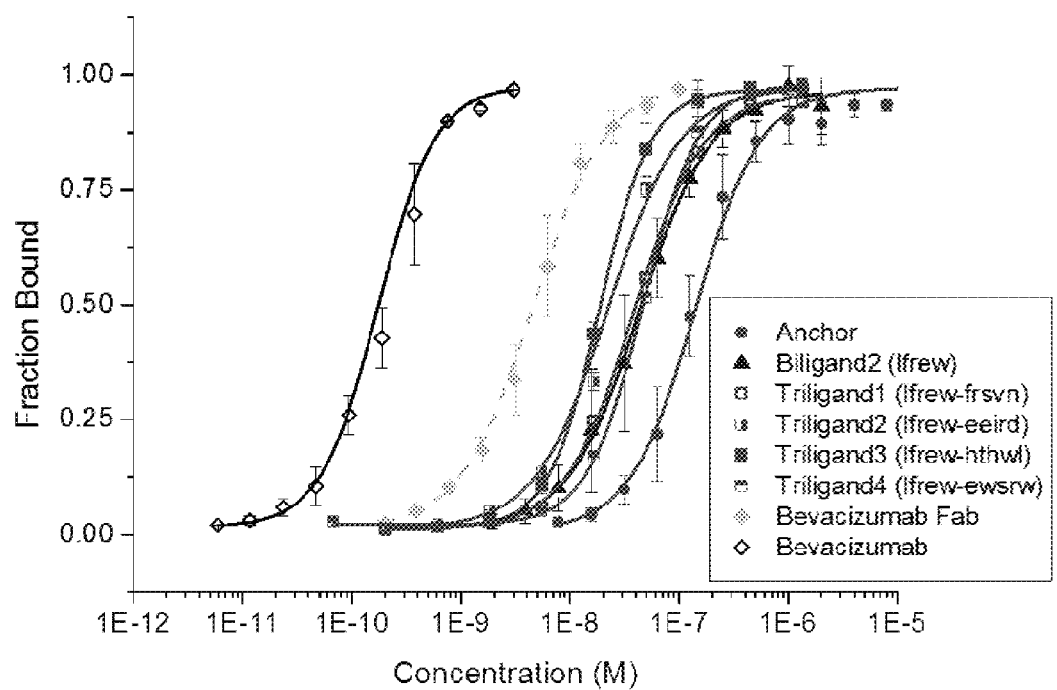
FIG. 70: Affinities of anti-VEGF PCC triligand candidates. VEGF165A was immobilized on NUNC MaxiSorp plates and incubated with varying concentrations of biotinylated PCC or bevacizumab (mAb or Fab). All values were normalized to the binding observed at saturation.
Figure 71:
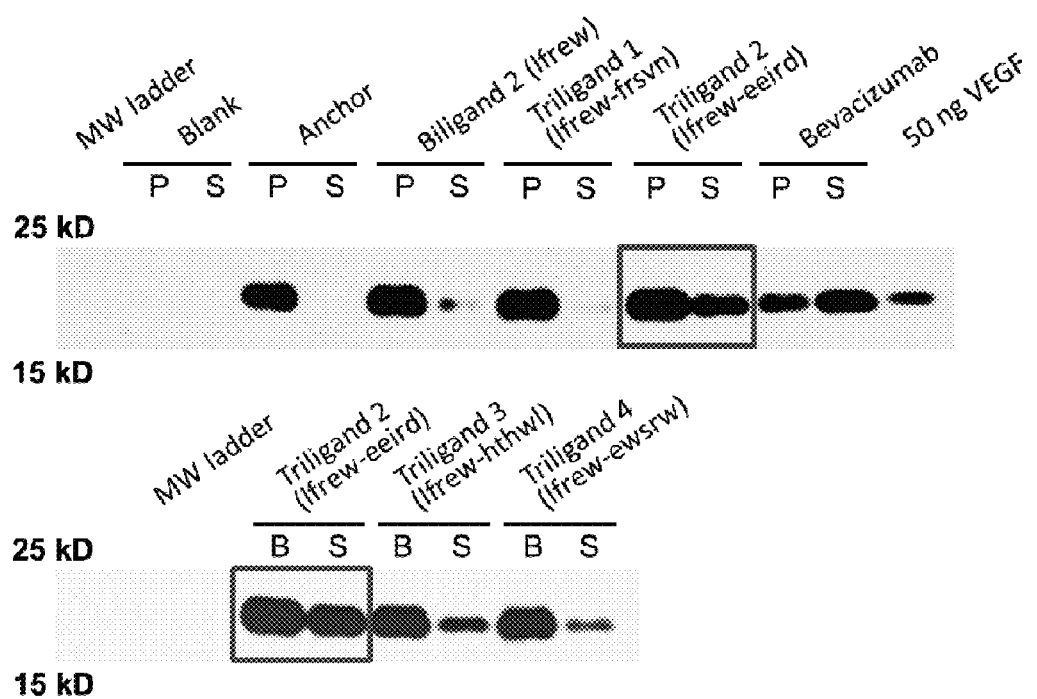
FIG. 71: Immunoprecipitation by anti-VEGF PCC triligand candidates from buffer and human serum. Biotinylated ligands were incubated with 0.5 µg/mL VEGF165A in PBS pH 7.4 (P) or 25% (v/v) human serum (S) for 16 h at 4° C., after which DynaBeads® M-280 Streptavidin were added for 3 h at 4° C. Beads were washed exhaustively, eluted with SDS-PAGE Laemmli sample buffer, and analyzed for VEGF165A by Western blotting compared to control (50 ng VEGF).

The affinity of Triligands 2 and 3, Biligand 2, and the anchor ligand of these capture agents are shown in FIG. 15. The affinity of Biligand 1 and Triligands 1 and 4 are further shown in FIGS. 67 and 70, respectively. As a detection agent, Biligand 2 showed five-fold improvement in its affinity for VEGF relative to the anchor ligand alone, while the best triligands showed an additional affinity gain (2-3 fold, KD~15 nM). These results suggest that the capture agent selection process inherently develops affinity. The affinities of Avastin® and Avastin® Fab were measured as KD~0.2 nM and KD~4.5 nM, respectively, and it appears that the decreased avidity of Avastin® Fab is manifested as loss in affinity in this experiment. In the same way that Avastin® divalency confers affinity and avidity over the Fab fragment, a dimeric triligand capture agent provides additional affinity gains.

Example 4

Binding Specificity Analysis

A pull-down assay was used to assess capture agent specificity for VEGF by measuring the ability of the capture agents to purify VEGF165 from buffer or complex media such as human serum. Capture agents were immobilized on streptavidin-functionalized magnetic beads, and the resultant resins were panned with VEGF165-spiked serum or buffer.

Pull-down detection of VEGF165 was performed using a modified immunoprecipitation technique that incorporated capture agents rather than antibody. First, biotinylated capture agent (400 nM; 0.1% DMSO, v/v) was incubated with 1 µg/mL VEGF165 in 2 mL TBS at 4° C. overnight. Separately, biotinylated capture agent (400 nM; 0.1% DMSO, v/v) was incubated with 1 µg/mL VEGF165 in 2 mL of 25% (v/v) human AB male serum (#HS-20, Omega Scientific, Tarzana, Calif.) under the same conditions (4° C., overnight). A vehicle-only control (0.1% DMSO, v/v) accompanied each sample.

Proteins were captured by BSA-blocked Dynabeads® M-280 Streptavidin (Invitrogen, #112-05D) under rotation at 4° C. for 4 hours (100 µL of 50% slurry per pull-down condition). Beads were separated from the serum or buffer matrix by application of the DynaMag™-Spin magnet (Invitrogen, #123-20D), and captured proteins were eluted from the beads in 30 µL of reducing Laemmli buffer. Eluted samples were subjected to 12% SDS-PAGE separation at 200 V for 30 minutes in 1×TGS (25 mM Tris, 192 mM Glycine, 0.1% SDS (w/v), pH 8.3). Samples were subsequently electrophoretically transferred to a nitrocellulose membrane in 25 mM Tris, 192 mM Glycine, pH 8.3, containing 20% (v/v) methanol (Bio-Rad Laboratories, Hercules, Calif.) at 100 V for 45 minutes. Following transfer, the nitrocellulose membrane was blocked at 4° C. for 2 hours in 5% non-fat dry milk in TBS. The membrane was then washed with TBS (3×), and 1 µg/mL mouse anti-human VEGF165 antibody [6B7] (#ab69479; Abcam, Mass.) in 0.5% non-fat dry milk in TBS was incubated at 4° C. overnight. After washing with TBS containing 0.02% Tween20 (v/v) (5×), 0.2 µg/mL HRP-conjugated goat polyclonal secondary antibody to mouse IgG (H+L) (#ab6789; Abcam, Mass.) in 0.5% non-fat dry milk in TBS was added to the membrane (4° C., 1 hour incubation). After washing with TBS containing 0.02% Tween20 (v/v) (5×), followed by TBS (5×), the membrane was developed with SuperSignal West Pico Chemiluminescent Enhancer and Substrate Solutions (Pierce, Ill.) and then immediately exposed to HyBlot CL AR film. Separately, a duplicate 12% gel was visualized for total protein content by silver stain (Bio-Rad Laboratories, Hercules, Calif.) to estimate specificity of capture agents in comparison to the Western result.

Results of pull-down assays are set forth in FIGS. 16, 68, 71, and 73. Probing the elutions via Western blot with a VEGF antibody confirms the increase in capture efficiency as the combined affinity/specificity metrics of the capture agent are increased by translating from anchor to biligand to triligand. Analysis of the total immunoprecipitated protein by SDS-PAGE showed tolerable to low non-selective binding for all capture agents, and correlates well with the capture efficiency for VEGF. VEGF detection from human serum was observed only after the anchor ligand was developed into biligand and then triligand capture agents. Triligand 2 captures equivalent amounts of VEGF in buffer and serum (lanes B vs. S), indicating the highest attainable capture agent specificity, and compares well with the Avastin® result.

These results suggest that the capture agent selection process not only develops affinity, but also inherently develops specificity. The results also suggest that triligands of equivalent affinity are not necessarily equivalent in specificity (compare Triligands 2 and 3); therefore, both affinity and specificity are critical performance parameters of capture agents that can mature independently.

Example 5

Serum Stability

Proteolytic stability is an important factor for the use of peptides in in vivo applications and for serum protein diagnostics. Most natural peptides have to be modified to prevent enzymatic degradation. Several approaches including the use of D-amino acids, non-natural amino acids, and cyclization have been used to improve capture agent stability.

Stability was studied by mixing 200 µg capture agent in TBS containing 25% (v/v) human AB male serum (HS-20, Omega Scientific, Tarzana, Calif.) in 800 µL total volume (see, e.g., Pakkala 2007). Peptides were incubated at 37° C., and 100 µL aliquots were taken at 0 minutes, 30 minutes, and then after every hour up to 4 hours. A final aliquot was taken after 24 hours. The peptide was separated from plasma proteins on a Microcon centrifugal filter device (Microcon YM-10, MWCO=10 kDa, Millipore, Bedford, Mass.) by centrifugation at 12,000 rpm using a Beckman Coulter refrigerated microcentrifuge (Brea, Calif.) for 20 min. The filtrates were examined by analytical HPLC (C18 column, linear gradient of 0→100% B over 60 min, where A=$H_2O$+0.1% TFA and B=ACN+0.1% TFA), followed by Bruker UltrafleXtreme MALDI mass spectrometry.

Two control assays were performed in parallel and subjected to the same conditions as above: 1) Biligand 2 in TBS, and 2) TBS containing 25% (v/v) human AB male serum.

Figure 17:
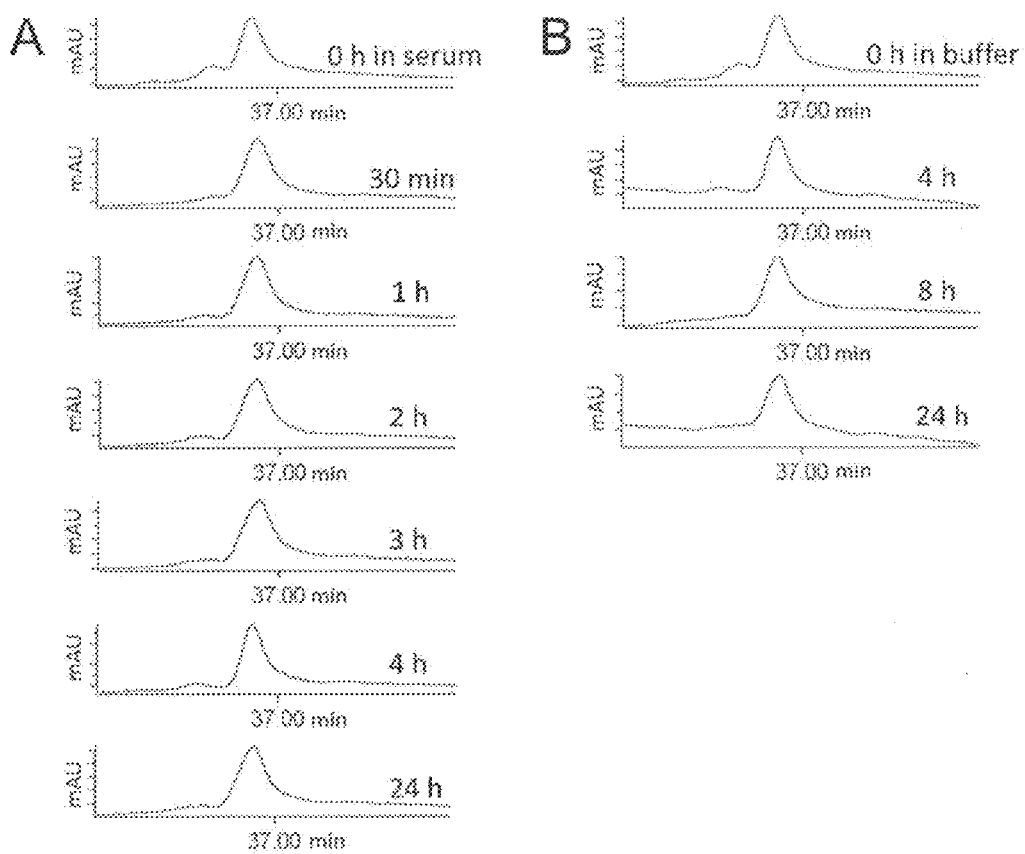
FIG. 17: HPLC analysis of in vitro stability for anti-VEGF PCC triligand at 37° C. (A) In 25% (v/v) human AB male serum. (B) In TBS pH 7.25. The PCC (200 µg) was incubated at 37° C. in the presence or absence of 25% (v/v) human AB male serum (HS-20, Omega Scientific, Tarzana, Calif.) in TBS. Aliquots were taken at various time points. The PCC was separated from plasma proteins on a Microcon centrifugal filter device (Microcon YM-10, MWCO=10 kDa, Millipore, Bedford, Mass.) by centrifugation at 12,000 rpm. The filtrates were examined by analytical HPLC on a $C_{18}$ column.

The capture agent was still intact after incubation with either human serum or buffer for 24 hours at 37° C. (FIG. 17), suggesting that the capture agent is stable to proteolytic degradation in human serum for more than 24 hours at physiological temperature and buffer. The results indicate that cyclization is an efficient and simple approach to improve resistance to proteolytic digestion for sequence segments containing (natural) L-amino acids, and that D-amino acids and non-natural amino acids are intrinsically stable elements. This approach, without any sequence modifications, could be useful for designing peptides for in vivo studies.

Example 6

Inhibition of HUVEC Proliferation

Human umbilical vein endothelial cells (HUVECs) constitutively secrete VEGF, which binds to VEGFR2 in an autocrine fashion. Avastin® binds directly to VEGF and blocks formation of the VEGF-VEGFR2 complex, thereby attenuating proliferation by blocking receptor signaling. Biligand capture agents were evaluated for their ability to inhibit HUVEC proliferation.

HUVECs were cultured in M199 medium (pH 7.4) in 5% $CO_2$ at 37° C. for 18 hours. Test compound and/or vehicle were incubated with cells ($1.1 \times 10^5$/mL) in the presence of heparin (10 µg/mL) and 0.5% FBS at 37° C. for 48 hours. Capture agents were screened at 10, 1, 0.1, 0.01 and 0.001 µM and in duplicate. Avastin® was screened at 100, 10, 1, 0.1 and 0.01 nM and in duplicate. VEGF165 (agonist, $EC_{50}$=0.079 nM) and SU5416 (antagonist, $IC_{50}$=48 nM) were assayed as standard references. Subsequently, the reagent Calcein AM dye (20 µg/ml) was added for an additional 50 minute incubation period. Fluorescence intensity was read on SpectroFluor Plus plate reader.

Figure 18:
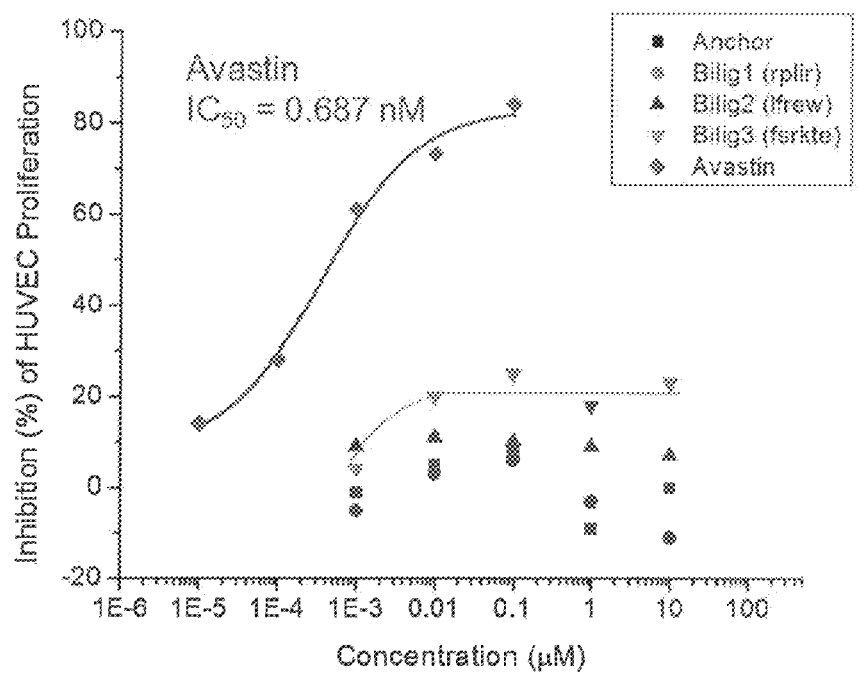
FIG. 18: Inhibition of HUVEC proliferation by Biligand 1("Bilig1 (rplir)"), Biligand 2 ("Bilig2 (Ifrew)"), Biligand 3 ("Bilig3-fsrkte"), the anchor ligand ("Anchor") of the biligands, and Avastin®.

Response curves illustrating percent inhibition versus test compound concentration are set forth in FIG. 18. Test compound-induced stimulation of cell proliferation by 50% or more, relative to 1 nM VEGF165 control response, indicates significant agonist activity, while test compound-induced suppression of 0.2 nM VEGF165-induced cell proliferation by 50% or more indicates significant antagonist activity. Results are shown in FIG. 18. Tabulated $IC_{50}$ values confirm Avastin®-mediated antagonism ($IC_{50}$=0.687 nM) as a positive control.

Binding of capture agents to soluble VEGF prevents ligation to VEGFR2 on the cell surface and attenuates proliferation by blocking signaling through the receptor.

Example 7

Pharmacokinetics

A preliminary pharmacokinetic assessment of Biligand 2 was performed following intravenous (IV) and intraperitoneal (IP) dosing to mice.

HPLC-MS Optimization. Test compound solutions were prepared as specified in Tables 1 and 2 and infused into the TSQ Quantum source via syringe pump at a constant rate. Full scan MS analysis was conducted and total ion current chromatograms and corresponding mass spectra were generated for the test compound in both positive and negative ionization modes. The precursor ions for MS/MS were selected from either the positive or the negative mass spectrum, as a function of the respective ion abundance. In addition, product ion MS/MS analysis was performed in order to determine the appropriate selected fragmentation reaction for use in quantitative analysis. The final reaction monitoring parameters were chosen to maximize the ability to quantify the test compound when present within a complex mixture of components. Following identification of the specific SRM transition to be used for each test compound, the detection parameters were optimized using the automated protocol in the TSQ Quantum Compound Optimization workspace. Finally, the chromatographic conditions to be used for LC-MS analysis were identified by injection and separation of the analyte on a suitable LC column and adjustment of the gradient conditions as necessary.

TABLE 1

General procedures

| Assay | Sample Preparation | Bibliography |
|---|---|---|
| HPLC-MS optimization | | Watt 2000 |
| Linearity (plasma, mouse) | Calibration curve; acetonitrile precipitation | Watt 2000 |
| Quantitative bioanalysis (plasma, mouse) | Calibration curve; acetonitrile precipitation | Watt 2000 |

TABLE 2

Experimental conditions

| Assay | Test Compound | Detection Methods |
|---|---|---|
| HPLC-MS optimization | 1000 ng/mL | HPLC-MS and HPLC-MS/MS |
| Linearity (plasma, mouse) | 0, 1, 2.5, 5, 10, 50, 250, 1000, 2500, 5000 ng/mL | HPLC-MS/MS |
| Quantitative bioanalysis (plasma, mouse) | Unknown in plasma samples | HPLC-MS/MS |

Linearity in Plasma. Aliquots of plasma were spiked with the test compound at the specified concentrations. The spiked samples were processed using acetonitrile precipitation and analyzed by HPLC-MS or HPLC-MS/MS. A calibration curve of peak area versus concentration was constructed. The reportable linear range of the assay was determined, along with the lower limit of quantitation (LLQ).

Quantitative Bioanalysis (Plasma). The plasma samples were processed using acetonitrile precipitation and analyzed by HPLC-MS/MS. A plasma calibration curve was generated. Aliquots of drug-free plasma were spiked with the test compound at the specified concentration levels. The spiked plasma samples were processed together with the unknown plasma samples using the same procedure. The processed plasma samples were stored at −20° C. until the HPLC-MS/MS analysis, at which time peak areas were recorded, and the concentrations of the test compound in the unknown plasma samples were determined using the respective calibration curve. The reportable linear range of the assay was determined, along with the lower limit of quantitation (LLQ).

Formulation. The solubility of the test compound is first evaluated in phosphate-buffered saline, pH 7.4 (PBS) by visual inspection. PBS is used as the vehicle if the compound is soluble at the target concentrations. Other vehicles that are compatible with IV dosing may be evaluated if the compound is not fully soluble in PBS. Such vehicles include DMSO, Solutol® HS 15, and Cremophor EL among others. For IP dosing, DMSO/Solutol® HS 15/PBS (5/5/90, v/v/v), or DMSO/1% methylcellulose (5/95, v/v) may be used as the vehicle if the test compound is not fully soluble in PBS. Customized formulations can be accommodated.

Plasma Sample Collection from Mice (parallel sampling). In vivo pharmacokinetic characterization was performed as specified in Tables 3-5. Animals were sedated under general inhalant anesthesia (3% isoflurane) for blood collection by cardiac puncture. Each mouse was subject to one blood draw. Blood aliquots (300-400 μL) were collected in tubes coated with lithium heparin, mixed gently, then kept on ice and centrifuged at 2,500×g for 15 minutes at 4° C., within 1 hour of collection. The plasma was then harvested and kept frozen at −20° C. until further processing.

TABLE 3

General procedures, in vivo PK

| Assay | Source | Dose | Technique | Bibliography |
|---|---|---|---|---|
| PK in-life (mouse, IV, parallel sampling) | Male mice CD-1, weighing 20-30 g | 1 mg/kg | Tail vein injection/blood collection | Hosten 2008 |
| PK in-life (mouse, IP, parallel sampling) | Male mice CD-1, weighing 20-30 g | 5 mg/kg | Gastric gavage/blood collection | Hosten 2008 |

TABLE 4

Experimental conditions, in vivo PK

| Assay | Sampling Time Points |
|---|---|
| PK in-life (mouse, IV, parallel sampling) | 3, 10, 30, 60, 120, 240, 360, 1440 min |
| PK in-life (mouse, IP, parallel sampling) | 10, 30, 60, 120, 240, 360, 480, 1440 min |

TABLE 5

Animal dosing design, in vivo PK (non-cannulated, non-fasted mice)

| Group | Experiment* |
|---|---|
| 1 | Biligand 2, IV, n = 3 mice per time point (24 animals total) |
| 2 | Biligand 2, IP, n = 3 mice per time point (24 animals total) |
| 3 | Control animals (for drug-free blood), n = 6 mice |

Plots of plasma concentration of compound versus time were constructed. The fundamental pharmacokinetic parameters of compound after IP and IV dosing (AUClast, AUCINF, Tv2, CI, VZ, Vss, Tmax, and Cmax) were obtained from the non-compartmental analysis (NCA) of the plasma data using WinNonlin. The bioavailability was calculated, if applicable. Noncompartmental analysis does not require the assumption of a specific compartmental model for either drug or metabolite. NCA allows the application of the trapezoidal rule for measurements of the area under a plasma concentration-time curve (Gabrielsson, J. and Weiner, D. Pharmacokinetic and Pharmacodynamic Data Analysis: Concepts and Applications. Swedish Pharmaceutical Press. 1997).

Figure 19:
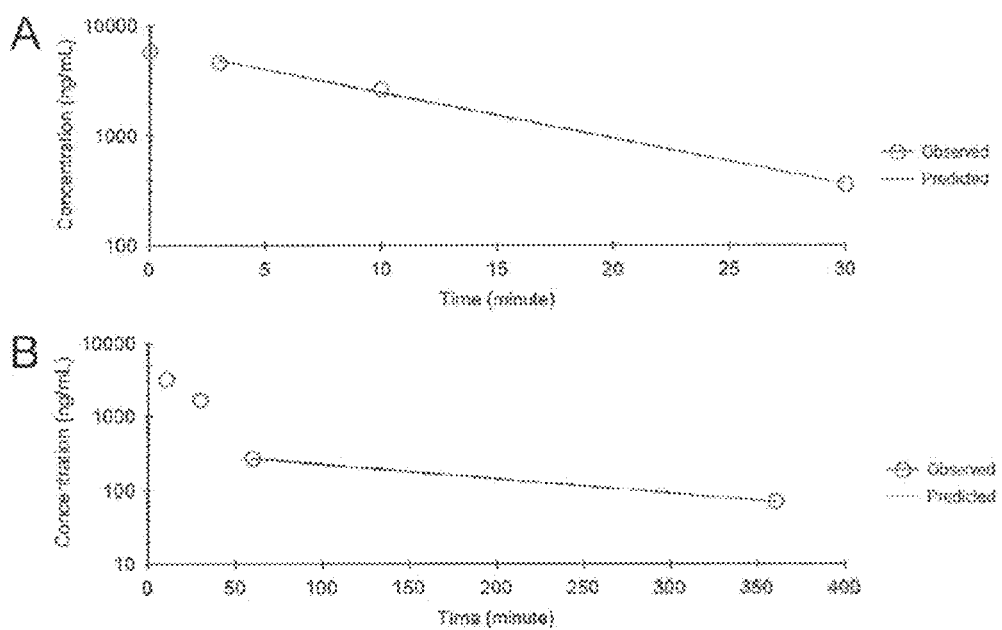
FIG. 19: A. Concentration-time profile after IV administration (1 mg/kg) of Biligand 1 to mice. Calculated $T_{1/2}$=7.2613 minutes (3 points, uniform weighting). B. Concentration-time profile after IP administration (5 mg/kg) of Biligand 1 to mice. Calculated $T_{1/2}$=154.3283 minutes (2 points, uniform weighting).

Graphs of the half-life for each route of administration are shown in FIG. 19, and the calculated PK parameters are summarized in Tables 6 and 7. As expected for peptides, the compound is cleared rapidly upon IV administration ($T_{1/2}$=7 min). Interestingly, there is a significant difference between the IV half-life and the IP half-life ($T_{1/2}$=154 min). There also appears to be two phases to the half-life for IP administration. These results suggest that IP is the superior route of administration.

TABLE 6

In vivo mouse PK analysis, IV administration of Bilig2-Itrew (Biligand 2)

| ROA | Dose (mg/kg) | T½ (min) | CL (mL/min/kg) | Vz (mL/kg) | Vss (mL/kg) | AUClast (min*ng/mL) | AUCINF (min*ng/mL) | Terminal Points |
|---|---|---|---|---|---|---|---|---|
| IV | 1 | 7 | 15 | 158 | 160 | 62760 | 66512 | 3 |

TABLE 7

In vivo mouse PK analysis, IP administration of Bilig2-Itrew (Biligand 2)

| ROA | Dose (mg/kg) | T½ (min) | Bioavailability (%) | Tmax (min) | Cmax (ng/mL) | AUClast (min*ng/mL) | AUCINF (min*ng/mL) | Terminal Points |
|---|---|---|---|---|---|---|---|---|
| IP | 5 | 154 | 41 | 10 | 3207 | 130030 | 145410 | 2 |

Example 8

Inhibition of VEGF Binding to VEGFR2

To measure the ability of capture agents to inhibit human VEGF165 binding to VEGFR2 (KDR), ELISA plates were coated with 10 µg/mL rabbit F(ab')2 to human IgG Fc (#309-006-008; Jackson ImmunoResearch, West Grove, Pa.) in 50 mM carbonate buffer, pH 9.6, at 25° C. for 2 hours and blocked overnight at 4° C. with 5% non-fat dry milk in TBS (25 mM Tris, 150 mM NaCl, pH 7.25) containing 0.1% (v/v) Triton X-100. Recombinant human VEGFR2 (KDR), Fc chimera (#357-KD, 10 µg/mL; R&D Systems, Minneapolis, Minn.) in TBS containing 0.1% (v/v) Triton X-100 was incubated on the plate for 1 hour at 25° C. Three-fold serial dilutions of capture agent or Avastin® Fab were incubated with 10 nM biotinylated VEGF165 (biotinylated using #21435 EZ-Link Sulfo-NHS-LC-Biotinylation kit, Pierce, Ill.) in 1% non-fat dry milk in TBS containing 0.1% (v/v) Triton X-100 for 2 hours in tubes. The solutions from the tubes were then transferred to the ELISA plates and incubated for 5 minutes. Bound biotinylated VEGF165 was detected using 0.2 pg/mL horseradish peroxidase-labeled streptavidin (#ab7403; Abcam, Mass.) prepared in TBS containing 0.1% (v/v) Triton X-100 and then developed by adding QuantaRed™ Enhanced Chemifluorescent HRP Substrate. Using an excitation wavelength of 535 nm, fluorescent emission at 595 nm was recorded by Beckman Coulter DTX880 photometer (Brea, Calif.) as a function of capture agent concentration. The titration curves were fit using a four-parameter regression curve fitting program (Origin 8.5, Northampton, Mass.). Concentrations of peptides corresponding to the mid-point absorbance of the titration curve were calculated and used as the $IC_{50}$ values.

Figure 20:
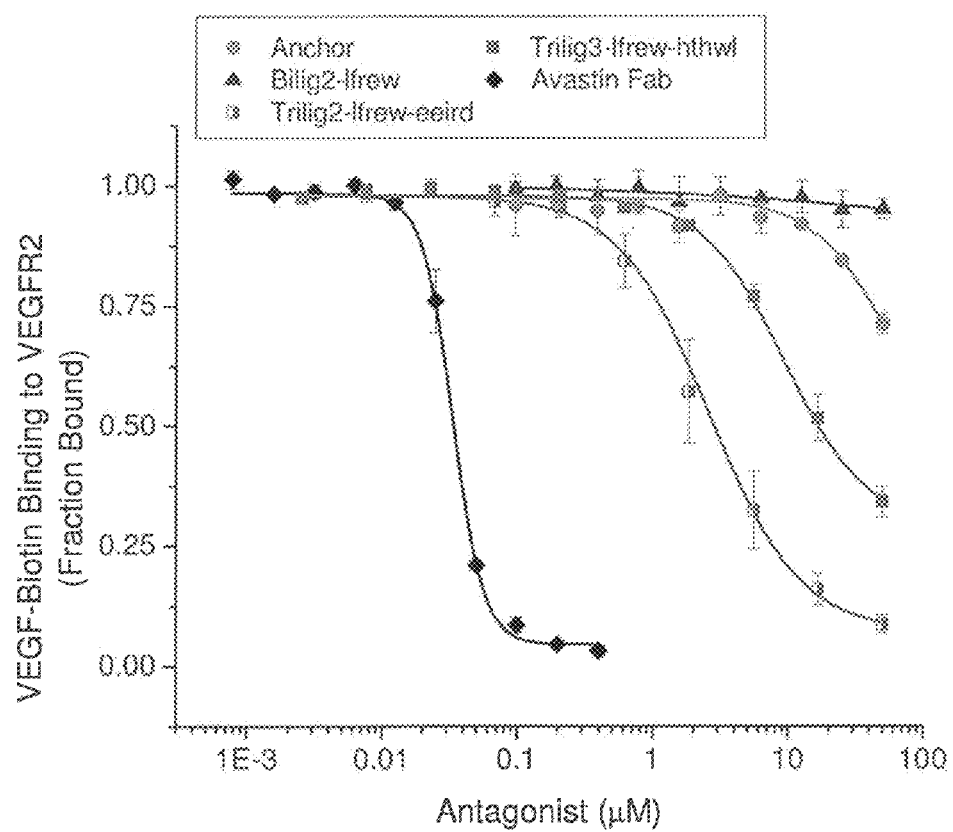
FIG. 20: Inhibition of VEGF165 binding to VEGFR2 by Triligand 2 ("Trilig2-Ifrew-eeird"), Triligand 3 ("Trilig3-Ifrew-hthwl"), Biligand 2 ("Bilig2-Ifrew"), the anchor ligand ("Anchor") of the bi- and triligands, and Avastin® Fab as measured by competitive ELISA.
Figure 72:
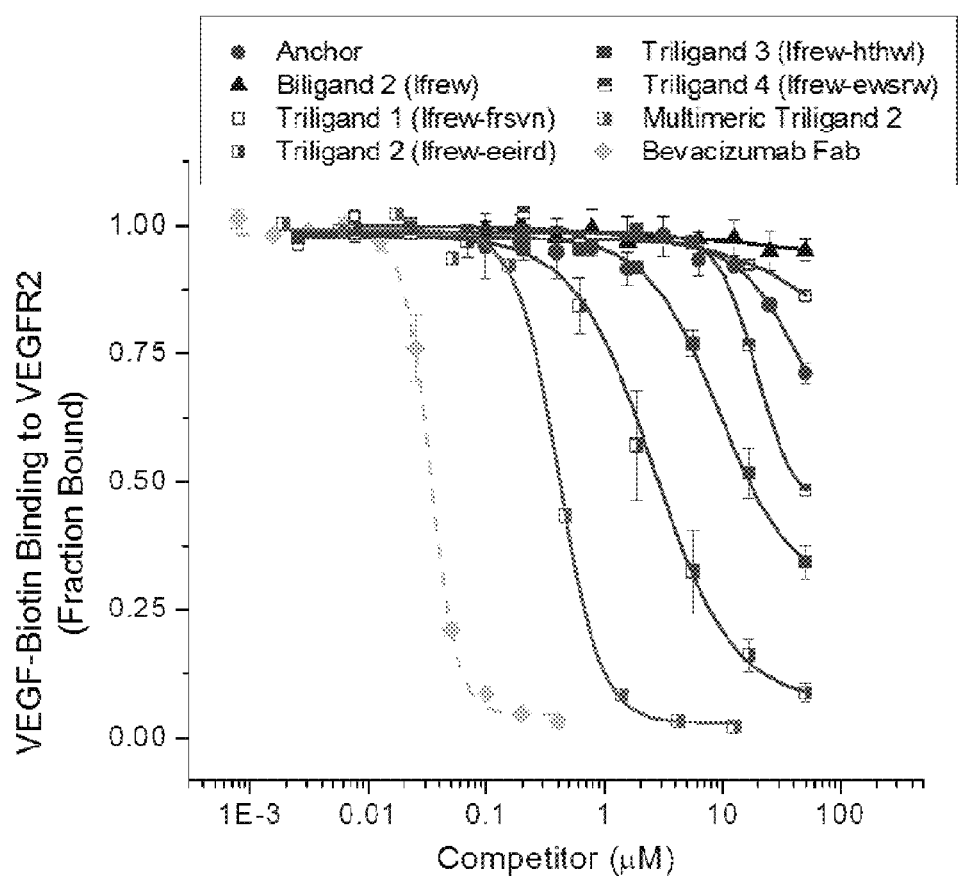
FIG. 72: Inhibition of VEGF binding to VEGFR2 by anti-VEGF PCC triligand candidates. Receptor blocking activities were screened by measuring biotinylated VEGF165A binding to VEGFR2-coated wells in the presence of serial dilutions of PCC or bevacizumab Fab. All values were normalized to the binding observed at saturation.
Figure 73:
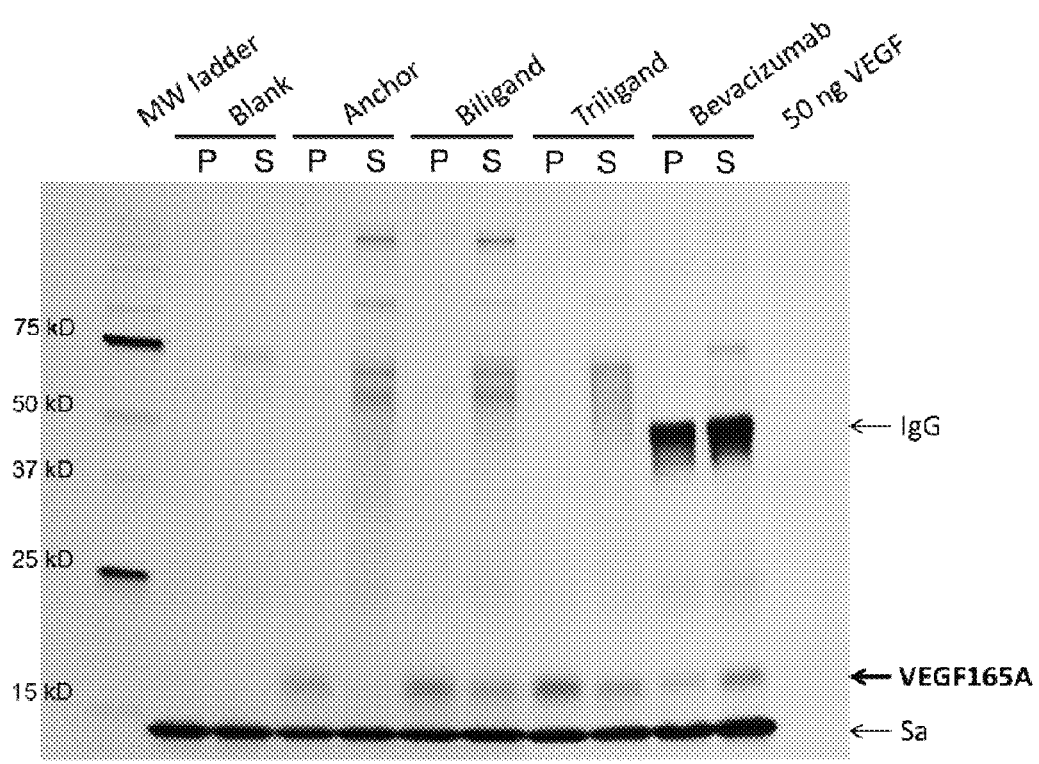
FIG. 73: Silver-stained gel visualizing total immunoprecipitated protein. Biotinylated ligands were incubated with 0.5 µg/mL VEGF165A in PBS pH 7.4 (P) or 25% (v/v) human serum (S) for 16 h at 4° C., after which DynaBeads® M-280 Streptavidin were added for 3 h at 4° C. Beads were washed exhaustively, eluted with SDS-PAGE Laemmli sample buffer, and analyzed by SDS-PAGE (12% gel) with silver staining.

The in vitro blocking potential of Triligands 2 and 3, Biligand 2, and the anchor ligand of these capture agents is shown in FIG. 20. The in vitro blocking potential of Triligands 1 and 4 are further shown in FIG. 72. Neither the anchor nor Biligand 2 blocked receptor binding at the concentrations tested (<50 µM). Therefore, the tertiary ligand component of the triligand capture agent appears to contribute significantly to the blocking activity, while the anchor and secondary ligand components provide enhancements in affinity and specificity. Three classes of triligand capture agents identified in this application (Triligands 2-4) were each found to each have binding sites that overlap significantly with the receptor-binding site. The largest in vitro blocking effect was observed for triligand 2 ($IC_{50}$=2 µM), which is within 100-fold of the $IC_{50}$ measured for Avastin® Fab. Even a partial blockade of VEGF may be sufficient to block in vivo tumor angiogenesis (Liang 2006).

Example 9

Inhibition of VEGF Binding to Avastin® Fab

A solid-phase competitive assay was used to quantify capture agent binding to the receptor interaction surface on VEGF in the presence of Avastin® Fab. Since the triligand capture agents and Avastin® Fab share similar binding affinities, concentration-dependent competition would confirm that they share binding epitopes.

NUNC MAXISORP™ microtiter plates were coated with 10 µg/mL Avastin® Fab in 50 mM carbonate buffer, pH 9.6, at 25° C. for 2 hours and blocked overnight at 4° C. with 5% non-fat dry milk in TBS (25 mM Tris, 150 mM NaCl, pH 7.25) containing 0.1%(v/v) Triton X-100. Two-fold serial dilutions of capture agent were incubated with 10 nM biotinylated VEGF165 in 1% non-fat dry milk in TBS containing 0.1%(v/v) Triton X-100 for 1 hour on the Fab-immobilized plate. Bound biotinylated VEGF165 was detected using 0.2 µg/mL horseradish peroxidase-labeled streptavidin (#ab7403; Abcam, MA) prepared in TBS containing 0.1% (v/v) Triton X-100 and then developed by adding QuantaRed™ Enhanced Chemifluorescent HRP Substrate. Using an excitation wavelength of 535 nm, fluorescent emission at 595 nm was recorded by Beckman Coulter DTX880 photometer (Brea, Calif.) as a function of capture agent concentration. The titration curves were fit using a four-parameter regression curve fitting program (Origin 8.5, Northampton, Mass.). Concentrations of peptides corresponding to the mid-point absorbance of the titration curve were calculated and used as the $IC_{50}$ values.

Figure 21:
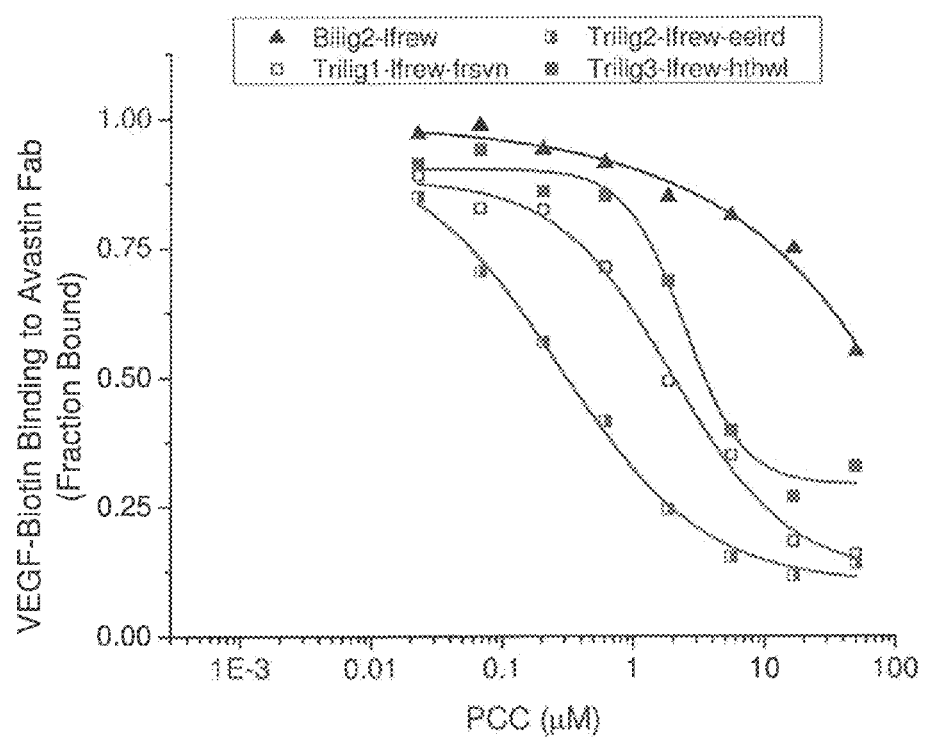
FIG. 21: Inhibition of VEGF165 binding to Avastin® Fab by Triligand 1 ("Trilig1-Ifrew-frsvn"), Triligand 2 ("Trilig2-Ifrew-eeird"), Triligand 3 ("Trilig3-Ifrew-hthwl"), and Biligand 2 ("Bilig2-Ifrew") as measured by competitive ELISA.

In vitro competition between Avastin® Fab and capture agents is shown in FIG. 21. VEGF blocking was observed with Triligand 2 ($IC_{50}$=0.4 µM) and Triligands 1 and 3 ($IC_{50}$=2 µM), suggesting that the triligand-binding epitopes on VEGF overlap with the epitope for Avastin® Fab. Biligand 2 also displayed concentration-dependent competition but was not as significant as the triligand capture agents, suggesting again that the tertiary ligand component appears to confer specific binding properties that result in greater coverage of the epitope.

Example 10

Plasma Protein Binding

Equilibrium dialysis techniques were used to separate the fraction of unbound test compound from the fraction that is bound to protein.

Assays were carried out in a 96-well format in a dialysis block constructed from Teflon. The protein matrix was spiked with the test compound at 10 µM (n=2) with a final DMSO concentration of 1% (v/v). The dialysate compartment was loaded with 150 µL phosphate buffer (pH 7.5) and the sample side was loaded with equal volume of the spiked protein matrix. The dialysis plate was then sealed and incubated at 37° C. overnight (18±2 hours). After the incubation, samples were taken from each compartment, diluted with the phosphate buffer followed by addition of acetonitrile and centrifugation. The supernatants were then used for HPLC-MS/MS analysis. A control sample (n=2) was prepared from the spiked protein matrix in the same manner as the assay samples (without dialysis). This control sample served as the basis for the recovery determination. Samples were analyzed by HPLC-MS/MS using selected reaction monitoring. The HPLC conditions consisted of a binary LC pump with autosampler, a C18 column (2×20 mm), and gradient elution. The percent bound to proteins and the recovery were calculated as follows:

$$\text{Protein binding } (\%) = \frac{(Area_{pe} - Area_{be}) \times \frac{V_{pe}}{V_{pi}}}{(Area_{pe} - Area_{be}) \times \frac{V_{pe}}{V_{pi}} + Area_{be}} \times 100$$

$$\text{Recovery } (\%) = \frac{(V_{pe} \times Area_{pe} + V_{be} \times Area_{be})}{V_{pi} \times Area_{cs}} \times 100$$

where $Area_{pe}$ is the peak area of analyte in the protein matrix at equilibrium, $Area_{be}$ is the peak area of analyte in the Assay Buffer at equilibrium, $V_{pe}$ is the volume of the protein matrix at equilibrium, VP; is the initial volume of the protein matrix, and Area$_{cs}$ is the peak area of analyte in control sample. The recovery determination served as an indicator of reliability of the calculated protein binding value.

Figure 22:
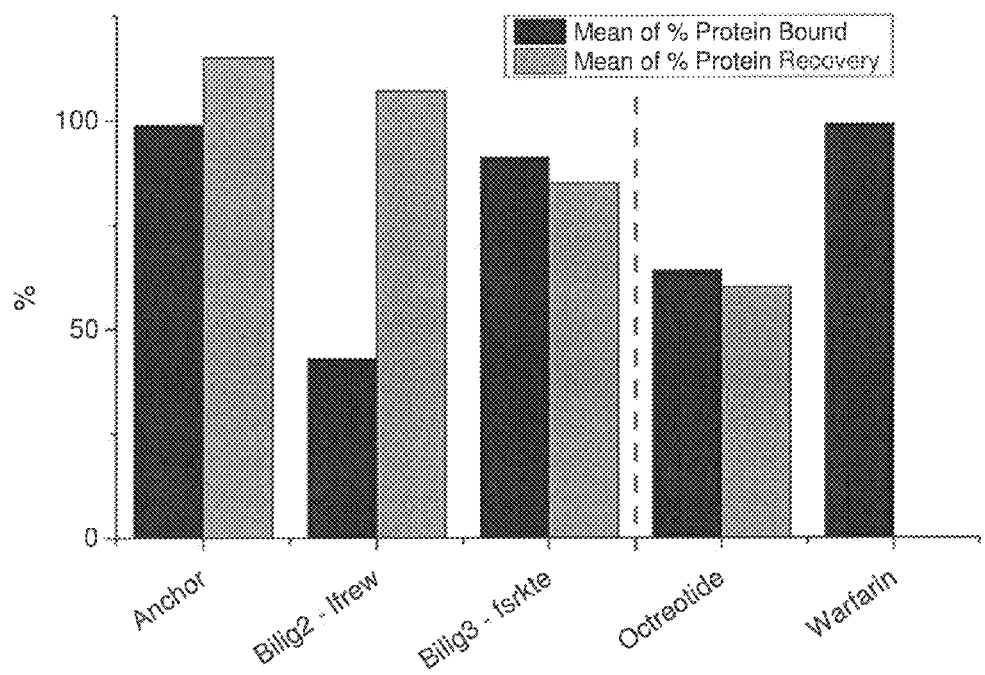
FIG. 22: Plasma protein binding by Biligand 2 ("Bilig2-Ifrew"), Biligand 3 ("Bilig3-fsrkte"), the anchor ligand ("Anchor") of the biligands and the reference compounds octreotide and warfarin.

Most successful drugs have a plasma binding component. Low plasma protein binding illustrates high specificity, while higher degrees of plasma protein binding predict that a compound will display longer circulation times and potentially increased access to the target at the expense of poorer specificity. Analysis of the plasma protein binding results indicates that Biligand 2 (Bilig2-Ifrew) displays low plasma protein binding (FIG. 22), while Biligand 3 (Bilig3-fsrkte) exhibited higher levels of plasma protein binding. Plasma protein binding by capture agents compares well against octreotide (a peptide therapeutic) and warfarin (a small molecule drug). The trends in plasma protein binding for capture agents mirror the trends in pull-down assay and Western blot results (Example 4). The percent protein recovery was high for all capture agents, suggesting there is no sample degradation during the course of the assay.

Example 11

Stability in Human Plasma and Mouse Liver Microsomes

Capture agent stability in human plasma was quantified at multiple timepoints by HPLC-MS/MS analysis.

Human plasma was pre-warmed at 37° C. water bath for 5 minutes, followed by addition of 5 µM test compound with a final DMSO concentration of 0.5% (v/v). The incubation was performed in a 37° C. water bath for 0, 15, 30, 45, and 60 minutes. At each time point, an aliquot of the incubation mixture was transferred to acetonitrile. Samples were then mixed and centrifuged. Supernatants were used for HPLC-MS/MS analysis. Samples were analyzed by HPLC-MS/MS using selected reaction monitoring. The HPLC system consisted of a binary LC pump with autosampler, a C-18 column, and a gradient. Peak areas corresponding to the test compound were recorded. The compound remaining (%) was calculated by comparing the peak area at each time point to time zero.

The test compound was pre-incubated with pooled mouse liver microsomes (male CD-1, 0.3 mg/mL) in phosphate buffer (pH 7.4) for 5 minutes in a 37° C. shaking waterbath. Concentration of the test compound was 1 µM with 0.01% DMSO, 0.25% acetonitrile and 0.25% methanol. The reaction was initiated by adding NADPH-generating system (1.3 mM NADP, 3.3 mM G6P, and 0.4 U/mL G6PDHase) and incubated for 0, 15, 30, 45, and 60 minutes. The reaction was stopped by transferring the incubation mixture to equal volume of acetonitrile/methanol (1/1, v/v). Samples were then mixed and centrifuged. Supernatants were used for HPLC-MS/MS analysis. Samples were analyzed by HPLC-MS/MS using selected reaction monitoring. The HPLC system consisted of a binary LC pump with autosampler, a C-18 column, and a gradient. Peak areas corresponding to the test compound were recorded. The compound remaining was calculated by comparing the peak area at each time point to time zero. The half-life was calculated from the slope of the initial linear range of the logarithmic curve of compound remaining (%) vs. time, assuming first order kinetics. In addition, the intrinsic clearance was calculated from the half-life.

Figure 23:
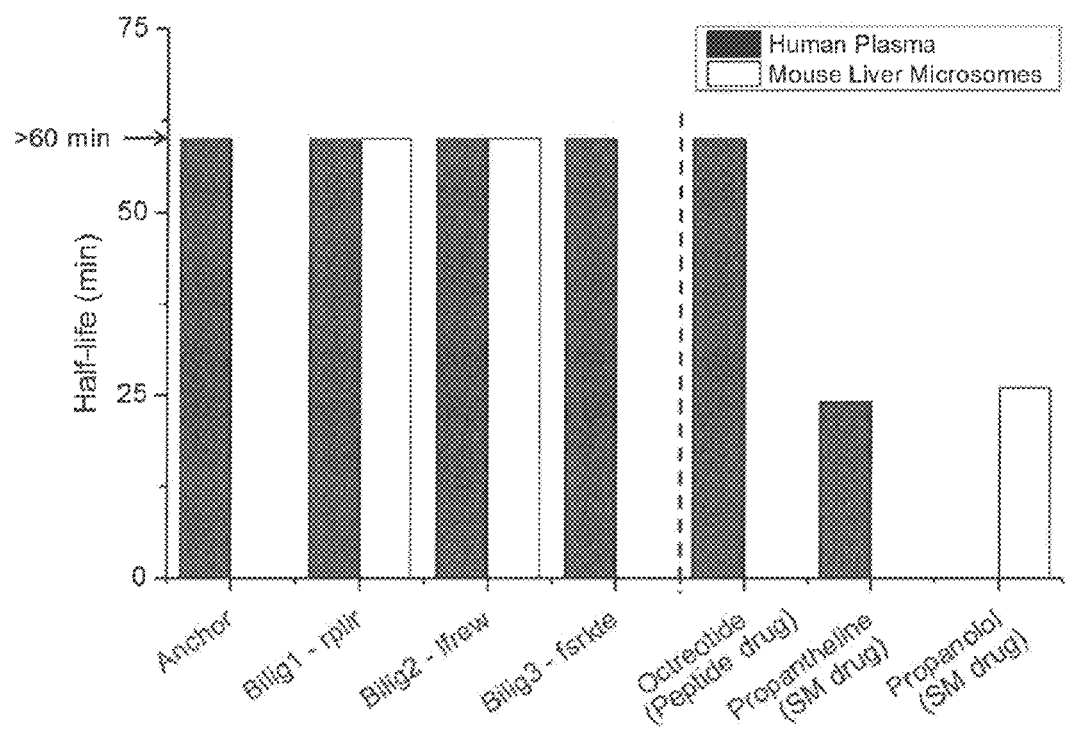
FIG. 23: Stability of Biligand 1 ("Bilig1-rplir"), Biligand 2 ("Bilig2-Ifrew"), Biligand 3 ("Bilig3-fsrkte"), the anchor ligand ("Anchor") of the biligands, and the reference compounds octreotide, propantheline, and propanolol in human plasma and mouse liver microsomes as measured by HPLC and MS/MS.

All capture agents tested were found to be stable in human plasma and mouse liver microsomes at 37° C. over the assay period of 60 minutes (FIG. 23). Capture agent stability is similar to that of peptides (e.g., octreotide) and surpasses that of some small molecules (e.g., propantheline, propanolol). This is an indication that capture agents may be administered in vivo without anticipation of degradation.

Example 12

Tetrameric Variant of Triligand Capture Agent

A tetrameric variant of Triligand 2 was prepared via non-covalent assembly on a streptavidin scaffold. Streptavidin is a tetrameric protein produced by Streptomyces avidinii that binds to biotin with an extremely high affinity (KD~1×10$^{-15}$ M) and specificity and represents an ideal scaffold to enhance the functional potential of the triligand capture agent. A single streptavidin tetramer may bind to four different biotin molecules, or, as set forth below, to four biotinylated capture agents.

Figure 24:
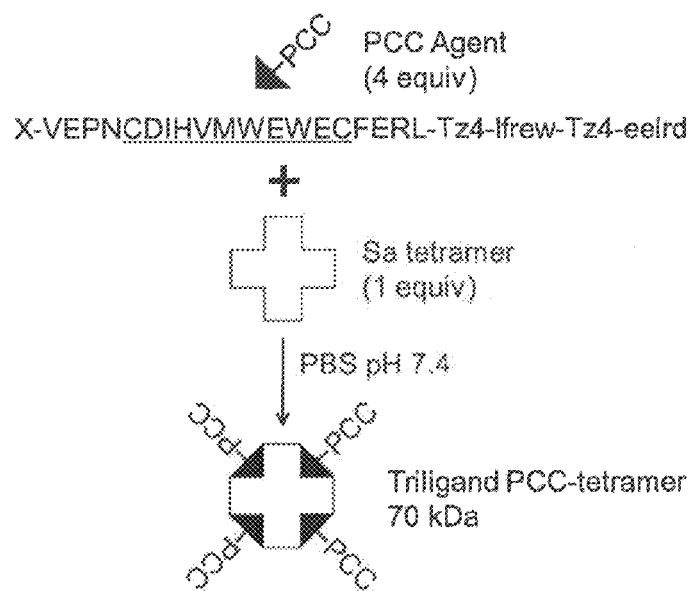
FIG. 24: Method for preparing tetrameric form of Triligand 2 (SEQ ID NO: 71).

To prepare the triligand tetramer, 4.1 µL of 4.19 mM Triligand 2 stock solution (4.5 equiv) in DMSO and 200 µL of 19 µM streptavidin tetramer (1 equiv; Promega, #Z7041) in phosphate-buffered saline (PBS; pH 7.4) were incubated on a rotator at 4° C. for 60 minutes (FIG. 24). To remove conjugates containing unoccupied biotin binding sites (i.e., conjugates with less than four triligands per Sa tetramer), Pierce Biotin Agarose (#20218) was subsequently added and this mixture was incubated at 4° C. for 60 minutes on the rotator. This treatment was followed by addition of 2 mL of Dynabeads® M-280 Streptavidin (10 mg/mL slurry, 650-900 pmol/mg biotin binding capacity; Invitrogen, #112-06D) and incubation for 30 minutes on the rotator at 4° C. to remove all excess biotinylated molecules. Finally, the Sa-Dynabeads were pelleted by applying a magnetic field (DynaMag™-Spin; Invitrogen, #123-20D) to obtain the purified triligand tetramer.

Figure 25:
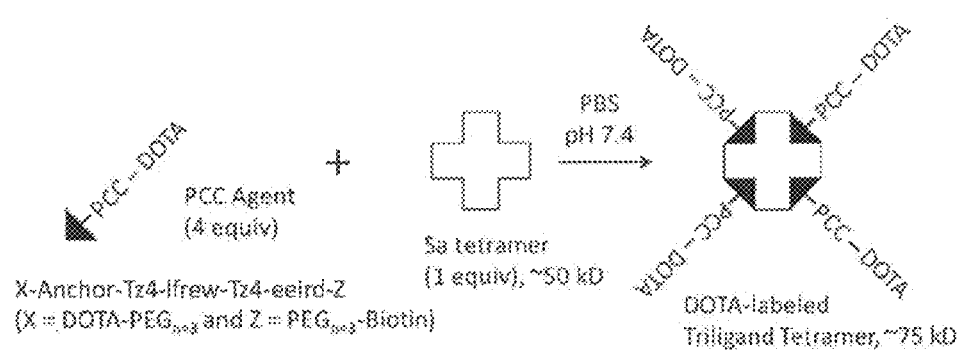
FIG. 25: Method for preparing DOTA-labeled tetrameric form of Triligand 2 by assembling bifunctional (DOTA- and biotin-conjugated) Triligand 2 on streptavidin scaffold.
Figure 27:
FIG. 27: Method for preparing DOTA-labeled tetrameric form of Triligand 2 by assembling using chemical modification of an engineered streptavidin scaffold.
Figure 50:
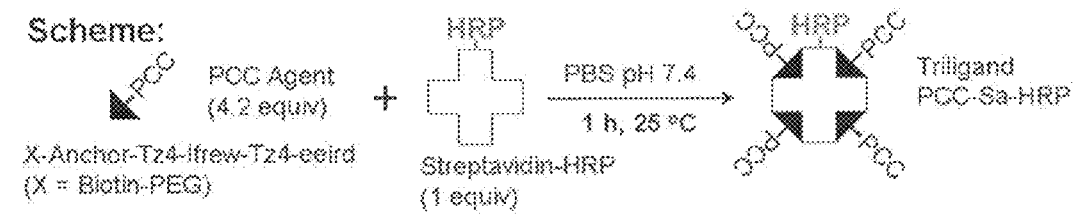
FIG. 50: Method for preparing horseradish peroxidase (HRP)-labeled tetrameric form of Triligand 2 by assembling biotinylated Triligand 2 on HRP-conjugated streptavidin scaffold.

Variants of the triligand tetramer described above may be generated that incorporate one or more covalently linked probes or functional groups (e.g., DOTA, fluorophore, enzymatic tag, additional biotin molecules). Exemplary methods of preparing a DOTA-labeled Triligand 2 tetramer are shown in FIGS. 25 and 27. An exemplary method of preparing an HRP-labeled Triligand 2 tetramer is shown in FIG. 50. These methods are generally applicable to any biotin-conjugated capture agent combined with any functional group of interest.

Figure 26:
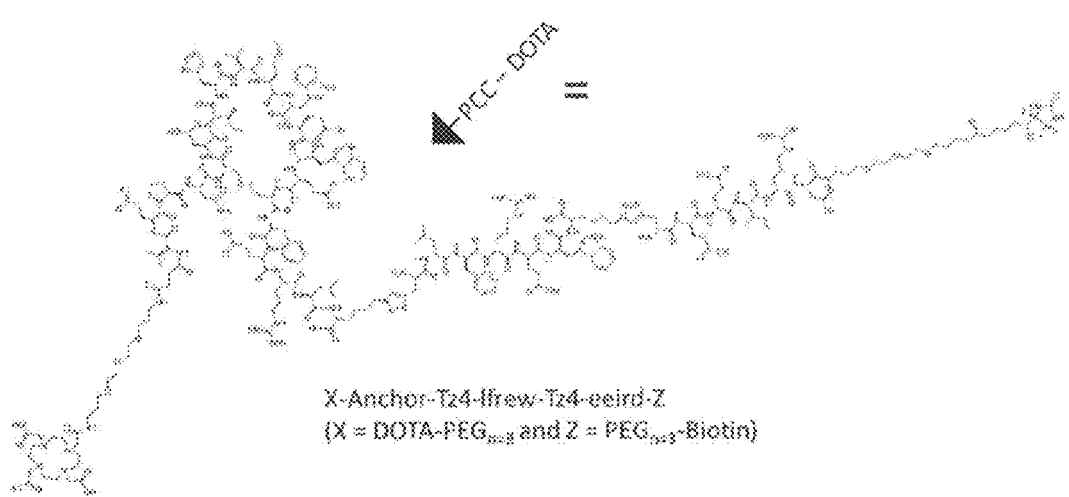
FIG. 26: Structure of bifunctional (DOTA- and biotin-conjugated) Triligand 2 (SEQ ID NO: 74).

The method set forth in FIG. 25 takes advantage of a bifunctional Triligand 2 presenting both covalent C-terminal biotin and N-terminal DOTA labels within a single molecule (FIG. 26). The labeled Triligand 2 tetramer is prepared by non-covalent assembly on a streptavidin scaffold as described above for the non-labeled triligand.

Figure 28:
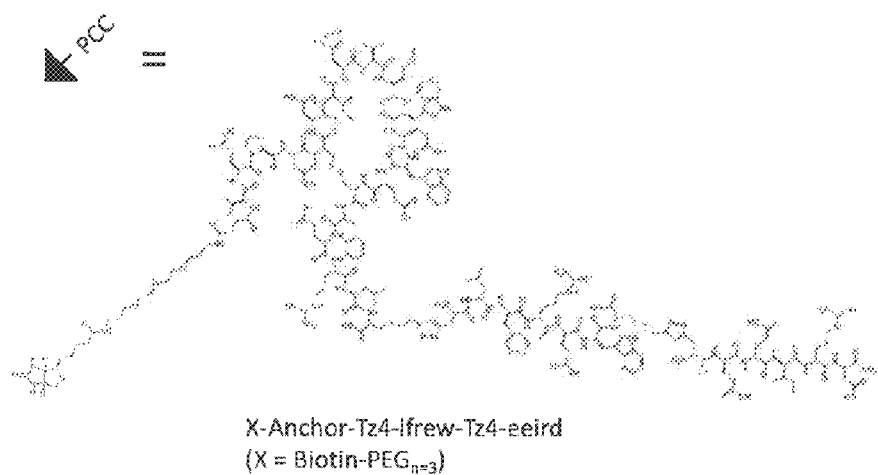
FIG. 28: Structure of biotin-conjugated Triligand 2 (SEQ ID NO: 75).
Figure 29:
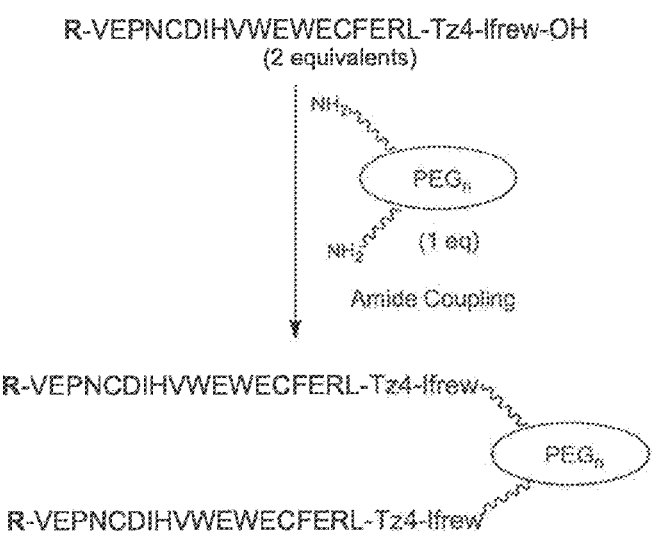
FIG. 29: Method for preparing multimeric capture agent via amide bond formation: 2 equivalents of Biligand 2 (SEQ ID NO: 68) are joined by $PEG_n$.

The method set forth in FIG. 27 utilizes an engineered variant of streptavidin expressing a C-terminal cysteine residue (Kwong 2009). This C-terminal cysteine residue may be used to install various labeling groups (e.g., DOTA, biotin, or fluorophore) on the triligand tetramer via thiol-reactive coupling (see, e.g., US Patent Publication No. 2011/0039717). In FIG. 27, the C-terminal cysteine is used to generate a DOTA-labeled streptavidin tetramer. In this example, the streptavidin tetramer is reacted with Maleimido-mono-amide-DOTA (B-272; Macrocyclics, Tex.). After dialysis to remove excess DOTA label, biotin-labeled Triligand 2 (FIG. 28) is linked to the tetramer as described above.

The method set forth in FIG. 50 results in a Triligand 2 tetramer linked to horseradish peroxidase.

Isolated triligand tetramers will be characterized by SDS-PAGE (7.5% gel). To retain the intact tetramer, samples will be prepared under non-reducing conditions and without boiling. The tetrameric triligand capture agent will be evaluated for affinity and specificity towards VEGF, and will also be evaluated for biological activity in vitro (e.g., displacement of VEGF from VEGFR and/or antagonism resulting in decreased cell growth) and in vivo (e.g., reduction of angiogenesis).

Example 13

Other Multimeric Variants of Capture Agents

Multimeric variants (e.g., dimers, trimers, and tetramers) of the biligands and triligands disclosed herein will be synthesized by various methods.

Figure 31:
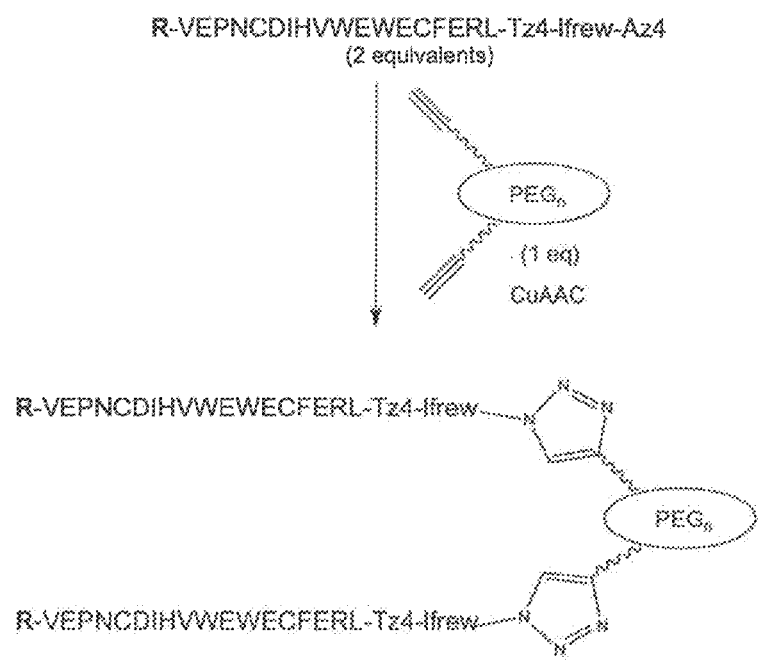
FIG. 31: Method for preparing multimeric capture agent via CuAAC:2 equivalents of Biligand 2 (SEQ ID NO: 68) are joined by $PEG_n$.

Homomultimeric biligand capture agents may also be synthesized using the method shown in FIG. 31 for Biligand 2. A multimeric variant will be synthesized from side-chain protected X-VEPNCDIHVMWEWECFERL-Tz4-Ifrew (SEQ ID NO: 68), where X is a pegylated reporter tag (e.g., biotin-PEG, DOTA-PEG, etc.) or an N-terminal capping group (e.g., acetyl). The syntheses will begin with a commercially available pegylated linker consisting of multiple (2, 3, or 4) reactive sites and will follow an amide coupling procedure.

Homomultimeric biligand capture agents may also be synthesized using the method shown in FIG. 31 for Biligand 2. A multimeric variant will be synthesized from side-chain protected X-VEPNCDIHVMWEWECFERL-Tz4-Ifrew-Az4 (SEQ ID NO: 68), where X is a pegylated reporter tag (e.g., biotin-PEG, DOTA-PEG, etc.) or an N-terminal capping group (e.g., acetyl). The syntheses will begin with a commercially available pegylated linker consisting of multiple reactive sites. Each site is first appended with an alkyne moiety, then conjugated to a capture agent through a CuAAC.

Figure 30:
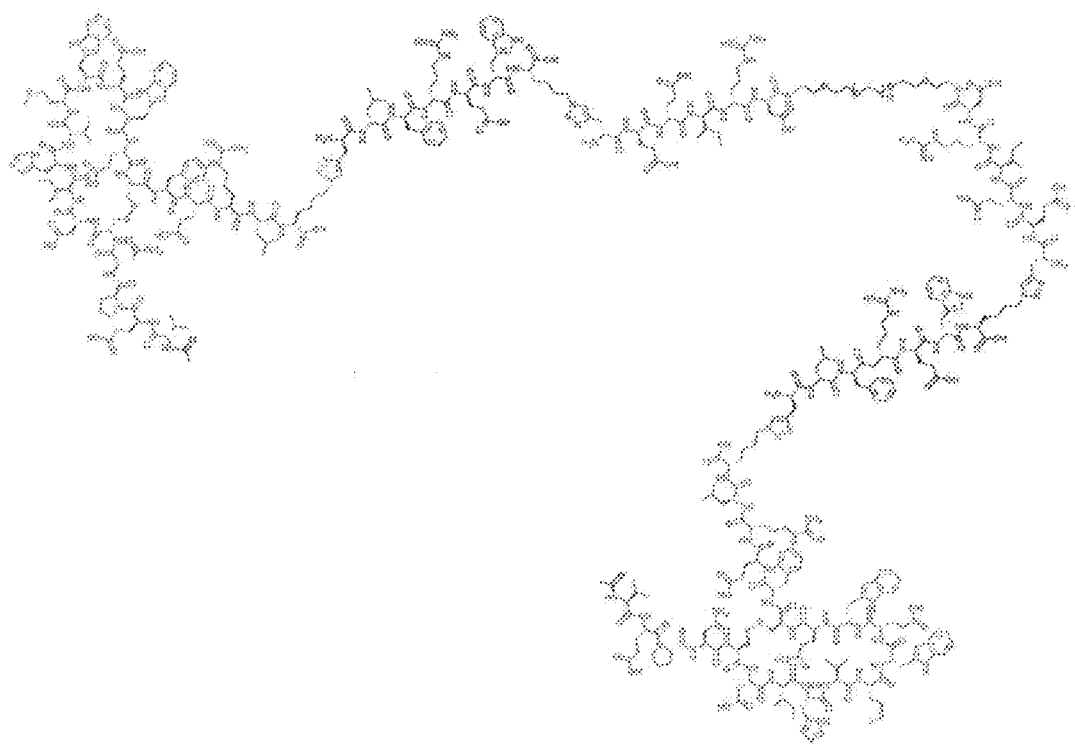
FIG. 30: Structure of Triligand 2 homodimer (SEQ ID NO: 76) prepared by amide bond formation.
Figure 32:
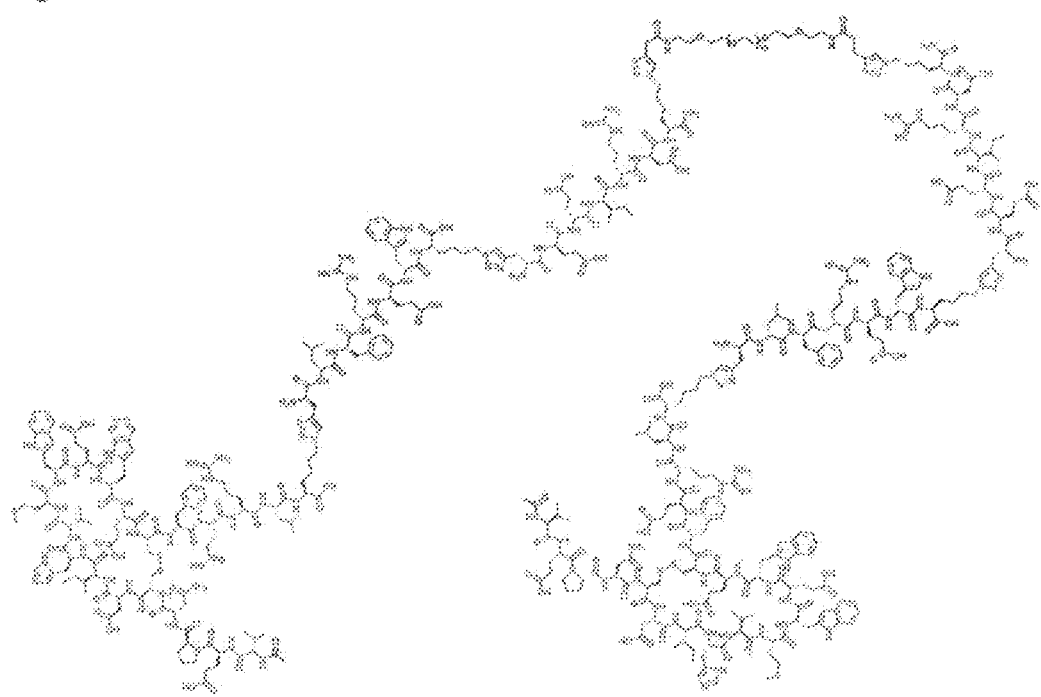
FIG. 32: Structure of Triligand 2 homodimer (SEQ ID NO: 77) prepared by CuAAC.

Homomultimeric triligand capture agents will also be generated. For example, multimeric variants of Triligand 2 may be synthesized from X-VEPNCDIHVMWEWECFERL-Tz4-Ifrew-Tz4-eeird (SEQ ID NO: 71), where X is a pegylated reporter tag (e.g., biotin-PEG, DOTA-PEG, etc.) or an N-terminal capping group (e.g., acetyl). The structure of an exemplary Triligand 2 homodimer generated by this method is set forth in FIG. 30. Similarly, multimeric variants of Triligand 2 may be synthesized from X- VEPNCDIHVMWEWECFERL-Tz4-Ifrew-Tz4-eeird-Az4 (SEQ ID NO: 71), where X is a pegylated reporter tag (i.e., biotin-PEG, DOTA-PEG, etc.) or an N-terminal capping group (i.e., acetyl), will be synthesized and subsequently evaluated as above. The structure of an exemplary Triligand 2 homodimer generated by this method is set forth in FIG. 32.

Figure 33:
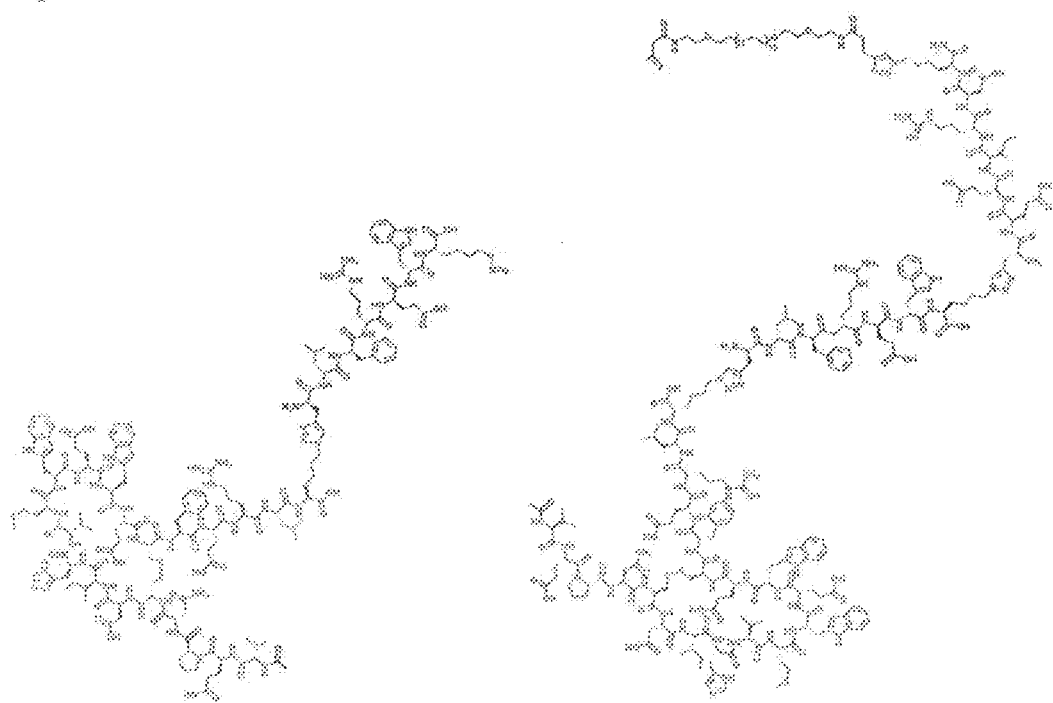
FIG. 33: Structure of Triligand 2 Triligand 3 heterodimer (SEQ ID NO: 78) joined via CuAAC.

Heteromultimeric variants of the biligand and triligand capture agents may also be synthesized by various methods. For example, a heterodimer of Triligands 2 and 3 as set forth in FIG. 33 may be prepared via covalent conjugation as described above. A synthetically produced heterodimer (where each peptide of the dimer is different in sequence and each interacts with a discrete, non-overlapping epitope on a single protein) may maximize the improvement in binding affinity and/or receptor blocking with the appropriate length linker joining the two peptides.

Multimeric biligands and triligands will be evaluated for improved affinity and specificity towards VEGF. Multimeric capture agents will also be evaluated for improvements in biological activity both in vitro (e.g., displacement of VEGF from VEGF receptor and/or antagonism resulting in decreased cell growth) and in vivo (e.g., reduction of angiogenesis). Multimeric capture agents may be comparatively evaluated with various non-covalent mixtures of capture agents and/or other peptides.

Example 14

Synthesis of PEGylated Triligand 2

Figure 34:
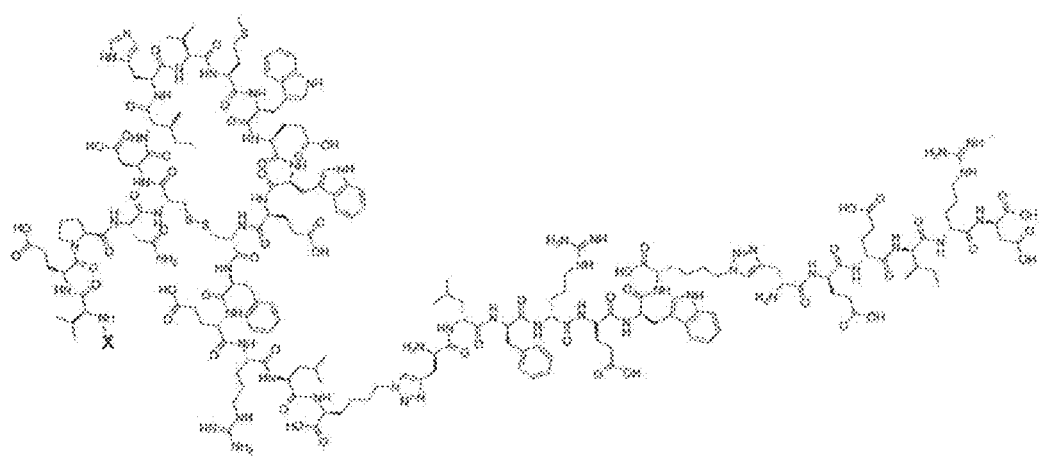
FIG. 34: Structure of X-Triligand 2 (SEQ ID NO: 79), where X is Ac, biotin-PEG, DOTA-PEG, etc.

PEGylated variants of X-Triligand 2 (FIG. 34), where X is a biotin-PEG3 linker or N-terminal capping group (e.g., acetyl) were prepared. Using an amide coupling procedure, Triligand 2 was covalently conjugated to a commercially available PEGylation module that is linear or branched.

Preparation of side-chain protected N-acetyl triligand on CTC resin. X-Triligand 2 was prepared using microwave-assisted Fmoc-based solid phase peptide synthesis (SPPS) on 2-chlorotrityl chloride (CTC) resin. The first amino acid was attached to the resin following the vendor's protocol. The resin was transferred to a CEM Liberty 1 microwave peptide synthesizer for the preparation of the remaining triligand. Each amino acid coupling reaction incorporated 4 equiv of Fmoc-amino acid, 4 equiv of HBTU (O-Benzotriazole-N,N,N',N'-tetramethyl-uronium-hexafluoro-phosphate), and 10 equiv of N,N-Diisopropylethylamine (DIEA). Deprotection of the Fmoc group required 20% piperidine/NMP, followed by wash with NMP. Coupling conditions of the two Tz4 linkers were modified to include 4 equiv of Fmoc-amino acid, 4 equiv of HATU (O-(7-azabenzotriazol-1-yl)-N,N,N',N'-tetramethyluronium hexafluorophosphate) and 10 equiv of DIEA. Deprotection of the Fmoc group required 20% piperidine/NMP, followed by wash with NMP.

Option (A): For final N-terminal capping (0.125 mmol scale), the resin was subjected to a solution of DIEA (1.1 mL), NMP (1.0 mL), and acetic anhydride (0.6 mL). After shaking at room temperature for 30 minutes, the resin was filtered and washed with NMP (3×), DCM (3×) and MeOH (3×). The resin was dried under vacuum for ~10 min.

Option (B): For the preparation of N-terminal biotinylated triligand, the PEG3 linker and biotin group were coupled to the resin containing triligand using a CEM Liberty 1 microwave peptide synthesizer. Coupling conditions were 4 equiv of Fmoc containing PEG3 linker, 4 equiv of HBTU and 10 equiv of DIEA. Deprotection of the Fmoc group required 20% piperidine/NMP, followed by wash with NMP. Coupling conditions for biotin were 4 equiv of biotin dissolved in DMSO/NMP (1:1), 4 equiv of HBTU and 10 equiv of DIEA. The resin was filtered and washed with NMP (3×), DCM (3×) and MeOH (3×), dried under vacuum for ~10 minutes.

Cleavage of Side-Chain Protected Triligand from CTC resin (0.25 mmol scale). To the dried side-chain protected triligand resin was added 3-4 mL of DCM/TFE (8:2) solution. After stirring at room temperature for 1 hour, the resin was filtered through cotton or glass wool into a centrifuge tube containing ~30 mL cold ether. A white precipitate formed. The resin was washed with 8:2 DCM/TFE until no more precipitate formed (~3-4 mL). Additional ether was added to a total volume of 50 mL, then the crude product was centrifuged (4500 rpm, 5 min, 4° C.). Following centrifugation, the supernatant was removed and the crude solid was dried by lyophilization.

Preparation of Ac-Triligand with C-terminal Linear PEG40 PEGylation. Side-chain protected Ac-triligand (125 mg, 17.2 µmol) was added to a vial, purged with Ar, and dissolved in anhydrous DMF (0.5 mL). A solution of 0.5 M HATU/HOAt (34 µL, 17 µmol) and DIEA (2.9 µL, 16.6 µmol) were then added and stirred for 15 min at room temperature. During this time, PEG40 amine (100 mg, 2.5 µmol: Jenkem #M-NH2-40K) was separately dissolved in anhydrous DCM (0.5 mL). The reaction mixture containing Ac-triligand was added to PEG40 amine solution at room temperature and then stirred overnight (12-16 hours). This reaction mixture was added dropwise to a centrifuge tube with 30 mL cold ether, resulting in the formation of a white precipitate. After filling the tube to ~45 mL with cold ether, the sample was centrifuged 3× (4500 rpm, 5 min, 4° C.). Following centrifugation, the supernatant was removed and the crude solid was dried by lyophilization.

Preparation of Ac-Triligand with C-terminal Branched PEG40 PEGylation. Side-chain protected Ac-triligand (125 mg, 17.2 µmol) was added to a vial, purged with Ar, and dissolved in anhydrous DMF (0.5 mL). A solution of 0.5 M HATU/HOAt (34 µL, 17 µmol) and DIEA (2.9 µL, 16.6 µmol) were then added and stirred for 15 min at rt. During this time, Y-shape PEG40 amine (100 mg, 2.5 µmol: Jenkem #Y-NH2-40K) was separately dissolved in anhydrous DCM (0.5 mL). The reaction mixture containing Ac-triligand was added to Y-shape PEG40 amine solution at room temperature and then stirred overnight (12-16 h). This reaction mixture was added dropwise to a centrifuge tube with 30 mL cold ether, resulting in the formation of a white precipitate. After filling the tube to ~45 mL with cold ether, the sample was centrifuged 3× (4500 rpm, 5 min, 4° C.). Following centrifugation, the supernatant was removed and the crude solid was dried by lyophilization.

Biotinylated PEGylated triligands were prepared by similar methods, but with a starting material of side-chain protected triligand presenting an N-terminal biotin linker.

Deprotection and Disulfide Cyclization. Each of the crude PEGylated triligands (from above) was dissolved in 2.5-3.5 mL of TFA/H$_2$O/triisopropylsilane[TIS]/2,2'-(ethylenedioxy)-diethanediol[DODT] (92.5/2.5/2.5/2.5) and then stirred at room temperature for 4 hours. Cold ether (~45 mL) was then added to each tube. Tubes were shaken vigorously and then centrifuged (4500 rpm, 5 minutes, 4° C.). After removing the supernatant, the crude solid was resuspended in another 45 mL of cold ether and centrifuged twice more. The final supernatant was removed and the crude solid was dried by lyophilization.

For disulfide cyclization, the crude solid was dissolved in 250 µL of DMSO. After the solid was mostly dissolved, H$_2$O (2.5 mL) was added and the pH was adjusted dropwise with ammonium carbonate (5%) solution until pH 6-7 was reached. This mixture was stirred at room temperature for ≥4 hours. This solution was further diluted with methanol and then purified directly by HPLC.

Figure 35:
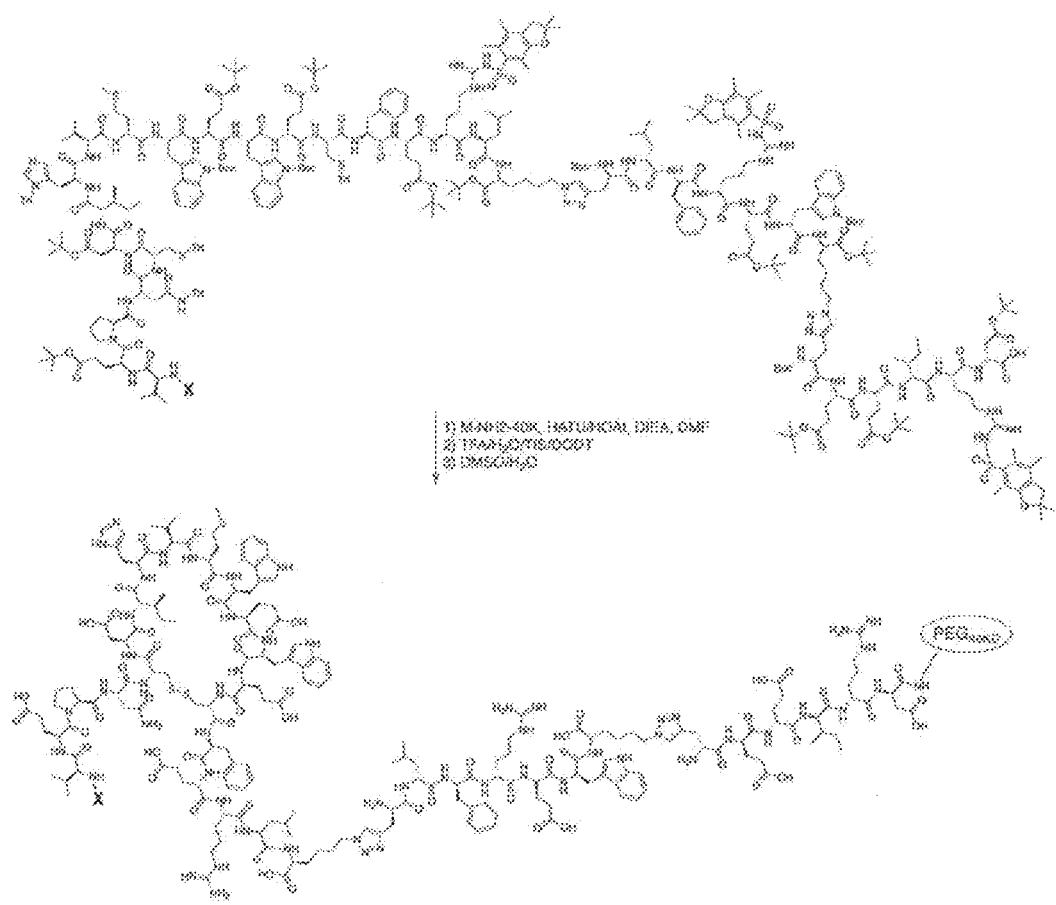
FIG. 35: Synthesis of PEGylated Triligand 2 (SEQ ID NO: 80). Non-restrained Triligand 2 of SEQ ID NO: 86 is coupled to linear PEG40 followed by disulfide cyclization.
Figure 36:
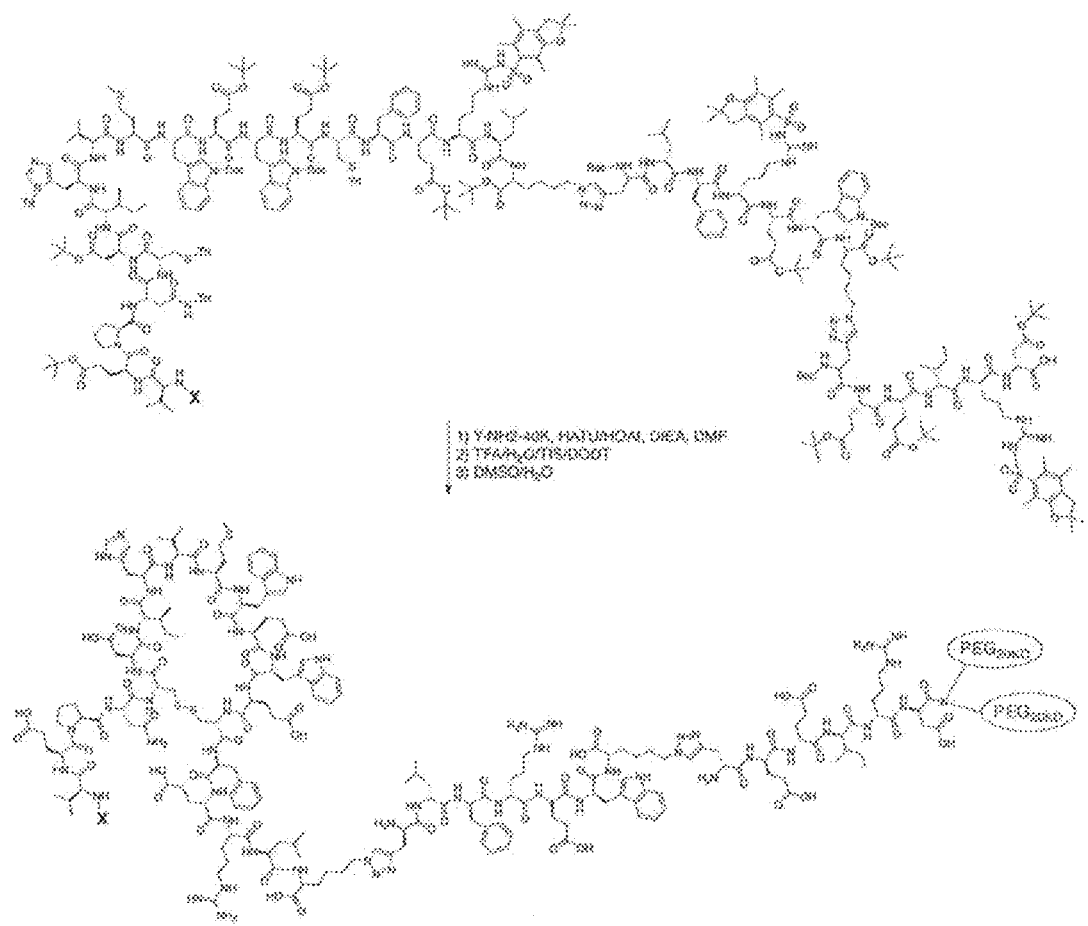
FIG. 36: Synthesis of PEGylated Triligand 2 (SEQ ID NO: 80). Non-restrained Triligand 2 (SEQ ID NO: 86) is coupled to branched PEG40 followed by disulfide cyclization.

The PEGylation synthesis reactions are summarized in FIGS. 35 and 36. PEGylated triligands will be evaluated for affinity and specificity for VEGF, as well as for biological activity in vitro and in vivo.

Example 15

Triligand Multimerization on Multi-Arm PEGylation Scaffolds

Dimeric and tetrameric variants of X-Triligand 2 (FIG. 34), where X is a biotin-PEG3 linker or N-terminal capping group (e.g., acetyl) were prepared. Using an amide coupling procedure, Triligand 2 was covalently conjugated to a commercially available multi-arm PEGylation linker consisting of multiple (two or four) reactive sites.

Preparation of Side-Chain Protected Triligand on CTC resin. X-Triligand 2 was prepared using microwave-assisted Fmoc-based solid phase peptide synthesis (SPPS) on 2-chlorotrityl chloride (CTC) resin. The first amino acid was attached to the resin following the vendor's protocol. The resin was transferred to a CEM Liberty 1 microwave peptide synthesizer for the preparation of the remaining triligand. Each amino acid coupling reaction incorporated 4 equiv of Fmoc-amino acid, 4 equiv of HBTU (O-Benzotriazole-N,N,N',N'-tetramethyl-uronium-hexafluoro-phosphate), and 10 equiv of N,N-Diisopropylethylamine (DIEA). Deprotection of the Fmoc group required 20% piperidine/NMP, followed by wash with NMP. Coupling conditions of the two Tz4 linkers were modified to include 4 equiv of Fmoc-amino acid, 4 equiv of HATU (O-(7-azabenzotriazol-1-yl)-N,N,N',N'-tetramethyluronium hexafluorophosphate) and 10 equiv of DIEA. Deprotection of the Fmoc group required 20% piperidine/NMP, followed by wash with NMP.

Option (A): For final N-terminal capping (0.125 mmol scale), the resin was subjected to a solution of DIEA (1.1 mL), NMP (1.0 mL), and acetic anhydride (0.6 mL). After shaking at room temperature for 30 minutes, the resin was filtered and washed with NMP (3×), DCM (3×) and MeOH (3×). The resin was dried under vacuum for ~10 minutes.

Option (B): For the preparation of N-terminal biotinylated triligand, the PEG3 linker and biotin group were coupled to the resin containing triligand using a CEM Liberty 1 microwave peptide synthesizer. Coupling conditions were 4 equiv of Fmoc containing PEG3 linker, 4 equiv of HBTU and 10 equiv of DIEA. Deprotection of the Fmoc group required 20% piperidine/NMP, followed by wash with NMP. Coupling conditions for biotin were 4 equiv of biotin dissolved in DMSO/NMP (1:1), 4 equiv of HBTU and 10 equiv of DIEA. The resin was filtered and washed with NMP (3×), DCM (3×) and MeOH (3×), dried under vacuum for ~10 minutes.

Cleavage of Side-Chain Protected Triligand from CTC resin (0.25 mmol scale). To the dried side-chain protected triligand resin was added 3-4 mL of DCM/TFE (8:2) solution. After stirring at room temperature for 1 hour, the resin was filtered through cotton or glass wool into a centrifuge tube containing ~30 mL cold ether. A white precipitate formed. The resin was washed with 8:2 DCM/TFE until no more precipitate formed (~3-4 mL). Additional ether was added to a total volume of 50 mL, then the crude product was centrifuged (4500 rpm, 5 minutes, 4° C.). Following centrifugation, the supernatant was removed and the crude solid was dried by lyophilization.

Preparation of Ac-Tetramer. Side-chain protected Ac-triligand (760 mg, 0.105 mmol) was added to a vial, purged with Ar, and dissolved in anhydrous DMF (2.0 mL). HATU (38 mg, 0.100 mmol), HOAt (13.6 mg, 0.100 µmol), and DIEA (17 µL, 97.6 µmol) were then added and stirred for 15 min at rt. During this time, 4ARM PEG40 amine (200 mg, 5.0 µmol; Jenkem #4ARM-NH2-40K) was separately dissolved in anhydrous DCM (1.5 mL). The reaction mixture containing Ac-triligand was added to 4ARM PEG40 amine solution at rt, and then stirred overnight (12-16 hours). This reaction mixture was added dropwise to two centrifuge tubes with 30 mL cold ether, resulting in the formation of a white precipitate. After filling each tube to ~45 mL with cold ether, samples were centrifuged 3× (4500 rpm, 5 min, 4° C.). Following centrifugation, the supernatant was removed and the crude solid was dried by lyophilization.

Preparation of Ac-Dimer. Side-chain protected Ac-triligand (208 mg, 28.7 µmol) was added to a vial, purged with Ar, and dissolved in anhydrous DMF (2.0 mL). HATU (18.7 mg, 49.2 µmol), HOAt (7.15 mg, 52.5 µmol), and DIEA (8.5 µL, 48.8 µmol) were then added and stirred for 15 min at rt. During this time, 2ARM PEG7.5 amine (37.5 mg, 5.0 µmol; Jenkem #NH2-PEG7500-NH2) was separately dissolved in anhydrous DCM (1.5 mL). The reaction mixture containing Ac-triligand was added to 2ARM PEG7.5 amine solution at rt, and then stirred overnight (12-16 hours). This reaction mixture was added dropwise to two centrifuge tubes with 30 mL cold ether, resulting in the formation of a white precipitate. After filling each tube to ~45 mL with cold ether, samples were centrifuged 3× (4500 rpm, 5 minutes, 4° C.). Following centrifugation, the supernatant was removed and the crude solid was dried by lyophilization.

Biotinylated triligand dimers and tetramers were prepared by similar methods, but with a starting material of side-chain protected triligand presenting an N-terminal biotin linker.

Deprotection and Disulfide Cyclization. The crude PEGylated PCC dimer or tetramer (from above) was dissolved in 2.5-3.5 mL of TFA/$H_2$O/triisopropylsilane[TIS]/2,2'-(ethylenedioxy)-diethanediol[DODT] (92.5/2.5/2.5/2.5) and then stirred at room temperature for 4 hours. Cold ether (~45 mL) was then added to each tube. Tubes were shaken vigorously and then centrifuged (4500 rpm, 5 minutes, 4° C.). After removing the supernatant, the crude solid was resuspended in another 45 mL of cold ether and centrifuged twice more. The final supernatant was removed and the crude solid was dried by lyophilization.

For disulfide cyclization, the crude solid was dissolved in 250 μL of DMSO. After the solid was mostly dissolved, $H_2O$ (2.5 mL) was added and the pH was adjusted dropwise with ammonium carbonate (5%) solution until pH 6-7 was reached. This mixture was stirred at room temperature for ≥4 hours. This solution was further diluted with methanol (2.5 mL or more if needed) and then purified directly by HPLC.

Figure 37:
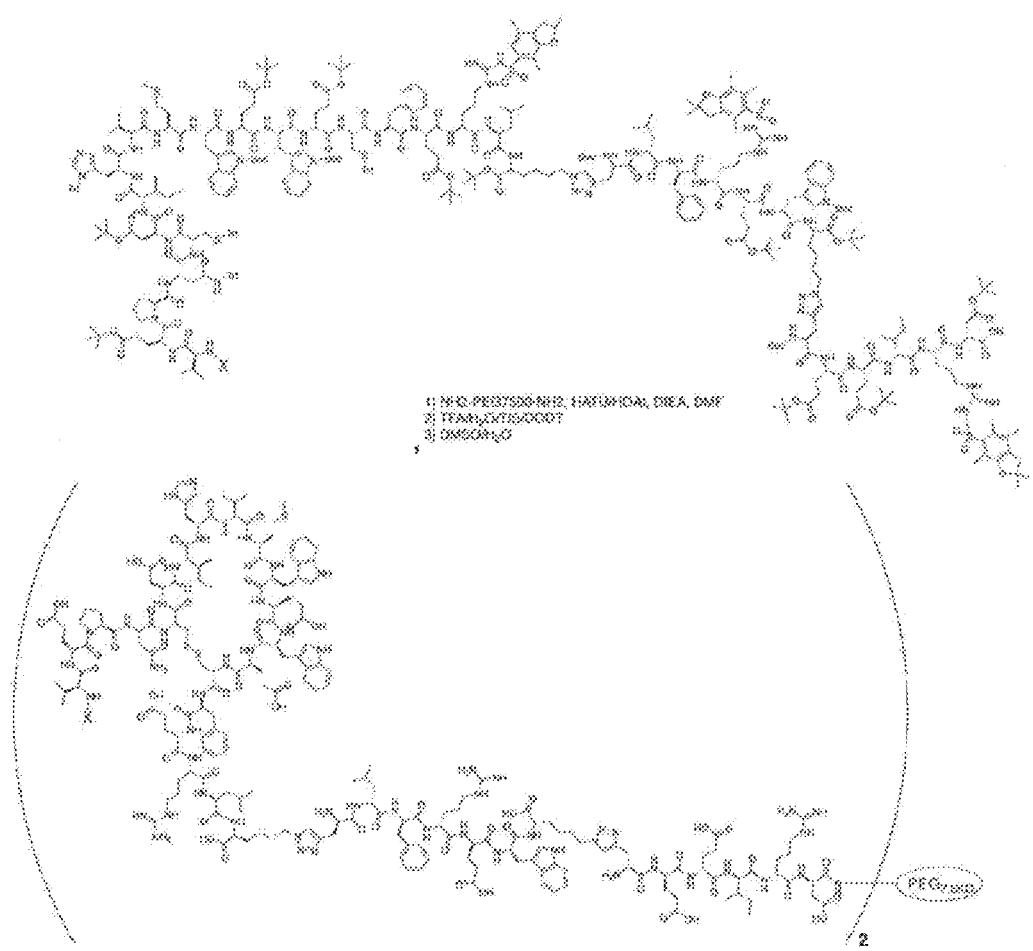
FIG. 37: Synthesis of multimeric Triligand 2 (SEQ ID NO: 82). 2 equivalents of non-restrained Triligand 2 (SEQ ID NO: 86) are joined by 2ARM PEG7.5 followed by disulfide cyclization.
Figure 38:
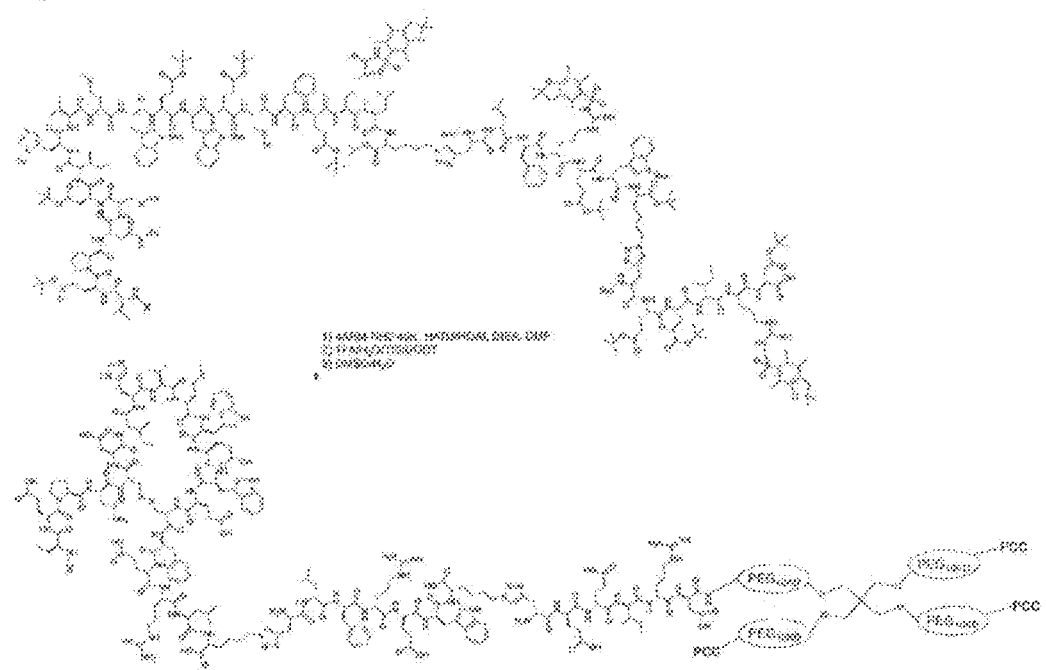
FIG. 38: Synthesis of multimeric Triligand 2 (homotetramer) (SEQ ID NO: 83). 4 equivalents of non-restrained Triligand 2 (SEQ ID NO: 86) are joined by 4ARM PEG40 followed by disulfide cyclization.

The multimerization synthesis reactions are summarized in FIGS. 37 and 38. PEGylated triligands will be evaluated for affinity and specificity for VEGF, as well as for biological activity in vitro and in vivo.

Example 16

Evaluation of Triligand Multimerization and Modifications

The C-terminus of a VEGF capture agent provides a potential site for medicinal chemistry optimization. A carboxylic acid terminus (—COOH) would be negatively charged at physiological pH, while a carboxamide terminus (—CONH$_2$) would be charge-neutral. Depending on the nature of the protein epitope targeted by the capture agent, one C-terminus may have improved properties over the other.

Figure 39:
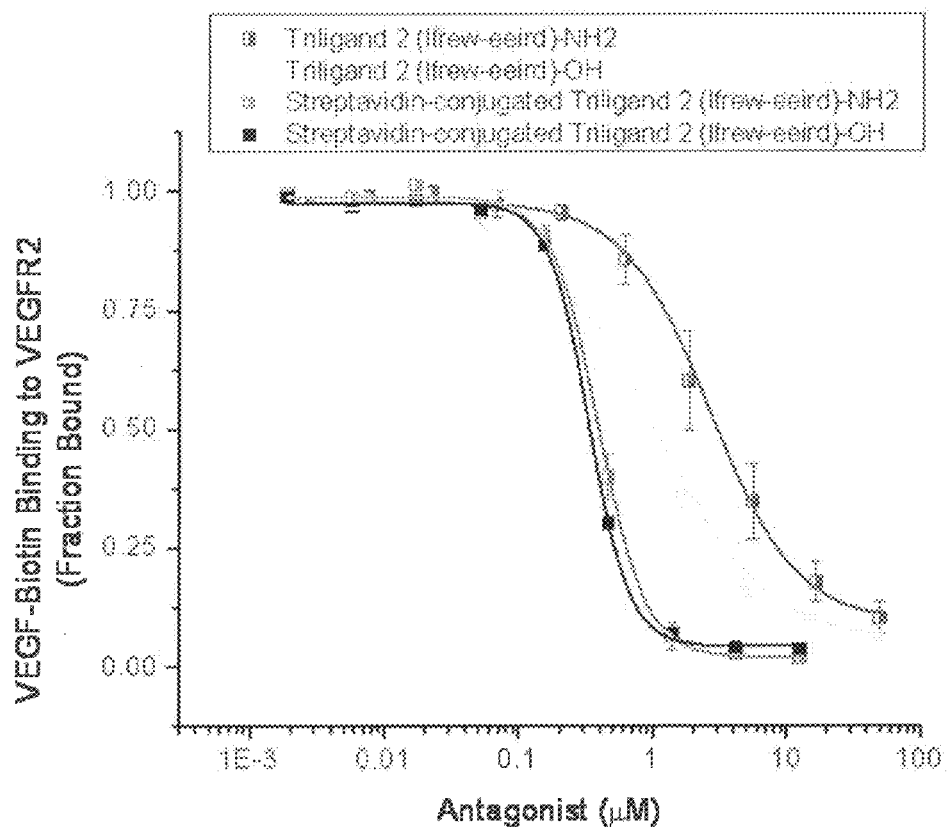
FIG. 39: Inhibition of VEGF165 binding to VEGFR2 by modified C-terminus Triligand 2 as measured by competitive ELISA.
Figure 40:
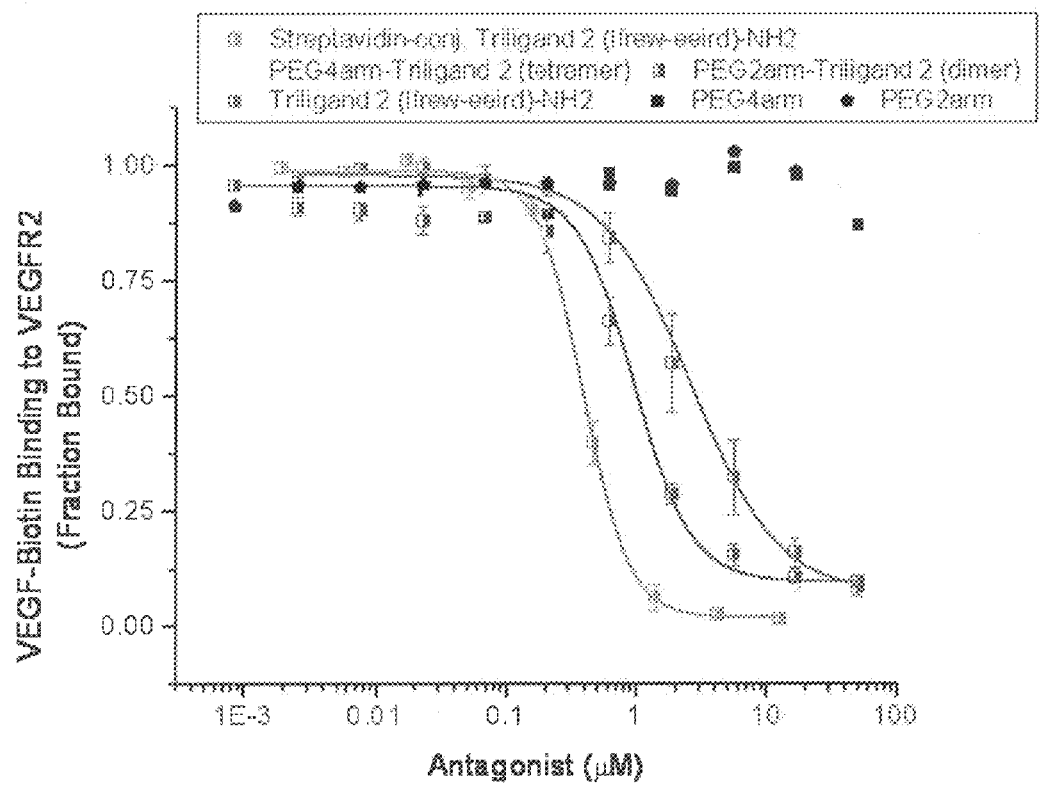
FIG. 40: Inhibition of VEGF165 binding to VEGFR2 by multimeric Triligand 2 as measured by competitive ELISA.

An in vitro competitive binding assay was performed as set forth in Example 8 using immobilized rhVEGFR2. Triligand 2-COOH displayed ~4× improvement in blocking over the original Triligand 2 with a carboxamide terminus, with blocking approaching that of multimeric streptavidin-conjugated Triligand 2 (FIG. 39). Multimeric streptavidin conjugates of Triligand 2-COOH and Triligand 2-CONH$_2$ were found to block similarly (FIG. 39). These results suggest that transforming the C-terminal carboxamide to a C-terminal carboxylic acid in the anti-VEGF triligand is important for in vitro blocking, but that optimization is important for the monomer only. In another competitive binding experiment, PEG2arm-Triligand 2 (dimer) displayed enhanced binding versus monomeric Triligand 2, while blocking by PEG4arm-Triligand 2 (tetramer) suggested an additional improvement and approaches the blocking of multimeric streptavidin-conjugated Triligand 2 (FIG. 40). Overall, these results suggest that multimerization may be a dominating influence on blocking, and may arise from both affinity and size contributions.

Figure 41:
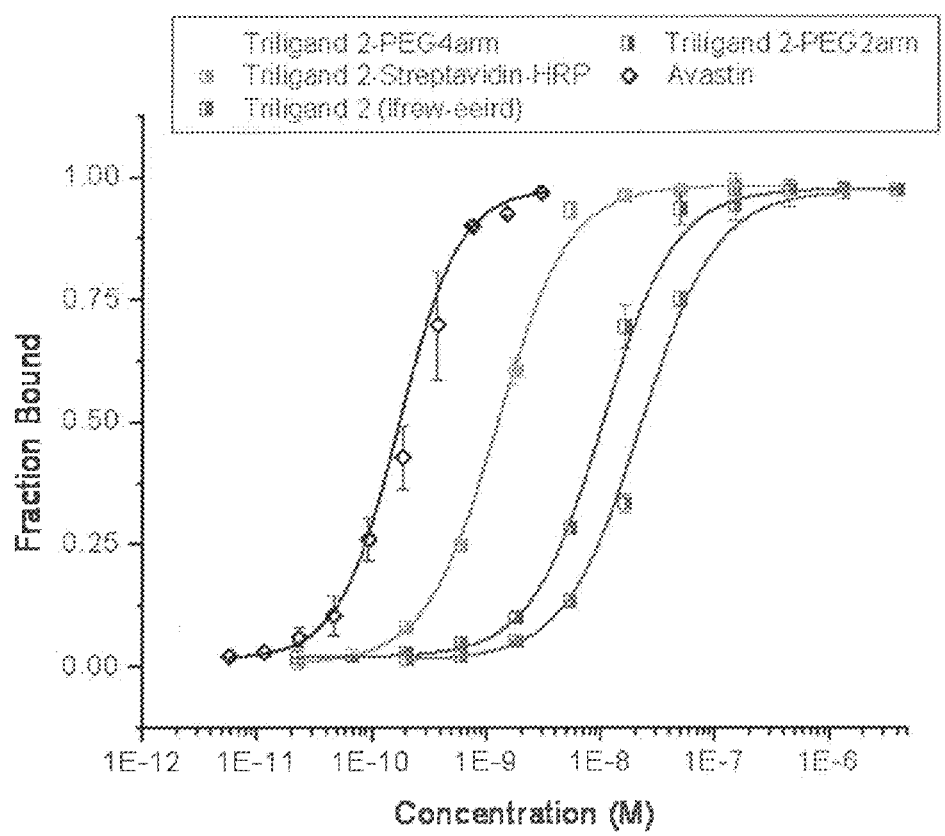
FIG. 41: Binding affinity of multimeric Triligand 2.

A binding affinity ELISA assay was performed as set forth in Example 3. Multimeric streptavidin-conjugated Triligand 2 and PEG4arm-Triligand 2 (tetramer) were found to share similar binding affinity for rhVEGF165 (FIG. 41). Further, the affinity of PEG2arm-Triligand 2 (dimer) (KD=~7.5 nM) was lower than that of the tetramer (KD=~1 nM) but higher than that of the monomer (KD=~15 nM) (FIG. 41). These results suggest that multimerization and size appear to be critical factors for binding affinity.

Figure 42:
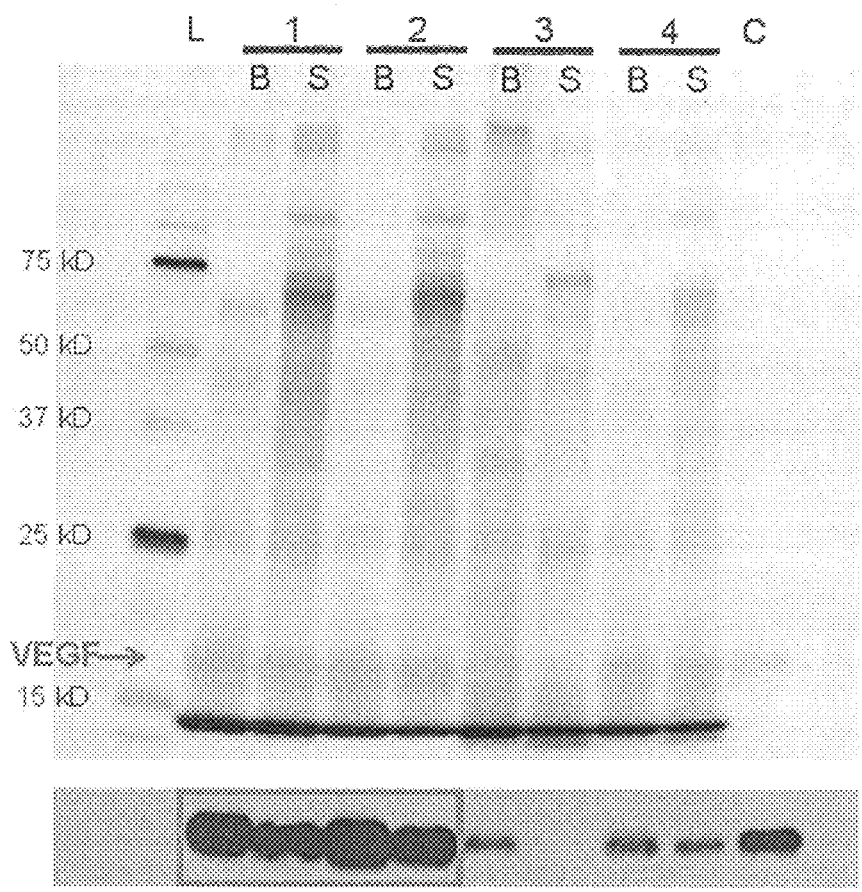
FIG. 42: Comparison of triligand modifications by VEGF pull-down assay. L: MW ladder; 1 B/S: Triligand 2-$NH_2$; 2B/S: Triligand 2-OH; 3B/S: Triligand 2-PEG4OKD; 4B/S: Triligand 2-branched PEG4OKD; C: VEGF control (50 ng).
Figure 43:
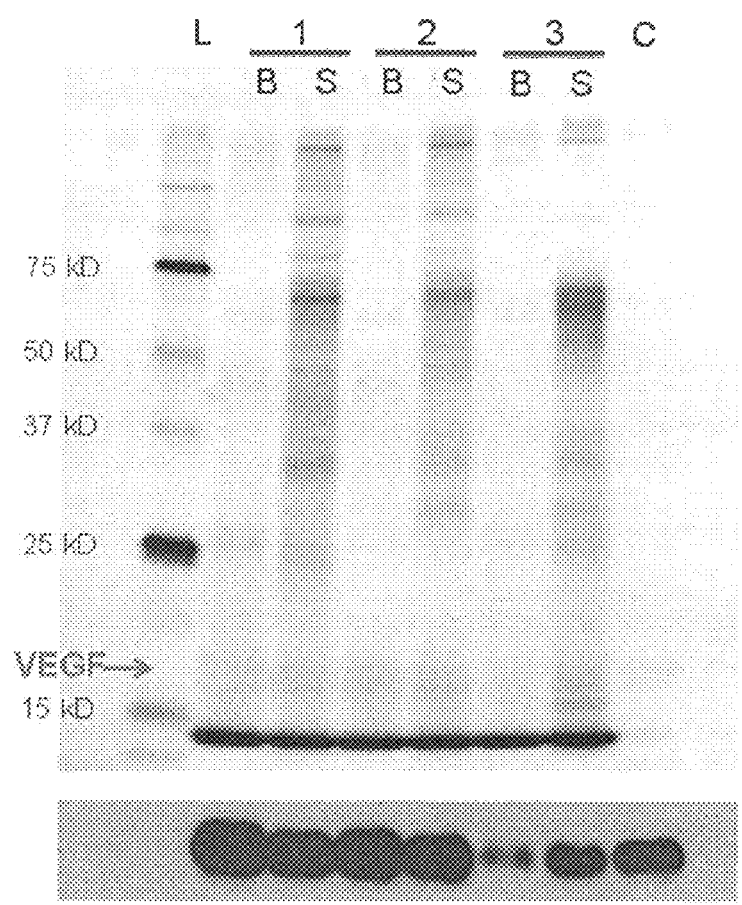
FIG. 43: Comparison of triligand modifications by VEGF pull-down assay. L: MW ladder; 1 B/S: Triligand 2-$NH_2$; 2B/S: PEG2arm-Triligand 2 (dimer); 3B/S: PEG4arm-Triligand 2 (tetramer); C: VEGF control (50 ng).
Figure 45E:
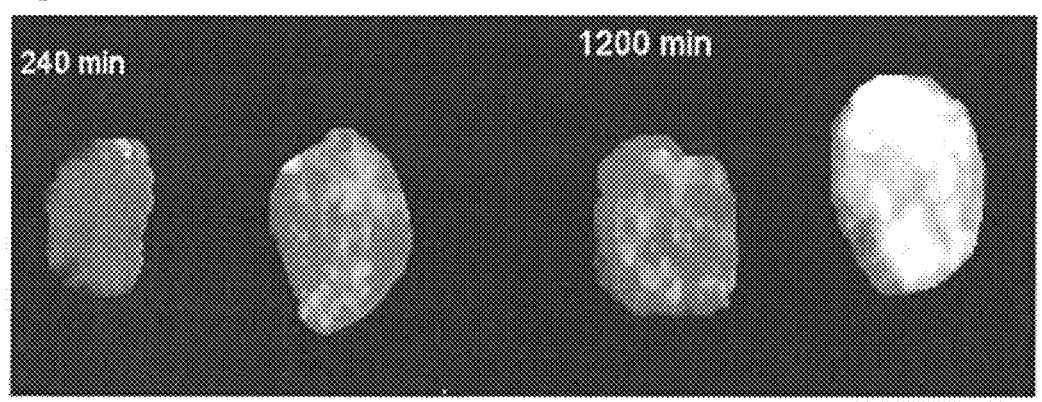
FIG. 45: Biodistribution study results for mouse 1010. A. Maximum intensity projections (MIPs). Gaussian filter (0.200 mm FWHM) applied to the images, scaled to fixed percentile of image. B. Cropped MIPs. Gaussian filter (0.100 mm FWHM) applied to the images, scaled to fixed percentile of image. C. Cropped coronal slices. Gaussian filter (0.100 mm FWHM) applied to the images. D. Tumors extracted using 3D ROI Tool in vivoQuant™. Left tumor is in red, right tumor is in green. E. MIP of extracted tumors. At 240 minutes, the color scale min (black) was 0 and the color scale max (white) was $3.9 \times 10\text{-}5$ μCi. At 1200 minutes, the color scale min (black) was 0 and the color scale max (white) was $1.63 \times 10\text{-}5$ μCi (corrected for isotope decay).
Figure 46E:
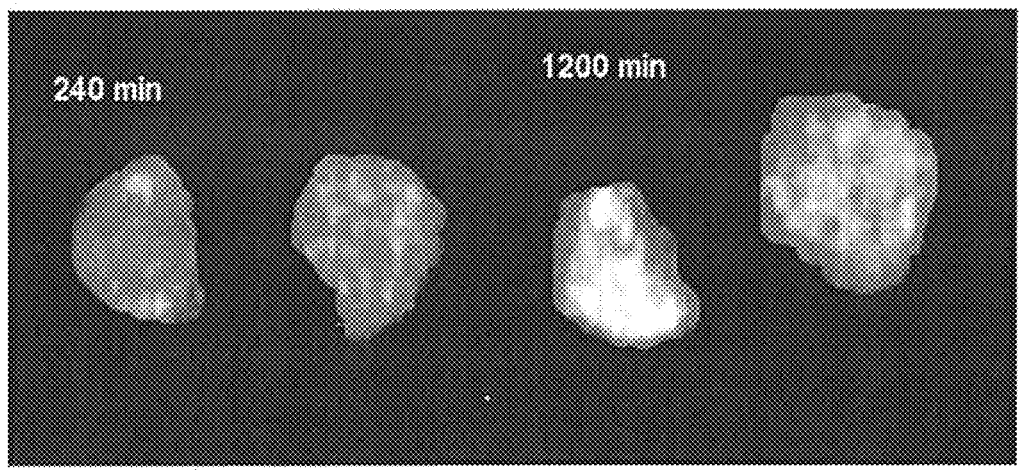
FIG. 46: Biodistribution study results for mouse 1011. A. Maximum intensity projections (MIPs). Gaussian filter (0.200 mm FWHM) applied to the images, scaled to fixed percentile of image. B. Cropped MIPs. Gaussian filter (0.100 mm FWHM) applied to the images, scaled to fixed percentile of image. C. Cropped coronal slices. Gaussian filter (0.100 mm FWHM) applied to the images. D. Tumors extracted using 3D ROI Tool in vivoQuant™. Left tumor is in red, right tumor is in green. E. MIP of extracted tumors. At 240 minutes, the color scale min (black) was 0 and the color scale max (white) was $3.9 \times 10\text{-}5$ μCi. At 1200 minutes, the color scale min (black) was 0 and the color scale max (white) was $1.63 \times 10\text{-}5$ μCi (corrected for isotope decay).
Figure 47:
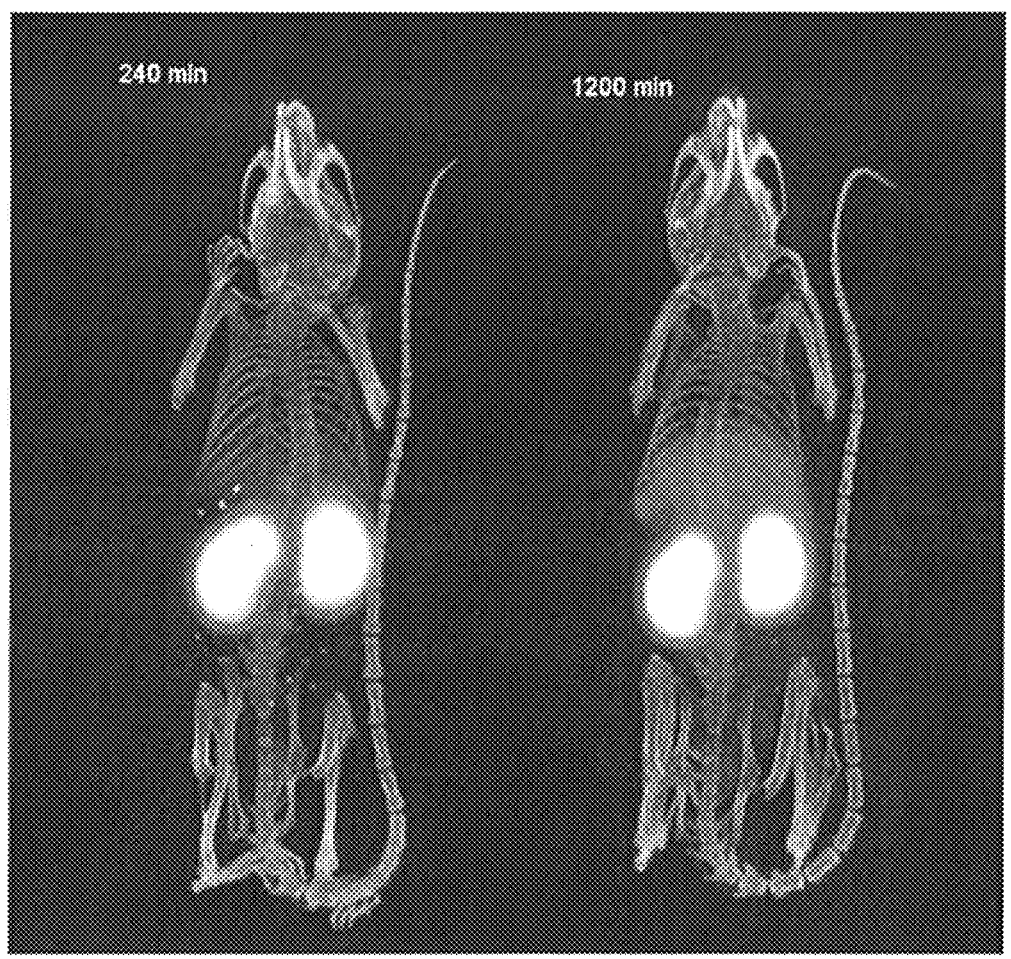
FIG. 47: Biodistribution study results for mouse 1012. A. Maximum intensity projections (MIPs). Gaussian filter (0.200 mm FWHM) applied to the images, scaled to fixed percentile of image. B. Cropped MIPs. Gaussian filter (0.100 mm FWHM) applied to the images, scaled to fixed percentile of image. C. Cropped coronal slices. Gaussian filter (0.100 mm FWHM) applied to the images. D. Tumors extracted using 3D ROI Tool in vivoQuant™. Left tumor is in red, right tumor is in green. E. MIP of extracted tumors. At 240 minutes, the color scale min (black) was 0 and the color scale max (white) was $3.9 \times 10\text{-}5$ μCi. At 1200 minutes, the color scale min (black) was 0 and the color scale max (white) was $1.63 \times 10\text{-}5$ μCi (corrected for isotope decay).

Pull-down assays and Western blots were performed as described in Example 4 to evaluate binding specificity. VEGF was immunoprecipitated from VEGF-spiked buffer (B) or 25% v/v human serum (S) using functionalized magnetic beads. C-terminal PEGylation was found to have a positive impact on specificity (i.e., less capture of serum proteins), but a negative impact on affinity (i.e., less capture of VEGF) (FIG. 42). No difference was observed for the C-terminal amide versus acid. The specificity of PEG2arm-Triligand 2 (dimer) was found to be approximately the same as the monomer (FIG. 43).

Example 17

Triligand Biodistribution

VEGF triligand was prepared as an N-terminal DOTA conjugate by solid-phase reaction with DOTA-tris (t-Bu ester) (B-260; Macrocyclics, Dallas, Tex.) prior to release of the peptide from resin and purification by HPLC. DOTA conjugated Avastin® was generated by reacting Avastin® with DOTA-NHS-ester (Macrocyclics, Dallas, Tex.) in 0.1 M Na$_2$HPO$_4$ buffer. After conjugation of Avastin®, reaction mixtures were centrifuged repeatedly through a YM-30 Centricon® centrifugal filters (Millipore, Billerica, Mass.) with 0.1 M pH 6.5 ammonium citrate buffer to remove unconjugated small molecules. The concentrations of purified DOTA conjugates were determined by measuring the absorbance at 280 nm of a UV spectrophotometer (Eppendorf, Westbury, N.Y.). For radiolabeling, DOTA-conjugated triligand and Avastin® were incubated with $^{64}$Cu in 0.1 M ammonium citrate, pH 6.5, at 43° C. for one hour. Labeled $^{64}$Cu-DOTA-test agent was purified by size-exclusion column (Bio-Spin6, BIO-RAD Laboratories). Radiochemical purity was determined by integrating areas on HPLC. This analysis was conducted on a size-exclusion column and characterized by the percentage of radioactivity associated with the 150 kDa protein peak.

30 female immunocompromised NU/J mice were obtained from Jackson Laboratories (25 tumor bearing, five non-tumor bearing). All mice were weighed and subjected to general clinical observations. For tumor bearing mice, subcutaneous human HT29 colon adenocarcinoma tumor cells (VEGF-positive) were implanted on the left rear flank and human MSTO-211 H mesothelioma tumor cells (VEGF-negative) were implanted on the right rear flank. HT29 cells were implanted two weeks after implantation of MSTO-211 H cells. Co-implantation of VEGF-positive and VEGF-negative tumor cells resulted in asymmetric tumors with localized VEGF expression.

Fourteen of the mice were selected for the study. These fourteen mice were divided into Groups 1-6. Groups 1 and 2 were non-tumor bearing (three mice in total), while Groups 3-6 were tumor bearing (11 mice in total). Groups 1-4 and 6 were administered $^{64}$Cu-DOTA radiolabeled VEGF triligand either intraperitoneally (IP) (Groups 1, 3, 4, and 6) or intravenously (IV) (Group 2). Positive control mice (Group 5) received $^{64}$Cu-DOTA radiolabeled Avastin® as test agent. Group 6 mice were administered IV Avastin® or vehicle control as a blocker 24 hours prior to $^{64}$Cu-DOTA radiolabeled VEGF triligand, administration. Test agent was administered to Group 3 at 1 week, Groups 4 and 5 at 2 weeks, and Group 6 at 3 weeks after implantation of HT29 cells. The study protocol is summarized in Table 8.

TABLE 8

Biodistribution study protocol

| Group | Route | Test agent | Mouse ID # | MSTO tumor mass size at selection (mm³) | HT29 tumor mass size at selection (mm³)2 | Dose volume (µL) | $^{64}$Cu (µCi/animal) | Dose level (µg/animal) |
|---|---|---|---|---|---|---|---|---|
| 1 (Pretest) | IP | $^{64}$Cu-DOTA-Triligand | 1001 | NA | NA | 240 | 202.6 | 64.8 |
|  |  |  | 1102R | NA | NA | 270 | 193.02 | 72.9 |
| 2 (Pretest) | IV | $^{64}$Cu-DOTA-Triligand | 1003 | NA | NA | 250 | 167.9 | 67.5 |
| 3 | IP | $^{64}$Cu-DOTA-Triligand | 1004 | 267.696 | 283.9655 | 150 | 193.69 | 52.5 |
|  |  |  | 1105R | 435.896 | 299.568 | 170 | 210.41 | 66.3 |
|  |  |  | 1106R | 621.075 | 340.805 | 230 | 211.81 | 89.7 |
| 4 | IP | $^{64}$Cu-DOTA-Triligand | 1005 | 465.7465 | 539.055 | 110 | 208.22 | 52.8 |
|  |  |  | 1007 | 744.185 | 463.736 | 130 | 208.12 | 62.4 |
|  |  |  | 1008 | 793.5 | 499.023 | 160 | 203.13 | 76.8 |
| 5 (Positive control) | IV | $^{64}$Cu-Avastin | 1005 | 441.8 | 499.234 | 250 | 204.82 | 52.5 |
| 6 (Blocker-vehicle) | IP | $^{64}$Cu-DOTA-Triligand | 1009 | 953.344 | 775.284 | 100 | 210.8 | 47.8 |
|  |  |  | 1011 | 1230.08 | 714.07 | 100 | 203.47 | 46.1 |
| 6 (Blocker-Avastin) |  |  | 1010 | 1131.588 | 707.868 | 110 | 215.06 | 52.1 |
|  |  |  | 1012 | 1139.9085 | 697.832 | 110 | 208.91 | 50.6 |

After dosing, mice were individually housed in suspended stainless steel wire mesh cages. Mice were fed irradiated block PicoLab Diet Rodent Diet 20 #5K75 (PMI Nutrition International, Inc.) ad libitum. Body weight was measured prior to biligand/triligand administration and weekly thereafter. Tumor size (length and width) was measured by caliper prior to administration and three times per week thereafter. Tumor volumes were calculated by the formula: Tumor volume=Length×Width$^2$/2, where length was always the longer dimension. Where there was more than one tumor per mouse, the location and dimensions of all tumors was recorded on a mass map.

Biodistribution was evaluated by MicroPET/CT imaging using dynamic and/or static scans. A CT scan preceded the first PET scan in each animal. Groups 1-4 and 6 were subjected to a dynamic PET scan at 0 to 2 hours after administration, and static scans at 4 and 20 hours after administration. Group 5 was subjected to a single static scan at 20 hours after administration. Static scans at 4 hours were performed for 15 minutes, while static scans at 20 hours were performed for 30 minutes. At the completion of scanning (approximately 21 hours after test agent administration), mice from Groups 1-4 and 6 were sacrificed for tissue biodistribution analysis. The following tissues were collected: tumors (groups 3, 4, and 6 only), liver, spleen, kidney, blood, muscle, heart, bladder, gall bladder, brain, femur, and lung. Tissues were weighed and counted for radioactivity concentration using a gamma counter or dose calibrator. Two samples of the remaining test article formulation equivalent to one thousandth of the injected radioactivity dose was also counted using the gamma counter and used a reference standard. Radioactivity was normalized by organ/tissue weight.

Biodistribution results for animal 1102R (Group 1) and 1004 (Group 3) are set forth in FIGS. 48 and 49, respectively.

Figure 74:
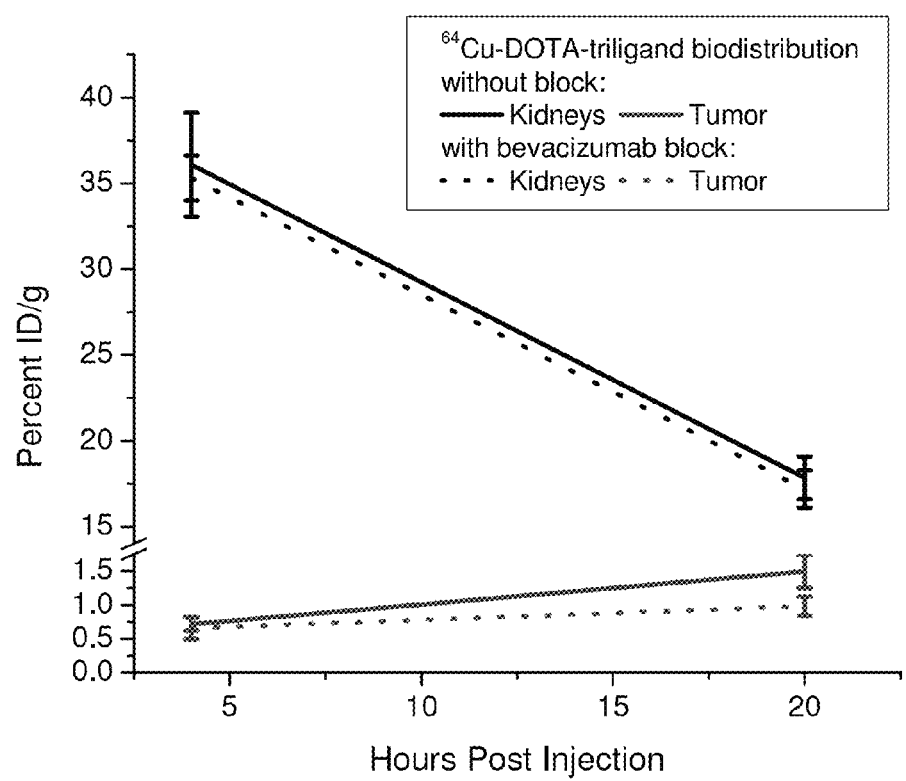
FIG. 74: Tissue distribution of $^{64}$Cu-DOTA-triligand in HT-29 xenograft-bearing nude mice after intraperitoneal injection. Percent ID/g was calculated from microPET images acquired at 4 and 20 h post injection. For blocking human VEGF-A, unlabeled bevacizumab (1 mg) was administered i.v. 48 h prior to $^{64}$Cu-DOTA-triligand. The data represents the average levels±SD from 4 mice per time point.

Tissue distribution data at 4 and 20 h post injection suggest that $^{64}$Cu-DOTA-triligand accumulates in the tumor as a function of time (FIG. 74).

Figure 57:
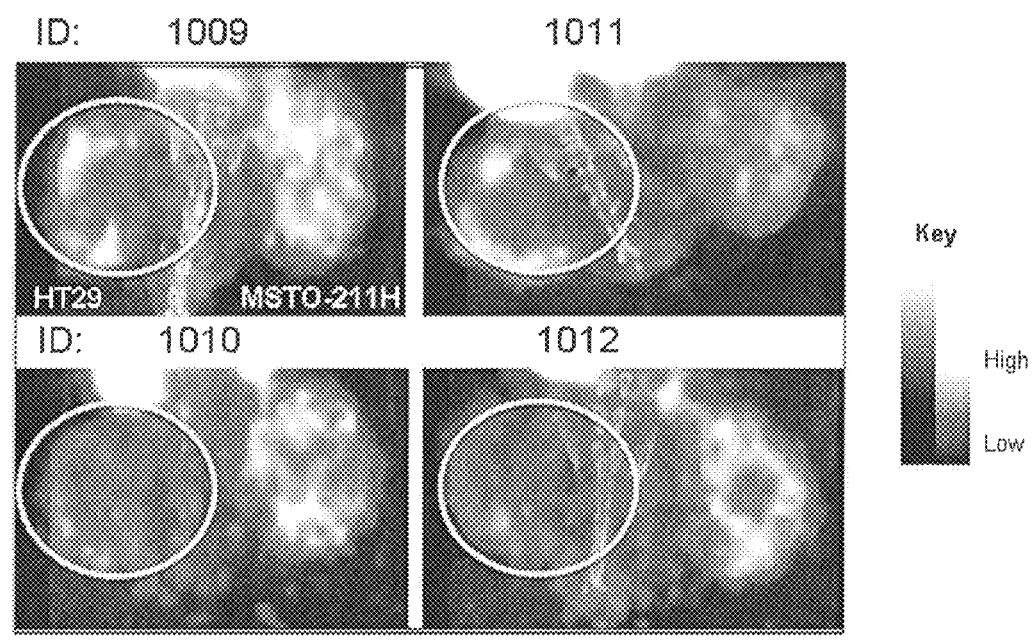
FIG. 57: Biodistribution results for mice 1009 and 1011 (control) and 1010 and 1012 (24 hour Avastin® blockade) at 20 hours post-VEGF triligand administration. Left=HT29, right=MSTO-211 H.
Figure 58E:
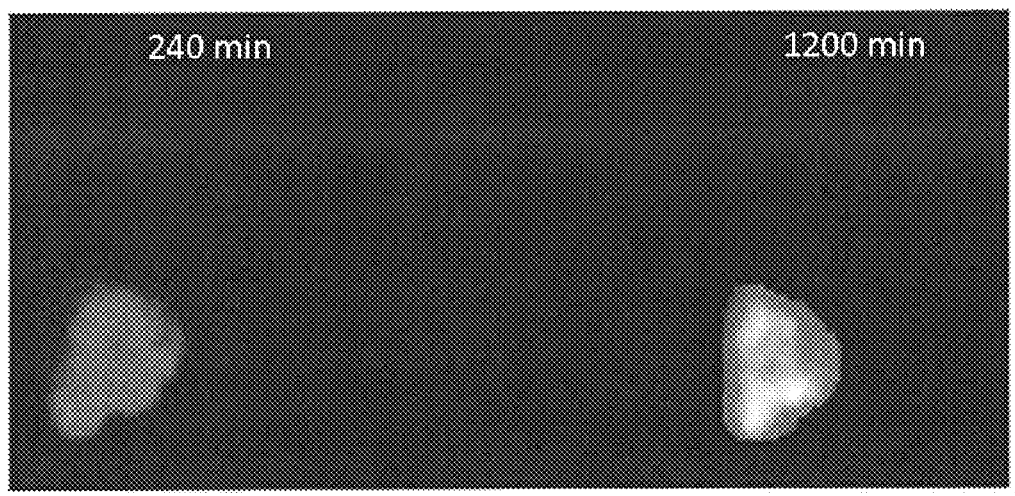
FIG. 58: Biodistribution study results for mouse 1013. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI Tool in vivoQuant™. Gaussian filter (0.200 mm FWHM) applied to the images, color scale max corrected for isotope decay.
Figure 59E:
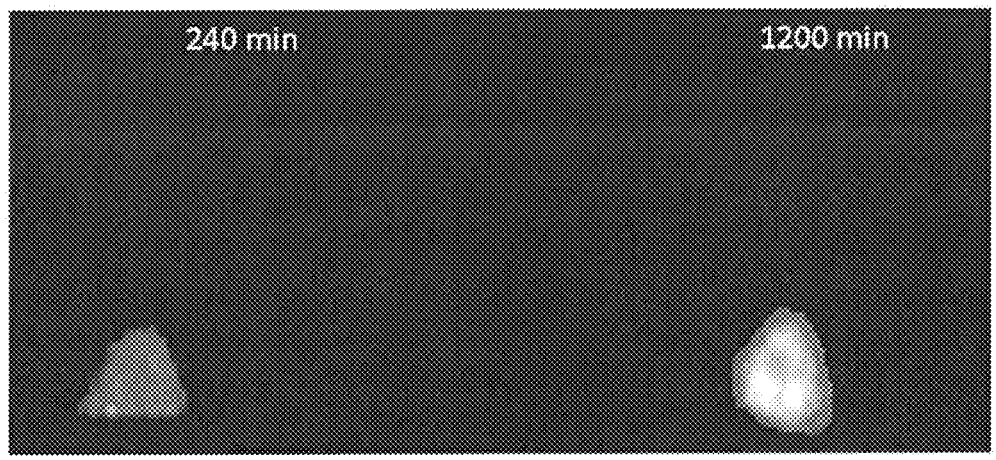
FIG. 59: Biodistribution study results for mouse 1014. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI Tool in vivoQuant™. Gaussian filter (0.200 mm FWHM) applied to the images, color scale max corrected for isotope decay.
Figure 60:
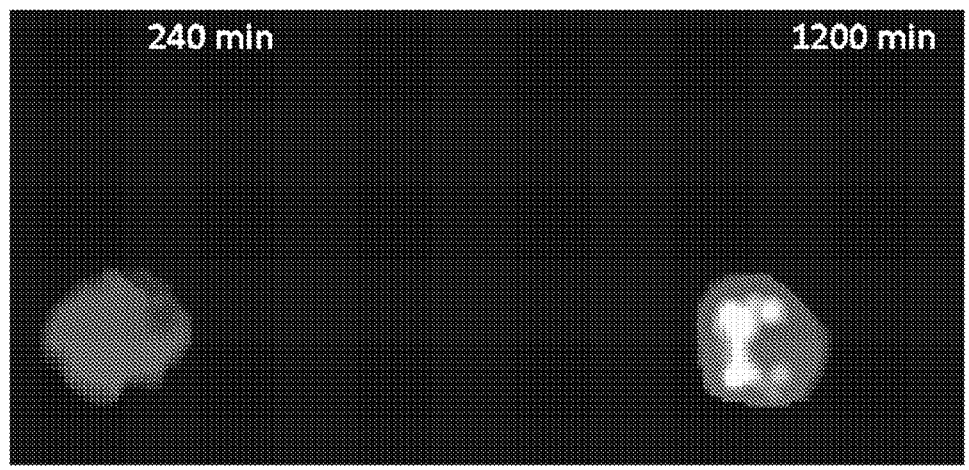
FIG. 60: Biodistribution study results for mouse 1017. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI Tool in vivoQuant™. Gaussian filter (0.200 mm FWHM) applied to the images, color scale max corrected for isotope decay.
Figure 61E:
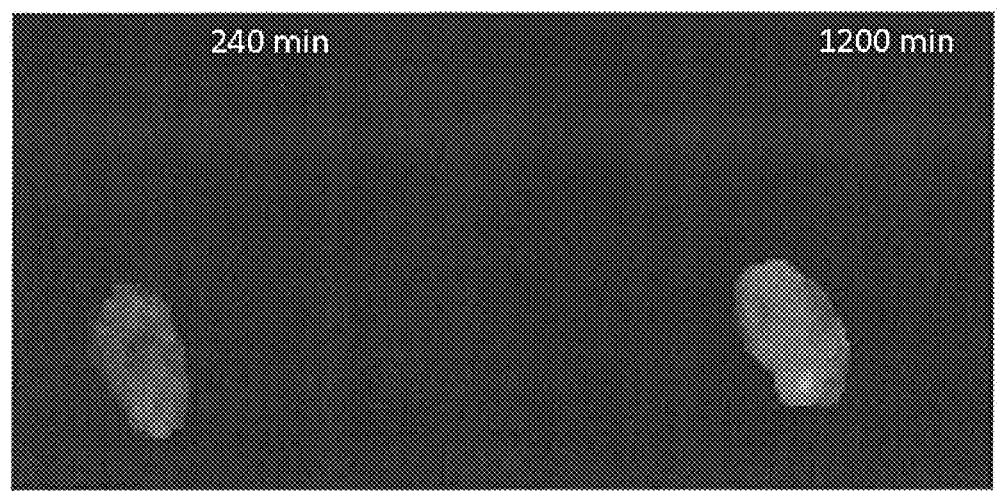
FIG. 61: Biodistribution study results for mouse 1018. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI Tool in vivoQuant™. Gaussian filter (0.200 mm FWHM) applied to the images, color scale max corrected for isotope decay.
Figure 62E:
FIG. 62: Biodistribution study results for mouse 1021. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI ool in vivoQuant™. Gaussian filter (0.200 mm FWHM) applied to the images, color scale max corrected for isotope decay.
Figure 63E:
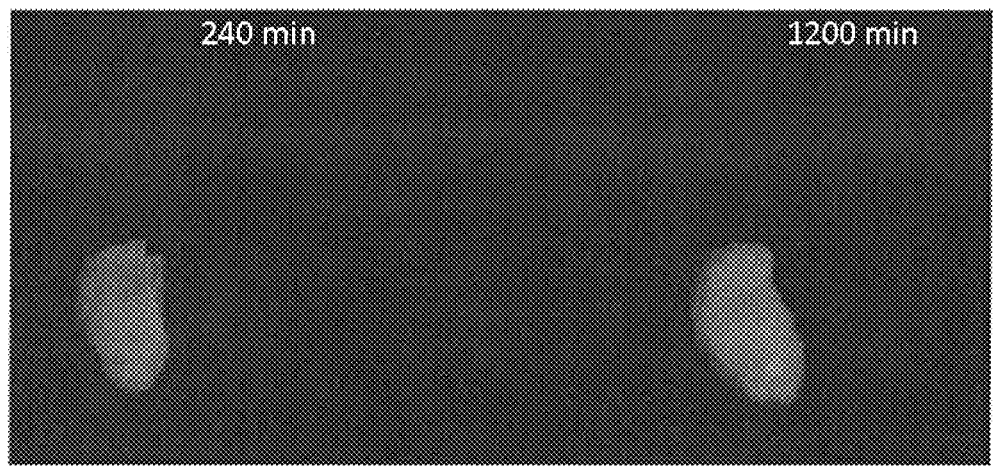
FIG. 63: Biodistribution study results for mouse 1022. A. Kidney maximum intensity projections (MIPs). Gaussian filter (0.200 mm FWHM) applied to the images, color scale max corrected for isotope decay. B. Tumor cropped MIPs. Gaussian filter (0.200 mm FWHM) applied to the images, color scale max corrected for isotope decay. C. Tumor cropped coronal slices. Gaussian filter (0.200 mm FWHM) applied to the images, color scale max corrected for isotope decay. D. Tumors extracted using 3D ROI Tool in vivoQuant™. Gaussian filter (0.200 mm FWHM) applied to the images, color scale max corrected for isotope decay. E. MIP of extracted tumors using 3D ROI Tool in vivoQuant™. Gaussian filter (0.200 mm FWHM) applied to the images, color scale max corrected for isotope decay.

Biodistribution results for animals 1009-1012 (Group 6) are set forth in FIGS. 44-47, respectively. A side-by-side comparison of the non-blockade mice (1009 and 1011) and the Avastin® blockade mice (1010 and 1012) is set forth in FIG. 57. These results show that pre-treatment with Avastin® decreases the intensity of VEGF triligand signal in HT29 tumors, which further supports the results from Example 9 suggesting that Avastin® and the VEGF triligand bind a shared epitope.

Example 18

Triligand Biodistribution

The in vitro binding affinity and blockade of VEGF receptor:ligand interactions by peptides synthesized using PCC technology suggested that similar molecular interactions may be modulated in vivo by the VEGF biligands and triligands disclosed herein. As shown in Example 17, pre-treatment with Avastin® decreased VEGF triligand signal in vivo in an HT29 mouse model. To further evaluate this effect, a follow-up biodistribution experiment was performed to phenotype VEGF expressed by HT29 xenografts in a murine model.

Radiolabeled VEGF triligand and HT-29 mice were prepared as described above in Example 17. After tumors had achieved sufficient volume, four control mice (mice 1013, 1015, 1016, and 1114R) were IV administered vehicle control, while test mice were IV administered Avastin® in molar excess. After 24 hours (test mice 1014, 1017, and 1018) or 48 hours (test mice 1021, 1022, 1023, and 1024), mice were IP administered radiolabeled VEGF triligand (~65 µg, 3.4 µCi/µg). Biodistribution was evaluated by MicroPET/CT imaging using a static scan at 0, 4, and 20 hours after triligand administration.

Figure 51:
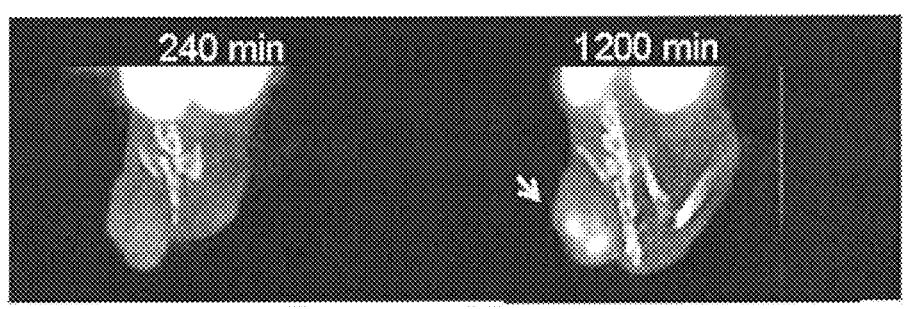
FIG. 51: Biodistribution results for mouse 1114R. Left=HT29. Results were corrected for isotope decay.
Figure 52:
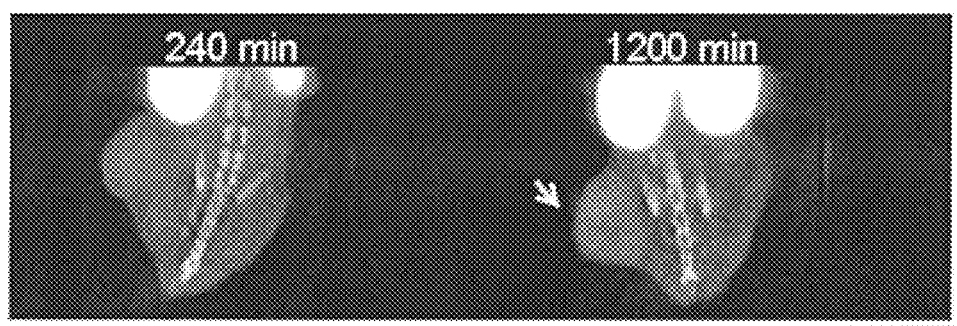
FIG. 52: Biodistribution results for mouse 1017. Left=HT29. Results were corrected for isotope decay.
Figure 53:
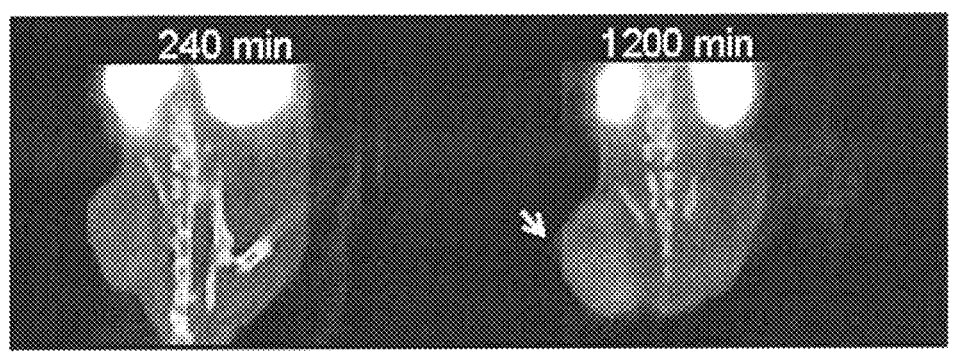
FIG. 53: Biodistribution results for mouse 1022. Left=HT29. Results were corrected for isotope decay.
Figure 54:
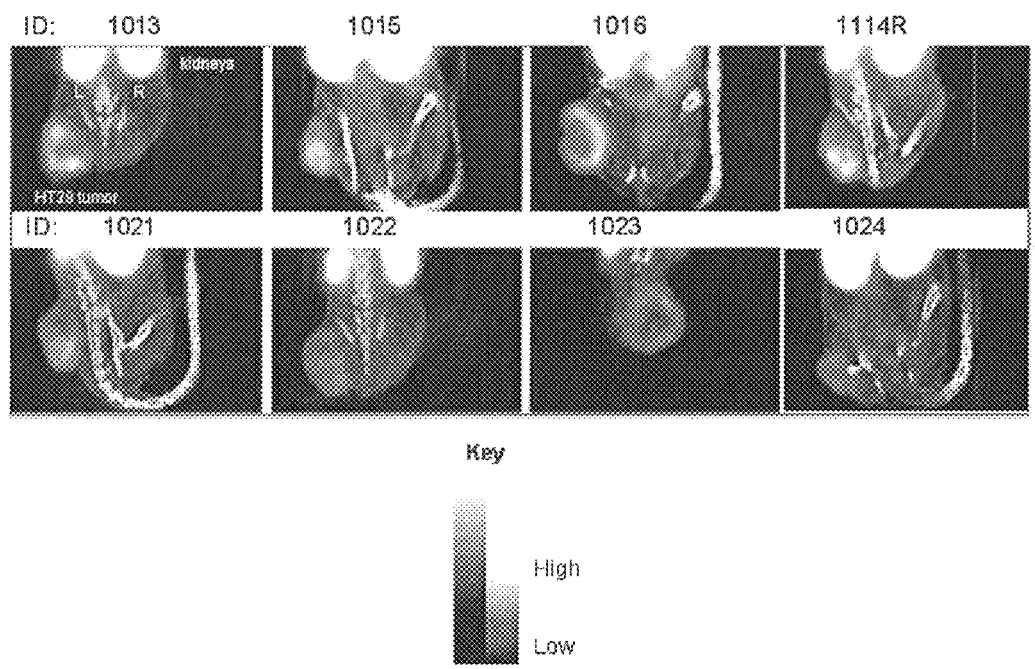
FIG. 54: Biodistribution results for mice 1013, 1015, 1016, and 1114R (control) and 1021-1024 (48 hour Avastin® blockade) at 20 hours post-VEGF triligand administration. Left=HT29.

Biodistribution results for animals 1013 (control), 1014 (24 hour blockade), 1017 (24 hour blockade), 1018 (24 hour blockade), 1021 (48 hour blockade), and 1022 (48 hour blockade) are set forth in FIGS. 58-63, respectively. Additional biodistribution results for animals 1114R (control), 1017, and 1022 are set forth in FIGS. 51-53, respectively. A side-by-side comparison of the control mice and the 48 hour blockade mice at 20 hours is set forth in FIG. 54. These results show that Avastin® blockade attenuates tumor binding by the VEGF triligand, suggesting that Avastin® and the VEGF triligand bind a shared epitope.

Figure 55:
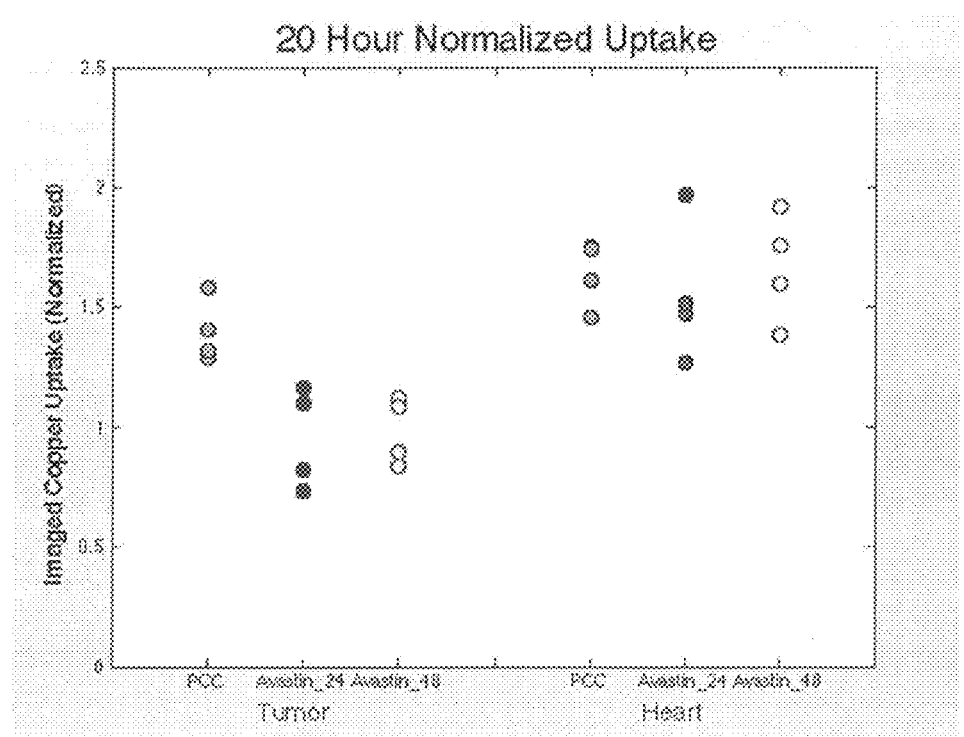
FIG. 55: Tumor versus heart tissue distribution of Example 17.
Figure 56:
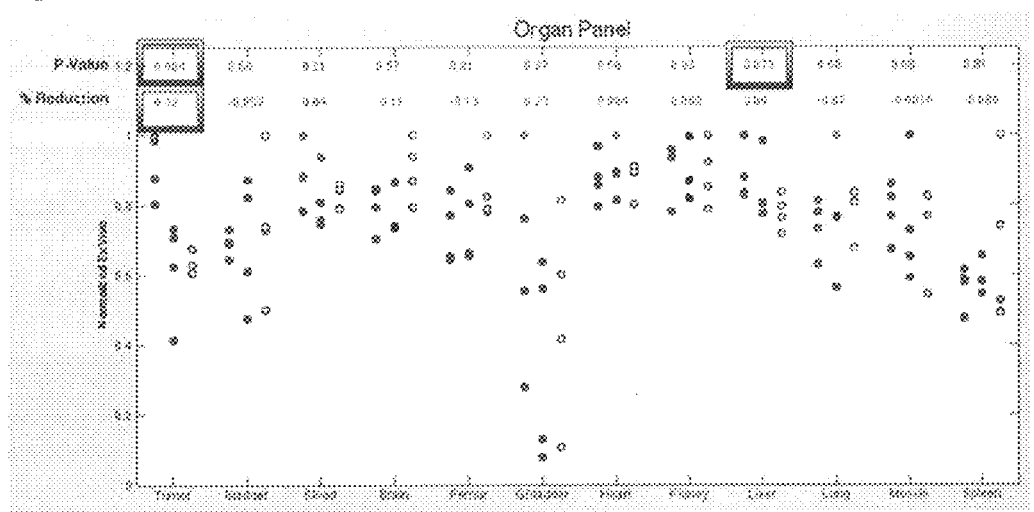
FIG. 56: Tumor versus other tissue distribution of Example 17.

At the completion of scanning, mice were sacrificed for tissue biodistribution analysis as described above in Example 17. FIG. 55 summarizes the results for tumor versus heart tissue samples. The reduction in VEGF triligand uptake in tumor tissue was 29% with 24 hour Avastin® blockade and 27% with 48 hour Avastin® blockade, with a Mann-Whitney non-parametric p-value of 0.004. The reduction in heart tissue, on the other hand, was only 11% with 24 hour Avastin® blockade and 0% with 48 hour Avastin® blockade, with a p-value of 0.933. Results across all tissue types are set forth in FIG. 56. These results show that although $^{64}$Cu was detectable in the bladder, blood, brain, femur, gallbladder, heart, kidney, liver, lung, muscle, and spleen, pre-administration of Avastin® only resulted in $^{64}$Cu signal attenuation in tumor tissue.

HT29 tumors suggest that VEGF triligand binds specifically to hVEGF expressed in vivo. Detection of the $^{64}$Cu signal in the other 11 tissues without Avastin® attenuation suggests non-specific localization of the VEGF triligand. However, these data are similar to those reported for metal-chelated Avastin® in similar studies of VEGF-overexpressing human tumors in murine xenograft models (Nagengast 2011; Paudyal 2011). The data suggest the potential for either non-specific binding of VEGF-epitope targeting proteins, binding to other VEGF isoforms, or organ-specific clearance, as demonstrated by the kidney signals. These results suggest that the VEGF triligands disclosed herein may be used in clinical applications such as in vivo molecular tumor epitope phenotyping, e.g. "molecular imaging," which may be beneficial in patient and tumor stratification for therapeutic decision-making.

Example 19

Plasma Concentrations and Pharmacokinetics of VEGF-PCC Following a Single Intravenous (IV) or Intraperitoneal (IP) Dose in Mice Materials and Methods
Test Article
Test article: VEGF-PCC (IN-VT-1001 Triligand) (PCC monomer) Ac-VEPNCDIHVMWEWECFERL-Tz4-lfrew-Tz4-eeird (SEQ ID NO: 71). The underlined region inclusive of the Cys residues is cyclized by a disulfide bond, Ac=N-terminal acetylation, and Tz4=1,4-disubstituted 1,2,3-triazole.

Storage condition: Approximately −20° C.
Samples and Storage
Samples were received from the sponsor on 20 Mar. and 10 Apr. 2012 and stored at approximately −70° C. before and after analysis.
LC-MS/MS Analysis
Sample Analysis
The LC-MS/MS system for analysis was comprised of an Agilent 1200 high performance liquid chromatography (HPLC) and a 5500 Qtrap mass spectrometer (Applied Biosystems by Life Technologies, Carlsbad, Calif.).

Concentrations of VEGF-PCC in mouse plasma were determined using a non-validated LC MS/MS assay with Angiotensin I as the internal standard following a solid phase extraction method. Individual VEGF-PCC calibration and QC standards were prepared from the respective intermediate stock solutions by addition to naïve mouse plasma. The target working range of the calibration curve was 50 to 5,000 ng/mL in plasma and the target concentrations of the QC standards were 150 to 3,750 ng/mL in plasma for VEGF-PCC.

Batch 1
Calibration curves for VEGF-PCC in mouse plasma ranged from 50 to 5,000 ng/mL, with a correlation coefficient value of 0.9936.

Duplicate QC samples at concentrations ranging from 150 to 3,750 ng/mL in mouse plasma were included in the analysis group. In addition, duplicate dilution (10-fold) QC samples at a concentration of 20,000 ng/mL in mouse plasma were also included in the analysis group.

The assay lower limit of quantitation (LLOQ) for VEGF-PCC in mouse plasma was 50 ng/mL for Batch 1.

Batch 2
Calibration curves for VEGF-PCC in mouse plasma ranged from 100 to 5,000 ng/mL, with a correlation coefficient value of 0.9915.

Duplicate QC samples at concentrations ranging from 150 to 3,750 ng/mL in mouse plasma were included in the analysis group. In addition, duplicate dilution (10-fold) QC samples at a concentration of 20,000 ng/mL in mouse plasma were also included in the analysis group.

The assay lower limit of quantitation (LLOQ) for VEGF-PCC in mouse plasma was 100 ng/mL for Batch 2.

The calibration and QC results were evaluated and, based on review by the study director, it was concluded that the method performance was acceptable. Data for calibration standards and QC samples are presented in Appendix 1.

Figure 64:
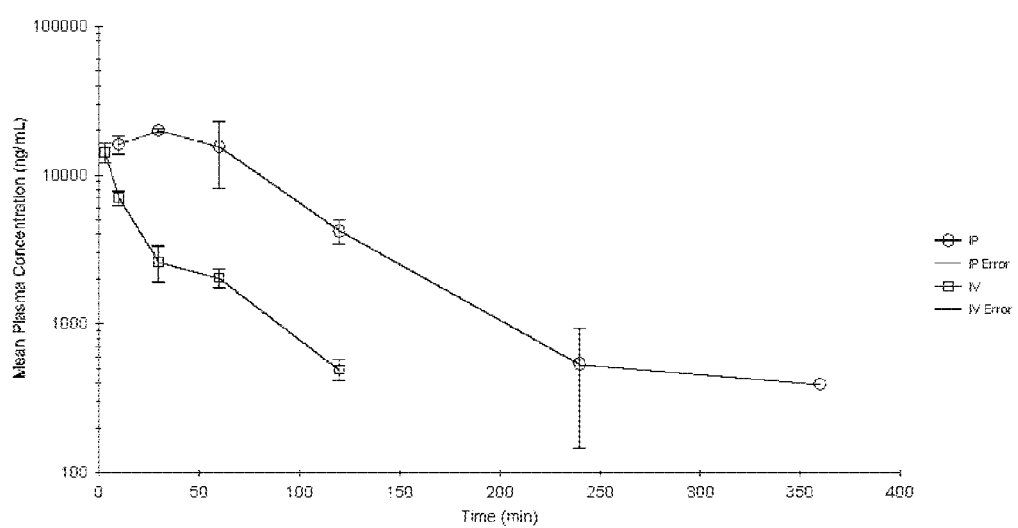
FIG. 64: Mean (±SD) plasma concentrations (ng/mL) of VEGF-PCC following a single intravenous (IV) or intraperitoneal (IP) dose in mouse.
Figure 75:
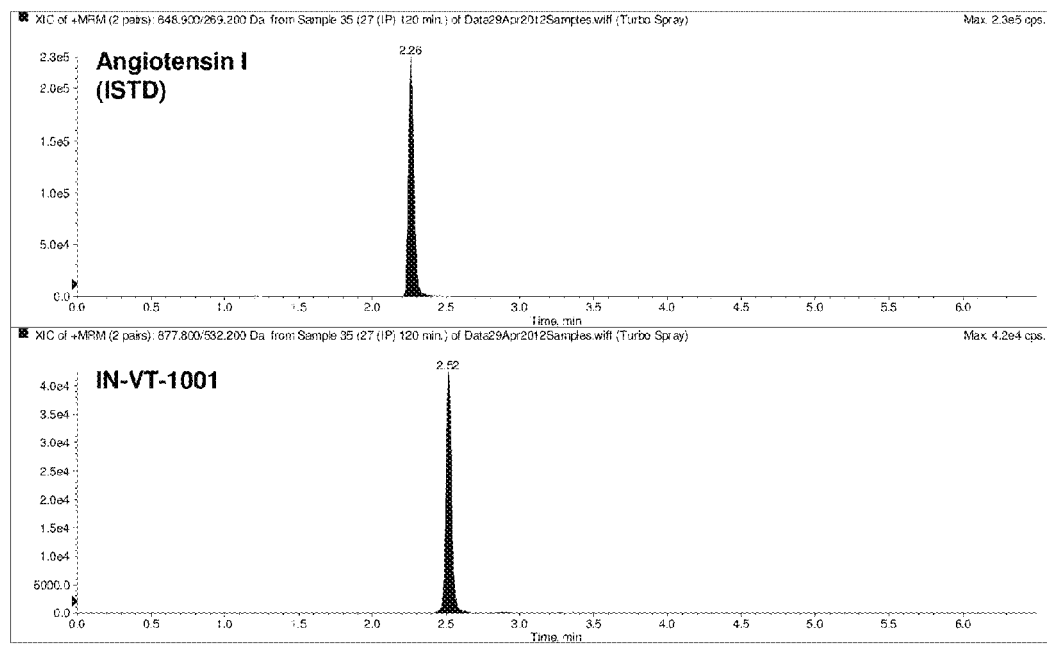
FIG. 75: Representative chromatogram of IN-VT-1001 in mouse plasma Animal Number 27 (IP), 120 minutes.

Concentrations of Test Article
Concentrations of VEGF-PCC in mouse plasma are presented in Tables A and B and are presented graphically in FIG. 64. A representative chromatogram is presented in FIG. 75.

TABLE A

Plasma concentrations of IN-VT-1001 (ng/mL) in mouse plasma following a single intravenous dose

| Animal Number | Collection Time Point (Minutes Postdose) | | | | | | | |
|---|---|---|---|---|---|---|---|---|
| | 3 | 10 | 30 | 60 | 120 | 240 | 360 | 1440 |
| 46 | 14200 | | | | | | | |
| 47 | 16200 | | | | | | | |
| 48 | 12000 | | | | | | | |
| 40 | | 7220 | | | | | | |
| 41 | | 7550 | | | | | | |
| 42 | | 6110 | | | | | | |
| 34 | | | 2170 | | | | | |
| 35 | | | 2210 | | | | | |
| 36 | | | 3420 | | | | | |
| 28 | | | | 1840 | | | | |
| 29 | | | | 2380 | | | | |
| 30 | | | | 1870 | | | | |
| 22 | | | | | 551 | | | |
| 23 | | | | | 400 | | | |
| 24 | | | | | 514 | | | |
| 16 | | | | | | BLQ | | |
| 17 | | | | | | BLQ | | |
| 18 | | | | | | BLQ | | |
| 10 | | | | | | | BLQ | |
| 11 | | | | | | | BLQ | |
| 12 | | | | | | | BLQ | |
| 4 | | | | | | | | BLQ |
| 5 | | | | | | | | BLQ |
| 6 | | | | | | | | BLQ |
| Mean | 14100 | 6960 | 2600 | 2030 | 488 | 0.00 | 0.00 | 0.00 |
| SD | 2100 | 754 | 710 | 303 | 78.7 | 0.00 | 0.00 | 0.00 |

TABLE B

Plasma concentrations of IN-VT-1001 (ng/mL) in mouse plasma following a single intraperitoneal dose

| Animal Number | Collection Time Point (Minutes Postdose) | | | | | | | |
|---|---|---|---|---|---|---|---|---|
| | 10 | 30 | 60 | 120 | 240 | 360 | 480 | 1440 |
| 43 | 17500 | | | | | | | |
| 44 | 17000 | | | | | | | |
| 45 | 13400 | | | | | | | |
| 37 | | 19400 | | | | | | |
| 38 | | 20200 | | | | | | |
| 39 | | BLQ | | | | | | |
| 31 | | | 10800 | | | | | |
| 32 | | | 23900 | | | | | |
| 33 | | | 11500 | | | | | |
| 25 | | | | BLQ | | | | |
| 26 | | | | 4730 | | | | |
| 27 | | | | 3640 | | | | |
| 19 | | | | | 259 | | | |
| 20 | | | | | 807 | | | |
| 21 | | | | | BLQ | | | |
| 13 | | | | | | 390 | | |
| 14 | | | | | | BLQ | | |
| 15 | | | | | | BLQ | | |
| 7 | | | | | | | BLQ | |
| 8 | | | | | | | BLQ | |
| 9 | | | | | | | BLQ | |
| 1 | | | | | | | | BLQ |
| 2 | | | | | | | | BLQ |
| 3 | | | | | | | | BLQ |
| Mean | 16000 | 13200 | 15400 | 2790 | 355 | 130 | 0.00 | 0.00 |
| SD | 2240 | 11400 | 7370 | 2480 | 412 | 225 | 0.00 | 0.00 |

Batch 1

Intravenous samples at 3, 10, and 30 minutes and intraperitoneal samples at 10, 30, and 60 minutes were diluted 10-fold with naïve mouse plasma prior to extraction and analysis. All other samples were extracted and analyzed undiluted.

One intraperitoneal sample at 120 minutes was above the upper limit of quantitation (ULOQ) for VEGF-PCC (5,000 ng/mL).

Batch 2

The one sample that was above the ULOQ from Batch 1 was diluted 10-fold and re analyzed in Batch 2 where it was now within the calibration curve range.

Pharmacokinetics

Intravenous

Mice received a single IV dose of VEGF-PCC at 1 mg/kg. A summary of the plasma concentrations for individual animals is shown in Table A. Plasma pharmacokinetic parameters are listed in Table 9.

The mean plasma concentration vs. time curve is shown in FIG. 64.

The mean systemic plasma clearance (CL) and steady state volume of distribution (Vss) values for VEGF-PCC following single IV dose administration at 1 mg/kg were 2.57 mL/min/kg and 0.0967 L/kg, respectively. The mean half-life (t1/2) was 0.598 hours.

The mean back-calculated C0 for VEGF-PCC was 19,100 ng/mL. The theoretical C0 for VEGF-PCC [assuming a mean IV dose of 1 mg/kg and an average body weight of 33 g and assuming a mean blood volume of approximately 1.7 mL (Davies and Morris, 1993)] was approximately 19,400 ng/mL.

Intraperitoneal

Mice received a single IP dose of VEGF-PCC at 5 mg/kg. A summary of the plasma concentrations for individual animals is shown in Table B. Plasma pharmacokinetic parameters are listed in Table 9. The mean plasma concentration vs. time curve is shown in FIG. 64.

The mean plasma exposure (AUCinf) of VEGF-PCC at 5 mg/kg was 32,200 ng*hr/mL. The mean Cmax and corresponding Tmax values were 19,800 ng/mL and 0.50 hours, respectively. The relative bioavailability of VEGF-PCC at 5 mg/kg IP in mice was approximately 99%.

Conclusions

The purpose of this study was to determine plasma concentrations and pharmacokinetics of VEGF-PCC in mice following a single IV or IP dose of VEGF-PCC at 1 or 5 mg/kg, respectively, using a liquid chromatography with tandem mass spectrometric (LC MS/MS) method.

Samples were analyzed using a non-validated LC-MS/MS method. Plasma concentrations of VEGF-PCC were determined using a non-validated LC MS/MS assay following a solid phase extraction method. The working range of the calibration curve was 50 to 5,000 ng/mL in plasma for VEGF-PCC.

Mice received a single IV dose of VEGF-PCC at 1 mg/kg. The mean systemic plasma clearance (CL) and steady state volume of distribution (Vss) values for were 2.57 mUmin/kg and 0.0967 L/kg, respectively. The mean half-life (t1/2) was 0.598 hours. The mean back-calculated C0 for VEGF-PCC was 19,100 ng/mL. The theoretical C0 for VEGF-PCC [assuming a mean intravenous dose of 1 mg/kg and an average body weight of 33 g and assuming a mean blood volume of approximately 1.7 mL (Davies and Morris, 1993)] was approximately 19,400 ng/mL.

Mice received a single IP dose of VEGF-PCC at 5 mg/kg. The mean plasma exposure (AUCinf) of VEGF-PCC at 5 mg/kg was 32,200 ng*hr/mL. The mean Cmax and corresponding Tmax values were 19,800 ng/mL and 0.50 hours, respectively. The relative bioavailability of VEGF-PCC at 5 mg/kg IP in mice was approximately 99%.

TABLE 9

Mean pharmacokinetic parameters for VEGF-PCC in mouse plasma following a single intravenous or intraperitoneal dose

| Dose Route | Dose (mg/kg) | $AUC_{0-t}$ (hr * ng/mL) | $AUC_{inf}$ (hr * ng/mL) | AUC % Ext (%) | CL (mL/min/kg) | F (%) | $T_{1/2}$ (hr) | $C_0$ (ng/mL) | $C_{max}$ (ng/mL) | $T_{max}$ (hr) | $V_{ss}$ (L/kg) |
|---|---|---|---|---|---|---|---|---|---|---|---|
| IV | 1 | 6070 | 6490 | 6.49 | 2.57 | NA | 0.598 | 19100 | NA | NA | 0.0967 |
| IP | 5 | 31500 | 32200 | 2.04 | NA | 99 | NA | NA | 19800 | 0.50 | NA |

NA Not applicable

Example 20

Iterative in Situ Click Chemistry Produces a VEGF-Targeted Capture Agent for in Vivo Molecular Imaging The development of Protein-Catalyzed Capture agents (PCCs) against VEGF began with a phage display-derived peptide that was previously demonstrated to interact at the receptor-binding domain.1 The peptide was modified with a pendant azide at the C-terminus to provide the anchor ligand X-VEPNCDIHVMWEWECFERL-Az4 (SEQ ID NO: 65) [where Az4=L-azidolysine, X=biotin-PEG3 linker or N-terminal capping group (i.e., acetyl), and underlined=cyclized]. PEG3 was attached as N-Fmoc-N"-succinyl-4,7,10-trioxa-1, 13-tridecanediamine (Sigma-Aldrich, 671517-5G). N-terminal capping was by acetic anhydride. Intramolecular disulfide cyclization was run over 4-16 h in 0.05 M ammonium acetate +10% (v/v) DMSO at pH 7-8 (adjusted accordingly with 5% (w/v) aq. ammonium carbonate).

Biligands and triligands discovered by the target-guided in situ click chemistry screens were prepared in bulk by solid-phase synthesis [where Tz4=1,4-disubstituted 1,2,3-triazole linker, FIG. 65], purified by RP-HPLC, and analyzed by mass spectrometry prior to assaying for in vitro or in vivo binding to VEGF.

X-VEPNCDIHVMWEWECFERL-Az4 (SEQ ID NO: 65). For X=acetyl, MALDI-MS (m/z): calcd. for $C_{117}H_{165}N_{31}O_{33}S_3$ (M+) 2628.1; found 2628.7. For X=biotin-PEG3, MALDI-MS (m/z): calcd. for $C_{139}H_{203}N_{35}O_{39}S_4$ (M+) 3114.4; found 3114.5.

X-VEPNCDIHVMWEWECFERL-Tz4-rplir (SEQ ID NO: 67). For X=acetyl, MALDI-MS (m/z): calcd. for $C_{151}H_{226}N_{44}O_{39}S_3$ (M+) 3375.6; found 3375.8. For X=biotin-PEG3, MALDI-MS (m/z): calcd. for $C_{173}H_{264}N_{48}O_{45}S_4$ (M+) 3861.9; found 3861.4.

X-VEPNCDIHVMWEWECFERL-Tz4-lfrew (SEQ ID NO: 68). For X=acetyl, MALDI-MS (m/z): calcd. for $C_{159}H_{222}N_{42}O_{41}S_3$(M+) 3471.6; found (M+H) 3473.3. For X=biotin-PEG3, MALDI-MS (m/z): calcd. for $C_{181}H_{260}N_{46}O_{47}S_4$ (M+) 3957.8; found 3957.1.

Biotin-PEG3-VEPNCDIHVMWEWECFERL-Tz4-lfrew-Az4 (SEQ ID NO: 66). MALDI-MS (m/z): calcd. for $C_{187}H_{270}N_{50}O_{48}S_4$ (M+) 4112.9; found (M+H) 4115.0.

X-VEPNCDIHVMWEWECFERL-Tz4-lfrew-Tz4-eeird (SEQ ID NO: 71). For X=acetyl, MALDI-MS (m/z): calcd. for $C_{196}H_{281}N_{55}O_{55}S_3$ (M+) 4382.0; found (M+H) 4383.3. For X=biotin-PEG3, MALDI-MS (m/z): calcd. for $C_{218}H_{319}N_{59}O_{61}S_4$ (M+) 4867.3; found 4870.6.

X-VEPNCDIHVMWEWECFERL-Tz4-lfrew-Tz4-frsvn (SEQ ID NO: 70). For X=acetyl, MALDI-MS (m/z): calcd. for $C_{197}H_{280}N_{56}O_{51}S_3$ (M+) 4343.0; found (M+Na) 4368.0. For X=biotin-PEG3, MALDI-MS (m/z): calcd. for $C_{219}H_{318}N_{60}O_{57}S_4$ (M+) 4828.3; found 4830.6.

X-VEPNCDIHVMWEWECFERL-Tz4-lfrew-Tz4-hthwl (SEQ ID NO: 72). For X=acetyl, MALDI-MS (m/z): calcd. for $C_{203}H_{281}N_{57}O_{50}S_3$(M+) 4413.0; found (M+H) 4415.2.

X-VEPNCDIHVMWEWECFERL-Tz4-lfrew-Tz4-ewsrw (SEQ ID NO: 73). For X=acetyl, MALDI-MS (m/z): calcd. for $C_{206}H_{283}N_{57}O_{52}S_3$ (M+) 4483.0; found (M+H) 4484.6. For X=biotin-PEG3, MALDI-MS (m/z): calcd. for $C_{228}H_{321}N_{61}O_{58}S_4$ (M+) 4969.3; found (M+K) 5008.0.

DOTA-PEG3-VEPNCDIHVMWEWECFERL-Tz4-lfrew-Tz4-eeird (SEQ ID NO: 71). N-terminal conjugation of DOTA (1,4,7,10-tetraazacyclododecane-1,4,7,10-tetraacetic acid) proceeded by solid-phase reaction with DOTA-tris (t-Bu ester) (B-260; Macrocyclics, Dallas, TX) followed by release of the peptide from resin and purification by RP-HPLC. MALDI-MS (m/z): calcd. for $C_{224}H_{331}N_{61}O_{66}S_3$ (M+) 5027.4; found (M+H) 5030.7.

Figure 76:
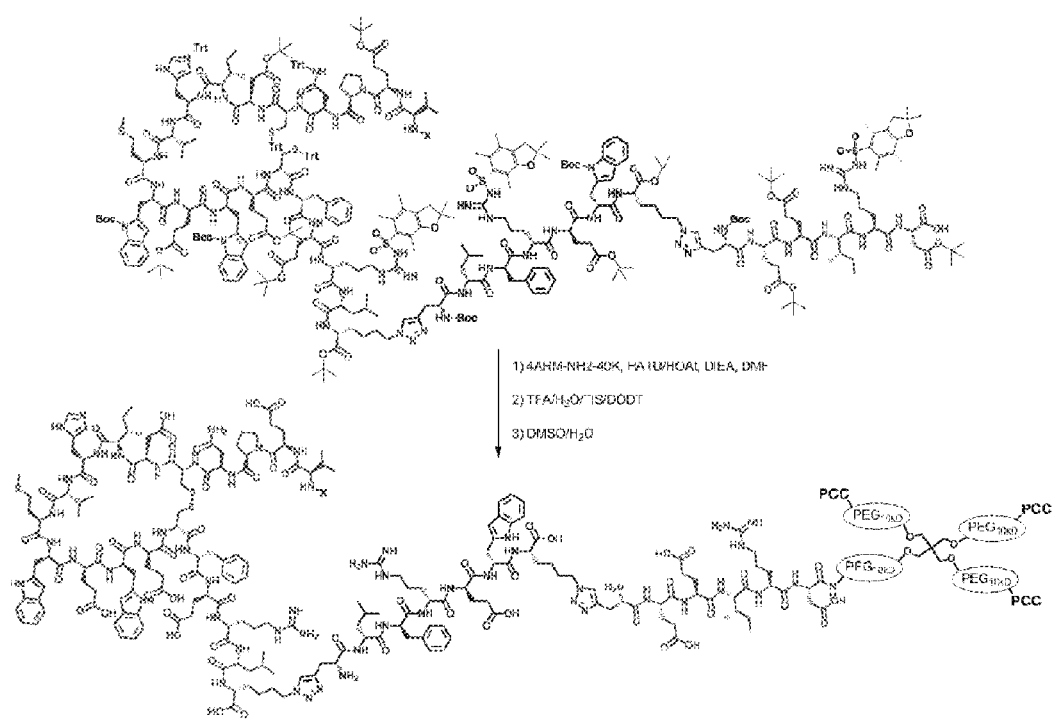
FIG. 76: Schematic of the reaction of the C-terminus of the triligand with a 4-arm PEG derivative (MW 40,000; Jenkem #4ARM-NH2-40K) resulting in the formation of a homotetramer, illustrated by a reaction of non-restrained Triligand 2 (SEQ ID NO: 86) and 4ARM PEG40 to form Triligand 2 homotetramer (SEQ ID NO: 83).

Multimeric PCC variants were designed and synthesized to explore the potential added benefit(s) from increased size and/or valency. Reaction of the C-terminus of the triligand with a 4-arm PEG derivative (MW 40,000; Jenkem #4ARM-NH2-40K) resulted in the formation of a homotetramer (FIG. 76). The homotetramer was purified by RP-HPLC and characterized by SDS-PAGE prior to assaying for in vitro binding to VEGF.

X-VEPNCDIHVMWEWECFERL-Tz4-lfrew-Tz4-eeird homotetramer (SEQ ID NO: 83). A molecular weight of 57,500 Da for X=acetyl or 59,500 Da for X=biotin-PEG3 was expected by 7.5% SDS-PAGE. Samples prepared in reducing Laemmli buffer were subjected to electrophoretic separation at 200 V for 30 min in 1× TGS (25 mM Tris, 192 mM Glycine, 0.1% SDS (w/v), pH 8.3) for duplicate gels. One gel was stained with Bio-Safe Coomassie (Bio-Rad, #161-0786) for 1 h to visualize the peptide-containing bands, while the other gel was stained with 5% (w/v) aq. barium chloride and then 0.05 M aq. iodine to visualize the PEG-containing bands.

For the biotinylated homotetramer, a third 7.5% gel was subsequently electrophoretically transferred to a nitrocellulose membrane in 25 mM Tris, 192 mM Glycine, pH 8.3, containing 20% (v/v) methanol (Bio-Rad Laboratories, Hercules, Calif.) at 100 V for 30 min. Following transfer, the nitrocellulose membrane was blocked at 4° C. for 2 h in 5% non-fat dry milk in TBS and probed with Streptavidin-HRP (Abcam, ab7403) for confirmation of the biotin label.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Agnew Angew Chem Int Ed Engl 48:4944 (2009)
2. Bell Cancer Lett 289:81 (2010)
3. Erlanson Proc Natl Acad Sci USA 97:9367 (2000)
4. Fairbrother Biochem 37:17754 (1998)
5. Fields Int J Pept Prot Res 35:161 (1990)
6. Hosten Drug Metab Dispos 36:1729 (2008)
7. Jencks Proc Natl Acad Sci USA 78:4046 (1981)
8. Kwong J Am Chem Soc 131:9695 (2009)
9. Lam Nature 354:82 (1991)
10. Lee J Comb Chem 10:807 (2008)
11. Lee Anal Chem 82:672 (2010)
12. Liang J Biol Chem 281:951 (2006)
13. Manetsch J Am Chem Soc 126:12809 (2004)
14. Mocharla Angew Chem Int Ed Engl 44:116 (2004)
15. Murray J Comput Aided Mol Des 16:741 (2002)
16. Nagengast Eur J Cancer 47:1595 (2011)
17. Pakkala J Pept Sci 13:348 (2007)
18. Paudyal Cancer Sci 102:117 (2011)
19. Shi Bioconjug Chem 20:750 (2009)
20. Shuker Science 274:1531 (1996)
21. Stollman Int J Cancer 122:2310 (2008)
22. Watt Anal Chem 72:979 (2000)
23. Whiting Angew Chem Int Ed Engl 45:1435 (2006)
24. Fairbrother, W. J.; Christinger, H. W.; Cochran, A. G.; Fuh, G.; Keenan, C. J.; Quan, C.; Shriver, S. K.; Tom, J. Y. K.; Wells, J. A.; Cunningham, B. C. *Biochemistry* 1998, 37, 17754-17764.
25. (a) Zimmerman, S. B.; Murphy, L. D. *Anal. Biochem.* 1996, 234, 190-193. (b) Kurfürst, M. M. *Anal. Biochem.* 1992, 200, 244-248.
26. Dhara, D.; Chatterji, P. R. *J. Phys. Chem. B* 1999, 103, 8458-8461.

What is claimed is:

1. A stable, synthetic capture agent that specifically binds VEGF, wherein the capture agent comprises a designed anchor ligand, a designed secondary ligand, and, optionally, a designed tertiary ligand, and wherein the anchor ligand and secondary ligand selectively bind VEGF, wherein the anchor ligand comprises an amino acid sequence 95% identical to the amino acid sequence of SEQ ID NO:1 and wherein the secondary ligand comprises a formula of X2-X3-X4-X5-X6, wherein X2 is selected from the group consisting of D-arginine, D-tryptophan, D-leucine, D-valine, glycine, D-proline, D-isoleucine and D-alanine; wherein X3 is selected from the group consisting of D-proline, D-phenylalanine, glycine, D-arginine, D-lysine, D-histidine, D-tryptophan and D-tyrosine; wherein X4 is selected from the group consisting of D-isoleucine, D-leucine, D-proline, D-alanine, D-arginine, D-phenylalanine, D-threonine and D-histidine; wherein X5 is selected from the group consisting of D-isoleucine, glycine, D-valine, D-leucine, D-alanine, D-proline, D-lysine, D-glutamate, D-histidine and D-arginine; and wherein X6 is selected from the group consisting of D-arginine, D-lysine, D-tryptophan, D-tyrosine, D-proline, D-valine, glycine, D-isoleucine, D-alanine and D-glutamine.

2. The capture agent of claim 1, wherein the anchor ligand and secondary ligand are linked together via a 1,4-substituted-1,2,3-triazole residue (Tz4).

3. The capture agent of claim 1, wherein the capture agent has a structure selected from the group consisting of:

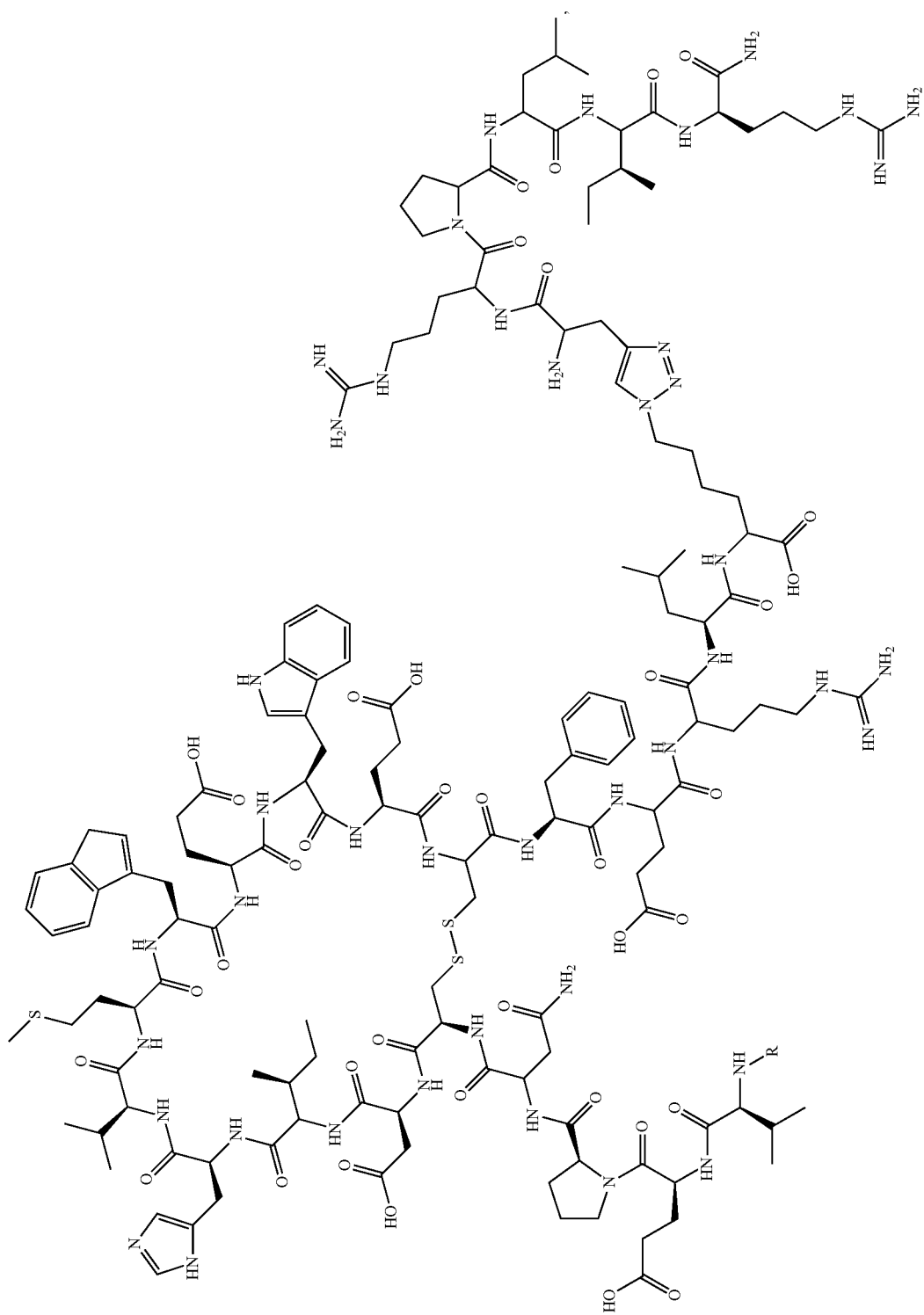

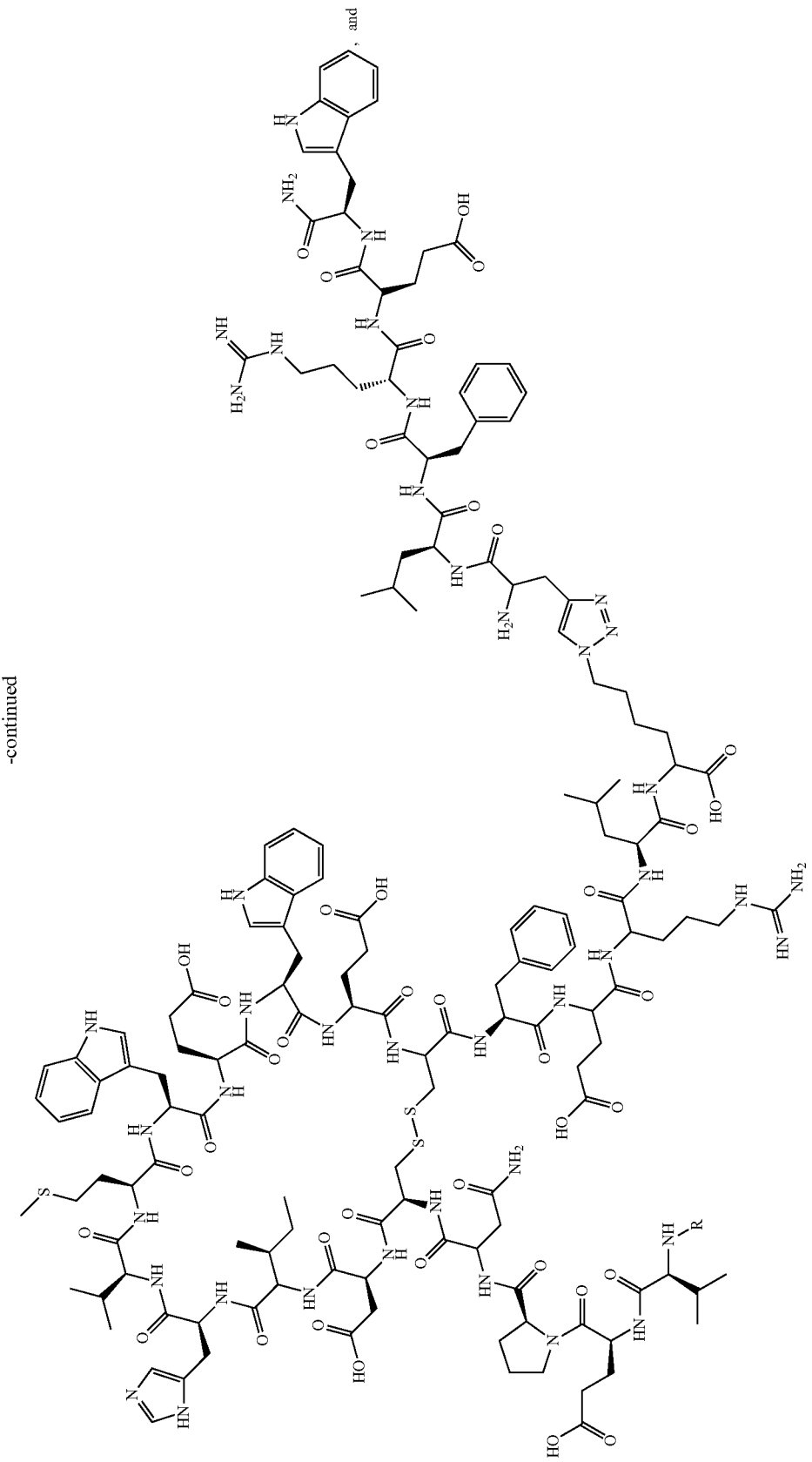

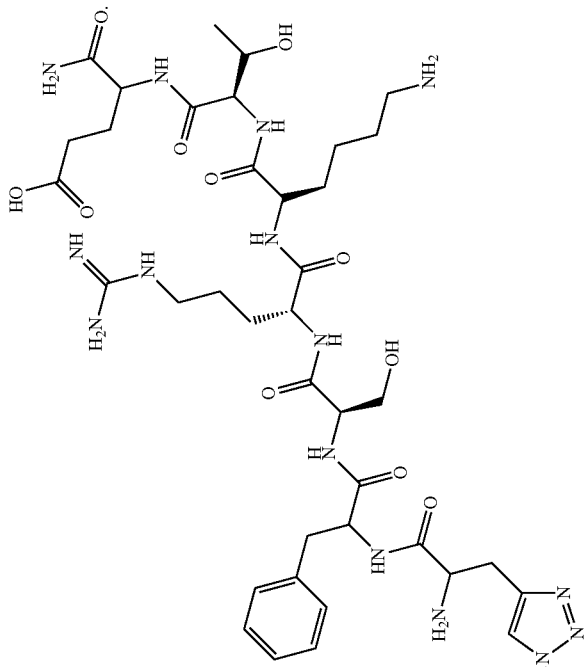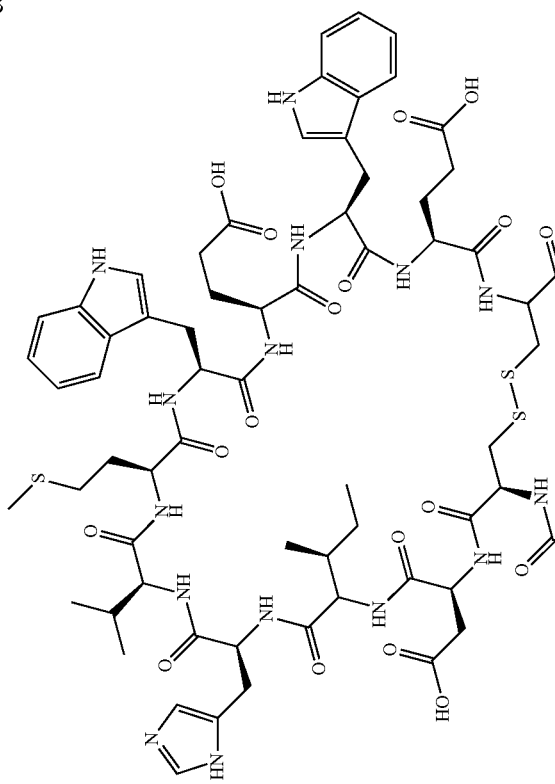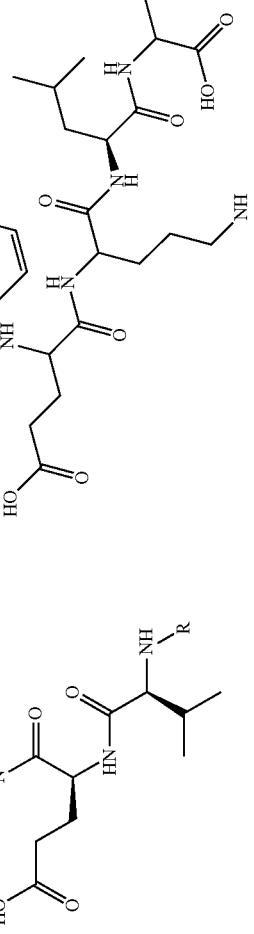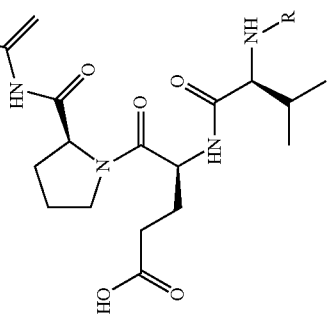

wherein R is a pegylated reporter tag or an N-terminal capping group.

4. The capture agent of claim 1, further comprising a designed tertiary ligand,
wherein the tertiary ligand comprises a formula of X2-X3-X4-X5-X6 wherein X2 is selected from the group consisting of D-histidine, D-arginine and D-lysine; X3 is selected from the group consisting of D-threonine, D-asparagine, D-leucine, D-proline, D-isoleucine, D-alanine, and D-glutamate; X4 is selected from the group consisting of D-histidine, D-lysine, D-arginine, D-tryptophan, D-phenylalanine, D-proline, D-leucine and D-tyrosine; X5 is selected from the group consisting of D-valine, D-proline, D-histidine, D-phenylalanine, D-tryptophan, D-asparagine, D-glutamine, D-serine and D-tyrosine; and X6 is selected from the group consisting of D-arginine, D-tyrosine, D-asparagine, D-glutamine, D-leucine, D-proline, D-lysine and D-histidine;

X2 is selected from the group consisting of D-tyrosine, D-phenylalanine and D-tryptophan; X3 is selected from the group consisting of D-proline, D-alanine, glycine, D-leucine, D-lysine, D-arginine and D-histidine; X4 is selected from the group consisting of D-arginine, D-histidine, D-tryptophan, D-phenylalanine, D-glutamate, D-proline, D-serine and D-threonine; X5 is selected from the group consisting of D-proline, D-aspartate, D-lysine, D-arginine, D-tyrosine, D-histidine, D-alanine, D-valine, D-leucine and D-asparagine; and X6 is selected from the group consisting of D-histidine, D-lysine, D-asparagine, D-threonine, D-glutamine, D-leucine, D-aspartate, D-serine, D-tyrosine, D-arginine, D-tryptophan, D-glutamate and D-valine; or X2 is selected from the group consisting of D-glutamate and D-aspartate; X3 is Selected from the group consisting of D-glutamate, D-phenylalanine, D-tryptophan, D-histidine, D-lysine, D-asparagine and D-serine; X4 is selected from the group consisting of D-isoleucine, D-proline, D-alanine, D-arginine, D-serine, D-aspartate, D-asparagine, D-proline, D-phenylalanine, D-tyrosine and D-histidine; X5 is selected from the group consisting of D-arginine, D-tyrosine, glycine, D-tryptophan, D-lysine, D-histidine, D-alanine, D-asparagine and D-leucine; and X6 is selected from the group consisting of D-aspartate, D-proline, D-tryptophan, D-tyrosine, D-leucine, D-asparagine, D-serine and D-threonine.

5. The capture agent of claim 4, wherein the anchor ligand and secondary ligand are linked together via a 1,4-substituted-1,2,3-triazole residue (Tz4).

6. The capture agent of claim 4, wherein the secondary ligand and tertiary ligand are linked together via a 1,4-substituted-1,2,3-triazole residue (Tz4).

7. The capture agent of claim 4, wherein the capture agent has a structure selected from the group consisting of

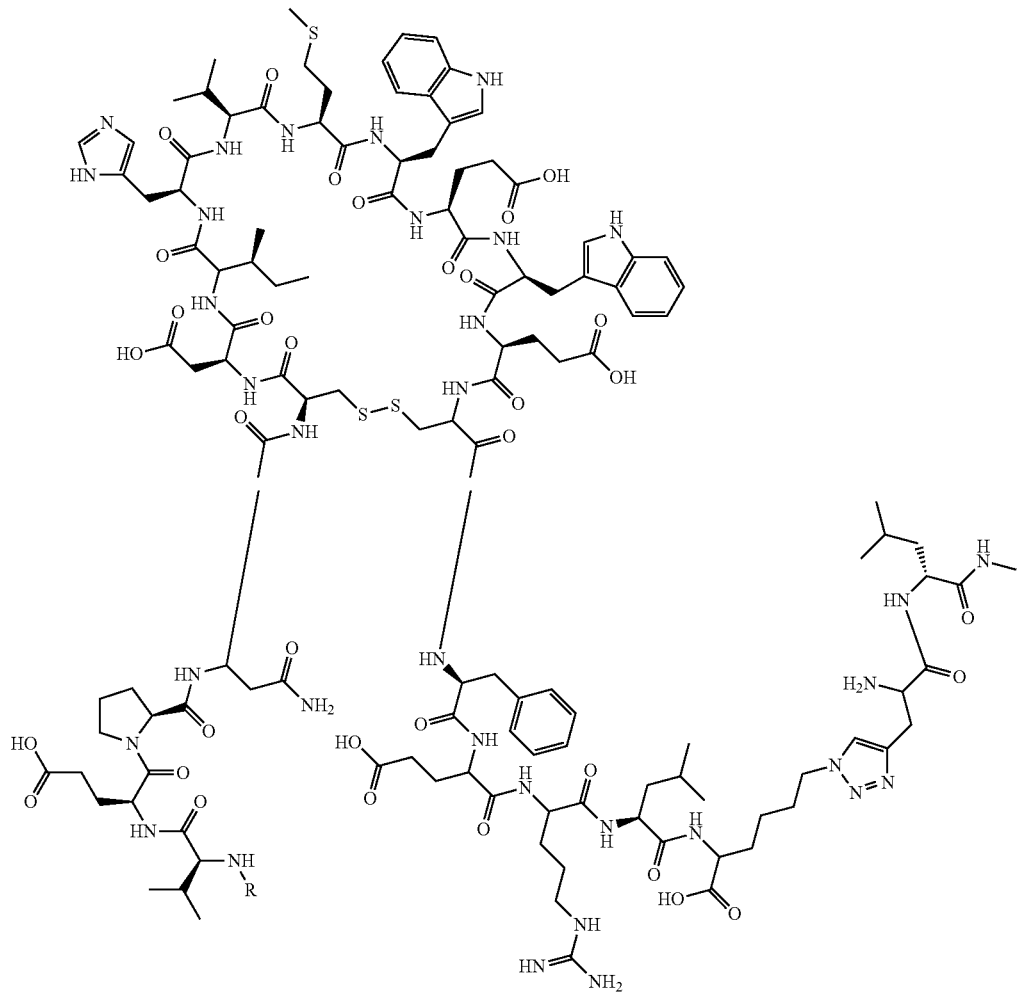

-continued
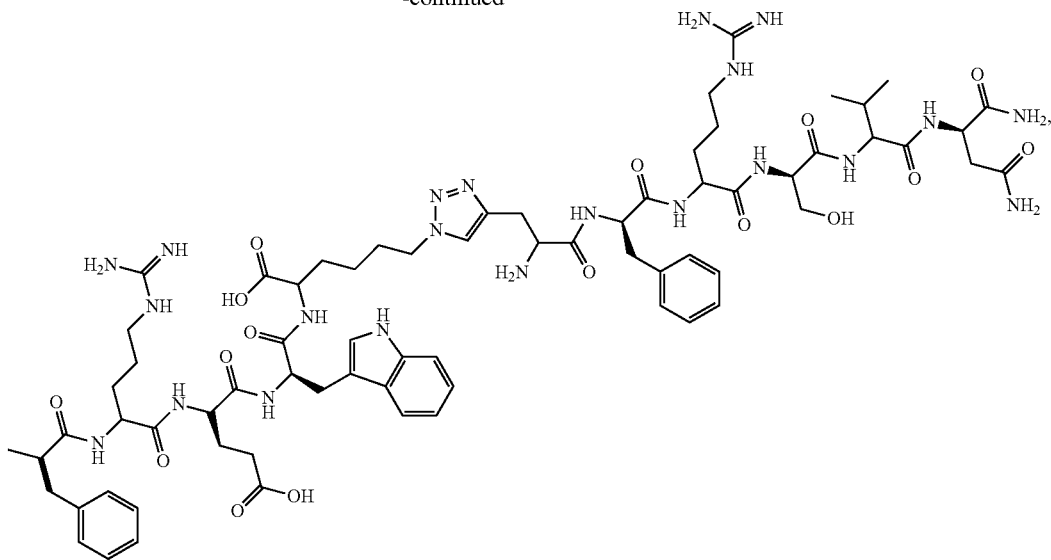
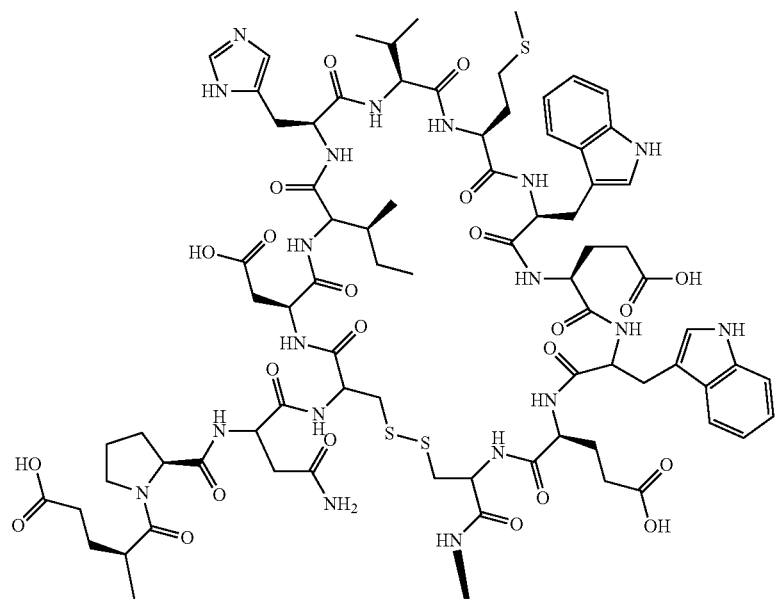
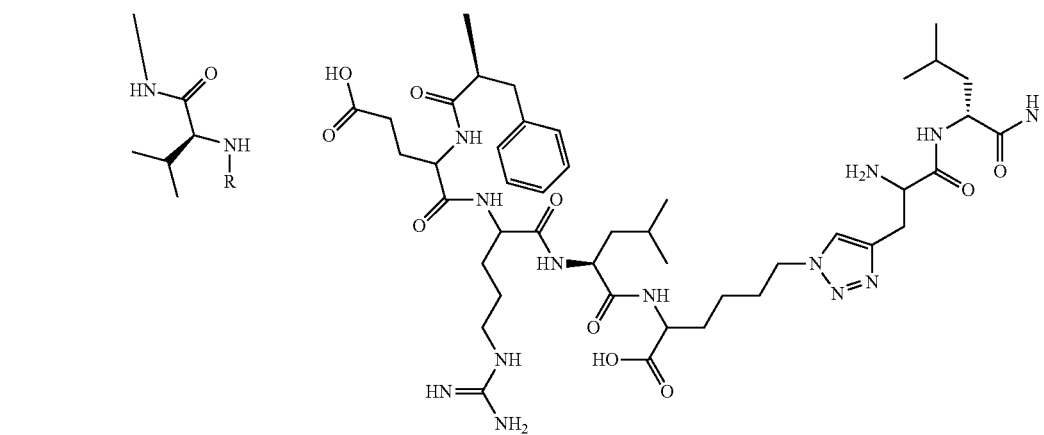

127                                    128
-continued
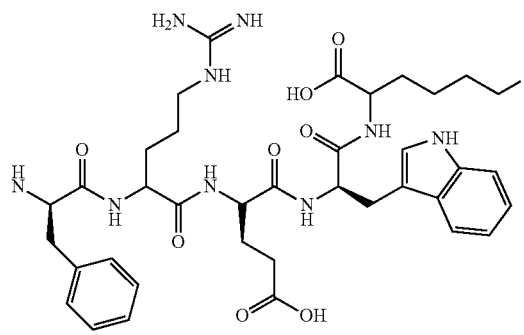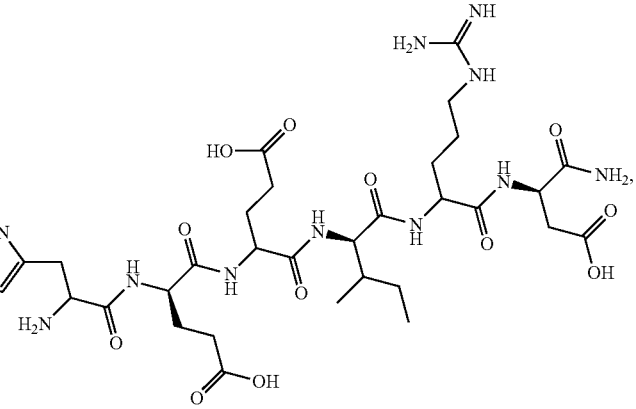
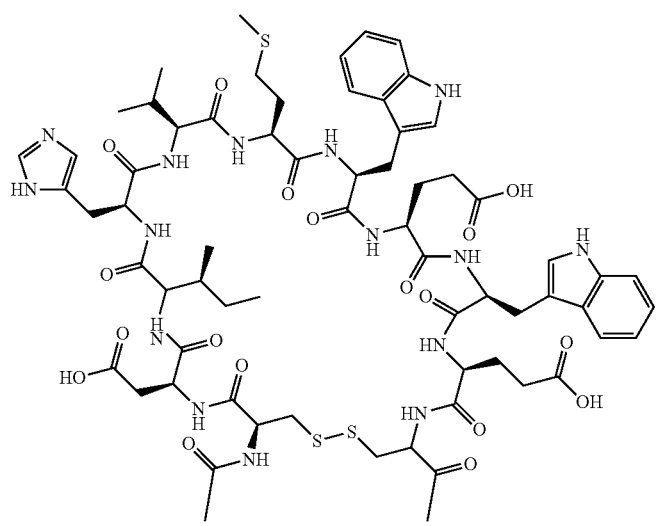
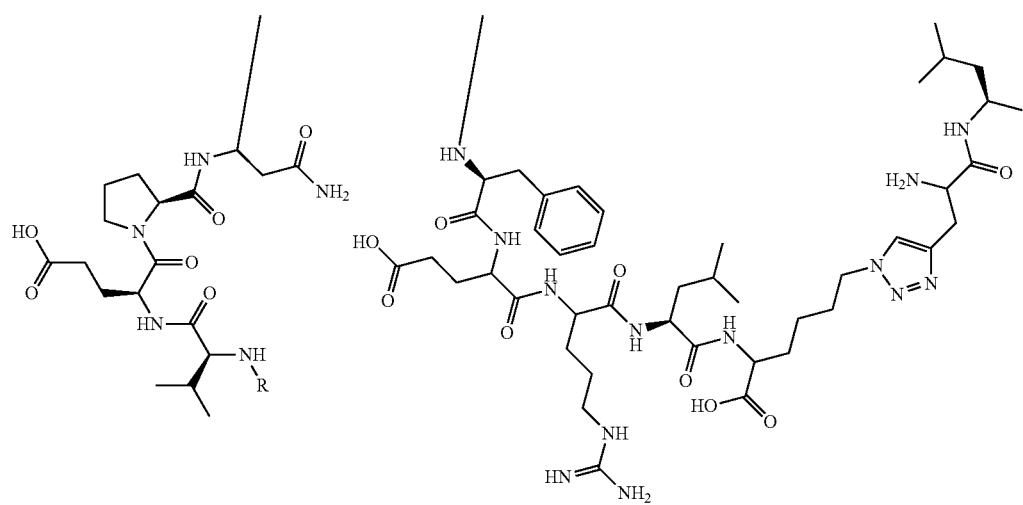

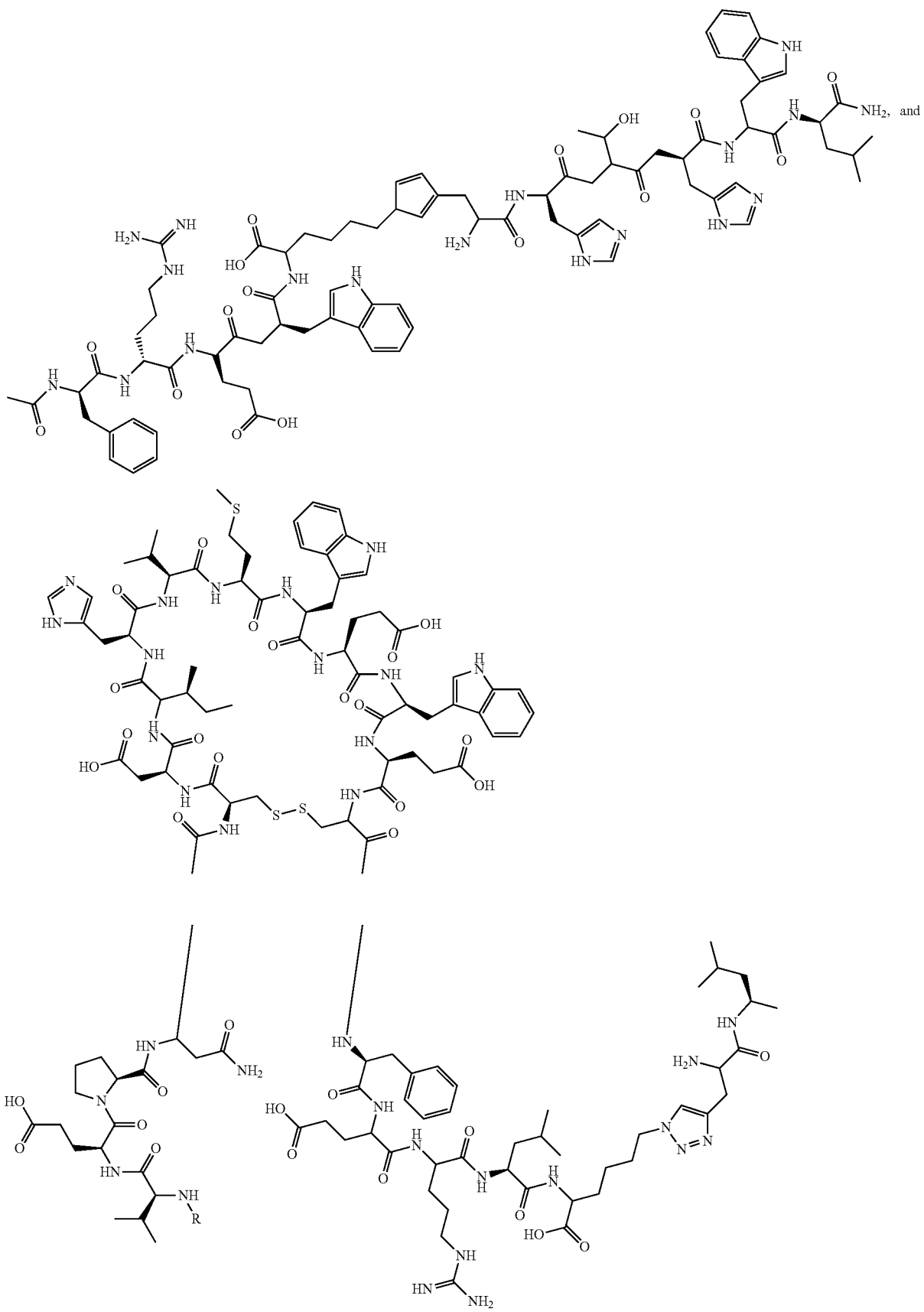

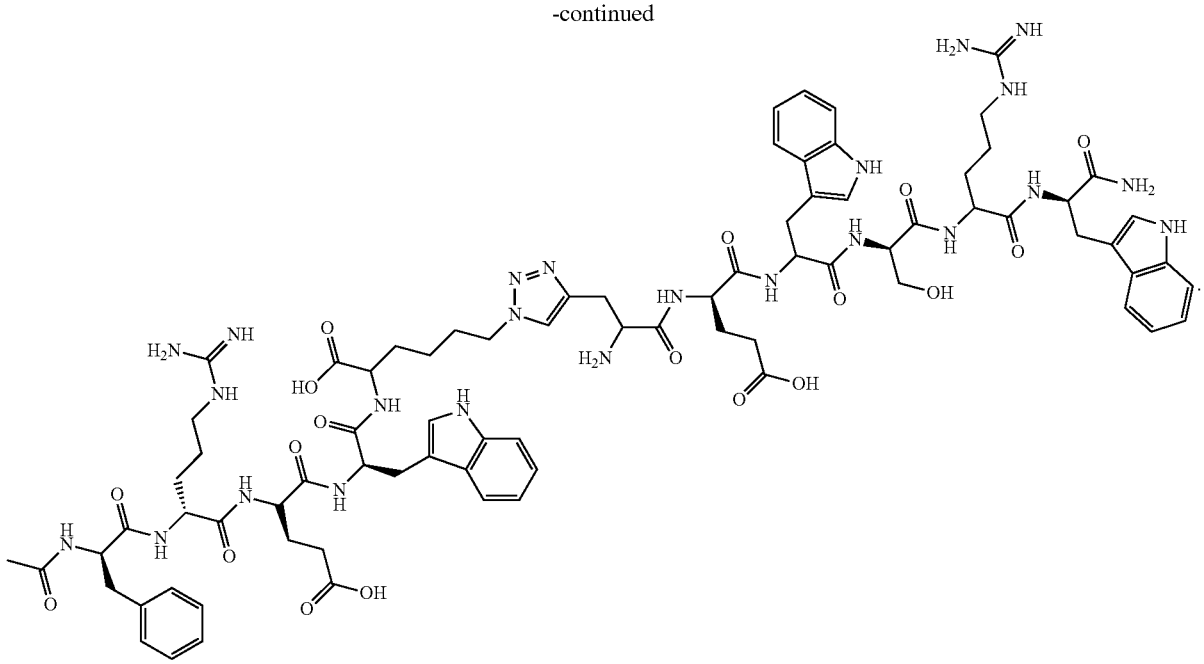

wherein R is a pegylated reporter tag or an N-terminal capping group.

8. The capture agent of claim 4, wherein binding of said capture agent to VEGF inhibits VEGF activity.

9. The capture agent of claim 4, wherein said capture agent inhibits binding of VEGF to VEGF receptor (VEGFR).

10. The capture agent of claim 4, wherein the capture agent is stable at a temperature of about about −80° C. to about 40° C.

11. The capture agent of claim 4, wherein the capture agent is stable at room temperature.

12. The capture agent of claim 4, wherein the capture agent is stable in blood serum or blood plasma for at least 24 hours.

13. The capture agent of claim 4, wherein the capture agent is stable at a pH in the range of from about 3 to about 12.

14. The capture agent of claim 4, wherein the capture agent is labeled with a label selected from the group consisting of biotin and copper-DOTA.

15. A method of detecting VEGF in a biological sample using an immunoassay, wherein the immunoassay utilizes a capture agent of claim 1 or claim 4, and wherein said capture agent replaces an antibody or its equivalent in the immunoassay.

16. The method of claim 15, wherein the immunoassay is selected from the group of Western blot, pull-down assay, dot blot, and ELISA.

17. A method of treating a condition associated with increased VEGF expression and/or activity in a subject in need thereof, comprising administering a therapeutically effective amount of a capture agent of claim 4.

18. The method of claim 17, wherein said condition is selected from the group consisting of cancer, proliferative retinopathy, disease pathology of wet form age-related macular degeneration (AMD), or rheumatoid arthritis.

19. A method of inhibiting VEGF activity in a subject comprising administering to the subject a therapeutically effective amount of the capture agent of claim 4.

20. The capture agent of claim 4, wherein the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C or $^{76}$Br.

21. A method of diagnosing a VEGF expressing cancer in a subject, the method comprising the steps of: a) administering to the subject the VEGF capture agent of claim 4, linked to a detectable moiety; and b) detecting the moiety linked to the VEGF capture agent in the subject; wherein detection of the moiety diagnoses a VEGF-expressing cancer in the subject.

22. The method of claim 21, wherein the capture agent is labeled with the detectable moiety consisting of $^{64}$Cu DOTA, $^{68}$Ga DOTA, $^{18}$F, $^{64}$Cu, $_{68}$Ga, $^{89}$Zr, $^{124}$I, $^{86}$Y, $^{94m}$Tc, $^{110}$In, $^{11}$C or $^{76}$Br.

23. A method of monitoring treatment of a subject receiving VEGF-directed therapy comprising
a) administering to the patient a small-molecule positron-emission-tomography ligand (PET ligand) that is bound to the VEGF capture agent of claim 2 or claim 5 on or near a VEGF-expressing cancer in the subject;
b) measuring the PET ligand that is bound to the VEGF capture agent associated with the VEGF-associated cancer at a first time;
c) measuring the PET ligand that is bound to the VEGF capture agent associated with the VEGF-associated cancer at a second time; and
d) comparing the amount of PET ligand that is bound to the VEGF capture agent associated with the VEGF-associated cancer at the first and second times, thereby monitoring treatment of the subject receiving VEGF-directed therapy.

24. A method for detecting VEGF in a sample comprising a) exposing the sample to the VEGF capture agent of claim 4, linked to a detectable moiety; and b) detecting the moiety linked to the VEGF capture agent in the sample; thereby detecting VEGF in the sample.

25. The method of claim 24, wherein the capture agent is labeled with the detectable moiety consisting of $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C or $^{76}$Br.

26. The method of claim 24, wherein the moiety linked to the VEGF capture agent is detected using PET or SPECT.

27. The method of claim 22, wherein the moiety linked to the VEGF capture agent is detected using PET or SPECT.

28. The capture agent of claim 3, wherein the pegylated reporter tag is selected from the group consisting of biotin-PEG and DOTA-PEG.

29. The capture agent of claim 3, wherein the N-terminal capping group is an acetyl group.

30. The capture agent of claim 7, wherein the pegylated reporter tag is selected from the group consisting of biotin-PEG and DOTA-PEG.

31. The capture agent of claim 7, wherein the N-terminal capping group is an acetyl group.

32. The capture agent of claim 14, wherein the label is bound to the capture agent by a linker.

33. The capture agent of claim 32, wherein the linker is a PEG linker.

34. The capture agent of claim 28, wherein the biotin-PEG is biotin-PEG3.

35. The capture agent of claim 34, wherein the biotin-PEG is biotin-PEG3.

* * * * *

SEQUENCE LISTING

<160> NUMBER OF SEQ ID NOS: 87

<210> SEQ ID NO 1
<211> LENGTH: 19
<212> TYPE: PRT
<213> ORGANISM: Artificial Sequence
<220> FEATURE:
<223> OTHER INFORMATION: Anchor Ligand
<220> FEATURE:
<221> NAME/KEY: Disulfide Restrained Residues
<222> LOCATION: (5)..(15)

<400> SEQUENCE: 1

Val Glu Pro Asn Cys Asp Ile His Val Met Trp Glu Trp Glu Cys Phe
1               5                   10                  15

Glu Arg Leu

<210> SEQ ID NO 2
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 2

Arg Pro Leu Ile Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 3

Leu Phe Arg Glu Trp
1               5

<210> SEQ ID NO 4
<211> LENGTH: 6
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(6)

<400> SEQUENCE: 4

Phe Ser Arg Lys Thr Glu
1               5

<210> SEQ ID NO 5
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

```
<400> SEQUENCE: 5

Phe Arg Ser Val Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 6

Glu Glu Ile Arg Asp
1               5

<210> SEQ ID NO 7
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 7

His Thr His Trp Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 8

Glu Trp Ser Arg Trp
1               5

<210> SEQ ID NO 9
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 9

Arg Pro Ile Ile Arg
1               5

<210> SEQ ID NO 10
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(3)
```

```
<220> FEATURE:
<221> NAME/KEY: D-amino acid
<222> LOCATION: (5)..(5)

<400> SEQUENCE: 10

Arg Phe Pro Gly Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(1)
<220> FEATURE:
<221> NAME/KEY: D-amino acid
<222> LOCATION: (3)..(5)

<400> SEQUENCE: 11

Trp Gly Ala Val Lys
1               5

<210> SEQ ID NO 12
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 12

Leu Arg Pro Ile Arg
1               5

<210> SEQ ID NO 13
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 13

Leu Arg Pro Leu Trp
1               5

<210> SEQ ID NO 14
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 14

Val Lys Arg Ala Tyr
1               5

<210> SEQ ID NO 15
<211> LENGTH: 5
<212> TYPE: PRT
```

```
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (2)..(5)

<400> SEQUENCE: 15

Gly His Arg Pro Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 16

Pro Arg Phe Lys Val
1               5

<210> SEQ ID NO 17
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(4)

<400> SEQUENCE: 17

Pro Trp Phe Ala Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(3)

<400> SEQUENCE: 18

Leu Trp Thr Gly
1

<210> SEQ ID NO 19
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 19

Ile Trp Arg Pro Ile
1               5

<210> SEQ ID NO 20
<211> LENGTH: 5
<212> TYPE: PRT
```

```
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (1)..(5)

<400> SEQUENCE: 20

Ala Tyr Arg His Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Secondary Ligand
<220> FEATURE:
<221> NAME/KEY: D-amino acid
<222> LOCATION: (2)..(5)

<400> SEQUENCE: 21

Gly Phe His Arg Gln
1               5

<210> SEQ ID NO 22
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 22

His Thr His Val Arg
1               5

<210> SEQ ID NO 23
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 23

His Thr His Pro Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 24

His Thr Lys His Asn
1               5

<210> SEQ ID NO 25
<211> LENGTH: 5
<212> TYPE: PRT
```

```
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 25

Arg Asn His Phe Gln
1               5

<210> SEQ ID NO 26
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 26

Arg Thr His Asn Leu
1               5

<210> SEQ ID NO 27
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 27

Arg Leu Arg Gln Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 28

Arg Pro Trp Ser Leu
1               5

<210> SEQ ID NO 29
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 29

Lys Ile Phe Ser Arg
1               5

<210> SEQ ID NO 30
<211> LENGTH: 5
<212> TYPE: PRT
```

```
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 30

His Pro Pro His Lys
1               5

<210> SEQ ID NO 31
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 31

His Ala Leu Trp His
1               5

<210> SEQ ID NO 32
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 32

His Ile Pro Tyr Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 33

His Glu Phe Phe Arg
1               5

<210> SEQ ID NO 34
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 34

His Glu Tyr Tyr Arg
1               5

<210> SEQ ID NO 35
<211> LENGTH: 5
<212> TYPE: PRT
```

```
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 35

Tyr Pro Arg Pro His
1               5

<210> SEQ ID NO 36
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 36

Tyr Pro Arg Pro Lys
1               5

<210> SEQ ID NO 37
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 37

Tyr Ala Arg Asp Asn
1               5

<210> SEQ ID NO 38
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(1)
<220> FEATURE:
<221> NAME/KEY: D-amino acid
<222> LOCATION: (3)..(5)

<400> SEQUENCE: 38

Phe Gly His Lys Thr
1               5

<210> SEQ ID NO 39
<211> LENGTH: 5
<212> TYPE: PRT
<213> ORGANISM: Artificial Sequence
<220> FEATURE:
<223> OTHER INFORMATION: Tertiary  Ligand
<220> FEATURE:
<221> NAME/KEY: D-amino acid
<222> LOCATION: (1)..(5)

<400> SEQUENCE: 39

Tyr Ala His Arg Gln
1               5
```

```
<210> SEQ ID NO 40
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 40

Trp Pro Trp Lys Leu
1               5

<210> SEQ ID NO 41
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 41

Phe Leu Trp Tyr Asp
1               5

<210> SEQ ID NO 42
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 42

Phe Lys Phe Lys Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 43

Trp Arg Glu Lys Tyr
1               5

<210> SEQ ID NO 44
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 44

Tyr His Pro His Arg
1               5
```

```
<210> SEQ ID NO 45
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 45

Trp Lys Pro His Trp
1               5

<210> SEQ ID NO 46
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 46

Trp Arg Ser His Glu
1               5

<210> SEQ ID NO 47
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 47

Tyr Arg Thr Ala Glu
1               5

<210> SEQ ID NO 48
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 48

Tyr Arg Thr Leu Gln
1               5

<210> SEQ ID NO 49
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 49

Phe Arg Ser Asn Gln
1               5
```

-continued

```
<210> SEQ ID NO 50
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 50

Phe Arg Thr Asn Val
1               5

<210> SEQ ID NO 51
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 51

Glu Glu Pro Tyr Pro
1               5

<210> SEQ ID NO 52
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)

<400> SEQUENCE: 52

Glu Glu Ala Gly Trp
1               5

<210> SEQ ID NO 53
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 53

Asp Phe Arg Trp Tyr
1               5

<210> SEQ ID NO 54
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)
```

```
<400> SEQUENCE: 54

Asp Trp Asp Gly Asp
1               5

<210> SEQ ID NO 55
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 55

Glu Trp Asn Lys Leu
1               5

<210> SEQ ID NO 56
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 56

Glu His Pro His Pro
1               5

<210> SEQ ID NO 57
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 57

Glu Lys Asn Lys Asn
1               5

<210> SEQ ID NO 58
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 58

Glu His Phe Trp Ser
1               5

<210> SEQ ID NO 59
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)
```

```
<400> SEQUENCE: 59

Glu His Tyr Ala Thr
1               5

<210> SEQ ID NO 60
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(3)
<220> FEATURE:
<221> NAME/KEY: D-amino acid
<222> LOCATION: (5)..(5)

<400> SEQUENCE: 60

Glu His His Gly Asn
1               5

<210> SEQ ID NO 61
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 61

Glu His His His Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 62

Glu Asn His His Asn
1               5

<210> SEQ ID NO 63
<211> LENGTH: 5
<212> TYPE: PRT
<213> ORGANISM: Artificial Sequence
<220> FEATURE:
<223> OTHER INFORMATION: Tertiary Ligand
<220> FEATURE:
<221> NAME/KEY: D-amino acid
<222> LOCATION: (1)..(5)

<400> SEQUENCE: 63

Glu Asn Arg Asn Leu
1               5

<210> SEQ ID NO 64
<211> LENGTH: 5
<212> TYPE: PRT
<213> ORGANISM: Artificial Sequence
<220> FEATURE:
<223> OTHER INFORMATION: Tertiary Ligand
<220> FEATURE:
```

```
<221> NAME/KEY: D-amino acid
<222> LOCATION: (1)..(5)

<400> SEQUENCE: 64

Glu Ser Asp Leu Pro
1               5

<210> SEQ ID NO 65
<211> LENGTH: 21
<212> TYPE: PRT
<213> ORGANISM: Artificial Sequence
<220> FEATURE:
<223> OTHER INFORMATION: Anchor Ligand Construct
<220> FEATURE:
<221> NAME/KEY: Biotin-PEG-
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Az4
<222> LOCATION: (21)..(21)

<400> SEQUENCE: 65

Xaa Val Glu Pro Asn Cys Asp Ile His Val Met Trp Glu Trp Glu Cys
1               5                   10                  15

Phe Glu Arg Leu Xaa
            20

<210> SEQ ID NO 66
<211> LENGTH: 27
<212> TYPE: PRT
<213> ORGANISM: Artificial Sequence
<220> FEATURE:
<223> OTHER INFORMATION: Biligand Construct
<220> FEATURE:
<221> NAME/KEY: Biotin-PEG-
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Az4
<222> LOCATION: (27)..(27)

<400> SEQUENCE: 66

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa
            20                  25

<210> SEQ ID NO 67
<211> LENGTH: 26
<212> TYPE: PRT
<213> ORGANISM: Artificial Sequence
<220> FEATURE:
<223> OTHER INFORMATION: Biligand 1
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
```

```
<220> FEATURE:
<221> NAME/KEY: D-amino acid
<222> LOCATION: (22)..(26)

<400> SEQUENCE: 67

Xaa Val Glu Pro Asn Cys Asp Ile His Val Met Trp Glu Trp Glu Cys
1               5                   10                  15

Phe Glu Arg Leu Xaa Arg Pro Leu Ile Arg
            20                  25

<210> SEQ ID NO 68
<211> LENGTH: 26
<212> TYPE: PRT
<213> ORGANISM: Artificial Sequence
<220> FEATURE:
<223> OTHER INFORMATION: Biligand 2
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)

<400> SEQUENCE: 68

Xaa Val Glu Pro Asn Cys Asp Ile His Val Met Trp Glu Trp Glu Cys
1               5                   10                  15

Phe Glu Arg Leu Xaa Leu Phe Arg Glu Trp
            20                  25

<210> SEQ ID NO 69
<211> LENGTH: 27
<212> TYPE: PRT
<213> ORGANISM: Artificial Sequence
<220> FEATURE:
<223> OTHER INFORMATION: Biligand 3
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)

<400> SEQUENCE: 69

Xaa Val Glu Pro Asn Cys Asp Ile His Val Met Trp Glu Trp Glu Cys
1               5                   10                  15

Phe Glu Arg Leu Xaa Phe Ser Arg Lys Thr Glu
            20                  25

<210> SEQ ID NO 70
<211> LENGTH: 32
<212> TYPE: PRT
<213> ORGANISM: Artificial Sequence
<220> FEATURE:
<223> OTHER INFORMATION: Triligand 1
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
```

<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 70

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Phe Arg Ser Val Asn
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Triligand 2
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 71

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Triligand 3
<220> FEATURE:
<221> NAME/KEY: Ac, Biotin-PEG, DOTA-PEG, etc
<222> LOCATION: (1)..(1)
<220> FEATURE:
<221> NAME/KEY: DisulfideRestrainedResidues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid

```
<222> LOCATION: (28)..(32)

<400> SEQUENCE: 72

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa His Thr His Trp Leu
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Triligand 4
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 73

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Trp Ser Arg Trp
            20                  25                  30

<210> SEQ ID NO 74
<211> LENGTH: 33
<212> TYPE: PRT
<213> ORGANISM: Artificial Sequence
<220> FEATURE:
<223> OTHER INFORMATION: Bifunctional Triligand 2
<220> FEATURE:
<221> NAME/KEY: DOTA-PEG
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)
<220> FEATURE:
<221> NAME/KEY: PEG-Biotin
<222> LOCATION: (33)..(33)

<400> SEQUENCE: 74

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30
```

```
<210> SEQ ID NO 75
<211> LENGTH: 32
<212> TYPE: PRT
<213> ORGANISM: Artificial Sequence
<220> FEATURE:
<223> OTHER INFORMATION: Biotin-conjugated Triligand 2
<220> FEATURE:
<221> NAME/KEY: Biotin-PEG
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 75

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
                20                  25                  30

<210> SEQ ID NO 76
<211> LENGTH: 63
<212> TYPE: PRT
<213> ORGANISM: Artificial Sequence
<220> FEATURE:
<223> OTHER INFORMATION: Triligand 2 Homodimer Prepared by Amide Bond
      Formation
<220> FEATURE:
<221> NAME/KEY: Disulfide Restrained Residues
<222> LOCATION: (5)..(15)
<220> FEATURE:
<221> NAME/KEY: Tz4
<222> LOCATION: (20)..(20)
<220> FEATURE:
<221> NAME/KEY: D-amino acid
<222> LOCATION: (21)..(25)
<220> FEATURE:
<221> NAME/KEY: Tz4
<222> LOCATION: (26)..(26)
<220> FEATURE:
<221> NAME/KEY: D-amino acid
<222> LOCATION: (27)..(31)
<220> FEATURE:
<221> NAME/KEY: PEG via Amide
<222> LOCATION: (32)..(32)
<220> FEATURE:
<221> NAME/KEY: D-amino acid
<222> LOCATION: (33)..(37)
<220> FEATURE:
<221> NAME/KEY: Tz4
<222> LOCATION: (38)..(38)
<220> FEATURE:
<221> NAME/KEY: D-amino acid
<222> LOCATION: (39)..(43)
<220> FEATURE:
<221> NAME/KEY: Tz4
<222> LOCATION: (44)..(44)
<220> FEATURE:
<221> NAME/KEY: Disulfide Restrained Residues
<222> LOCATION: (49)..(59)

<400> SEQUENCE: 76
```

-continued

```
Val Glu Pro Asn Cys Asp Ile His Val Met Trp Glu Trp Glu Cys Phe
1               5                   10                  15

Glu Arg Leu Xaa Leu Phe Arg Glu Trp Xaa Glu Glu Ile Arg Asp Xaa
            20                  25                  30

Asp Arg Ile Glu Glu Xaa Trp Glu Arg Phe Leu Xaa Leu Arg Glu Phe
        35                  40                  45

Cys Glu Trp Glu Trp Met Val His Ile Asp Cys Asn Pro Glu Val
    50                  55                  60
```

<210> SEQ ID NO 77
<211> LENGTH: 63
<212> TYPE: PRT
<213> ORGANISM: Artificial Sequence
<220> FEATURE:
<223> OTHER INFORMATION: Triligand 2 Homodimer Prepared by CuAAc
<220> FEATURE:
<221> NAME/KEY: Disulfide Restrained Residues
<222> LOCATION: (5)..(15)
<220> FEATURE:
<221> NAME/KEY: Tz4
<222> LOCATION: (20)..(20)
<220> FEATURE:
<221> NAME/KEY: D-amino acid
<222> LOCATION: (21)..(25)
<220> FEATURE:
<221> NAME/KEY: Tz4
<222> LOCATION: (26)..(26)
<220> FEATURE:
<221> NAME/KEY: D-amino acid
<222> LOCATION: (27)..(31)
<220> FEATURE:
<221> NAME/KEY: PEG via Tz4
<222> LOCATION: (32)..(32)
<220> FEATURE:
<221> NAME/KEY: D-amino acid
<222> LOCATION: (33)..(37)
<220> FEATURE:
<221> NAME/KEY: Tz4
<222> LOCATION: (38)..(38)
<220> FEATURE:
<221> NAME/KEY: D-amino acid
<222> LOCATION: (39)..(43)
<220> FEATURE:
<221> NAME/KEY: Tz4
<222> LOCATION: (44)..(44)
<220> FEATURE:
<221> NAME/KEY: Disulfide Restrained Residues
<222> LOCATION: (49)..(59)

<400> SEQUENCE: 77

```
Val Glu Pro Asn Cys Asp Ile His Val Met Trp Glu Trp Glu Cys Phe
1               5                   10                  15

Glu Arg Leu Xaa Leu Phe Arg Glu Trp Xaa Glu Glu Ile Arg Asp Xaa
            20                  25                  30

Asp Arg Ile Glu Glu Xaa Trp Glu Arg Phe Leu Xaa Leu Arg Glu Phe
        35                  40                  45

Cys Glu Trp Glu Trp Met Val His Ile Asp Cys Asn Pro Glu Val
    50                  55                  60
```

<210> SEQ ID NO 78
<211> LENGTH: 63
<212> TYPE: PRT
<213> ORGANISM: Artificial Sequence
<220> FEATURE:
<223> OTHER INFORMATION: Triligand 2/Triligand 3 Heterodimer Joined via
      CuAAC
<220> FEATURE:
<221> NAME/KEY: Disulfide Restrained Residues
<222> LOCATION: (5)..(15)
<220> FEATURE:

-continued

```
<221> NAME/KEY: Tz4
<222> LOCATION: (20)..(20)
<220> FEATURE:
<221> NAME/KEY: D-amino acid
<222> LOCATION: (21)..(25)
<220> FEATURE:
<221> NAME/KEY: Tz4
<222> LOCATION: (26)..(26)
<220> FEATURE:
<221> NAME/KEY: D-amino acid
<222> LOCATION: (27)..(31)
<220> FEATURE:
<221> NAME/KEY: PEG via Tz4
<222> LOCATION: (32)..(32)
<220> FEATURE:
<221> NAME/KEY: D-amino acid
<222> LOCATION: (33)..(37)
<220> FEATURE:
<221> NAME/KEY: Tz4
<222> LOCATION: (38)..(38)
<220> FEATURE:
<221> NAME/KEY: D-amino acid
<222> LOCATION: (39)..(43)
<220> FEATURE:
<221> NAME/KEY: Tz4
<222> LOCATION: (44)..(44)
<220> FEATURE:
<221> NAME/KEY: Disulfide Restrained Residues
<222> LOCATION: (49)..(59)

<400> SEQUENCE: 78

Val Glu Pro Asn Cys Asp Ile His Val Met Trp Glu Trp Glu Cys Phe
1               5                   10                  15

Glu Arg Leu Xaa Leu Phe Arg Glu Trp Xaa Glu Glu Ile Arg Asp Xaa
            20                  25                  30

Leu Trp His Thr His Xaa Trp Glu Arg Phe Leu Xaa Leu Arg Glu Phe
        35                  40                  45

Cys Glu Trp Glu Trp Met Val His Ile Asp Cys Asn Pro Glu Val
    50                  55                  60

<210> SEQ ID NO 79
<211> LENGTH: 32
<212> TYPE: PRT
<213> ORGANISM: Artificial Sequence
<220> FEATURE:
<223> OTHER INFORMATION: X-Triligand 2
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 79

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30

<210> SEQ ID NO 80
```

-continued

```
<211> LENGTH: 33
<212> TYPE: PRT
<213> ORGANISM: Artificial Sequence
<220> FEATURE:
<223> OTHER INFORMATION: PEGylated Triligand 2
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)
<220> FEATURE:
<221> NAME/KEY: PEG(40KD)
<222> LOCATION: (33)..(33)

<400> SEQUENCE: 80

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30

Xaa

<210> SEQ ID NO 81
<211> LENGTH: 33
<212> TYPE: PRT
<213> ORGANISM: Artificial Sequence
<220> FEATURE:
<223> OTHER INFORMATION: PEGylated Triligand 2
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: 2xPEG(20KD)
<222> LOCATION: (33)..(33)

<400> SEQUENCE: 81

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30

Xaa

<210> SEQ ID NO 82
<211> LENGTH: 65
<212> TYPE: PRT
<213> ORGANISM: Artificial Sequence
<220> FEATURE:
<223> OTHER INFORMATION: Multimeric Triligand 2
```

```
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)
<220> FEATURE:
<221> NAME/KEY: PEG(7.5KD)
<222> LOCATION: (33)..(33)
<220> FEATURE:
<221> NAME/KEY: D-amino acid
<222> LOCATION: (34)..(38)
<220> FEATURE:
<221> NAME/KEY: Tz4
<222> LOCATION: (39)..(39)
<220> FEATURE:
<221> NAME/KEY: D-amino acid
<222> LOCATION: (40)..(44)
<220> FEATURE:
<221> NAME/KEY: Tz4
<222> LOCATION: (45)..(45)
<220> FEATURE:
<221> NAME/KEY: Disulfide Restrained Residues
<222> LOCATION: (50)..(60)
<220> FEATURE:
<221> NAME/KEY: Ac, Biotin-PEG, DOTA-PEG, etc
<222> LOCATION: (65)..(65)

<400> SEQUENCE: 82

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
                20                  25                  30

Xaa Asp Arg Ile Glu Glu Xaa Trp Glu Arg Phe Leu Xaa Leu Arg Glu
            35                  40                  45

Phe Cys Glu Trp Glu Trp Met Val His Ile Asp Cys Asn Pro Glu Val
        50                  55                  60

Xaa
65

<210> SEQ ID NO 83
<211> LENGTH: 33
<212> TYPE: PRT
<213> ORGANISM: Artificial Sequence
<220> FEATURE:
<223> OTHER INFORMATION: Triligand 2 Homotetramer
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
```

```
<221> NAME/KEY: D-amino acid
<222> LOCATION: (28)..(32)
<220> FEATURE:
<221> NAME/KEY: PEG Tetramer
<222> LOCATION: (33)..(33)

<400> SEQUENCE: 83

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Glu Glu Ile Arg Asp
            20                  25                  30

Xaa

<210> SEQ ID NO 84
<211> LENGTH: 26
<212> TYPE: PRT
<213> ORGANISM: Artificial Sequence
<220> FEATURE:
<223> OTHER INFORMATION: Illustration of Biligand Structure
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D- or L-amino acid
<222> LOCATION: (22)..(26)

<400> SEQUENCE: 84

Xaa Val Glu Pro Asn Cys Asp Ile His Val Met Trp Glu Trp Glu Cys
1               5                   10                  15

Phe Glu Arg Leu Xaa Xaa Xaa Xaa Xaa Xaa
            20                  25

<210> SEQ ID NO 85
<211> LENGTH: 32
<212> TYPE: PRT
<213> ORGANISM: Artificial Sequence
<220> FEATURE:
<223> OTHER INFORMATION: Illustration of Triligand Structure
<220> FEATURE:
<221> NAME/KEY: Ac, Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D- or L-amino acid
<222> LOCATION: (28)..(32)

<400> SEQUENCE: 85

Xaa Val Glu Pro Asn Cys Asp Ile His Val Met Trp Glu Trp Glu Cys
1               5                   10                  15

Phe Glu Arg Leu Xaa Leu Phe Arg Glu Trp Xaa Xaa Xaa Xaa Xaa Xaa
            20                  25                  30

<210> SEQ ID NO 86
```

```
<211> LENGTH: 32
<212> TYPE: PRT
<213> ORGANISM: Artificial Sequence
<220> FEATURE:
<223> OTHER INFORMATION: Non-Restrained Triligand 2
<220> FEATURE:
<221> NAME/KEY: Biotin-PEG
<222> LOCATION: (1)..(1)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)
<220> FEATURE:
<221> NAME/KEY: D-amino acid
<222> LOCATION: (28)..(32)

<400> SEQUENCE: 86

Xaa Val Glu Pro Asn Cys Asp Ile His Val Met Trp Glu Trp Glu Cys
 1               5                  10                  15

Phe Glu Arg Leu Xaa Leu Phe Arg Glu Trp Xaa Glu Glu Ile Arg Asp
             20                  25                  30

<210> SEQ ID NO 87
<211> LENGTH: 27
<212> TYPE: PRT
<213> ORGANISM: Artificial Sequence
<220> FEATURE:
<223> OTHER INFORMATION: Biligand
<220> FEATURE:
<221> NAME/KEY: Biotin-PEG, DOTA-PEG, etc
<222> LOCATION: (1)..(1)
<220> FEATURE:
<221> NAME/KEY: Disulfide Restrained Residues
<222> LOCATION: (6)..(16)
<220> FEATURE:
<221> NAME/KEY: Tz4
<222> LOCATION: (21)..(21)
<220> FEATURE:
<221> NAME/KEY: D-amino acid
<222> LOCATION: (22)..(26)
<220> FEATURE:
<221> NAME/KEY: Tz4
<222> LOCATION: (27)..(27)

<400> SEQUENCE: 87

Xaa Val Glu Pro Asn Cys Asp Ile His Val Met Trp Glu Trp Glu Cys
 1               5                  10                  15

Phe Glu Arg Leu Xaa Leu Phe Arg Glu Trp Xaa
             20                  25
```